US011672846B2

(12) United States Patent
Howell et al.

(10) Patent No.: US 11,672,846 B2
(45) Date of Patent: Jun. 13, 2023

(54) SOLUBLE BACTERIAL AND FUNGAL PROTEINS AND METHODS AND USES THEREOF IN INHIBITING AND DISPERSING BIOFILM

(71) Applicants: The Hospital for Sick Children, Toronto (CA); The Royal Institution for the Advancement of Learning/McGill University, Montreal (CA)

(72) Inventors: Lynne P. Howell, Toronto (CA); Perrin Baker, Mississauga (CA); Noor Alnabelseya, San Francisco, CA (US); Natalie Bamford, Toronto (CA); Dustin Little, Burlington (CA); Donald Sheppard, Montreal (CA); Brendan Snarr, North Bethesda, MD (US); Mark Jae Lee, Burbank, CA (US)

(73) Assignees: The Hospital for Sick Children, Toronto (CA); The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 17/127,911

(22) Filed: Dec. 18, 2020

(65) Prior Publication Data
US 2021/0138044 A1   May 13, 2021

Related U.S. Application Data

(63) Continuation of application No. 15/316,394, filed as application No. PCT/CA2015/000361 on Jun. 5, 2015, now Pat. No. 10,905,749.

(60) Provisional application No. 62/008,836, filed on Jun. 6, 2014.

(51) Int. Cl.
| | | |
|---|---|---|
| *C12N 9/24* | (2006.01) |
| *A61K 38/47* | (2006.01) |
| *A61L 29/16* | (2006.01) |
| *A61L 27/54* | (2006.01) |
| *A61K 45/06* | (2006.01) |
| *A01N 63/50* | (2020.01) |
| *A01N 63/30* | (2020.01) |
| *A01N 63/10* | (2020.01) |
| *A01N 63/00* | (2020.01) |
| *A61K 35/74* | (2015.01) |
| *A61L 27/34* | (2006.01) |
| *A61L 29/08* | (2006.01) |
| *A61L 31/10* | (2006.01) |
| *A61L 31/16* | (2006.01) |

(52) U.S. Cl.
CPC ........... *A61K 38/47* (2013.01); *A01N 63/00* (2013.01); *A01N 63/10* (2020.01); *A01N 63/30* (2020.01); *A01N 63/50* (2020.01); *A61K 35/74* (2013.01); *A61K 45/06* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C12N 9/2402* (2013.01); *C12Y 302/01* (2013.01); *A61L 2300/252* (2013.01); *A61L 2300/254* (2013.01); *A61L 2300/404* (2013.01); *A61L 2420/00* (2013.01); *A61L 2430/24* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,726,878 B1 | 4/2004 | Flidlyander et al. |
| 6,830,745 B1 | 12/2004 | Budny et al. |
| 7,294,497 B2 | 11/2007 | Kaplan |
| 7,989,604 B2 | 8/2011 | Kaplan |
| 8,580,551 B2 | 11/2013 | Kaplan |

FOREIGN PATENT DOCUMENTS

| | | |
|---|---|---|
| JP | 2006511226 A | 4/2006 |
| WO | 2004061117 A2 | 7/2004 |
| WO | 2004062677 A1 | 7/2004 |
| WO | 2008157350 A2 | 12/2008 |

OTHER PUBLICATIONS

Johansen et al. Applied and Environmental Microbiology, vol. 63, No. 9, pp. 3724-3728, Sep. 1997.*
Uniprot Accession No. Q7VX64, Jan. 22, 2014.*
Uniprot Accession No. Q9HZE4, Mar. 19, 2014.*
Kaplan JB, Velliyagounder K, Ragunath C, Rohde H, Mack D, et al.: "Genes involved in the synthesis and degradation of matrix polysaccharide in Actinobacillus actinomycetemcomitans and Actinobacillus pleuropneumoniae biofilms", Journal of Bacteriology, vol. 186, No. 24, pp. 8213-8220, American Society for Microbiology, Washington DC, U.S.A., Dec. 2004.
A partial English translation of Ichinose, Y., et al: "Pseudomonas syringae", Jpn. J. Phytopathol, Nov. 2014, vol. 80, Special Issue 97-103, Review for the 100th Anniversary, pp. 97-103.

(Continued)

*Primary Examiner* — Richard G Hutson
(74) *Attorney, Agent, or Firm* — Melanie Szweras; Bereskin & Parr LLP/ S.E.N.C.R.L., s.r.l.

(57) ABSTRACT

The present disclosure relates to methods of treating or preventing a biofilm-related infection and methods of preventing and treating biofilm formation on indwelling medical devices, implants, and non-medical surfaces comprising administering at least one soluble microbial protein that is encoded by an exopolysaccharide biosynthetic operon or functional gene cluster, wherein the protein comprises a glycosyl hydrolase domain. The present disclosure further provides particular soluble glycosyl hydrolases and compositions thereof.

9 Claims, 57 Drawing Sheets

Specification includes a Sequence Listing.

(56) References Cited

OTHER PUBLICATIONS

Kaplan, J.B. et al.: "Biofilm Dispersal—Mechanisms, Clinical Implications, and Potential Therapeutic Uses", J. Dent. Res., Mar. 2010, vol. 89, No. 3, pp. 205-218.
Boyd, A. and Chakrabarty, A.M.: "Role of Alginate Lyase in Cell Detachment of Pseudomonas aeruginosa", Applied and Environmental Microbiology, Jul. 1994, vol. 60, No. 7, pp. 2355-2359.
Intra, J. et al.: "Phylogenetic analyses suggest multiple changes of substrate specificity within the Glycosyl hydrolase 20 family", BMC Evolutionary Biology, published Jul. 22, 2008, vol. 8, Article No. 214, pp. 1-17.
Henrissat, B.: "A classification of glycosyl hydrolases based on amino acid sequence similarities", Biochem J., Dec. 1, 1991, vol. 280, pp. 309-316.
Yoshida, K. et al.: Carbohydrate-Binding Module of a Rice Endo-β-1,4-glycanase, OsCel9A, Expressed in Auxin-Induced Lateral Root Primordia, is Post-Translationally Truncated, Plant and Cell Physiology, Nov. 1, 2006, vol. 47, Issue 11, pp. 1555-1571.
English translation of the Abstract; Yamagishi, A.: "Experimental Test on the Last Common Ancestor: Reproduction of the Ancient Proteins", Journal of Geography, Apr. 25, 2003, vol. 112, Issue 2, pp. 197-207.
Harry, S.: "The functions of paucimannose N-glycans in Caenorhabditis elegans", Trends in Glycoscience and Glycotechnology, released Sep. 2009, vol. 21, Issue 119, pp. 131-148.
Kriventseva, E., et al: "OrthoDB v10: sampling the diversity of animal, plant, fungal, protist, bacterial and viral genomes for evolutionary and functional annotations of orthologs", Nucleic Acids Research, Jan. 8, 2019, vol. 47, Database issue D807-D811.
Thorn, C. R., et al.: Pseudomonas Infection Responsive Liquid Crystals for Glycoside Hydrolase and Antibiotic Combination, American Chemical Society, ACS Appl. Bio Materials, Jul. 13, 2018, vol. 1, 2, pp. 281-288.
Kaplan, J. B.: "Therapeutic Potential of Biofilm-Dispersing Enzymes", Sep. 2009, The International Journal of Artificial Organs, vol. 32, No. 9, pp. 545-554.
Waterhouse R. M. et al.: "OrthoDB: A Hierarchical Catalog of Animal, Fungal and Bacterial Orthologs", Nucleic Acids Research, vol. 41, Database issue pp. D358-D365, published online Nov. 23, 2012.
MIZUNOE Yoshimitsu, Oto-Rhino-Laryngology, Tokyo (2013) vol. 56, No. 4, pp. 199-203 (English translation of Excerpt).
Ruperez, P. et al.: "Extracelluar Galactosaminogalactan From Aspergillus Parasiticus", received for publication Jan. 30, 1981, Trans. Br. Mycol. Soc. vol. 77, pp. 621-625.
Ramasubbu, N. et al. : "Structural Analysis of Dispersin B, a Biofilm-releasing Glycoside Hydrolase from the Periodontopathogen *Actinobacillus actinomycetemcomitans*", ePub Apr. 14, 2005, Journal of Molecular Biology, vol. 349(3), pp. 475-486.
Molecular Biology of the Cell, (2002), 1st edition, 5th impression, p. 153, the item "orthologs" (English translation of Excerpt).
Muszkieta, L et al.: "Investigation of Aspergillus Fumigatus Biofilm Formation By Various "Omics" Approaches", Feb. 12, 2013, Frontiers in Microbiol., vol. 4, Article 13, pp. 1-16.
Sheppard, D. et al.: "Sph3: A Glycosyl Hydrolase Required for Biofilm Formation by Aspergillus Fumigatus and Potential Therapeutic Agent", Oct. 2015, Mycoses vol. 58, P443, p. 212 (Abstract only).
Papers of the Week: "A New Glycoside Hydrolase Family Found in Common Human Pathogenic Fungus Sph3 Is a Glycoside Hydrolase Required for the Biosynthesis of Galactosaminogalactan in *Aspergillus fumigatus*", Nov. 13, 2015, The Journal of Biological Chemistry, vol. 290, No. 46, p. 27451.
Lee M.J.: "The Synthesis and Functions of Galactosaminogalactan in *Aspergillus* Species", Aug. 2014, A thesis submitted to McGill University, pp. 1-238.
Desai J. V. et al. "Fungal Biofilms, Drug Resistance, and Recurrent Infection", 2014, Cold Spring Harb. Perspect. Med. vol. 4, a019729, pp. 1-18.

Bugli, F. et al.: "In Vitro Interaction between Alginate Lyase and Amphotericin B against Aspergillus Fumigatus Biofilm Determined by Different Methods", 2012, Antimicrob. Agents Chemother., vol. 57 No. 3, pp. 1275-1282.
Baker, P. et al., "Exploiting exopolysaccharide biosynthetic machinery to develop therapeutics that inhibit and Disperse Pseudomonas aeruginosa biofilms", FASEB Conference on Microbial Glycobiology, Jun. 8, 2014 (online), Abstract.
Little, D. J. et al.: "PgaB is Required for the De-N-acetylation and Export of the Biofilm Polysaccharide PNAG", Abstract, presented at ACA Annual Meeting 2013, Honolulu, Hawaii, Jul. 2013.
Little, D.J. et al., "PgaB is Required for the De-N-acetylation and Recognition of the Biofilm Exopolysaccharide Poly-β-1,6-N-acetyl-D-glucosamine", Abstract, presented at CSHRF Health Research Forum 2013, Winnipeg, Manitoba, Jun. 2013.
Little, D.J. et al., "The Structure- and Metal-dependent Activity of *Escherichia coli* PgaB Provides Insight into the Partial De-N-acetylation of Poly-β-1,6-N-acetyl-D-glucosamine", The Journal of Biological Chemistry, Sep. 7, 2012, vol. 287, No. 37, pp. 31126-31137.
Little, D.J. et al.: "Structural insights for the N-deacetylation of poly-β-1,6-N-acetyl-D-glucosamine", Abstract, FASEB Summer Conference on Microbial Polysaccharides, Carefree, Arizona, U.S.A., Jun. 2011.
Little, D.J. et al.: "Characterizing the role of PgaB in exopolysaccharide modification and secretion during biofilm formation in *Escherichia coil*", Abstract, 21st Annual Buffalo-Hamilton-Toronto (BHT) Symposium, Hamilton, Ontario, Canada, Nov. 2, 2012.
Little, D.J. et al.: "Modification and periplasmic translocation of the biofilm exopolysaccharide poly-β-1,6-N-acetyl-D-glucosamine", PNAS, Jul. 29, 2014, vol. 111, No. 30, pp. 11013-11018.
Baker, P. et al.: "Slime Wars: Identification of Compounds that Inhibit PEL Polysaccharide Dependent Biofilm-Formation", Poster, presented at Biochemistry Research Day, Toronto, Ontario, Canada, Jun. 4, 2013.
Sheppard, D.: "New uses for old drugs . . . ", PowerPoint Presentation, presented at 19th Congress of the International Society for Human and Animal Mycology, Melbourne, Australia, May 2, 2015.
Colvin, K. M. et al.: "Pe1A Deacetylase Activity is Required for Pel Polysaccharide Synthesis in Pseudomonas Aeruginosa", Journal of Bacteriology, May 2013, vol. 195, No. 10, pp. 2329-2339.
Ma, L. et al., "Analysis of Pseudomonas Aeruginosa Conditional PsL Variants Reveals Roles for the Psl Polysaccharide in Adhesion and Maintaining Biofilm Structure Postattachment", Journal of Bacteriology, Dec. 2006, vol. 188, No. 23, pp. 8213-8221.
Billings, N. et al., "The Extracellular Matrix Component Psl Provides Fast-Acting Antibiotic Defense in Pseudomonas aeruginosa Biofilms", PLOS Pathogens, Aug. 8, 2013, vol. 9, Issue 8, e1003526, pp. 1-12.
Doss, RP. et al., "Adhesion of Germlings of Botrytis cinerea", Appl. Environ. MicrobioL., Jan. 1995, vol. 61, No. 1, pp. 260-265.
Snarr, B. and Sheppard, D.: "Crosstalk between biofilm exopolysaccharides of Aspergillus fumigatus and Pseudomonas aeruginosa", PowerPoint Presentation, presented at 2014 International Union of Microbiological Societies (IUMS), Montreal, Quebec, Canada, Jul. 29, 2014.
Little, D.J. et al: "Role of BpsB Bordetella Biofilm Formation and its Potential as a Therapeutic Agent", PowerPoint presentation, presented at Biofilm Retreat, Marblehead, Ohio, U.S.A., Sep. 2014.
Little, D.J. et al., "Modification and Translocation of the Biofilm Exopolysaccharide poly-β-1,6-N-acetyl-D-glucosamine (PNAG)", Abstract, presented at the International Union of Crystallography meeting, Montreal, Canada, Aug. 2014.
Little, D.J., "Modification and periplasmic translocation of the biofilm exopolysaccharide poly-β(1,6)-N-acetyl-D-glucosamine (PNAG)", PowerPoint Presentation, presented at FASEB Conference on Microbial Glycobiology, Itasca, Illinois, U.SA., Jun. 10, 2014.
Bamford, N.C. et al., "Characterizing the role of Sph3 in biofilm formation by Aspergillus fumigatus", Abstract, 23rd Annual Buffalo-Hamilton-Toronto (BHT) Symposium, Hamilton, Ontario, Canada, Nov. 7, 2014.

(56) References Cited

OTHER PUBLICATIONS

Bamford, N.C.: "Characterizing the role of Sph3 in biofilm formation by Aspergillus fumigatus", PowerPoint Presentation, presented at 23rd Annual Buffalo-Hamilton-Toronto (BHT) Symposium, Hamilton, Ontario, Canada, Nov. 7, 2014.

Bamford, N.C., "Structure and Function of Sph3 from Aspergillus fumigatus", PowerPoint Presentation, presented at the Wozniak/Parsek Retreat, Marblehead, Ohio, U.S.A., Sep. 2014.

Baker, P., "Exploiting exopolysaccharide biosynthetic machinery to develop therapeutics that inhibit and disperse Pseudomonas aeruginosa biofilms", PowerPoint Presentation, presented at FASEB Conference on Microbial Glycobiology, Itasca, Illinois, U.S.A., Sep. 16, 2014.

Baker, P. et al.: "Exploiting exopolysaccharide biosynthetic machinery to develop therapeutics that inhibit and disperse Pseudomonas aeruginosa biofilms", Poster, displayed at FASEB 2nd International Conference, Itasca, Illinois, U.SA., Sep. 16, 2014.

Baker, P. et al.: "Developing therapeutic enzymes that prevent and disperse Pseudomonas aeruginosa biofilms", PowerPoint presentation, presented at the Wozniak/Parsek Retreat, Marblehead, Ohio, U.SA., Jun. 12, 2014.

Chen, M. et al.: "Novel Strategies for the Prevention and Treatment of Biofilm Related Infections", Int. J. Mol. Sci., Sep. 6, 2013, vol. 14, No. 9, pp. 18488-18501.

Gravelat, F. et al.: "Identification of a gene cluster mediating the biosynthesis of the Aspergillus fumigatus cell wall and secreted polysaccharide, galactosaminogalactan", The Tenth International Aspergillus Meeting, Mar. 2013, Abstract.

Ngo et al: "Computational Complexity, Protein Structure Prediction, and the Levinthal Paradox", in "The Protein Folding Problem and Tertiary Structure Prediction", 1994, Merz et al., (ed.), Birkhauser, Boston, MA, pp. 433 and 492-495.

Loussert, C. et al.: "In vivo biofilm composition of Aspergillus fumigatus", Cellular Microbiology, Feb. 5, 2010, vol. 12, No. 3, pp. 405-410.

Yu, S. et al.: "PslG, a self-produced glycosyl hydrolase, triggers biofilm disassembly by disrupting exopolysaccharide matrix", Cell Research, Nov. 27, 2015, pp. 1-16.

Little, D. J.: "PgaB is Required for the De-N-acetylation and Export of the Biofilm Polysaccharide PNAG", PowerPoint presentation, presented at ACA Annual Meeting 2013, Honolulu, Hawaii, Jul. 23, 2013.

Little, D. J. et al., "PgaB is Required for the De-N-acetylation and Export of the Biofilm Exopolysaccharide Poly-β-1,6-N-acetyl-D-glucosamine (PNAG)", Poster, displayed at CSHRF Health Research Forum 2013, Winnipeg, Manitoba, Jun. 2013.

Little, D.J. et al.: "Structural insights for the N-deacetylation of poly-β-1,6-N-acetyl-D-glucosamine", Poster, displayed at FASEB Conference 2011, Polysaccharides of Medical, Agricultural and Industrial Importance, Carefree, Arizona, U.S.A., Jun. 2011.

Little, D.J. et al.: "Characterizing the role of PgaB in exopolysaccharide modification and secretion during biofilm formation in *Escherichia coil*", PowerPoint Presentation, presented at University of Toronto, Toronto, Canada, Oct. 17, 2012.

Little, D.J. et al.: "Modification and Translocation of the Biofilm Exopolysaccharide poly-β-1,6-N-acetyl-D-glucosamine (PNAG)", Poster, presented at the International Union of Crystallography Conference, Montreal, Quebec, Canada, Aug. 5-12, 2014.

Database UniProt [Online], Jul. 5, 2005, retrieved from EBI, Accession No. Q4WX17.

Database UniProt [Online], Jan. 23, 2007, retrieved from EBI, Accession No. A1CJQ5.

Database UniProt [Online], Apr. 26, 2005, retrieved from EBI, Accession No. Q5B928.

Turk, R. et al.: "In vitro evaluation of DispersinB on methicillin-resistant *Staphylococcus pseudintermedius* biofilm", Veterinary Microbiology, Oct. 1, 2013, vol. 166, pp. 576-579.

Darouiche, R.O. et al.: "Antimicrobial and antibiofilm efficacy of triclosan and DispersinB® combination", Journal of Antimicrobial Chemotherapy, May 14, 2009, vol. 64, pp. 88-93.

Erickson, D.L. et al.: "Loss of a Biofilm-Inhibiting Glycosyl Hydrolase during the Emergence of Yersinia pestis", Journal of Bacteriology, Dec. 15, 2008, vol. 190, No. 24, pp. 8163-8170.

Bamford, N.C. et al.: "Sph3 Is a Glycoside Hydrolase Required for the Biosynthesis of Galactosaminogalactan in Aspergillus fumigatus", The Journal of Biological Chemistry, Sep. 4, 2015, vol. 290, No. 46, pp. 27438-27450.

Snarr, B.D. et al.: "Microbial glycoside hydrolases as antibiofilm agents with cross-kingdom activity", PNAS, Jun. 20, 2017, vol. 114, No. 27, pp. 7124-7129.

P. Baker, N.C. Bamford, D.J. Little, B. Starr, P.J.Hill, M. Lee, D. Askar, T.S. Awad, L. Jennings, B. Hatton, M. Parsek, D. Wozniak, D. Sheppard, P.L. Howell: "Development of multi-platform enzyme-based microbial biofilm disruptors", PowerPoint Presentation, presented at the GlycoCOM Conference, Banff, May 5, 2015.

P. Baker, N.C. Bamford, D.J. Little, B. Starr, P.J.Hill, M. Lee, D. Askar, T.S. Awad, L Jennings, B. Hatton, M. Parsek, D. Wozniak, D. Sheppard, P.L. Howell: "Development of multi-platform enzyme-based microbial biofilm disruptors", Poster, displayed at th GlycoCOM Conference, Banff, May 5, 2015.

P. Baker, G.B. Whitfield, J. Rich, P.J. Hill, N. Alnabelseya, D.J. Little, B. Snarr, D. Sheppard, M. Parsek, D. Wozniak, J. J. Harrison, P. L. Howell: "The role of glycoside hydolases in Pseudononas aeruginosa Exopolysaccharide biosynthesis", Poster, Presented at the 11th Annual National Carbohydrate Symposium, Banff, May 6-8, 2015.

P. Baker, N.C. Bamford, D.J. Little, B. Starr, P.J. Hill, M. Lee, D. Askar, T.S. Awad, L. Jennings, B. Hatton, M. Parsek, D. Wozniak, D. Sheppard, P. L. Howell: "Development of multi-platform enzyme-based microbial biofilm disruptors", Powerpoint presentation, presented at the Department of Biochemistry, University of Toronto Retreat, Toronto, Ontario, May 21, 2015.

Turk et al.: "In vitro evaluation of DispersinB on methicillin-resistant *Staphylococcus pseudintermedius* biofilm", Oct. 25, 2013, Veterinary microbiology vol. 166, pp. 576-579.

Darouiche et al.: "Antimicrobial and antibiofilm efficacy of triclosan and DispersinB combination", Jul. 2009, The Journal of antimicrobial chemotherapy, vol. 64(1): 88-93.

Donelli et al.: "Synergistic activity of dispersin B and cefamandole iafate in inhibition of staphylococcal biofilm growth on polyurethanes", Aug. 2007, Antimicrobial agents and chemotherapy; vol. 51, pp. 2733-2740.

Gawande et al: "Antibiofilm and Antimicrobial Efficacy of DispersinB-KSL-W Peptide-Based Wound Gel Against Chronic Wound Infection Associated Bacteria", May 2014, Current microbiology, vol. 68, pp. 635-641.

Manuel et al.: "Role of active-site residues of dispersin B, a biofilm-releasing beta-hexosaminidase from a periodontal pathogen, in substrate hydrolysis", Nov. 2007, The FEBS journal vol. 274(22), pp. 5987-5999.

Baker et al.: "Exopolysaccharide biosynthetic glycoside hydrolases can be utilized to Disrupt and prevent Pseudomonas aeruginosa biofilms", May 2016, Science Advances, vol. 2, No. 5, pp. 1-9.

Fontaine et al. Galactosaminogalactan, a New Immunosuppressive Polysaccharide of Aspergillus fumigatus. PLOS Pathogens, published Nov. 10, 2011, vol. 7, No. 11, e1002372, pp. 1-13.

Bales et al. Purification and Characterization of Biofilm-Associated EPS Exopolysaccharides from ESKAPE Organisms and Other Pathogens. PLOS ONE, published Jun. 21, 2013, vol. 8, No. 6, e67950, pp. 1-8.

Wozniak et al. Alginate is not a significant component of the extracellular polysaccharide matrix of PA14 and PAO1 Pseudomonas aeruginosa biofilms. The Proceedings of the National Academy of Sciences USA, published Jun. 24, 2003, vol. 100, No. 13, pp. 7907-7912.

Bok et al. Purification, Characterization, and Molecular Analysis of Thermostable Cellulases CelA and CelB from Thermotoga neapolitana. Applied and Environmental Microbiology, published Dec. 1998, vol. 64, No. 12, pp. 4774-4781.

Le Mauff et al. Molecular mechanism of Aspergillus fumigatus biofilm disruption by fungal and bacterial glycoside hydrolases. The Journal of Biological Chemistry, published Jun. 5, 2019, vol. 294, No. 28, pp. 10760-10772.

(56) References Cited

OTHER PUBLICATIONS

Miyazawa et al. The mechanisms of hyphal pellet formation mediated by polysaccharides, α-1,3-glucan and galactosaminogalactan, in *Aspergillus* species. Fungal Biology and Biotechnology, published online Jul. 1, 2020, vol. 7, article No. 10, pp. 1-13.
Takada et al. Structure of Polygalactosamine Produced by Aspergillus parasiticus. The Journal of Biochemistry, published Apr. 1981, vol. 89, No. 4, pp. 1265-1274.
Bardalaye and Nordin. Galactosaminogalactan from Cell Walls of Aspergillus niger. Journal of Bacteriology, published Feb. 1976, vol. 125, No. 2, pp. 655-669.
Gomez-Miranda and Leal. Extracellular and cell wall polysaccharides of Aspergillus alliaceus. Transactions of the British Mycological Society, published Feb. 1981, vol. 76, No. 2, pp. 249-253.
Lee et al. Deacetylation of Fungal Exopolysaccharide Mediates Adhesion and Biofilm Formation. American Society for Microbiology, published Apr. 5, 2016, vol. 7, No. 2, e00252-16, pp. 1-14.

* cited by examiner

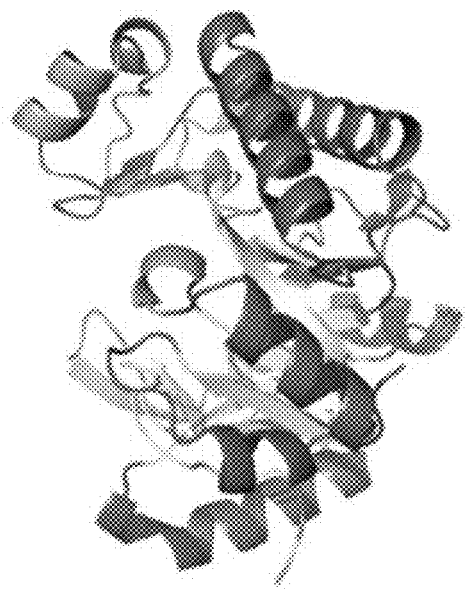
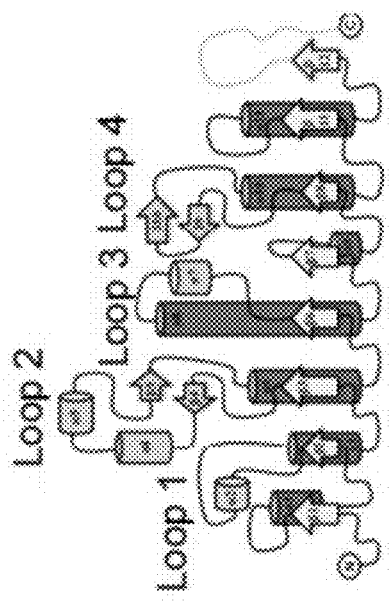
Fig. 13A
Fig. 13B
Fig. 13C

SOLUBLE BACTERIAL AND FUNGAL PROTEINS AND METHODS AND USES THEREOF IN INHIBITING AND DISPERSING BIOFILM

CROSS-REFERENCE TO RELATED APPLICATIONS

This application claims priority to U.S. patent application Ser. No. 15/316,394, filed on Dec. 6, 2016, now allowed, which itself was filed on Jun. 5, 2015 under 35 U.S.C. 371 as a national phase entry of International Patent Application No. PCT/CA2015/000361, now expired, which itself claimed the benefit of priority to U.S. Provisional application No. 62/008,836 filed Jun. 6, 2014, the contents of which are incorporated herein by reference in their entirety.

INCORPORATION OF SEQUENCE LISTING

A computer readable form of the Sequence Listing "9962-P46130US03_SequenceListing.txt" (45,056 bytes), submitted via EFS-WEB and created Dec. 18, 2020, is herein incorporated by reference.

FIELD

The present disclosure relates to glycosyl hydrolase-containing soluble microbial proteins. In particular, the present disclosure relates to compositions and methods and uses thereof in treating and preventing microbial biofilms.

BACKGROUND

Microbial Biofilms

The composition of microbial biofilms varies between strains/species and environmental conditions, but generally contains proteinaceous adhesins, nucleic acids, and exopolysaccharides as the main components (Branda et al 2005, Sutherland 2001a, Vu et al 2009). Exopolysaccharides are the predominant biofilm matrix component of many microbial organisms, contributing to biofilm adhesion, architecture, and resistance (Colvin et al 2011, Colvin et al 2012, Ma et al 2009, Ma et al 2006, Mah et al 2003, Matsukawa & Greenberg 2004). Biofilms form on biotic surfaces, such as lung epithelial cells or other organs, and abiotic surfaces including, but not limited to, medical devices, and implants, and are responsible for biofouling in industrial and commercial settings including, but not limited to; pipes and drains, water filtration apparatuses and food-contact surfaces (Bjarnsholt et al 2013, Kumar & Anand 1998). The hallmark of chronic, biofilm-related infections is an extreme resistance to antibiotics and the ability to evade the host immune system (Bjarnsholt 2013, Hoiby et al 2010, Kim et al 2009, Mishra et al 2012, Rybtke et al 2011, Stewart 2003, Stewart & Costerton 2001). The tolerance of bacterial biofilms to antibiotics and detergents is often 1,000 times higher compared to their planktonic counterparts (Alhede et al 2011, Costerton et al 1987, Costerton et al 1999, Davies 2003). Mature biofilms have a highly complex structure that allows for the movement of nutrients and waste products (Hall-Stoodley et al 2004, Sutherland 2001b). Biofilms act to sequester a large microbial population, including many pathogenic bacterial species, which symbiotically utilize the strengths of each organism for survival in the host (Wolcott et al 2013). Therefore, strategies to inhibit biofilms may have implications for reducing the total microbial biomass (Bragonzi et al 2012).

*P. aeruginosa* and Biofilm Formation.

During infection, the bacterium *P. aeruginosa* undergoes a life-style change from a free-swimming state to a surface attached, matrix embedded biofilm state (FIG. 1). Upon establishment of a biofilm, the infection becomes chronic and untreatable, as the biofilm is highly resistant to antibiotics and aids in the bacterial adaptation to changing environments (Colvin et al 2011, Mishra et al 2012, Zegans et al 2012). In CF patients this biofilm allows the bacteria to persist within the lungs for decades (Ma et al 2012, Mann & Wozniak 2012, Starkey et al 2009), while in wounds it allows for initial colonization and protection. *P. aeruginosa* biofilms are mainly composed of the exopolysaccharides; Psi, Pel and alginate. All three polysaccharides are important virulence factors and aid in genetic fitness of the bacterium (Skurnik et al 2013). Two common clinical biofilm forming strains *P. aeruginosa* PA14 and PAO1 have been extensively studied (Hare et al 2012, Kukavica-Ibrulj et al 2008). PA14, the most abundant strain worldwide (Wiehlmann et al 2007), was originally identified in burn wound isolates (Rahme et al 1995). This strain is highly virulent and exclusively utilizes Pel (Colvin et al 2012), while the second clinical strain PAO1 is a moderately virulent strain (Lee et al 2006) that primarily utilizes Psl for biofilm production (Colvin et al 2012). Under duress, PAO1 is able to utilize Pel if production of Psl is compromised (Colvin et al 2012), allowing it to maintain infection in the host (Byrd et al 2011). Several recent studies indicate that Pel and Psl are critical during early biofilm formation. In addition, Psl has been demonstrated to be important for continued maintenance in established biofilms as demonstrated in CF patients (Billings et al 2013, Huse et al 2013, Irie et al 2012, Wang et al 2013, Zhao et al 2013).

Psl Polysaccharide

Psl is composed of a pentasaccharide repeating unit of D-mannose, D-glucose and L-rhamnose, and is distinct from other known polysaccharides (FIG. 2). The psl operon, discovered in 2004 (Jackson et al 2004), consists of 15 open reading frames (ORFs) pslABCDEFGHIJKLMNO, encoding putative proteins required for the biosynthesis of the exopolysaccharide. Four of these ORFs, pslB, pslM, pslN, pslO are not required for Psl biosynthesis (Byrd et al 2009). The psl operon is present in numerous *Pseudomonas* strains (FIG. 3). The initial steps in Psl biosynthesis are proposed to occur in the cytoplasm and are then transferred to the periplasm prior to secretion through the outer membrane (Franklin et al 2011).

Psl functions as a "molecular glue" for bacterial adhesion and is important for initial adherence of planktonic or "free-swimming" bacteria to abiotic and biotic surfaces (Byrd et al 2010, Byrd et al 2009, Ma et al 2006). Psi also aids in the structural stability, and maintenance of the architecture of the mature biofilm (Ma et al 2009, Ma et al 2012). The polysaccharide provides protection against the immune system (Mishra et al 2012) and is a first line of defense during the initial stages of biofilm development, especially towards attack by antibiotics with diverse targets and biochemical properties (Billings et al 2013). For example, Psl-producing biofilms have a ~35-50% increase in resistance to Polymyxin B, Tobramycin and Ciprofloxacin which are standard antibiotics used in the clinic to treat *P. aeruginosa* infections, and a 75% increase in resistance to Colistin, one of the last-resort antibiotics for multi-drug resistant *P. aeruginosa* (Billings et al 2013). Non-Psi producing, antibiotic-sensitive *P. aeruginosa*, *Escherichia coli*, and *Staphylococcus aureus*, gain antibiotic tolerance by integrating into Psl-containing biofilms. Sub-inhibitory concentrations of these antibiotics induce further biofilm formation (Hoffman et al 2005) exacerbating the infection. While alginate is the major exopolysaccharide in chronic CF lung infection, recent evidence suggests that Psl is just as important during long-term colonization (40,000 bacterial generations) (Huse et al 2013). Patients recovering from *P. aeruginosa* infections have specific antibodies against Psl demonstrating that Psi is clinically relevant during infection (Digiandomenico et al 2012).

Pel Polysaccharide

Biofilms that form at the air-liquid interface are referred to as pellicles. Pellicles formed by the clinical isolate *P. aeruginosa* PA14 are encoded on the seven-gene operon pelABCDEFG, all of which are necessary for Pel-dependent biofilm formation (FIG. 4) (Colvin et al 2011, Friedman & Kolter 2004a). The pel operon was initially discovered in a transposon library in 2004 (Friedman & Kolter 2004b). The chemical composition of Pel and linkage is currently unknown. The biosynthesis is believed to start in the cytoplasm and the polymer is transported across the inner membrane for translocation through the periplasm. Recent work suggests that the Pel polysaccharide must be deacetylated or partially deacetylated by the multi-domain periplasmic protein PelA for biofilm formation to occur (Colvin et al 2013). *P. aeruginosa* PA14 largely relies on the Pel polysaccharide for adhesion and cell-to-cell interaction compared to other strains. The polysaccharide is crucial for maintaining cell-to-cell interactions and forms a structural scaffold for the biofilm community (Colvin et al 2011). Pel also serves a protective role against commonly used antibiotics tobramycin and ciprofloxacin (Colvin et al 2011).

PNAG Biofilms in Gram-Positive and Gram-Negative Bacteria

The polysaccharide PNAG (FIG. 5) has been found in the biofilms of *Staphylococcus epidermidis* (Mack et al 1996), *S. aureus* (McKenney et al 1999), *E. coli* (Wang et al 2004), *Pseudomonas fluorescens* (Itoh et al 2005), *Acinetobacter baumannii* (Choi et al 2009), *Actinobacillus pleuropneumoniae* (Izano et al 2007), *Yersinia pestis* (Jarrett et al 2004), *Aggregatibacter actinomycetemcomitans* (Izano et al 2008), *Bordetella bronchiseptica* (Sloan et al 2007), *Bordetella pertussis* (Conover et al 2010), and *Burkholderia* spp. (Yakandawala et al 2011). The biosynthesis of PNAG requires the icaADBC and pgaABCD operons in Gram-positive and Gram-negative bacteria, respectively. Interestingly, recent immunogenic studies probing the cellular surface of a wide variety of prokaryotic and eukaryotic pathogens that do not contain the canonical genetic loci for the biosynthesis of PNAG revealed the presence of surface-associated PNAG (Cywes-Bentley et al 2013). This included *Streptococcus pneumoniae, Streptococcus pyogenes, Streptococcus dysgalactiae, Enterococcus faecalis, Listeria monocytogenes, Clostridium difficile, Mycobacterium tuberculosis, Mycobacterium smegmatis, Neisseria meningitidis, Neisseria gonorrheae*, nontypable *Haemophilus influenzae, Haemophilus ducreyi, Helicobacter pylori, Campylobacter jejuni, Citrobacter rodentium, Salmonella enterica, Candida albicans, Aspergillus flavus, Fusarium solani, Cryptococcus neoformans, Trichomonas vaginalis, Plasmodium berghei*, and *Plasmodium falciparum* (Cywes-Bentley et al 2013). Furthermore, administration of monoclonal antibodies that bind to PNAG were able to mediate complement-dependent opsonic or bactericidal killing that protected mice against local or systemic infections from a number of the pathogens (Cywes-Bentley et al 2013).

PNAG Polysaccharide

PNAG is a homopolymer of repeating N-acetyl-D-glucosamine units, similar to chitin, however it is synthesized with a $\beta(1,6)$ linkage. The mature form of PNAG is partially deacetylated, is commonly referred to as dPNAG, and is required for the formation of the biofilm in a large number bacteria (FIG. 6). Given the differences in cell wall architecture between Gram-positive and Gram-negative bacteria, the sequence homology between the protein products of the two genetic loci is limited to IcaA and PgaC, and IcaB and the N-terminal domain of PgaB. PgaB, a two-domain outer-membrane lipoprotein, and IcaB, an extracellular single-domain protein, are required for the partial de-N-acetylation of PNAG (Little et al 2012a, Pokrovskaya et al 2013). Impairment of de-N-acetylation of PNAG has shown to prevent biofilm formation in *E. coli, S. aureus*, and *S. epidermidis* (Cerca et al 2007, Itoh et al 2008, Vuong et al 2004).

*Aspergillus fumigatus* and Biofilm Formation

*Aspergillus fumigatus* is a fungal pathogen and is one of the most common *Aspergillus* species to cause disease in immuno-compromised individuals (Geiser et al 2007). *Aspergillus* species are the second most common cause of fungal infection in the healthcare setting after *C. albicans* (Ellis et al 2000). The average person inhales several hundred *A. fumigatus* conidia (fungal spores) daily, which pass through the airways and are deposited in the alveoli of the lungs. Importantly, while these conidia account for less than 0.1% of all airborne fungal conidia, *A. fumigatus* conidia accounts for >80% of invasive infection in humans. In healthy individuals with normal lung function, conidia are removed by the mucociliary elevator or rapidly phagocytosed and killed by alveolar macrophages to prevent infection. However, in immune-compromised individuals, these conidia are not killed but instead adhere to pulmonary epithelial cells and macrophages before being internalized and germinating within host cells (Wasylnka et al 2005, Wasylnka & Moore 2002, Wasylnka & Moore 2003). Following germination, the newly formed hyphae remain intimately associated with host epithelial, endothelial and immune cells that can result in inflammation and tissue injury (Gravelat et al 2013, Wasylnka & Moore 2000). In patients with chronic lung disease whose immune system is intact, *Aspergillus* spores can germinate to produce hyphae that colonize the airways or pre-existing lung cavities but do not invade into tissues. These forms of *Aspergillus* infection are associated with persistent airway inflammation, allergic responses and declining lung function. In both invasive and chronic pulmonary aspergillosis infection, hyphae of the fungus are found within a dense extracellular matrix (Loussert et al 2010). It has been shown that biofilm formation and the adherence of hyphae to epithelial cells is mediated by the exopolysaccharide galactosaminogalactan (GAG) (Gravelat et al 2013). *Aspergillus* is also a cause of wound and corneal infections. Other *Aspergillus* species and some non-*Aspergillus* fungi, including the fungal pathogen *Fusarium*, as well as a number of plant pathogenic fungi have the genetic capability to produce GAG.

Galactosaminogalactan (GAG)

Galactosaminogalactan (GAG) is a heterogeneous, linear extracellular polysaccharide that is composed of $\alpha 1$-4 linked galactose and $\alpha 1$-4 linked N-acetylgalactosamine (Fontaine et al 2011). The exopolysaccharide is secreted by *A. fumigatus* to form a biofilm, encapsulating the hyphae and allowing adherence to both biotic (epithelial cells & fibronectin) and abiotic (glass & plastic) surfaces (Gravelat et al 2013). Additionally, GAG is a component of the *A. fumigatus* cell wall, constituting ~2% of the total polysaccharides from cell wall of static and aerial hyphae (Loussert et al 2010). The functions of GAG in *A. fumigatus* pathogenesis are as follows (Gravelat et al 2013); mediate adherence of *A. fumigatus* hyphae to biotic and abiotic surfaces (Gravelat et al 2013), act as an immunosuppressor (Fontaine et al 2011), modulate host immune responses through cloaking β-glucans and other pathogen-associated molecular pattern molecules on the surface of the hyphae (Gravelat et al 2013).

Hydrolytic Enzymes Involved in Exopolysaccharide Biosynthesis

Many exopolysaccharide biosynthetic machinery systems, including those of cellulose, alginate, Psl, Pel and GAG polysaccharide, encode a putative or functionally characterized glycosyl hydrolase. These enzymes may be required for biofilm formation to occur but the exact biological role in this process remains undetermined.

Putative Glycosyl Hydrolase PslG (Psl Polysaccharide System)

Although PslG is essential for polymer production (Byrd et al 2009), the biological role of PslG in the biosynthesis of Psl is not fully understood. Glycosyl hydrolases (GHs) are grouped into families based on amino acid sequence (Davies & Henrissat 1995, Henrissat & Bairoch 1996). Based on amino acid sequence identity, the Carbohydrate-active enzymes database (CAZy) (Lombard et al 2014) categorizes PslG as a member of the GH39 family. Interestingly, all current bacterial members of this family are currently annotated as β-xylosidases while human members are annotated as α-L-iduronidase. All structures are composed of a N-terminal $(\beta/\alpha)_8$ TIM-barrel containing a conserved active site, and a C-terminal β-sandwich domain. The catalytic reaction occurs via a retaining mechanism with two catalytic glutamate residues responsible for catalysis (Vocadlo et al 2002).

The Multi-Domain Protein PelA (Pel Polysaccharide System)

Bioinformatics analysis of PelA indicates that it is a multi-domain periplasmic protein with three potential catalytic activities. The Phyre$^2$ (Kelley & Sternberg 2009) server suggests that the protein may have upwards of five distinct domains (FIG. 7) (Colvin et al 2013) including a predicted TIM-barrel domain composing residues 47-303, a reductase domain from residues 304-409, a deacetylase domain from residues 520-800 and a β-jelly roll fold from residues 840-927 (Colvin et al 2013). It was previously demonstrated that site specific mutation of putative catalytic residues in the deacetylase domain abrogated biofilm formation (Colvin et al 2013). It is unknown whether the proposed catalytic function of the hydrolase domain is required for Pel biosynthesis.

PgaB/BpsB is a PNAG Deacetylase and Putative Glycosyl Hydrolase

Bioinformatics analysis indicates that PgaB is the only periplasmic protein in the pga biosynthetic operon with a catalytic de-N-acetylation domain and a predicted carbohydrate-binding domain. Although known to be essential for PNAG de-N-acetylation, the biological role of PgaB C-terminal domain ($PgaB_{310-672}$) in the de-N-acetylation of PNAG has only recently been determined (Little et al 2014). $PgaB_{310-672}$ was shown to bind PNAG oligomers and molecular dynamics simulations combined with structures in complex with N-acetylglucosamine (GlcNAc), glucosamine (GlcN), and a PNAG hexamer suggest the domain preferentially binds dPNAG. In *Bordetella* spp. the pgaABCD operon is known as bpsABCD (FIG. 6) (Parise et al 2007). BpsB from *B. bronchiseptica* is predicted to contain a deacetylase domain that shares 40% and 24% sequence identity to PgaB and IcaB, respectively (Parise et al 2007).

Based on amino acid sequence identity, the CAZy database (Lombard et al 2014) recently categorized both BpsB and PgaB C-terminal domains as members of the GH13 family. This GH superfamily contains a functional $(\beta/\alpha)_8$ TIM-barrel catalytic domain (Little et al 2014, Lombard et al 2014). Structural prediction servers suggest that the proteins have high structural similarity to families GH18 and GH20. However, previous and ongoing efforts to show $PgaB_{310-672}$ hydrolase activity with PNAG oligomers and artificial para-nitrophenyl (pNP) glycoside substrates have proven unsuccessful (Little et al 2012a). Interestingly, sequence and structural comparison of $PgaB_{310-672}$ to GH13, GH18 and GH20 family members reveals the absence of the catalytic consensus sequences AED, DXXDXDXE, or GGDE, respectively.

Clinical and Economic Significance of Microbial Biofilms.

Biofilm-related infections account for between 65-80% of all chronic, persistent bacterial infections and the number of infections and conditions involving biofilms continues to grow (Bjarnsholt et al 2013, Flemming & Wingender 2010). *P. aeruginosa* and the formation of highly-resistant biofilms are a dominant bacterial species in three specific areas; burn wound victims, chronic wound infections and cystic fibrosis (CF). Other bacteria such as, but not limited to; *S. epidermis, S. aureus* and *E. coli* are also significant in biofilm formation, especially in relation to medical-device related infections. In industry, biofouling—the accumulation of microorganisms embedded in a biofilm on abiotic surfaces—is a significant problem due to biotransfer potential between abiotic and biotic surfaces (Van Houdt & Michiels 2010), and reduced flow rates in pipes and other objects due to increased drag (Tian et al 2014).

*Aspergillus fumigatus* is a fungal pathogen and is one of the most common *Aspergillus* species to cause disease in immuno-compromised individuals. Importantly, while *A. fumigatus* conidia account for less than 0.1% of all airborne fungal conidia, *A. fumigatus* conidia accounts for >80% of invasive infection in humans. Invasive aspergillosis is associated with higher morbidity and mortality, particularity in immunocompromised patients (Tong et al 2009). Studies have reported mortality rates of over 80% in bone marrow transplantation, 90% in liver transplant recipients and 49% with patients with leukemia or lymphoma (Lin et al 2001, Singh 2000). *A. fumigatus* is the second most common cause of fungal infection found in hospitalized patients/healthcare settings after *C. albicans* (Ellis et al 2000).

Exopolysaccharide producing fungi are important plant pathogens. *Botrytis cinerea* affects over 200 species of flowering and bulb-producing plants including grapes, onions, strawberries, and ornamental cut flowers (Dean et al 2012). Crop losses due to *Botrytis* infections and the cost of fungicides to combat these costs are a significant economic problem. In 2001 an estimated €540 million was spent on the control of *Botrytis* infections alone (Dean et al 2012). Further, resistance to fungicides continues to increase (Bardas et al 2010, Grabke et al 2014, Leroch et al 2013, Rodriguez et al 2014). Other pathogens account for important economic losses: *Blumeria graminis* is an important pathogen of wheat and barley (Dean et al 2012); while *Fusarium oxysporum* can infect over 100 different plant hosts and is associated with important losses of crops such as tomato cotton, melon and banana (Michielse & Rep 2009).

Treatments Against Bacterial and Fungal Biofilms

The ability of microorganisms within biofilms to withstand the actions of antimicrobial agents and host defenses presents a substantial challenge. Apart from surgical intervention (when appropriate), antimicrobial agents remain the only treatment option and are administered for extended durations in an attempt to penetrate the protective biofilm barrier and eradicate the infection. This methodology is partly to blame for the increase in anti-microbial resistance by bacteria and fungi. The continued presence of non-lethal doses of antimicrobial agents leads to desensitization, thereby inducing selection for resistant mutants (Hoiby et al 2011). Evolutionary mutation rates in biofilms have been shown, both in vitro and in vivo, to occur more rapidly. Furthermore, it has been demonstrated that sub-inhibitory concentrations of antibiotics used to treat *P. aeruginosa* infections induce biofilm formation, exacerbating the inability to manage these bacterial infections (Hoffman et al 2005).

There is precedence that enzyme therapy is a viable treatment option for bacterial biofilms. One example is the glycosyl hydrolase DspB or DispersinB® (U.S. Pat. No. 7,989,604 B2) (Kaplan et al 2004, Manuel et al 2007). Initially isolated from *A. actinomycetemcomitans*, the enzyme degrades the biofilm exopolysaccharide poly-β-1, 6-N-acetylglucosamine (PNAG) used by several pathogenic organisms including but not limited to; *E. coli, S. aureus* and *S. epidermidis* (Darouiche et al 2009, Donelli et al 2007, Gawande et al 2014, Kaplan et al 2004, Turk et al 2013). DspB nor homologs of the enzyme are found within the PNAG biosynthetic operon of *A. actinomycetemcomitans*. DispersinB® does not have the capability of inhibiting and dispersing *P. aeruginosa* or *A. fumigatus* biofilms as these bacteria do not have the genetic capacity to produce PNAG.

SUMMARY

The inability of microorganisms to produce a biofilm diminishes attachment to biotic and abiotic surfaces, and increases susceptibility of microorganisms to antimicrobial agents (Davies 2003) and the host immune system (Bakkevig et al 2005, Jain & Ohman 1998, Maharaj et al 1993, Monday & Schiller 1996). The present inventors have demonstrated that exogenously applying soluble forms of glycosyl-hydrolase containing bacterial or fungal proteins: PelA, PslG, BpsB, PgaB, Sph3, Ega3 and their orthologs, results in prevention and/or inhibition of microbial biofilms. The inventors thus proposed the use any soluble glycosyl-hydrolase protein located in any exopolysaccharide biosynthetic operon or functional gene cluster in any microbial species for the inhibition and dispersal of the formed microbial biofilm resulting from the use of the biosynthetic operon or functional gene cluster in the formation of the biofilm.

Accordingly, in one aspect, the present disclosure provides a method of treating or preventing a biofilm-related infection comprising administering at least one soluble microbial protein encoded by an exopolysaccharide biosynthetic operon or functional gene cluster, such as a bacterial or fungal protein, comprising a glycosyl hydrolase domain. Also provided herein is use of at least one soluble microbial protein encoded by an exopolysaccharide biosynthetic operon or functional gene cluster, such as a bacterial or fungal protein, comprising a glycosyl hydrolase domain for treating or preventing a biofilm-related infection. Further provided is use of at least one soluble microbial protein encoded by an exopolysaccharide biosynthetic operon or functional gene cluster, such as a bacterial or fungal protein, comprising a glycosyl hydrolase domain in the manufacture of a medicament for treating or preventing a biofilm-related infection. Even further provided is at least one soluble microbial protein encoded by an exopolysaccharide biosynthetic operon or functional gene cluster, such as a bacterial or fungal protein, comprising a glycosyl hydrolase domain for use in treating or preventing a biofilm-related infection.

In one embodiment, the present disclosure provides a method of treating or preventing a biofilm-related infection comprising administering at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain, and (vi) a soluble protein comprising an Ega3 GH domain, or orthologs thereof, to an animal or plant in need thereof. Also provided is use of at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain, and (vi) a soluble protein comprising an Ega3 GH domain, or orthologs thereof, for treating or preventing a biofilm related infection in an animal or plant in need thereof. Further provided is use of at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain, and (vi) a soluble protein comprising an Ega3 GH domain, or orthologs thereof, in the preparation of a medicament for treating or preventing a biofilm-related infection in an animal or plant in need thereof. Even further provided is at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain, and (vi) a soluble protein comprising an Ega3 GH domain, or orthologs thereof, for use in treating or preventing a biofilm-related infection in an animal or plant in need thereof.

In an embodiment, the methods or uses disclosed herein comprise at least two of, at least three of, at least four of, at least five of, or all of the soluble proteins.

In an embodiment, the methods or uses disclosed herein further comprise administering other soluble proteins that degrade other components of biofilm, such as alginate and/or cellulose.

In one embodiment, the biofilm-related infection may be the result of a wound or burn infection in the animal.

In one embodiment, the biofilm-related infection may be the result of keratitis in the animal.

In another embodiment, the biofilm-related infection may be a lung infection in the animal, wherein the animal has chronic pulmonary disease.

In another embodiment, the biofilm-related infection is a result of microbial contamination on or of medical devices or implants in the animal.

In another embodiment, the biofilm-related infection may be a lung infection in the animal, which includes but is not limited to invasive aspergilliosis, an acute disease of the immunocompromised host or chronic *aspergillus* infection that occurs in immunocompetent individuals with compromised lung function.

In an embodiment, at least one soluble protein comprising a glycosyl hydrolase potentiates neutrophil killing of the microorganism. In a particular embodiment, the soluble protein is a PelA protein disclosed herein.

In yet another embodiment, the biofilm-related infection is mediated by a fungus producing an exopolysaccharide sheath in an animal or a plant. In an embodiment, the plant includes plant materials, such as fruit or flowers.

In yet another embodiment, the biofilm-related infection may be caused by any microorganism or group of microorganisms some or all of which have the genetic capacity to synthesize the exopolysaccharides, Pel, Psl, PNAG and/or GAG and combinations thereof. These organisms include, but are not limited to; *P. aeruginosa*, *S. aureus*, *E. coli*, *S. epidermidis*, *Y. pestis*, *B. pertussis*, *Burkholderia* spp., *Candida* spp., *Aspergillus* spp., *Acinetobacter* spp., *T. asahii*, *B. cineria* and *Fusarium* spp. In another embodiment, the biofilm may be dependent on the secretion of any exopolysaccharide that is able to be degraded by the soluble glycosyl hydrolases disclosed herein.

In yet another embodiment, the methods or uses disclosed herein further comprise co-administering an antimicrobial agent to the animal or plant in need thereof. In one embodiment, the antimicrobial agent is an antibiotic. In another embodiment, the antimicrobial agent is an antifungal agent. In yet another embodiment, the antimicrobial agent is a fungicide for use on plants.

In a further embodiment, the at least one soluble protein may be expressed by a vector and the methods or uses disclosed herein comprise use of or administration of the vector to the animal or plant in need thereof. In an embodiment, the vector is a lytic phage that is able to invade bacteria of the biofilm. In another embodiment, the vector is a mycovirus.

In another aspect, the present disclosure provides a method of preventing biofilm formation on an indwelling medical device or implant comprising coating the device with at least one soluble microbial protein encoded by an exopolysaccharide biosynthetic operon or functional gene cluster, such as a bacterial or fungal protein, comprising a glycosyl hydrolase domain.

In one embodiment, the present disclosure provides a method of preventing biofilm formation on an indwelling medical device or implant comprising coating the device with at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain, and (vi) a soluble protein comprising an Ega3 GH domain, or orthologs thereof, prior to use in an animal in need thereof. In an embodiment, the method comprises at least two of, at least three of, at least four of, or all of the soluble proteins.

The indwelling medical device or implant can be any device or implant that is inserted into the body of the animal and that is susceptible to biofilm formation. In an embodiment, the indwelling medical device or implant is a catheter, an intravenous tube, a bioprosthetic including, but not limited to a heart valve or a prosthetic joint.

In an embodiment, the biofilm is caused by any microorganism or microorganisms that have the genetic capacity to synthesize the exopolysaccharides, Pel, Psi, PNAG and/or GAG and combinations thereof. These organisms include, but are not limited to; *P. aeruginosa*, *S. aureus*, *E. coli*, *S. epidermidis*, *Y. pestis*, *B. pertussis*, *Burkholderia* spp., *Candida* spp. *Aspergillus* spp, *Botrytis* spp., *Trichosporon* spp., *Acinetobacter* spp. and *Fusarium* spp. In another embodiment, the biofilm may be dependent on the secretion of any exopolysaccharide that is able to be degraded by the soluble glycosyl hydrolases disclosed herein.

In yet another embodiment, the methods disclosed herein further comprise coating an antimicrobial agent on the indwelling medical device or implant. In one embodiment, the antimicrobial agent is an antibiotic. In another embodiment, the antimicrobial agent is an antifungal agent.

In yet a further aspect, provided herein is a method of preventing or treating biofilm on a non-medical surface that is susceptible to biofilm comprising coating with or applying to the surface at least one soluble microbial protein encoded by an exopolysaccharide biosynthetic operon or functional gene cluster, such as a bacterial or fungal protein, comprising a glycosyl hydrolase domain.

In one embodiment, the present disclosure provides a method of preventing or treating biofilm on a non-medical surface that is susceptible to biofilm formation comprising coating with or applying to the surface with at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain (v) a soluble protein comprising a Sph3 GH domain, and (vi) a soluble protein comprising an Ega3 GH domain, or orthologs thereof. In an embodiment, the method comprises at least two of, at least three of, at least four of, at least five of, or all of the soluble proteins.

In yet another embodiment, the methods disclosed herein further comprise coating or applying an antimicrobial agent on the non-medical surface. In one embodiment, the antimicrobial agent is an antibiotic. In another embodiment, the antimicrobial agent is an antifungal agent.

Also provided herein is an indwelling medical device or implant prepared by the methods disclosed herein.

In an embodiment, the soluble protein comprising a PslG GH domain comprises amino acids 31 to 442 of the PslG sequence deposited into GenBank under accession no. AAG05625.1 or a glycosyl hydrolase variant thereof.

In an embodiment, the soluble protein comprising a PelA GH domain comprises amino acids 47 to 303 of the PelA sequence deposited into GenBank under accession no. AAG06452.1 or amino acids 35-291 of the PelA sequence deposited into GenBank under accession no. AAY92244.2 or glycosyl hydrolase variants thereof.

In an embodiment, the soluble protein comprising a PelA GH domain ortholog comprises amino acids 61 to 317 of the RagA sequence deposited into GenBank under accession no. CAQ62201.1 or amino acids 23 to 277 of the PelA sequence deposited into GenBank under accession no. ABB32191.1 or glycosyl hydrolase variants thereof.

In an embodiment, the soluble protein comprising a BpsB GH domain comprises amino acids 318 to 670 or amino acids 27 to 701 of the BpsB sequence deposited into GenBank under accession no. CAE32265.1 or glycosyl hydrolase variants thereof.

In an embodiment, the soluble protein comprising a PgaB GH domain comprises amino acids 310 to 672 or amino acids 22 to 672 of the PgaB sequence deposited into GenBank under accession no. AAC74108.1 or glycosyl hydrolase variants thereof.

In an embodiment, the soluble protein comprising a Sph3 GH domain comprises amino acids 52 to 298 of the Sph3 sequence from *Aspergillus fumigatus* deposited into GenBank under accession no. EAL92786.1 or a glycosyl hydrolase variant thereof.

In an embodiment, the soluble protein comprising a Sph3 GH domain ortholog comprises amino acids 54 to 304 of the Sph3$_{AC}$ sequence from *Aspergillus clavatus* NRRL 1 deposited into GenBank under accession no. EAW09379.1 or a glycosyl hydrolase variant thereof.

In an embodiment, the soluble protein comprising a Sph3 GH domain ortholog comprises amino acids 43 to 299 of the Sph3AN sequence from *Aspergillus nidulans* FGSC A4 deposited into GenBank under accession no. EAA63523.1 or a glycosyl hydrolase variant thereof.

In an embodiment, the soluble protein comprising an Ega3 GH domain comprises amino acids 46 to 318 of the Ega3 sequence from *Aspergillus fumigatus* deposited into GenBank under accession no. EAL92787.1 or a glycosyl hydrolase variant thereof.

In yet further aspects, provided herein is an isolated protein consisting of amino acids 31 to 442 of the PslG sequence deposited into GenBank under accession no. AAG05625.1, an isolated protein consisting of amino acids 47 to 303 of the PelA sequence deposited into GenBank under accession no. AAG06452.1 or amino acids 35-291 of the PelA sequence deposited into GenBank under accession no. AAY92244.2, an isolated protein consisting of amino acids 61 to 317 of the RagA sequence deposited into GenBank under accession no. CAQ62201.1 or amino acids 23 to 277 of the PelA sequence deposited into GenBank under accession no. ABB32191.1, an isolated protein consisting of amino acids 318 to 670 or amino acids 27 to 701 of the BpsB sequence deposited into GenBank under accession no. CAE32265.1, an isolated protein consisting of amino acids 310 to 672 of the PgaB deposited into GenBank under accession no. AAC74108.1, an isolated protein consisting of amino acids 52 to 298 of the Sph3 sequence deposited into GenBank under accession no. EAL92786.1, an isolated protein consisting of amino acids 54 to 304 of the Sph3$_{AC}$ sequence from *Aspergillus clavatus* NRRL 1 deposited into GenBank under accession no. EA1109379.1, an isolated protein consisting of amino acids 43 to 299 of the Sph3AN sequence from *Aspergillus nidulans* FGSC A4 deposited into GenBank under accession no. EAA63523.1, and/or an isolated protein consisting of amino acids 46 to 318 of the Ega3 sequence deposited into GenBank under accession no. EAL92787.1.

In yet another aspect, the present disclosure provides a vector encoding at least one soluble microbial protein encoded by an exopolysaccharide biosynthetic operon or functional gene cluster, such as a bacterial or fungal protein, comprising a glycosyl hydrolase domain. In one embodiment, the vector is able to invade the microbial organism. In an embodiment, the vector is a lytic phage. In another embodiment, the vector is a mycovirus.

In one embodiment, the present disclosure provides a vector encoding (i) a soluble protein comprising a PslG glycosyl hydrolase (GH) domain, such as a PslG GH soluble protein or ortholog described herein, (ii) a soluble protein comprising a PelA GH domain, such as a PelA GH soluble protein or ortholog described herein, (iii) a soluble protein comprising a BpsB GH domain, such as a BpsB GH soluble protein or ortholog described herein, (iv) a soluble protein comprising a PgaB GH domain, such as a PgaB GH soluble protein or ortholog described herein, (v) a soluble protein comprising a Sph3 GH domain, such as a Sph3 GH soluble protein or ortholog described herein, or (vi) a soluble protein comprising an Ega3 GH domain, such as an Ega3 GH soluble protein or ortholog described herein, or orthologs thereof, or combinations thereof. In an embodiment, the vector is a lytic phage. In another embodiment, the vector is a mycovirus.

In yet another aspect, the present disclosure provides pharmaceutical compositions comprising at least one soluble microbial protein encoded by an exopolysaccharide biosynthetic operon or functional gene cluster, such as a bacterial or fungal protein comprising a glycosyl hydrolase domain; and a pharmaceutically acceptable carrier. In an embodiment, the pharmaceutically acceptable carrier is a gel, such as Poloxamer.

In one embodiment, the present disclosure provides pharmaceutical compositions comprising at least one, at least two, at least three, at least four of, at least five of, or all of: (i) a soluble protein comprising a PslG glycosyl hydrolase (GH) domain, such as a PslG GH soluble protein or ortholog described herein, (ii) a soluble protein comprising a PelA GH domain, such as a PelA GH soluble protein or ortholog described herein, (iii) a soluble protein comprising a BpsB GH domain, such as a BpsB GH soluble protein or ortholog described herein, (iv) a soluble protein comprising a PgaB GH domain, such as a PgaB GH soluble protein or ortholog described herein; (v) a soluble protein comprising a Sph3 GH domain, such as a Sph3 GH soluble protein or ortholog described herein, and (vi) a soluble protein comprising an Ega3 GH domain, such as a Ega3 GH soluble protein or ortholog described herein, or orthologs thereof, and a pharmaceutically acceptable carrier.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

*acearum* (not all species that contain the operon are depicted in this figure). PelA is located at the beginning of each operon.

Figure 5:
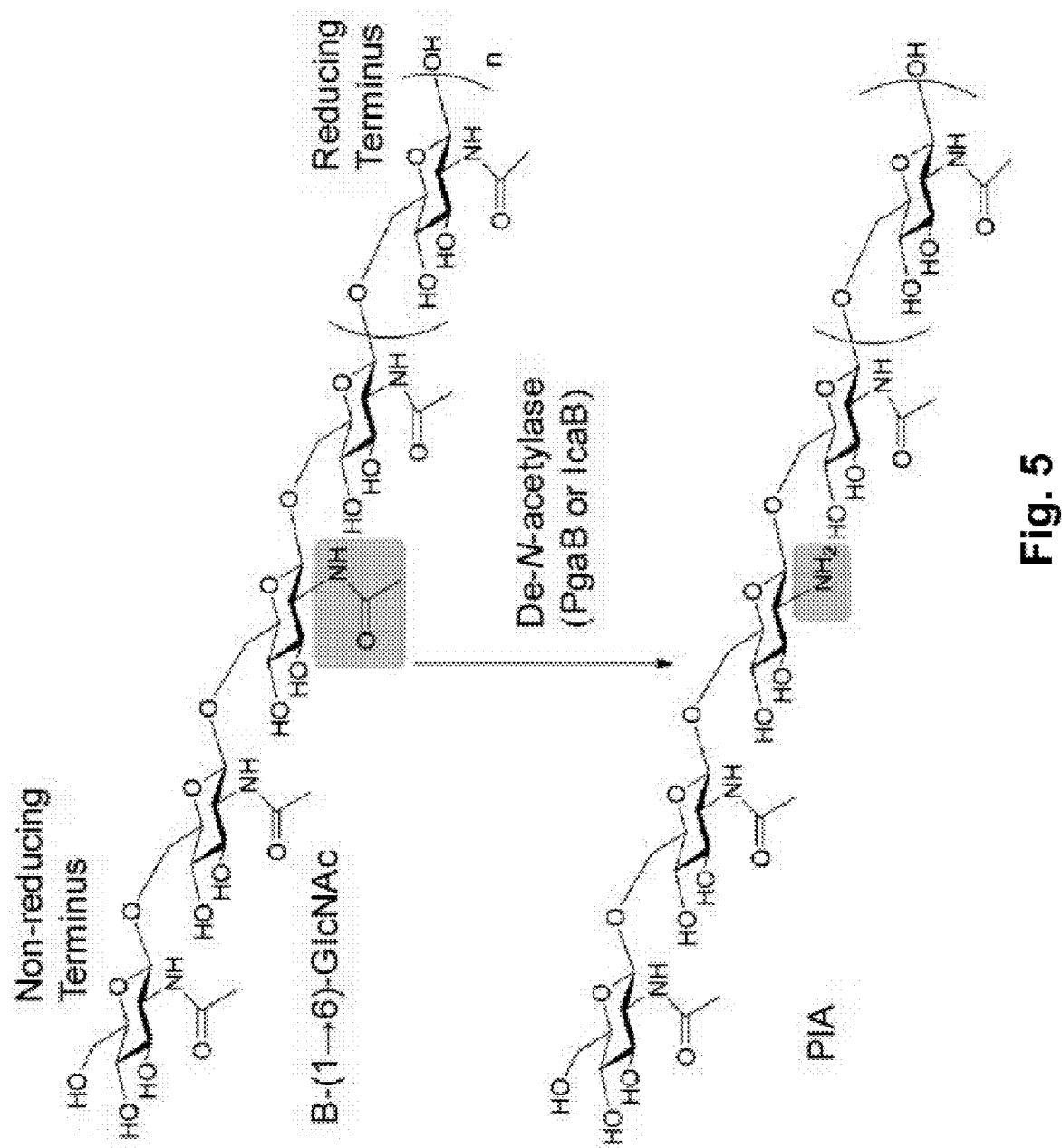

FIG. 5 shows the chemical structure of poly-β(1,6)-N-acetyl-D-glucosamine (PNAG). PNAG is a homopolymer of repeating N-acetyl-D-glucosamine units, similar to chitin, however it is synthesized with a β(1,6) linkage. PNAG present in the biofilm is often partially deacetylated. This form of the polymer is commonly referred to as dPNAG, and is the medically relevant form of the polymer.

Figure 6:
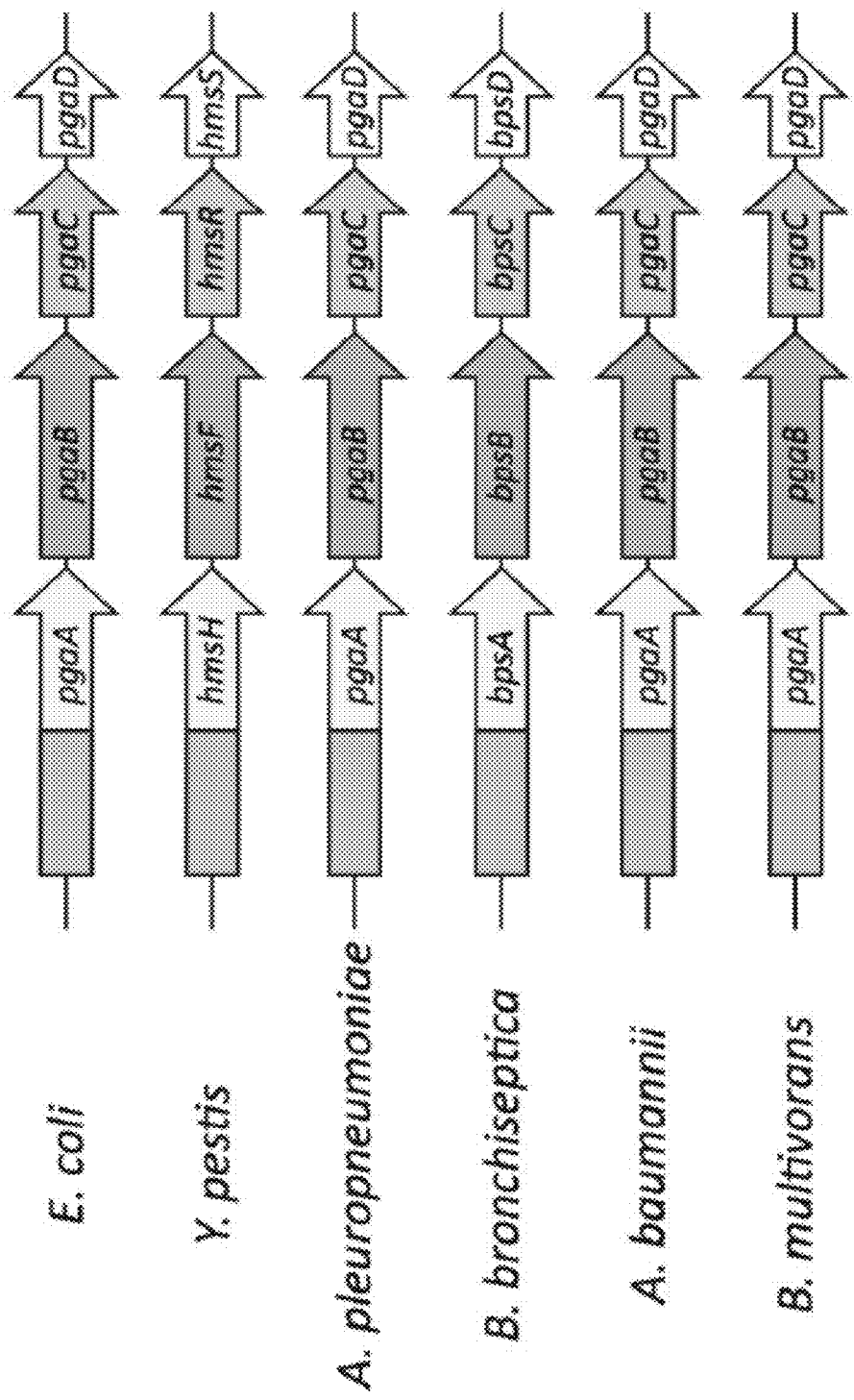

FIG. 6 shows Pga operons in several Gram-negative species. The pga operon is found in numerous bacterial species.

Figure 7:
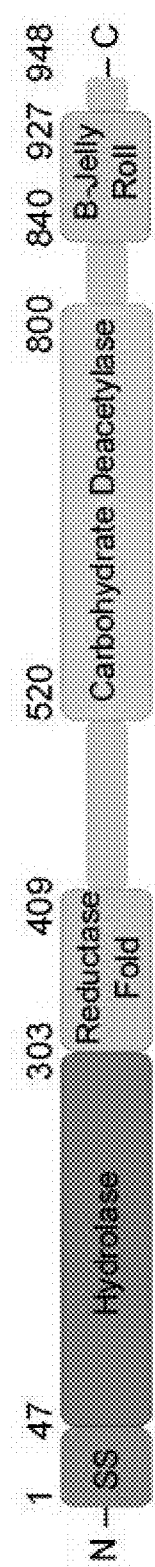

FIG. 7 shows the domain boundaries of PelA. The approximate boundaries for each domain are indicated on the diagram with the relative sizes proportional to the number of residues in each predicted region. The following domains represent those of PelA as predicted by Phyre$^2$ (Kelley & Sternberg 2009); GH (hydrolase), reductase, carbohydrate deacetylase and a region with no predicted function, the β-jelly roll. The small grey rectangles represent regions of the PelA$_{47-303}$ protein for which Phyre$^2$ was unable to make high confidence predictions, or for which the entire domain could not be modeled.

Figure 8:
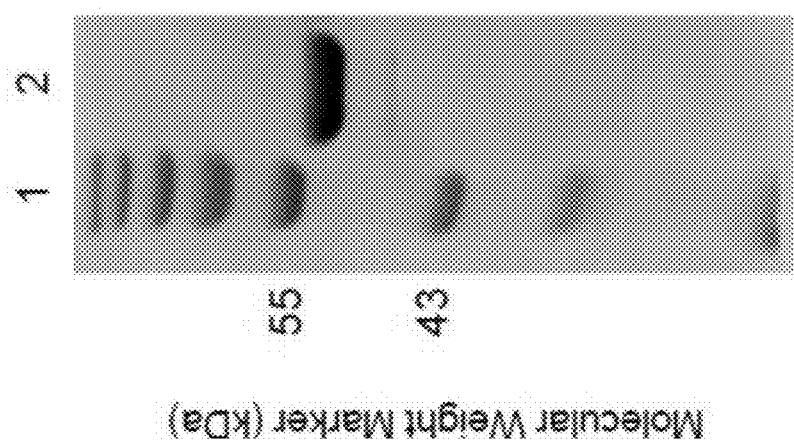

FIG. 8 shows sodium dodecyl sulfate polyacrylamide gel electrophoresis (SDS-PAGE) gel of PslG$_{31-442}$. Analysis from SDS-PAGE gel indicates that the protein is >95% pure and has a molecular weight of ~48 kDa which is consistent with the expected molecular weight of the purified protein.

Figures 9A, 9B:
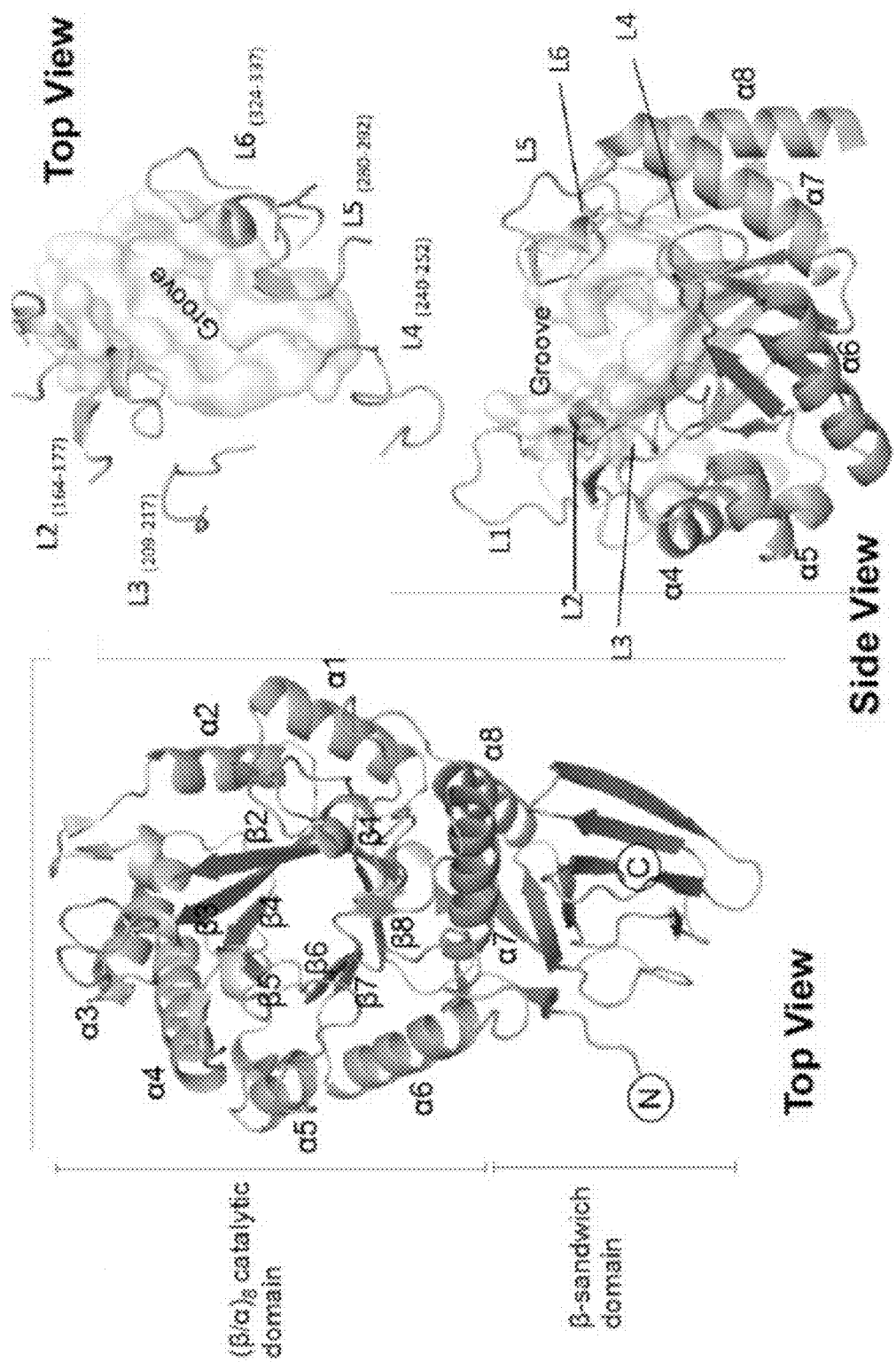

FIGS. 9A-9B show the X-ray crystal structure of PslG$_{31-442}$. (FIG. 9A) The enzyme is a two-domain protein composed of a TIM-barrel domain and a β-sandwich domain. (FIG. 9B) The putative active site groove, containing the proposed catalytic residues is ~40 Å in length and runs equatorially across the TIM-barrel domain.

Figure 10:
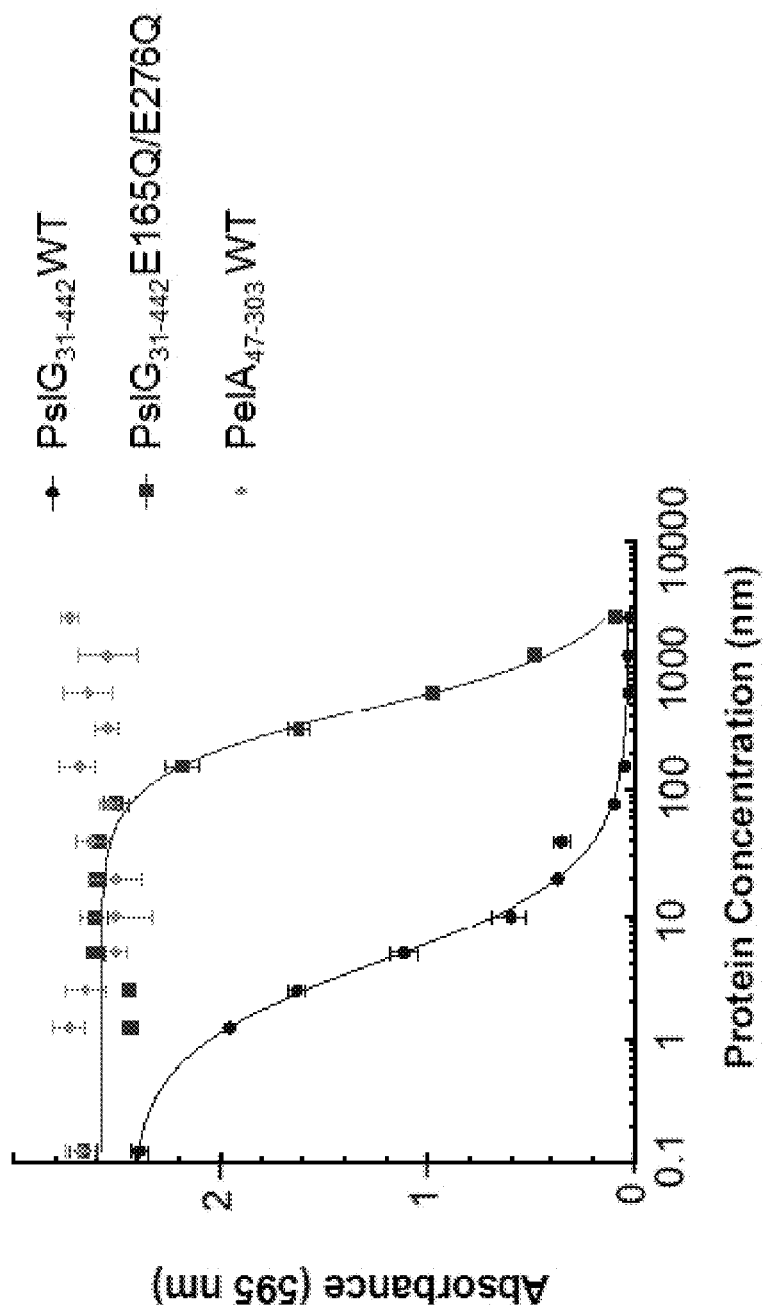

FIG. 10 shows inhibition of Psl Biofilm from *P. aeruginosa* PAO1 pBADpsl strain. Titration of PslG$_{31-442}$ into static *P. aeruginosa* cultures with inducible Psl production indicates that addition of >10 nM of PslG$_{31-442}$ is sufficient to inhibit Psl biofilm formation. Titration of PslG$_{31-442}$E165Q/E276Q (EC$_{50}$=466.5±1.1 nM) also results in biofilm inhibition but requires significantly higher concentrations of protein relative to the WT enzyme (EC$_{50}$=4.1±1.1 nM).

Figure 11A:
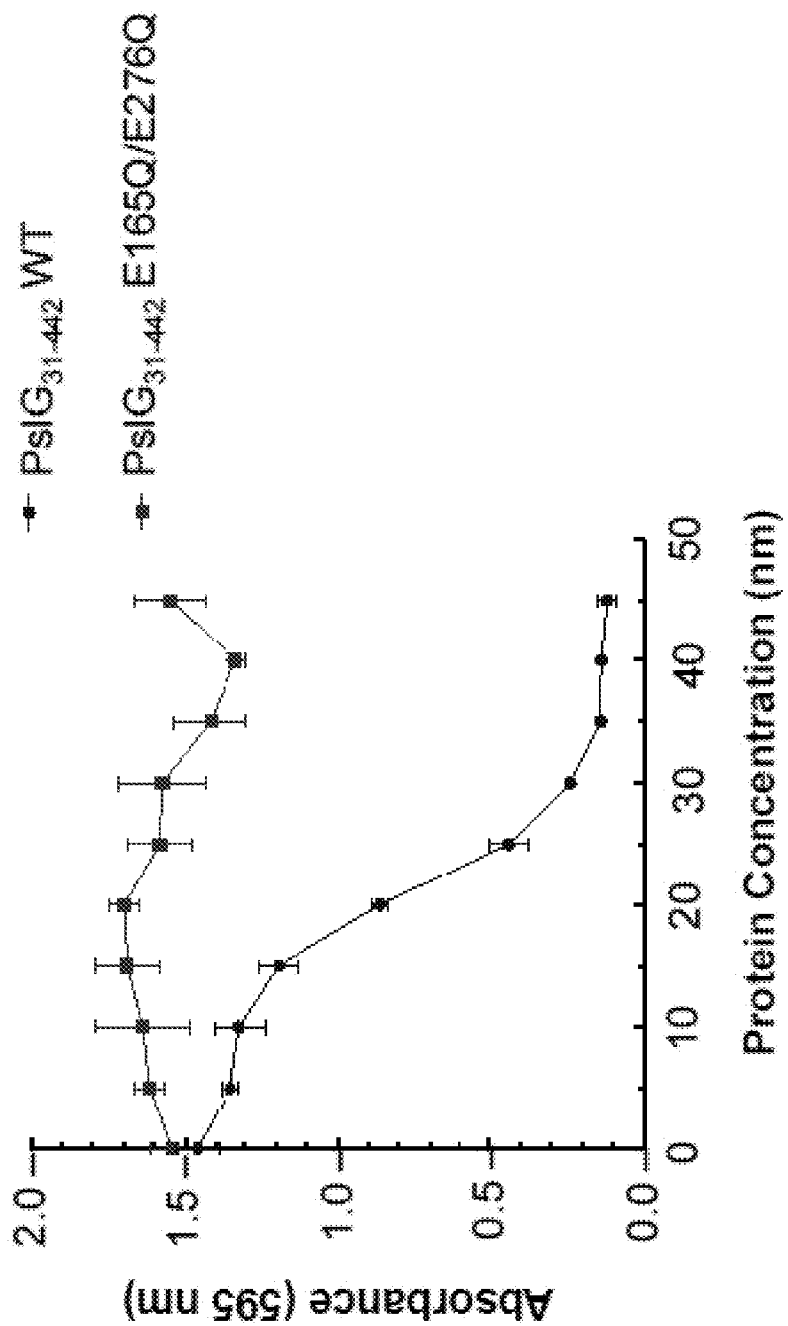
Figure 11B:
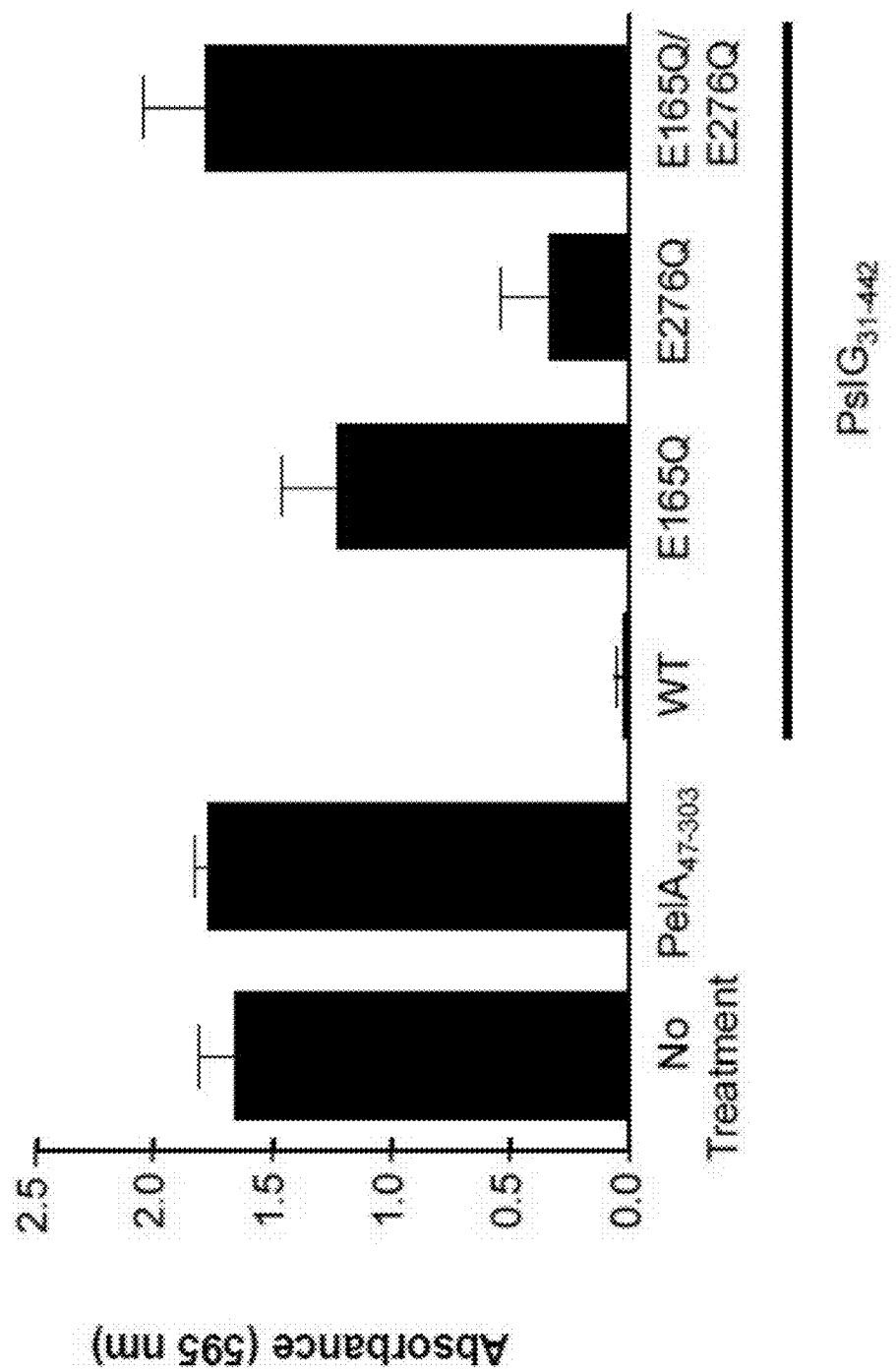

FIGS. 11A-11B show the dispersion of pre-formed Psl-biofilms. (FIG. 11A) Addition of 86 nM of PslG$_{31-442}$ to pre-formed Psl biofilms resulted in a significant reduction of the biofilm after 20 min and complete abolishment of the biofilm after 35 min. (FIG. 11B) Addition of 58 nM of PslG$_{31-442}$ was able to disperse the biofilm in 30 minutes. When PslG$_{31-442}$ E165Q/E276Q double catalytic variant was added in 100-fold excess compared to the non-variant enzyme (5 µM), no significant difference was observed compared to that of the untreated biofilm. Single enzyme catalytic variants were also impaired in their ability to disrupt the biofilm.

Figure 12:
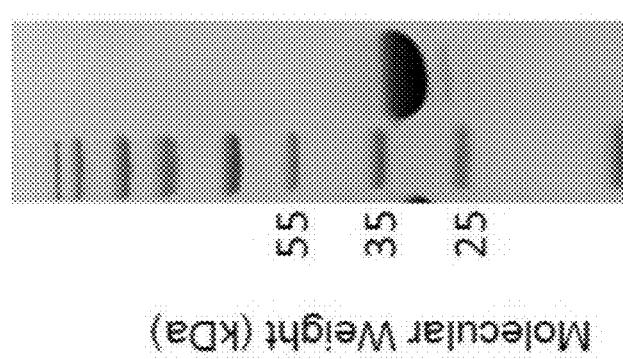

FIG. 12 shows sodium dodecyl sulfate polyacrylamide gel electrophoresis (SDS-PAGE) gel of PelA$_{47-303}$. Analysis from SDS-PAGE gel indicates that the protein is >95% pure and has a molecular weight of ~28 kDa which is consistent with the expected molecular weight of the purified protein.

FIGS. 13A-13C show the X-ray crystal structure of PelA$_{47-303}$. The core structure represents a β$_8$/α$_7$ TIM-barrel fold with the β-sheets in light grey and the α-helices in dark grey. Extra loop insertions within the core backbone structure are illustrated in light grey. (FIG. 13A) Top view of the cartoon representation of PelA$_{47-303}$. (FIG. 13B) Side view cartoon representation of PelA$_{47-303}$ showing the extra loops clustering in two main groups. (FIG. 13C) Topological representation showing in detail the eight β-sheets and seven α-helices of the core structure of the TIM-barrel. There are four loops inserted within the core structure labeled loop 1-loop 4. The light grey segment represents the C-terminus that connects to the following putative reductase domain. The N- and C-termini are indicated at either end by N and C, respectively.

Figures 14A, 14B:
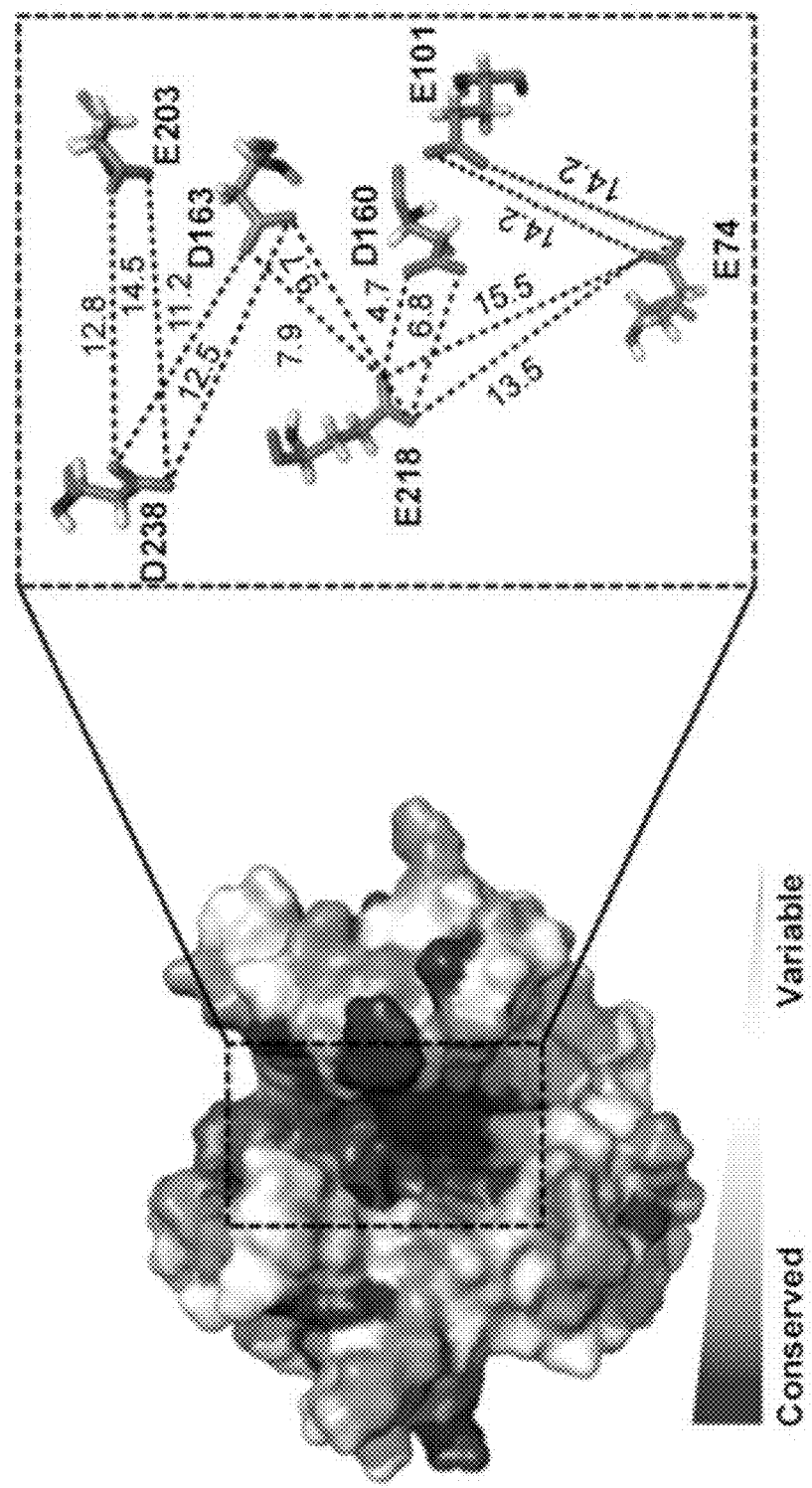

FIGS. 14A to 14B show conserved residues lining the putative binding cleft in PelA$_{47-303}$. (FIG. 14A) The conservation profile of PelA$_{47-303}$ as represented by the ConSurf server (Ashkenazy et al 2010) with the conservation bar shown. (FIG. 14B) A close up of the highly conserved region in PelA$_{47-303}$. Highly conserved acidic residues line the putative binding cleft of the protein. Spatial separation was measured between the carboxyl oxygens of the residues and indicated in angstroms (Å).

Figure 15:
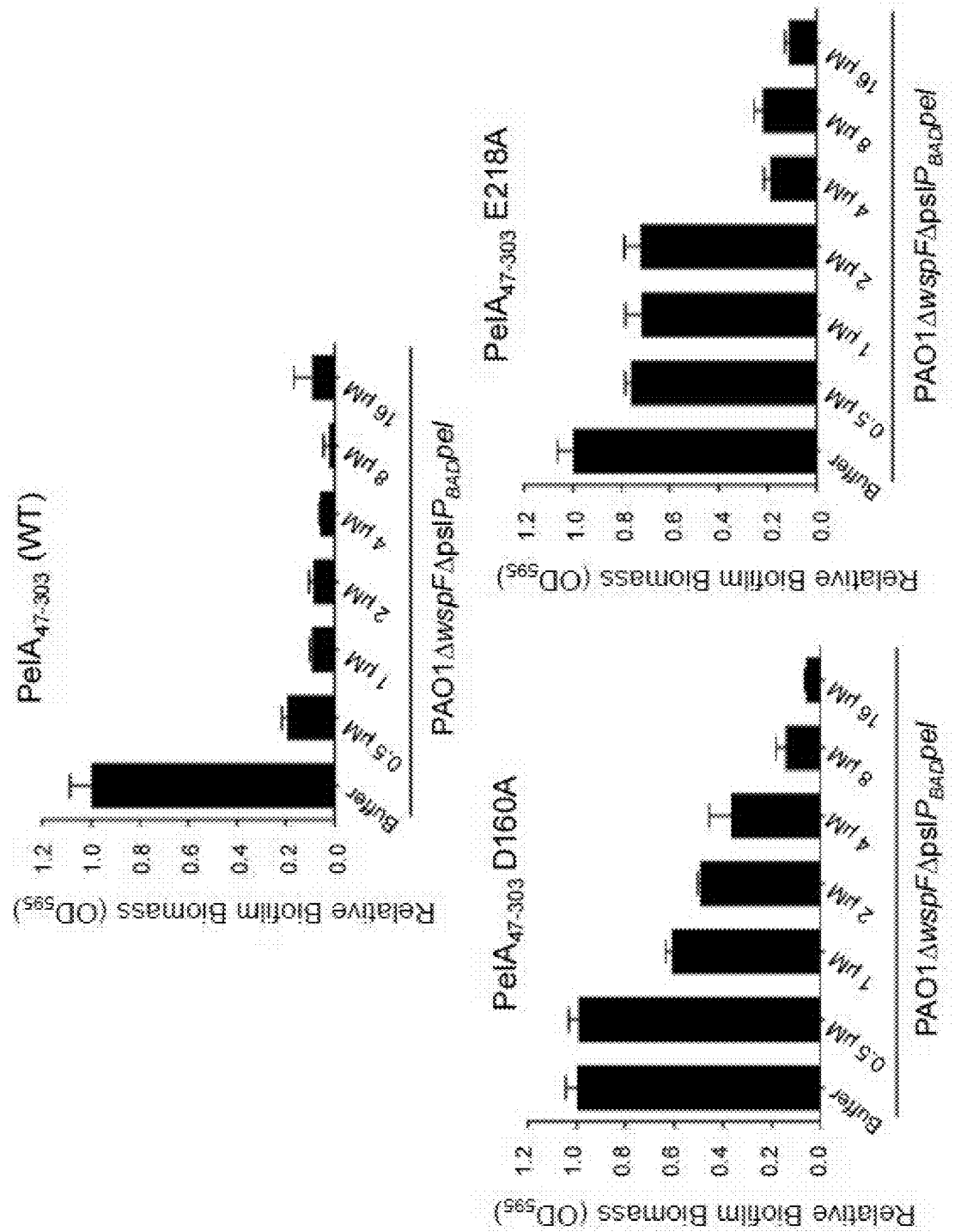

FIG. 15 shows inhibition of Pel biofilm formation by PelA$_{47-303}$. Purified PelA$_{47-303}$ and variants at increasing concentrations of 0.5, 1, 2, 4, 8 and 16 µM. Arabinose at 0.5% (w/v) was added to induce Pel polysaccharide production. The first bar in each graph contained buffer D and represents the positive control. The results were normalized against the buffer control in each plate. Triplicate reactions were incubated for 48 h at ambient temperature. Error bars represent the standard error of the mean.

Figure 16:
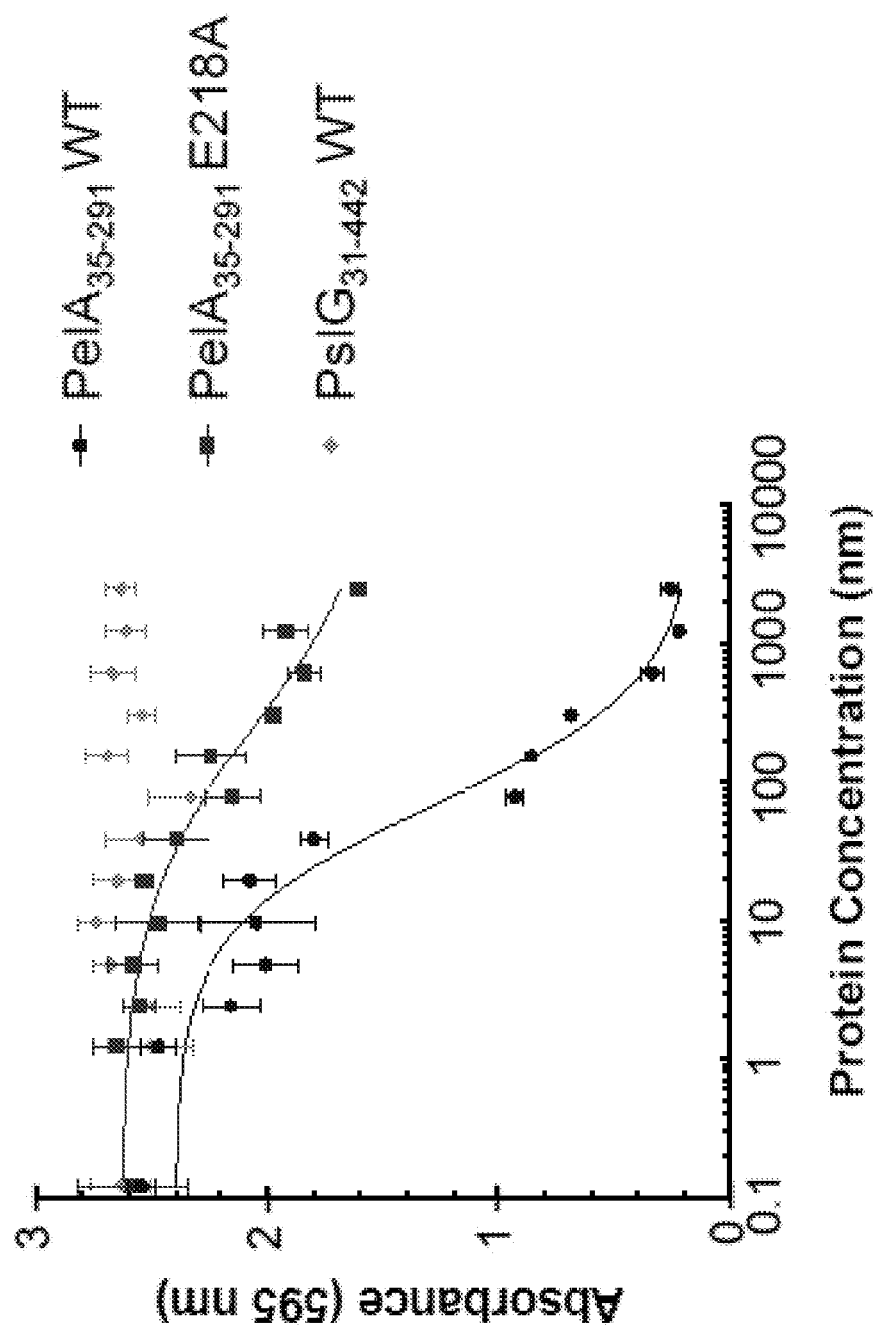

FIG. 16 shows inhibition of Pel biofilm by PelA$_{35-291}$ from *P. protogens* Pf-5. Titration of PelA$_{35-291}$ from *P. protogens* Pf-5 in static wild-type *P. aeruginosa* PAO1ΔwspFΔps/P$_{BAD}$pel culture. The addition of PelA$_{35-291}$ from *P. protogens* Pf-5 prevented biofilm formation at 70 nM and had an EC$_{50}$ of 69.3±1.2 nM. PslG$_{31-442}$ was unable at preventing biofilm formation indicating that this inhibition is enzyme specific.

Figure 17A:
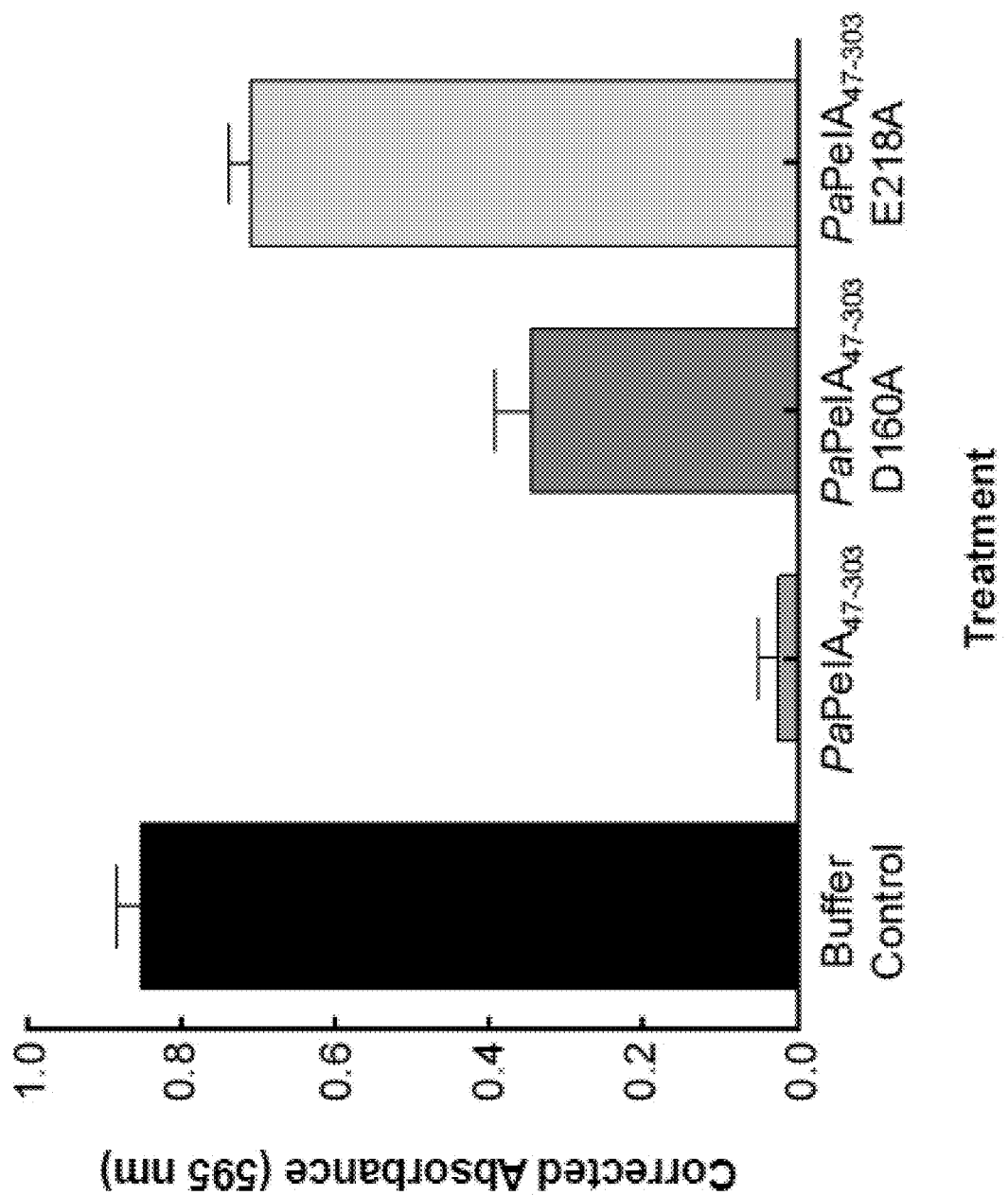
Figure 17B:
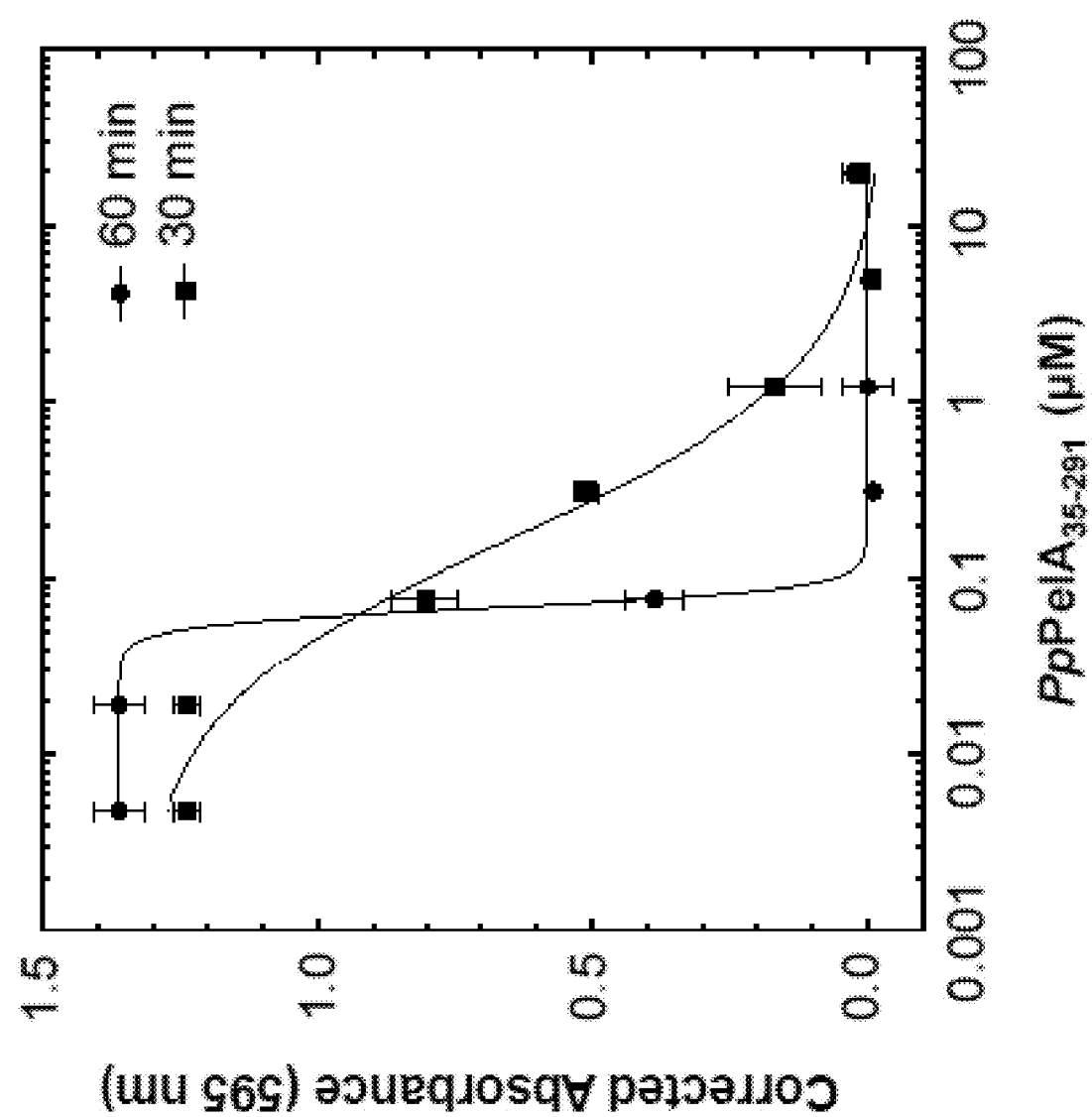

FIGS. 17A-17B show dispersion of pre-formed Pel-biofilms. (FIG. 17A) Addition of PelA$_{47-303}$ from *P. aeruginosa* PAO1 to pre-formed Pel biofilms resulted in biofilm dispersal after 2 hours while putative catalytic variants retained the majority of the biofilm. (FIG. 17B) Titration of wild-type PelA$_{35-291}$ from *P. protogens* Pf-5 into pre-formed Pel biofilms was able to disperse the biofilm in as little as 30 min.

FIGS. 18A to 18D show biofilm inhibition through the coating of PslG$_{31}$_442 and PelA$_{47-303}$ to polystyrene plastic. (FIG. 18A) Treatment of polystyrene plates with 40 µg/mL of PelA$_{47-303}$ or BSA at 4° C. overnight in 1×PBS buffer. The wells were washed prior to bacterial inoculation. (FIG. 18B) Treatment of polystyrene slides with 40 µg/mL of adsorbed PslG$_{31-442}$ prevented bacterial cell attachment and biofilm formation as visualized by the lack of SYTOX green staining using confocal microscopy. (FIG. 18C) Covalent attachment of PslG$_{31-442}$ to glass was also effective at preventing biofilm formation whereas a BSA (negative control) was unable to prevent biofilm formation. (FIG. 18D) Covalent attachment of PslG$_{31-442}$ to glass was effective at preventing cell attachment and biofilm formation for at least 8 days as visualized by a lack of SYTOX green staining.

Figure 19:
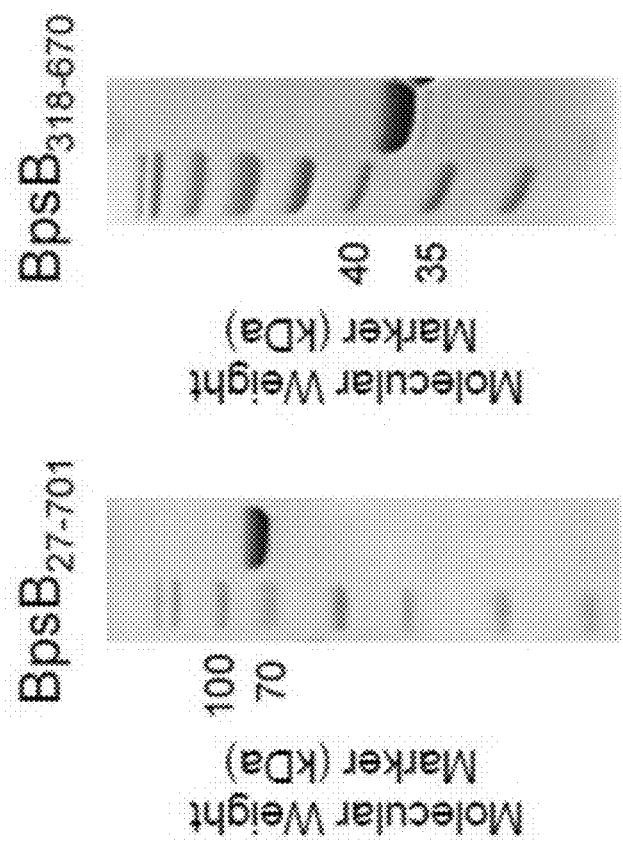

FIG. 19 shows sodium dodecyl sulfate polyacrylamide gel electrophoresis (SDS-PAGE) gel of BpsB constructs. Analysis from SDS-PAGE gel indicates that each protein is >95% pure and has a molecular weight of ~79 kDa for BpsB$_{27-701}$ and ~42 kDa for BpsB$_{318-670}$ which are consistent with the expected molecular weights of each purified protein.

Figure 20:
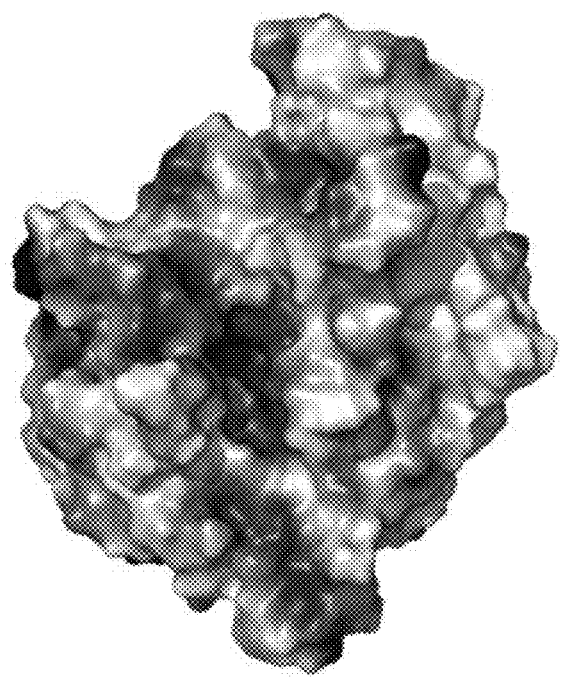
Figure 20:
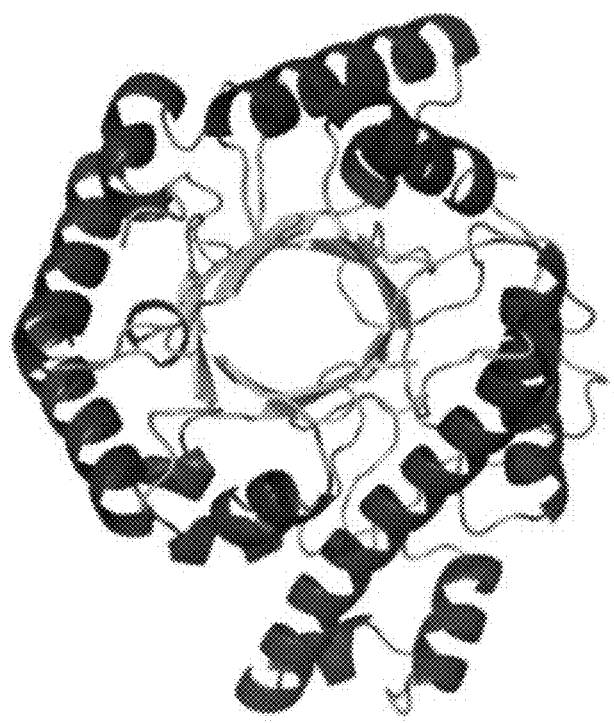

FIG. 20 shows the crystal structure of BpsB$_{318-670}$. The enzyme is a (β/α)$_8$ TIM-barrel fold with an electronegative groove ~41 Å long and 11 Å wide.

Figure 21:
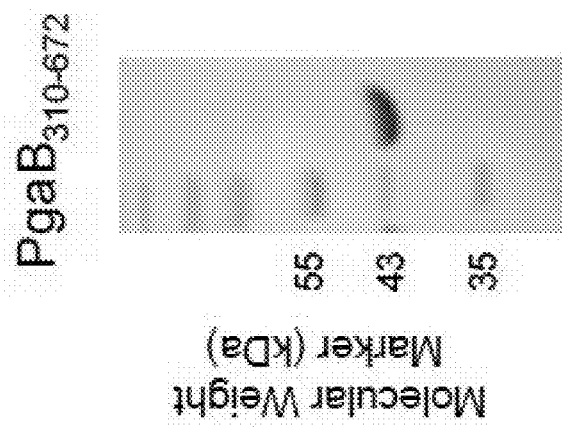

FIG. 21 shows sodium dodecyl sulfate polyacrylamide gel electrophoresis (SDS-PAGE) gel of PgaB$_{310-672}$. Analysis from SDS-PAGE gel indicates that the protein is >95% pure and has a molecular weight of ~42 kDa for PgaB$_{310-672}$ which is consistent with the expected molecular weights of the purified protein.

Figure 22A:
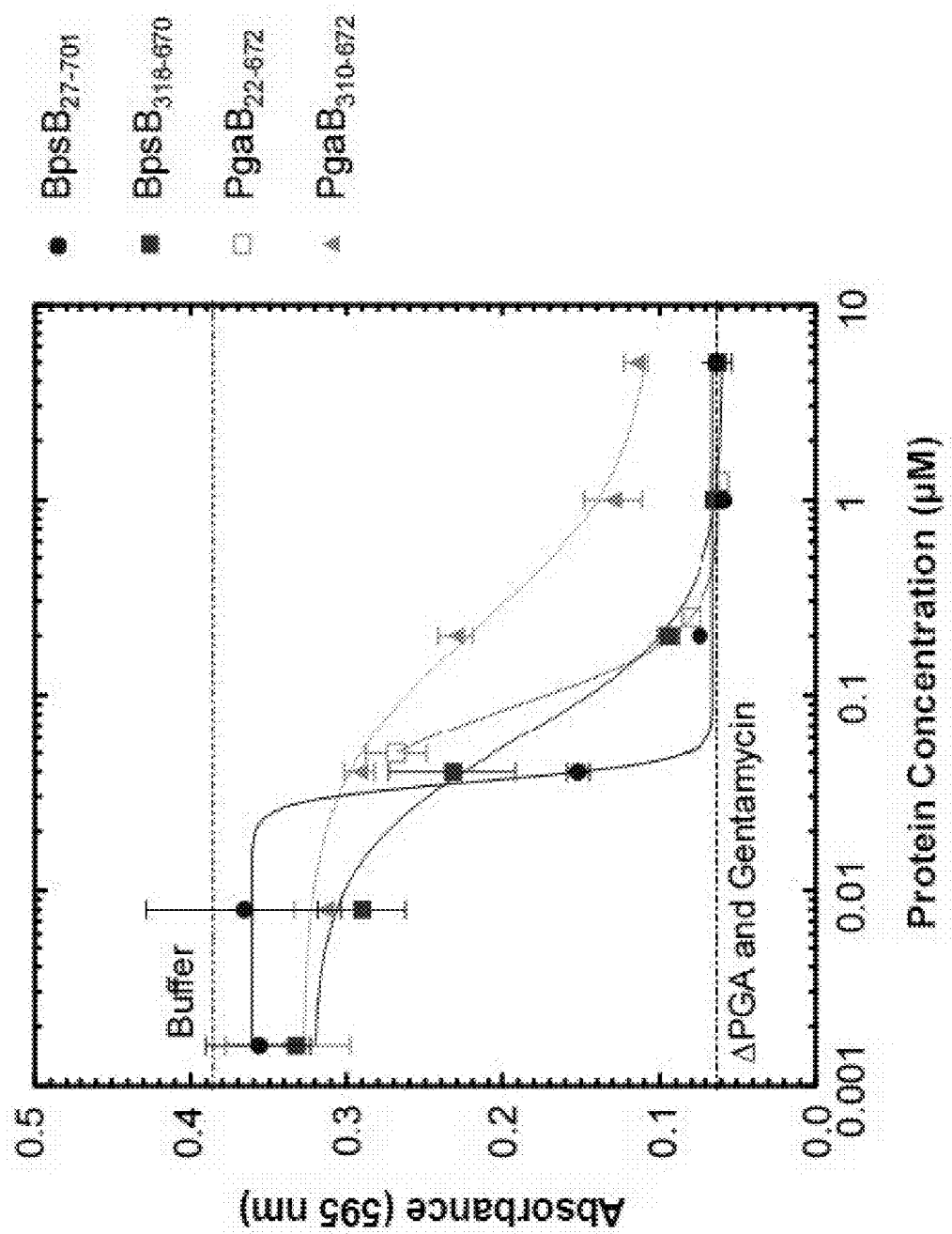
Figure 22B:
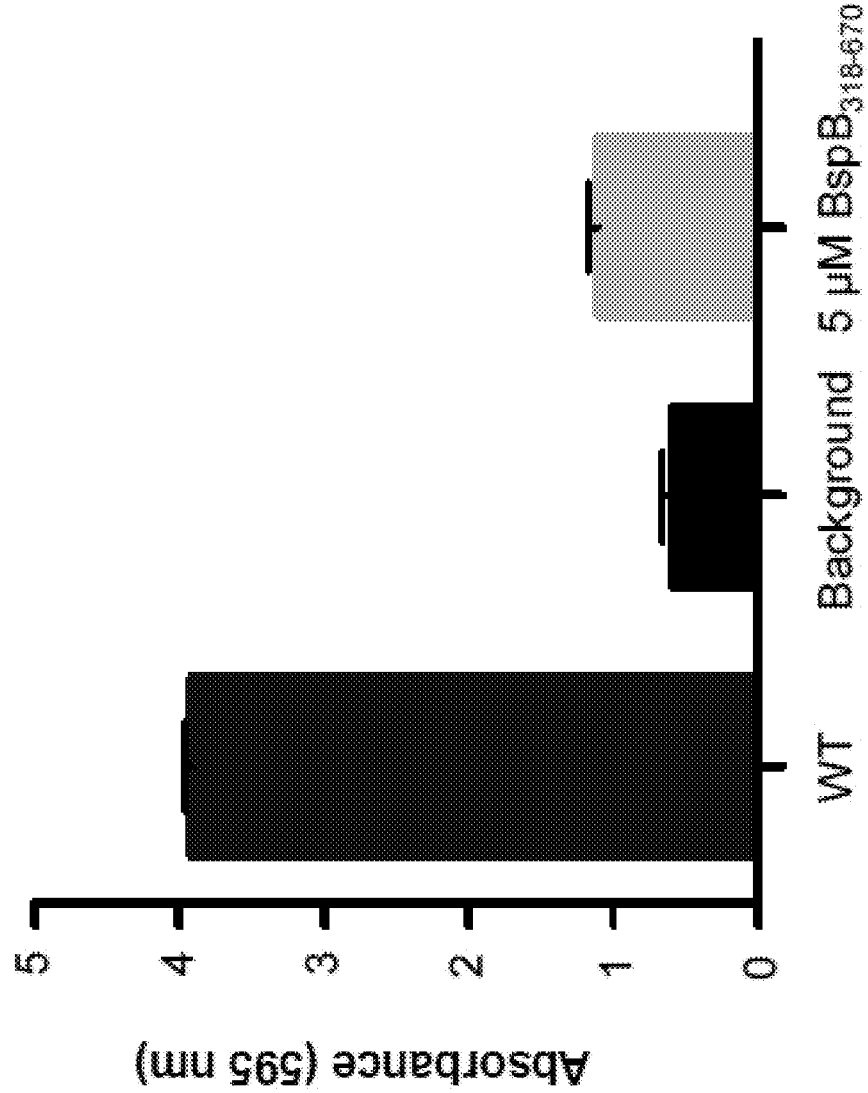

FIG. 22A-22B show inhibition of PNAG-dependent biofilms. (FIG. 22A) Titration curves of BpsB$_{27-701}$, BpsB$_{318-670}$, PgaB$_{22-672}$, and PgaB$_{310-672}$ added prior to inoculation for the inhibition of E. coli biofilms. (FIG. 22B) Testing of, BpsB$_{318-670}$, on the inhibition of Staphylococcus carnosus biofilm formation. Background staining represents S. carnosus treated with gentamycin.

Figure 23A:
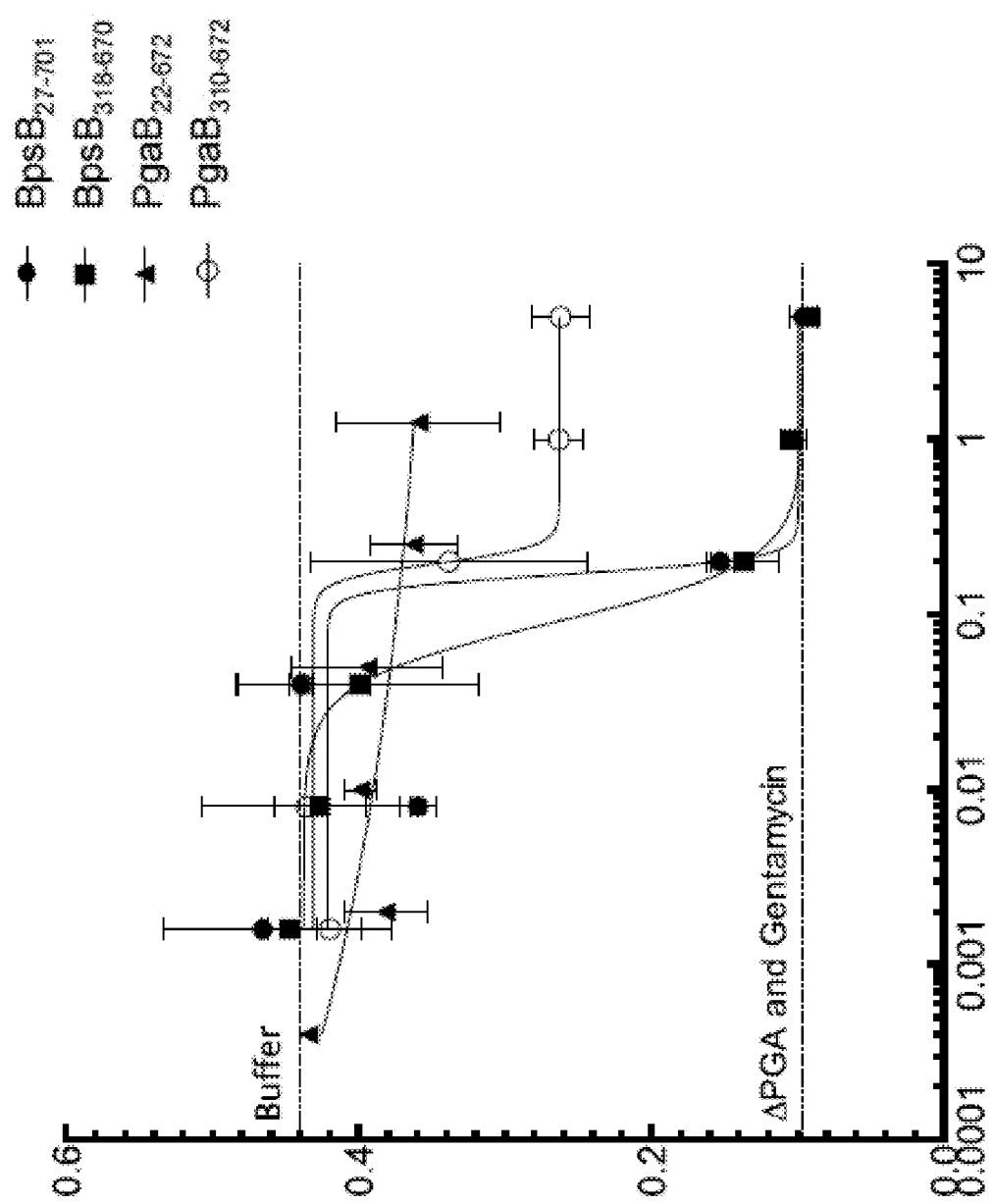
Figure 23B:
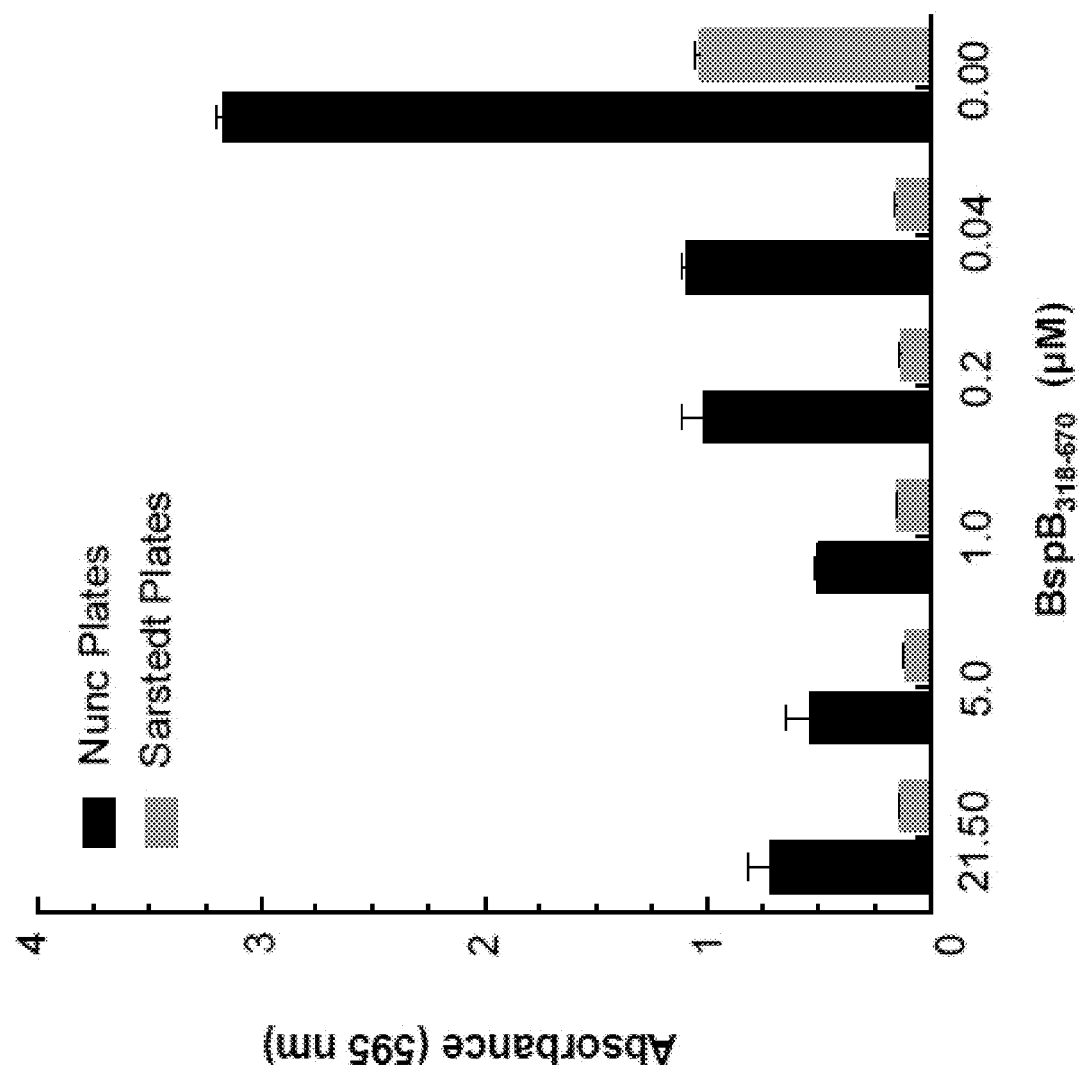
Figure 23C:
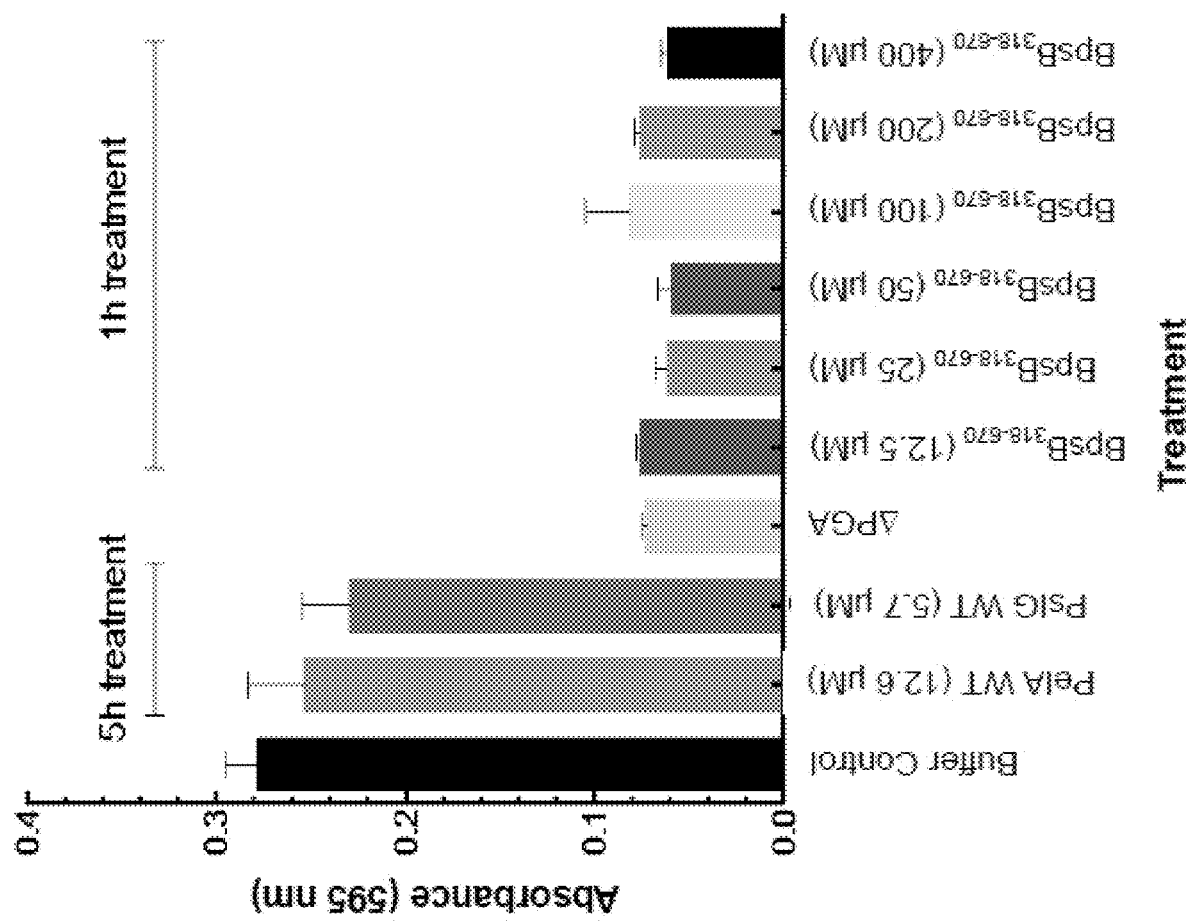

FIGS. 23A-23C show the dispersion of pre-formed PNAG-dependent biofilms. (FIG. 23A) Titration curves of BpsB$_{27-701}$, BpsB$_{318-670}$, PgaB$_{22-672}$, and PgaB$_{310-672}$ to preformed E. coli biofilms after 60 min incubation. (FIG. 23B) Testing of different 96-well plates for BpsB-mediated E. coli biofilm dispersal. (FIG. 23C) Comparing BpsB-mediated E. coli biofilm dispersal against other known biofilm degrading enzymes, PelA$_{47-303}$ and PslG$_{31-442}$.

Figure 24:
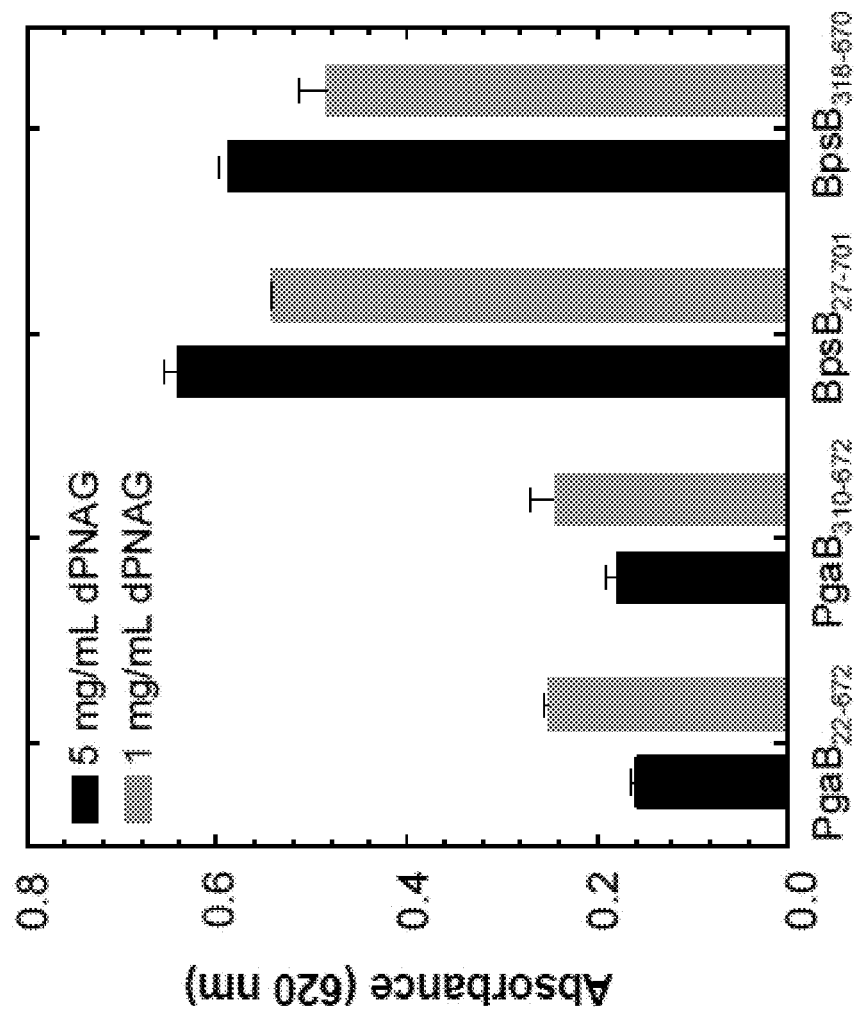

FIG. 24 shows a reducing sugar assay on dPNAG. BpsB$_{27-701}$, BpSB$_{318-670}$, PgaB$_{22-672}$, and PgaB$_{310-672}$ hydrolyze dPNAG. BpsB$_{27-701}$ and BpsB$_{318-670}$ show ~4 times higher rates of dPNAG hydrolysis using the reducing sugar assay than PgaB$_{22-672}$/PgaB$_{310-672}$.

Figure 25A:
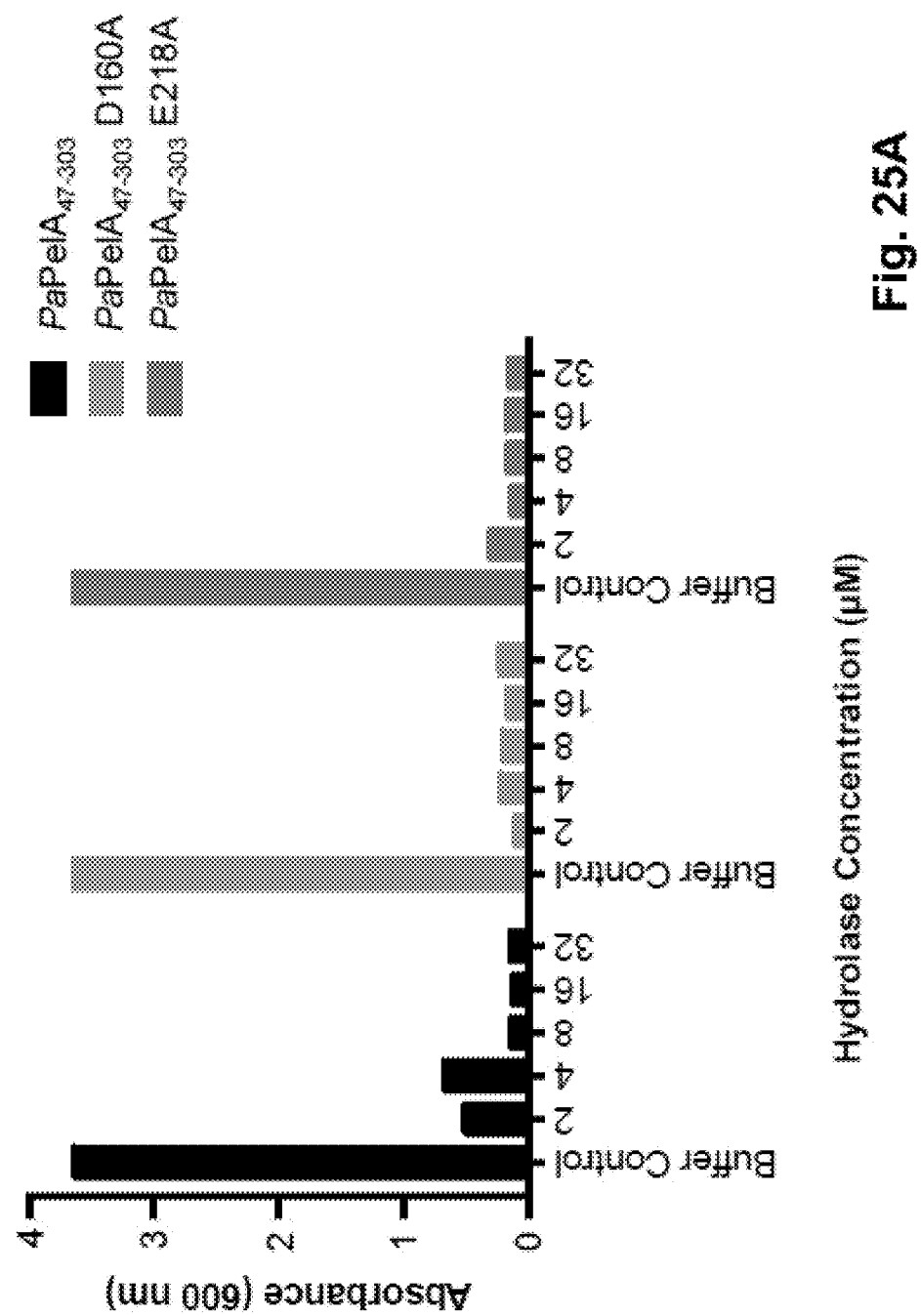
Figure 25B:
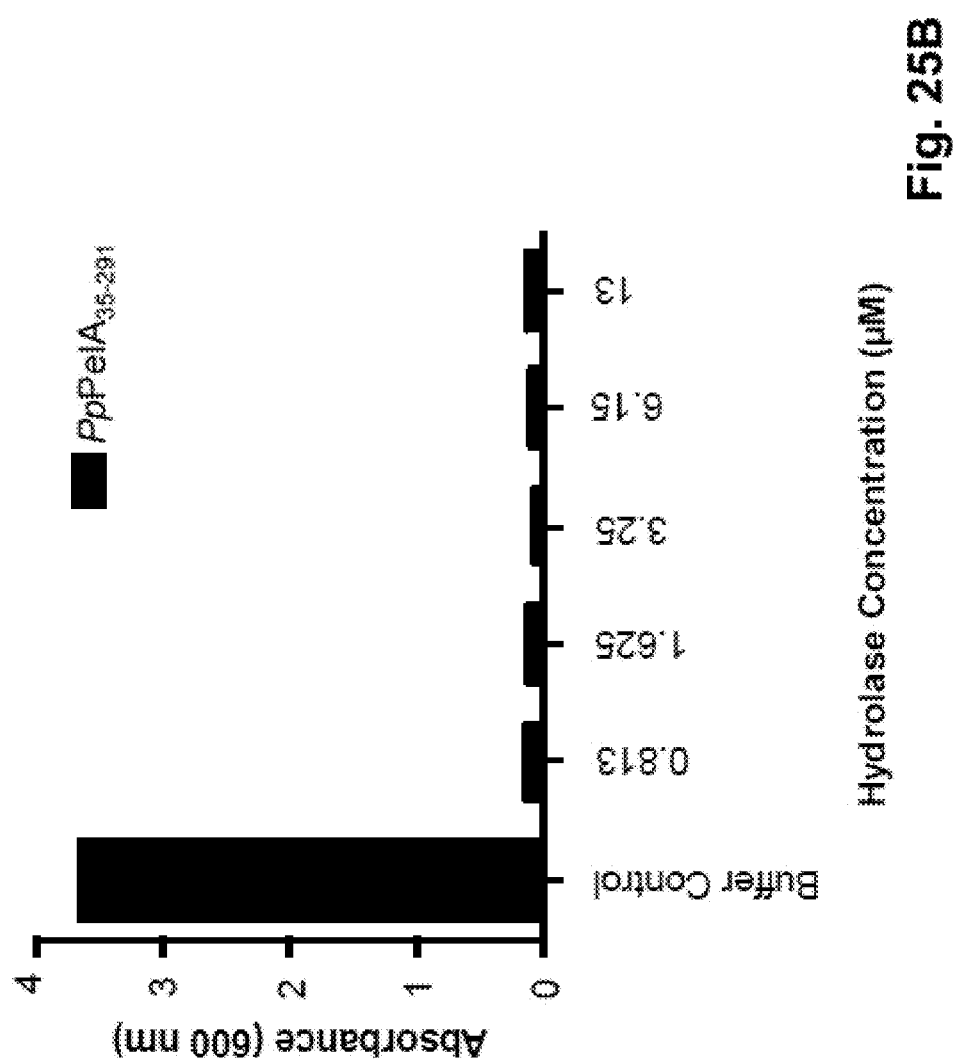

FIGS. 25A-25B show the inhibition of GAG-dependent biofilm formation by PelA$_{47-303}$. (FIG. 25A) Purified PelA$_{47-303}$ and variants were added to A. fumigatus cultures prior to biofilm formation. Cultures were grown for 20 hours in Brian media. (FIG. 25B) Purified P. protogens PelA$_{35-291}$ was added in the same manner and was also shown to prevent GAG-dependent biofilm formation. The amount of GAG biofilm present following growth was assessed using crystal violet staining.

Figure 26:
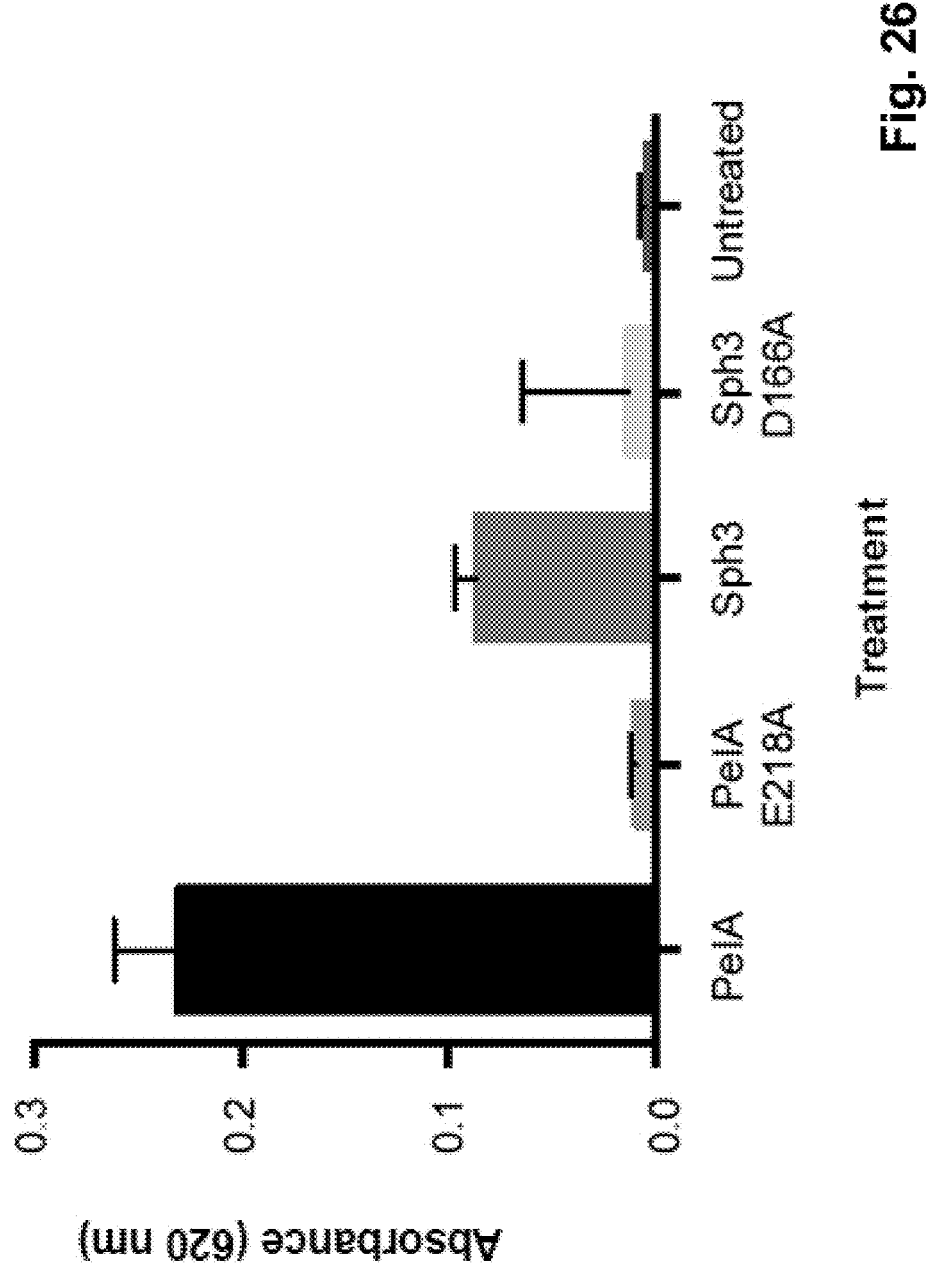

FIG. 26 shows the results of a reducing sugar assay when purified GAG, from A. fumigatus was treated with the glcosyl hydrolases PelA$_{47-303}$ and its inactive catalytic variant E218A and Sph3$_{52-298}$ and its inactive variant D166A. An increase in reducing ends indicates that the enzymes are capable of hydrolyzing the glycosidic bonds of the GAG polysaccharide. Under assay conditions, PelA$_{47-303}$ lead to the production of ~2-fold more reducing ends than Sph3$_{52-298}$. PelA refers to PelA$_{47-303}$ and Sph3 refers to Sph3$_{52-298}$.

Figure 27:
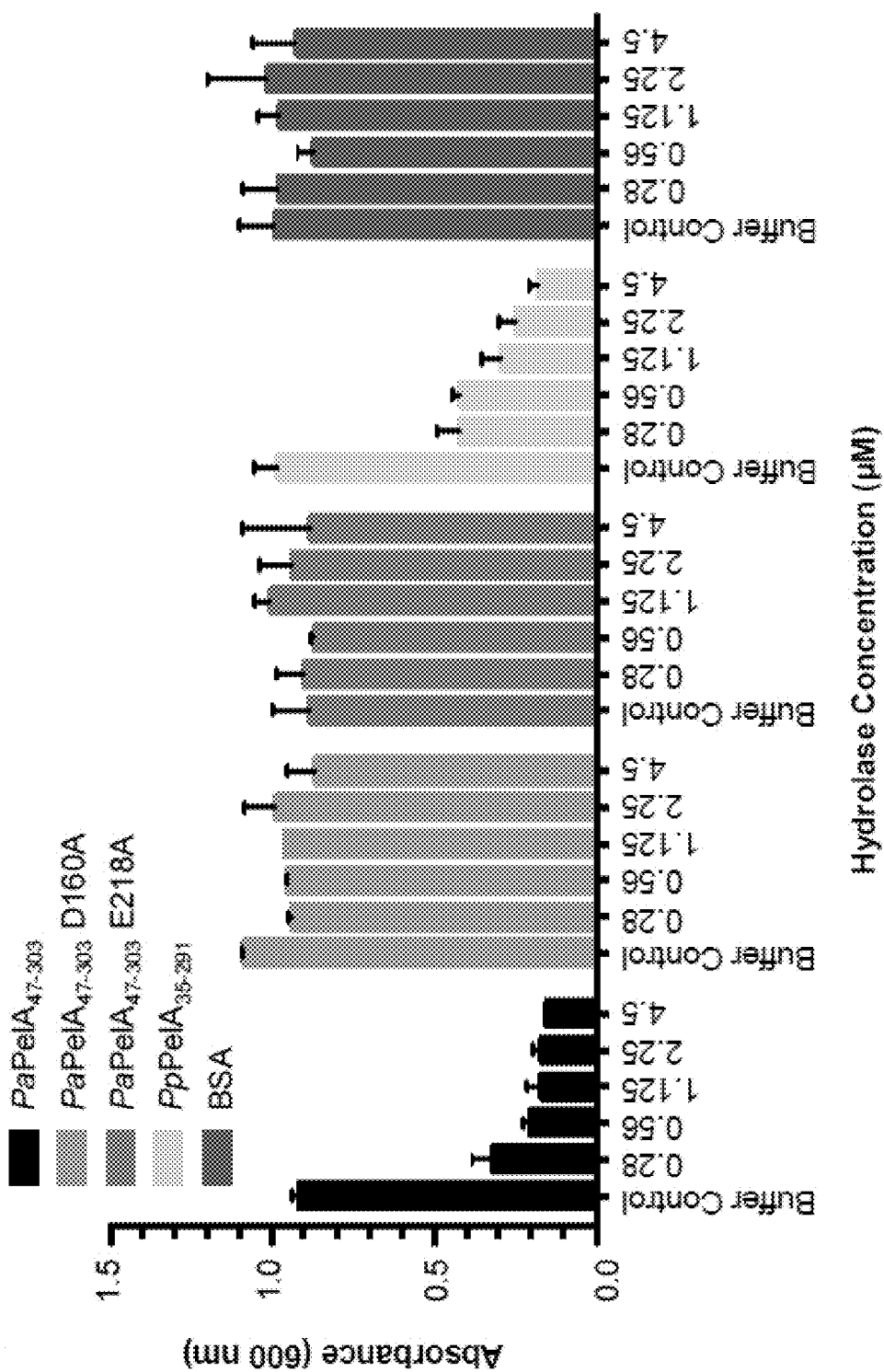

FIG. 27 shows the dispersion of pre-formed GAG biofilms using PelA$_{47-303}$ and P. protogens PelA$_{35-291}$. Exogenous addition of PelA$_{47-303}$ and P. protogens PelA$_{35-291}$ to pre-formed A. fumigatus GAG biofilms resulted in the elimination of the GAG biofilms as detected through the crystal violet assay. In comparison, PelA$_{47-303}$ variants D160A and E218A as well as a BSA control did not disperse the biofilm.

Figure 28:
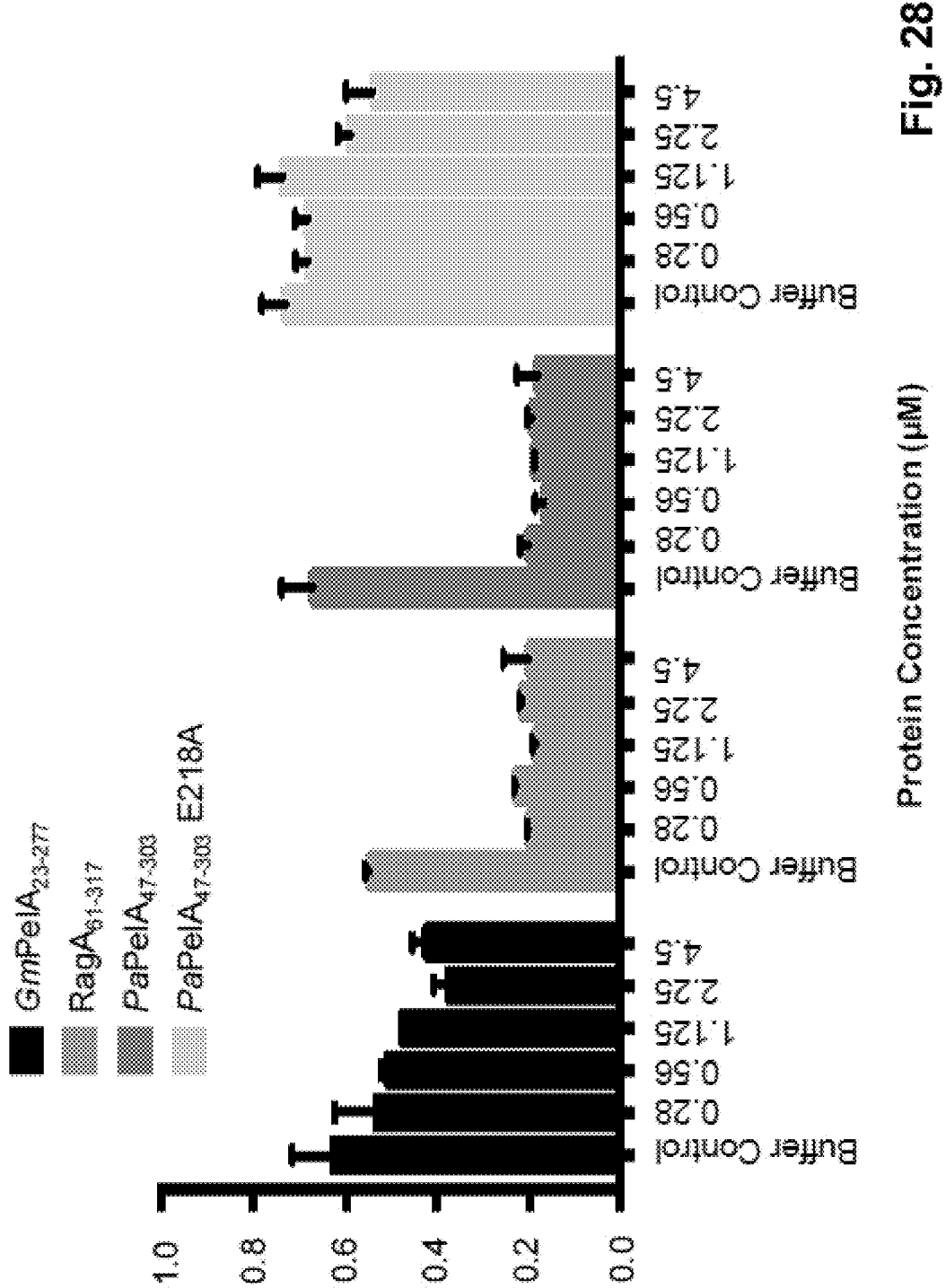

FIG. 28 shows the dispersion of pre-formed GAG biofilms using RagA$_{61-317}$ and GmPelA$_{23-277}$. Addition of RagA$_{61-317}$ to pre-formed A. fumigatus GAG biofilms resulted in the elimination of the GAG biofilms as detected through the crystal violet assay. The putative glycosyl hydrolase PelA$_{47-303}$ was used as a positive control while the PelA$_{47-303}$ variant E218A acts as negative control. GmPelA$_{23-277}$ was less effective at eliminating GAG biofilms as detected through the crystal violet assay than PelA and RagA.

Figure 29:
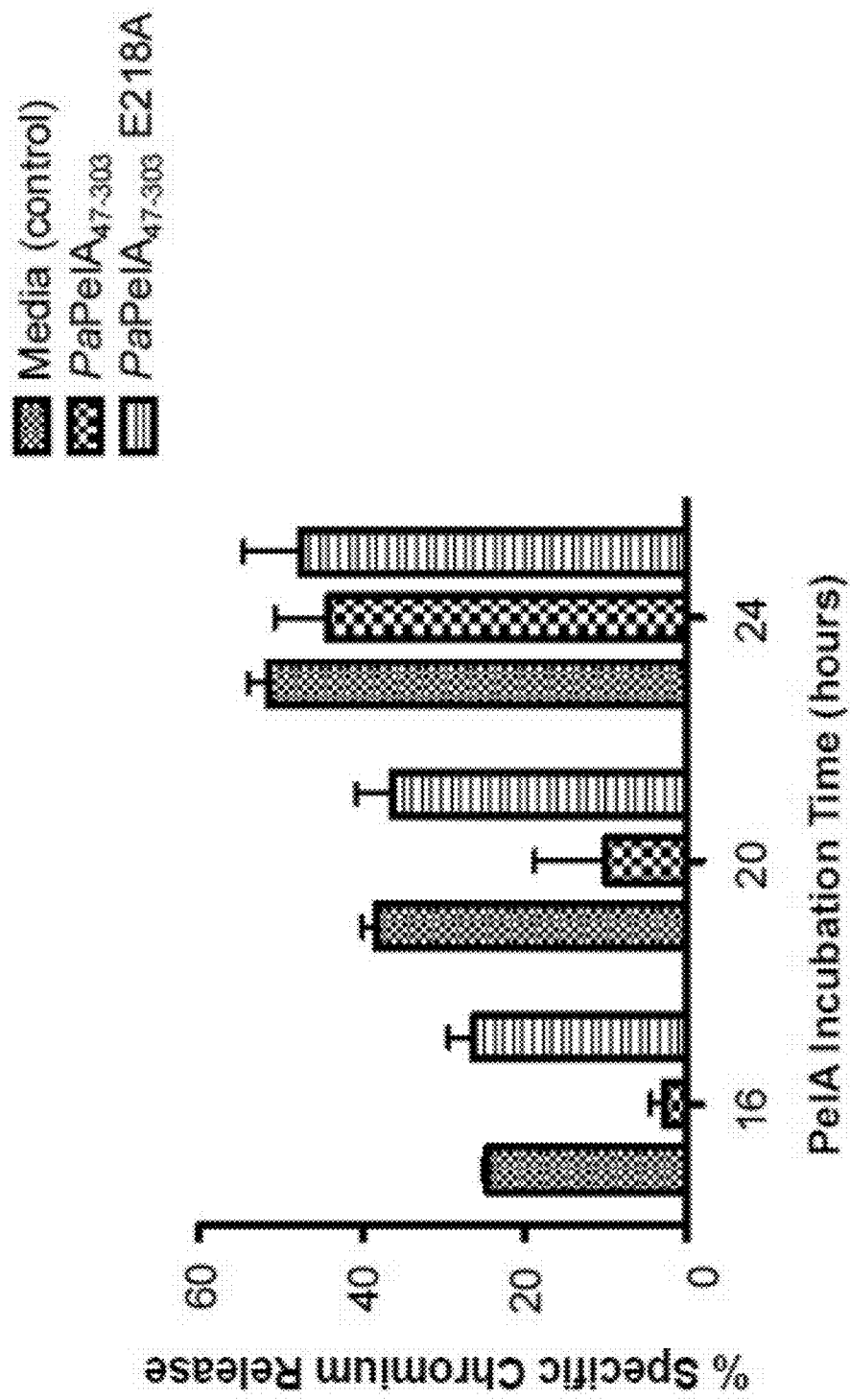

FIG. 29 show that PelA$_{47-303}$ protects epithelial cells from damage caused by A. fumigatus infection. The exogenous addition of wild-type PelA$_{47-303}$ blocked the ability of A. fumigatus to induce pulmonary epithelial cell injury as measured by a chromium release assay over a period of 16 h while PelA$_{47-303}$ E218A did not prevent epithelial cell damage. Cell damage results in Chromium release and thus less damage is visualized by a lower percentage of chromium release.

Figure 30:
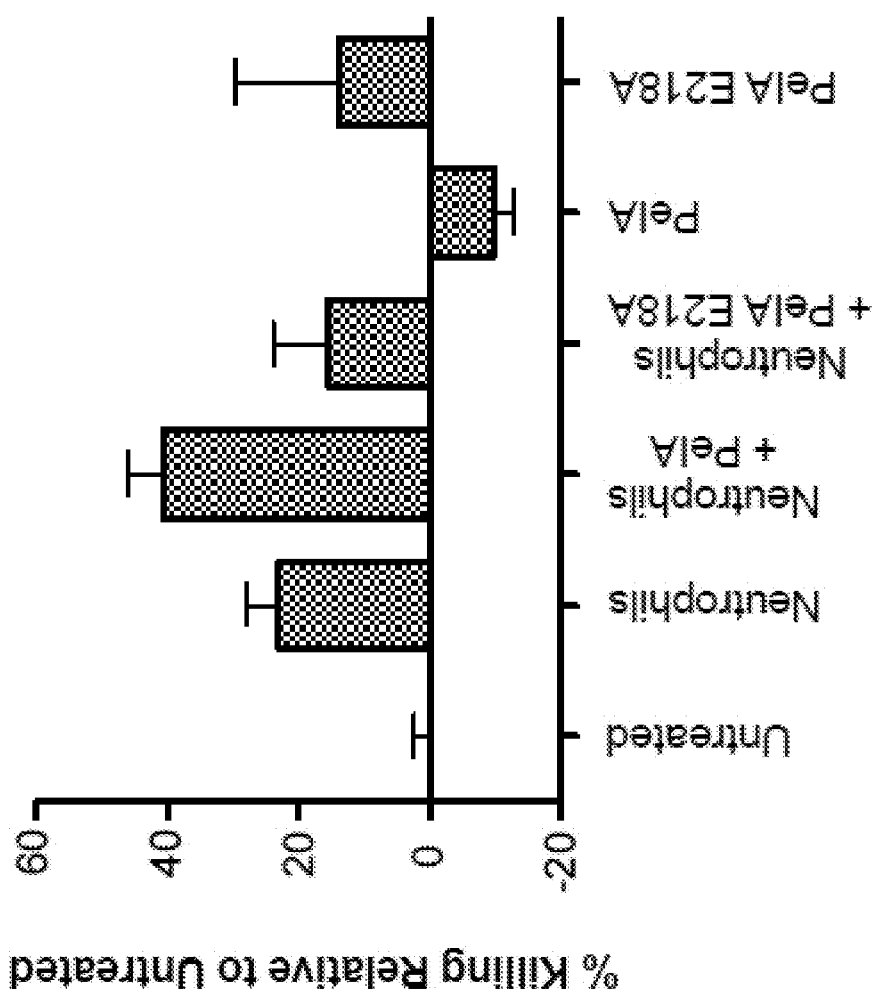

FIG. 30 depicts the enhancement of the bacteriocidal properties of the HL60 neutrophil-like cell line in the presence of PelA$_{47-303}$. Biofilms of P. aeruginosa overexpressing the pel operon were grown for 20 h and incubated with neutrophil-like differentiated HL60 cells for 2 h. P. aeruginosa killing was assessed by quantitative CFU plating. The presence of PelA$_{47-303}$ with neutrophils lead to ~2-fold more bacterial killing than neutrophils alone.

Figure 31:
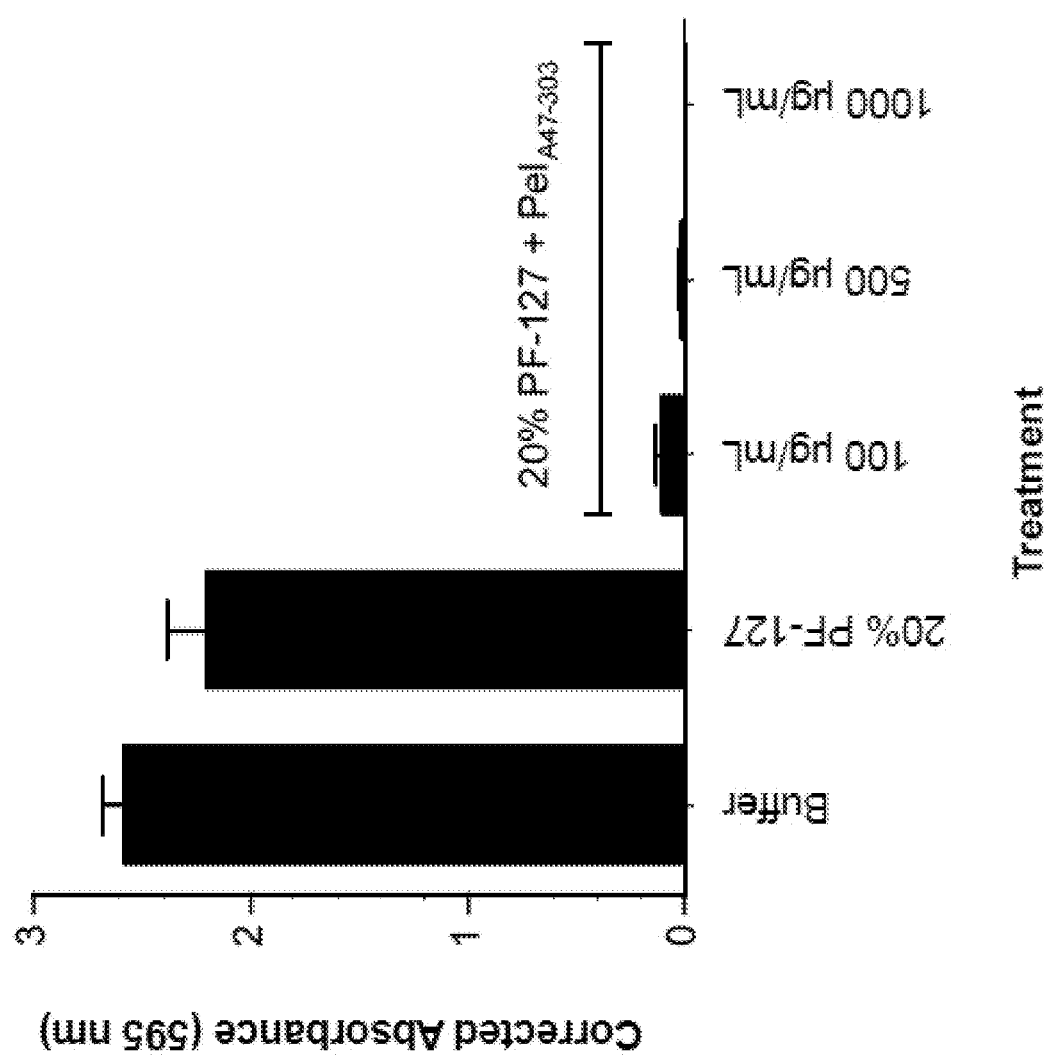

FIG. 31 shows the results of encapsulation of PelA$_{47-303}$ into the thermoreversible gel PF-127. Addition of 1×PBS or 20% PF-127 did not result in dispersal of the Pel-dependent biofilm however addition of PelA$_{47-303}$ at three different concentrations was able to disperse the biofilm in a 1 hour period.

Figure 32:
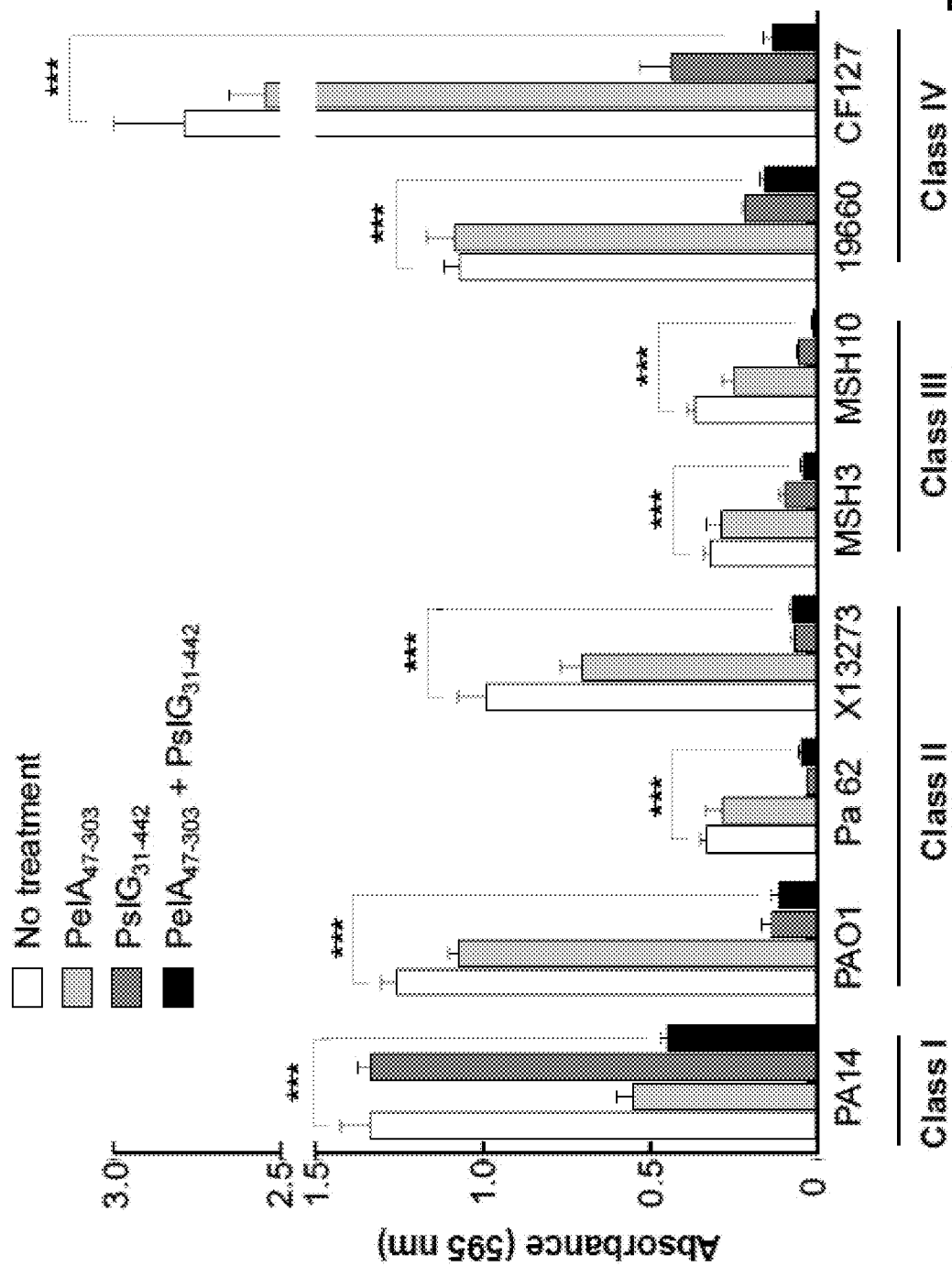

FIG. 32 shows the result of biofilm dispersal of clinical and environmental isolates of P. aeruginosa by PelA$_{47-303}$, PslG$_{31-442}$ and when these enzymes used in combination. A combination of PelA$_{47-303}$ and PslG$_{31-442}$ resulted in ≥90% reduction in biofilm biomass as detected through crystal violet staining. Class I and Class II strains are solely dependent on Pel and Psi production, respectively. Class III strains are redundant exopolysaccharide matrix producers as mutations in both the pel and psl operons are necessary to eliminate the biofilm production in the microtiter dish assay. Finally, Class IV strains are matrix over-producers that form biofilms characterized by Pel and Psl overproduction.

Figure 33:
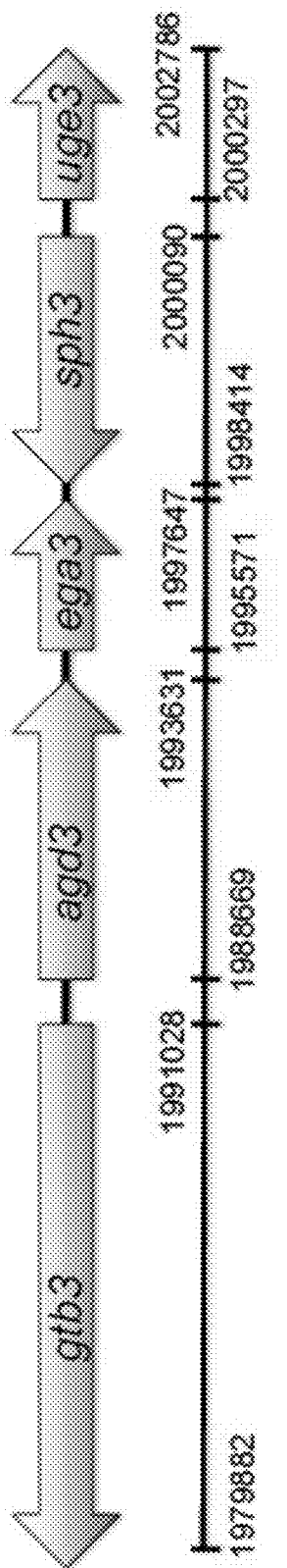

FIG. 33 shows a diagram of genes required for the biosynthesis of GAG on chromosome 3 of A. fumigatus.

Figure 34:
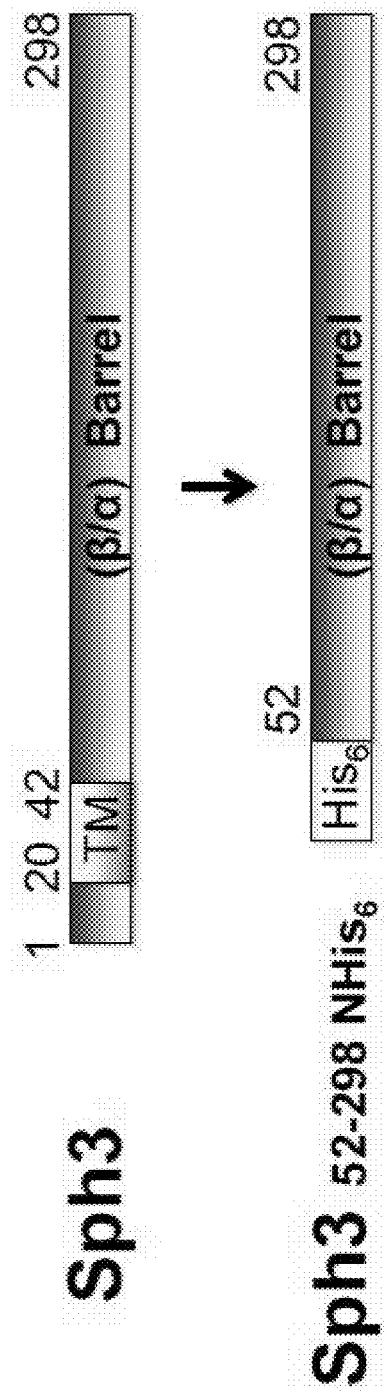

FIG. 34 shows the construct generation of Sph3$_{52-298}$. The TMHMM server indicates that amino acids 20-42 compose a transmembrane domain. A construct composed of residues 52-298 was used to generate a soluble protein.

Figure 35:
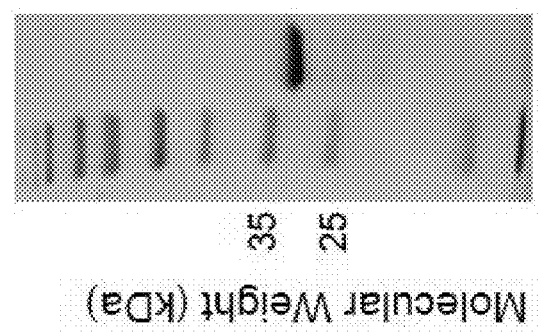

FIG. 35 shows a sodium dodecyl sulfate polyacrylamide gel electrophoresis (SDS-PAGE) gel of Sph3$_{52-298}$. Analysis from SDS-PAGE gel indicates that the protein is >95% pure and has a molecular weight of ~30 kDa which is consistent with the expected molecular weight of the purified protein.

Figure 36:
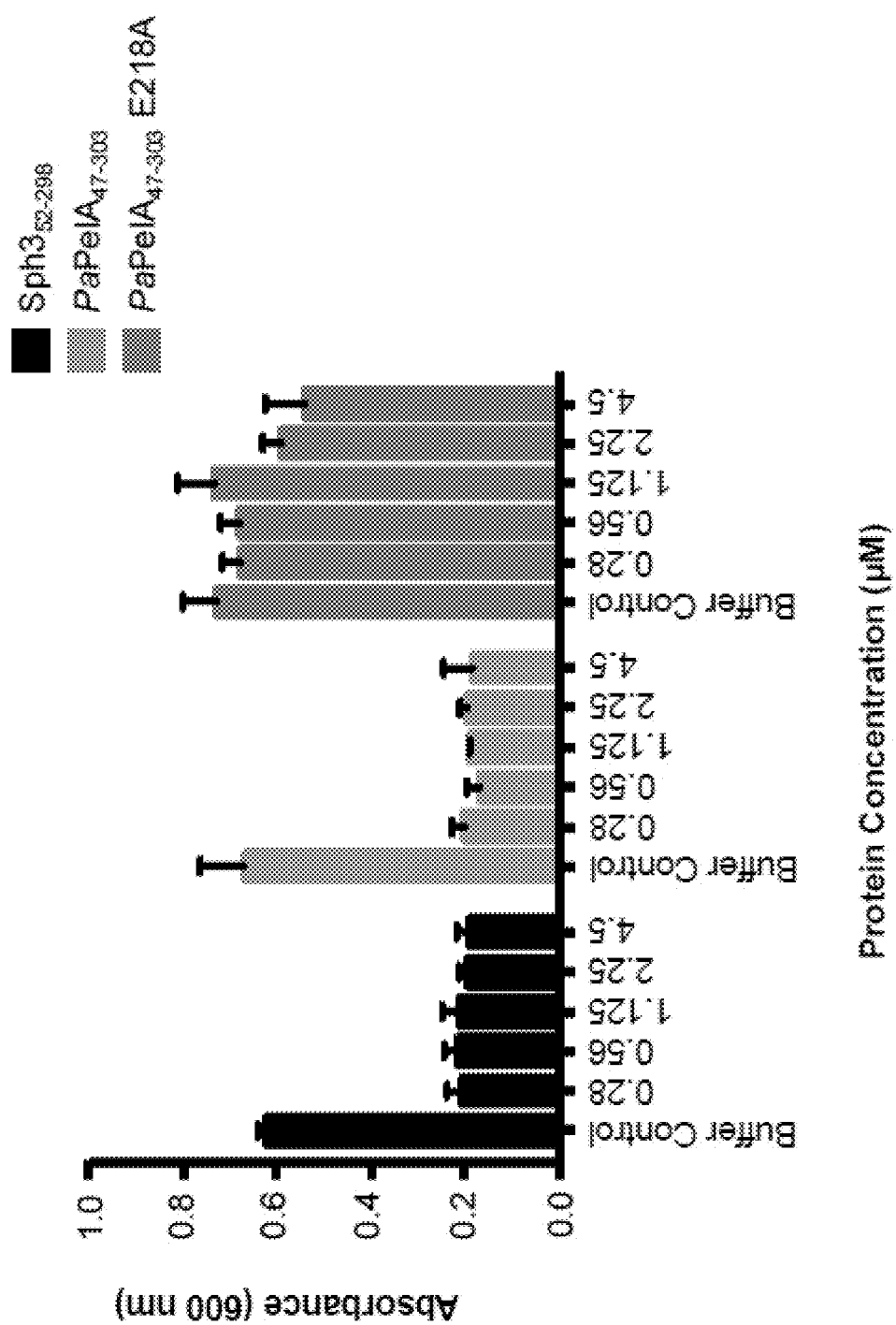

FIG. 36 shows the dispersion of pre-formed GAG biofilms using Sph3. Addition of Sph3$_{52-298}$ to pre-formed A. fumigatus GAG biofilms resulted in the elimination of the GAG biofilms as detected through the crystal violet assay. The putative glycosyl hydrolase PelA$_{47-303}$ was used as a positive control while the PelA$_{47-303}$ variant E218A acts as negative controls.

Figure 37:
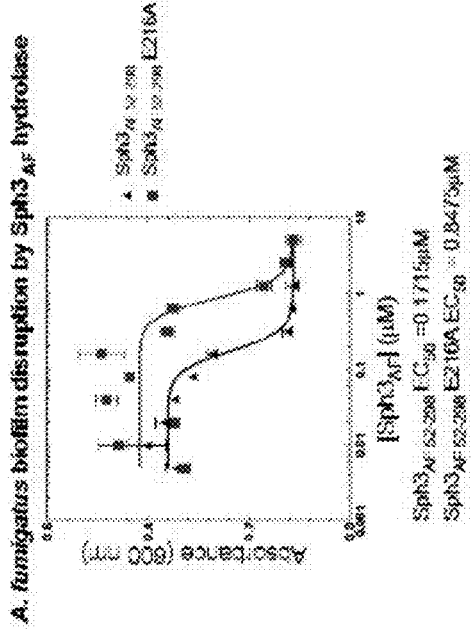
Figure 37:
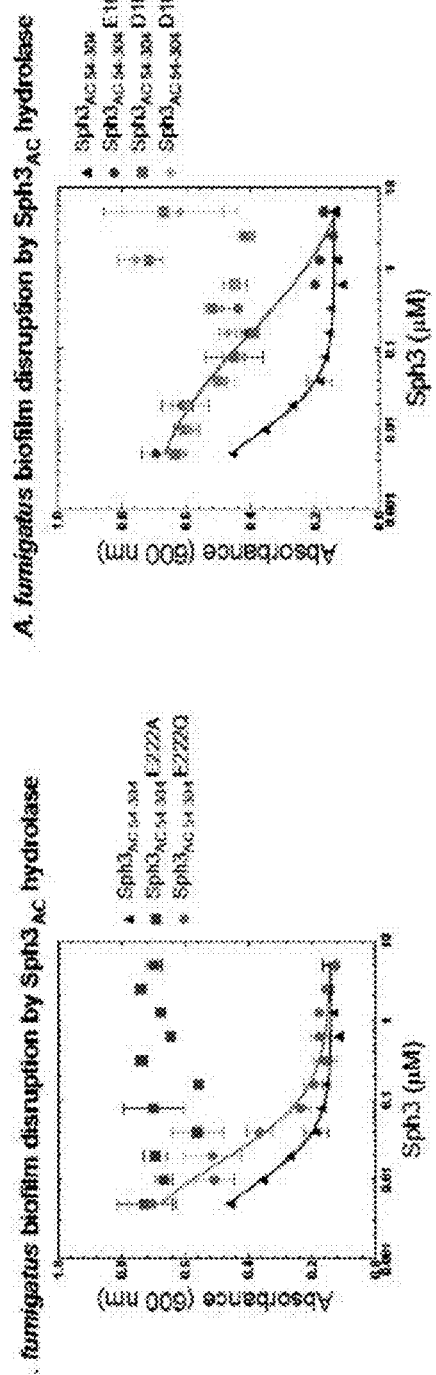

FIG. 37 shows that orthologs Sph3$_{52-298}$ and Sph3$_{AC(54-304)}$ from different Aspergillus species are capable of disrupting GAG-dependent biofilms. The mutation of putative catalytic residues abrogates biofilm disruption by the enzyme. Sph3$_{AC}$ refers to Sph3$_{AC(54-304)}$.

Figure 38:
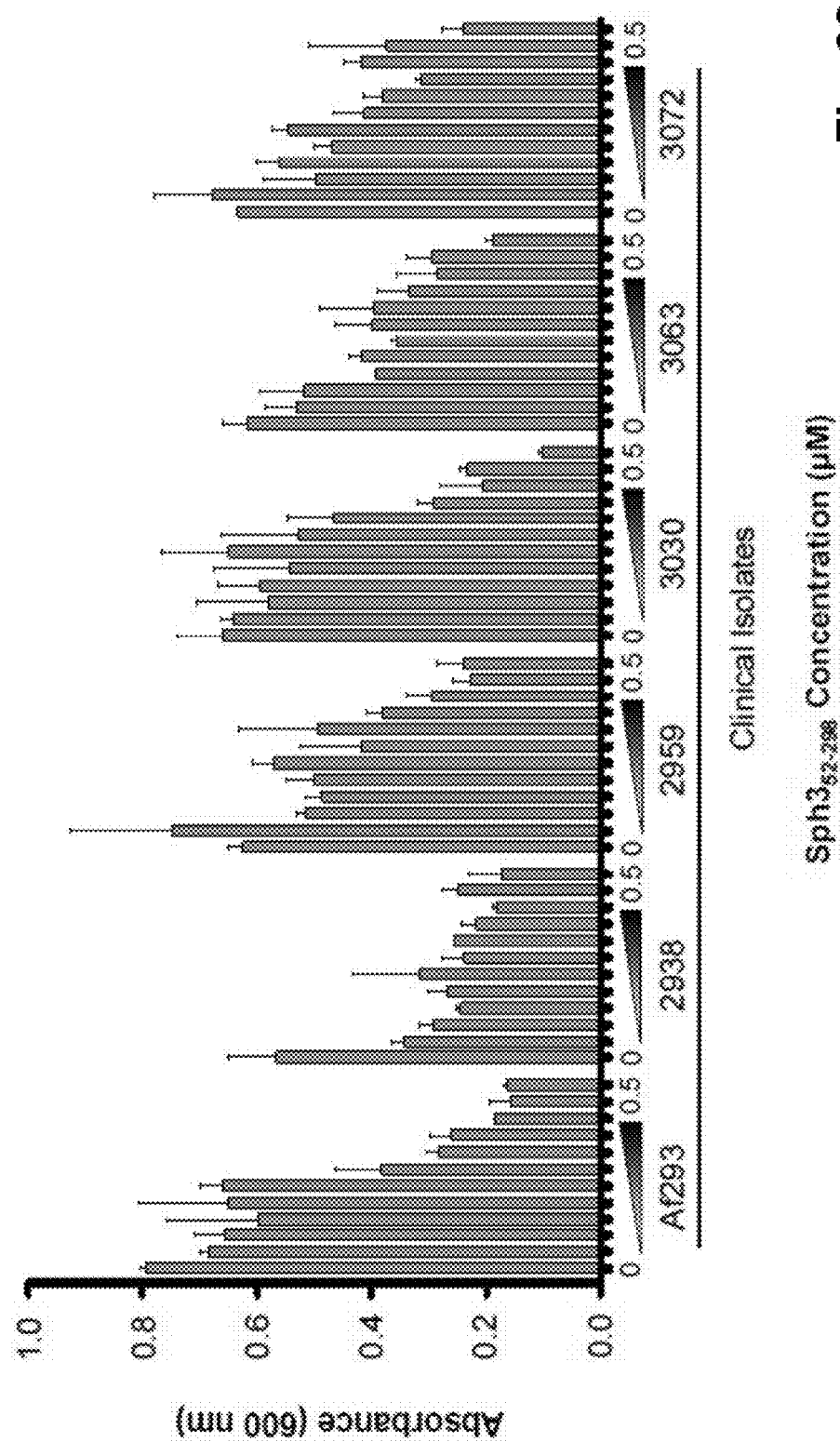

FIG. 38 shows dose-dependent activity of recombinant Sph3$_{52-298}$ against preformed biofilms of multiple clinical isolates. Biofilms of the indicated A. fumigatus strains were grown for 24 hours, and then incubated for 1 hour with the indicated concentration of Sph3$_{52-298}$. Biofilm disruption was measured by crystal violet staining of the residual biofilm mass after gentle washing.

Figure 39:
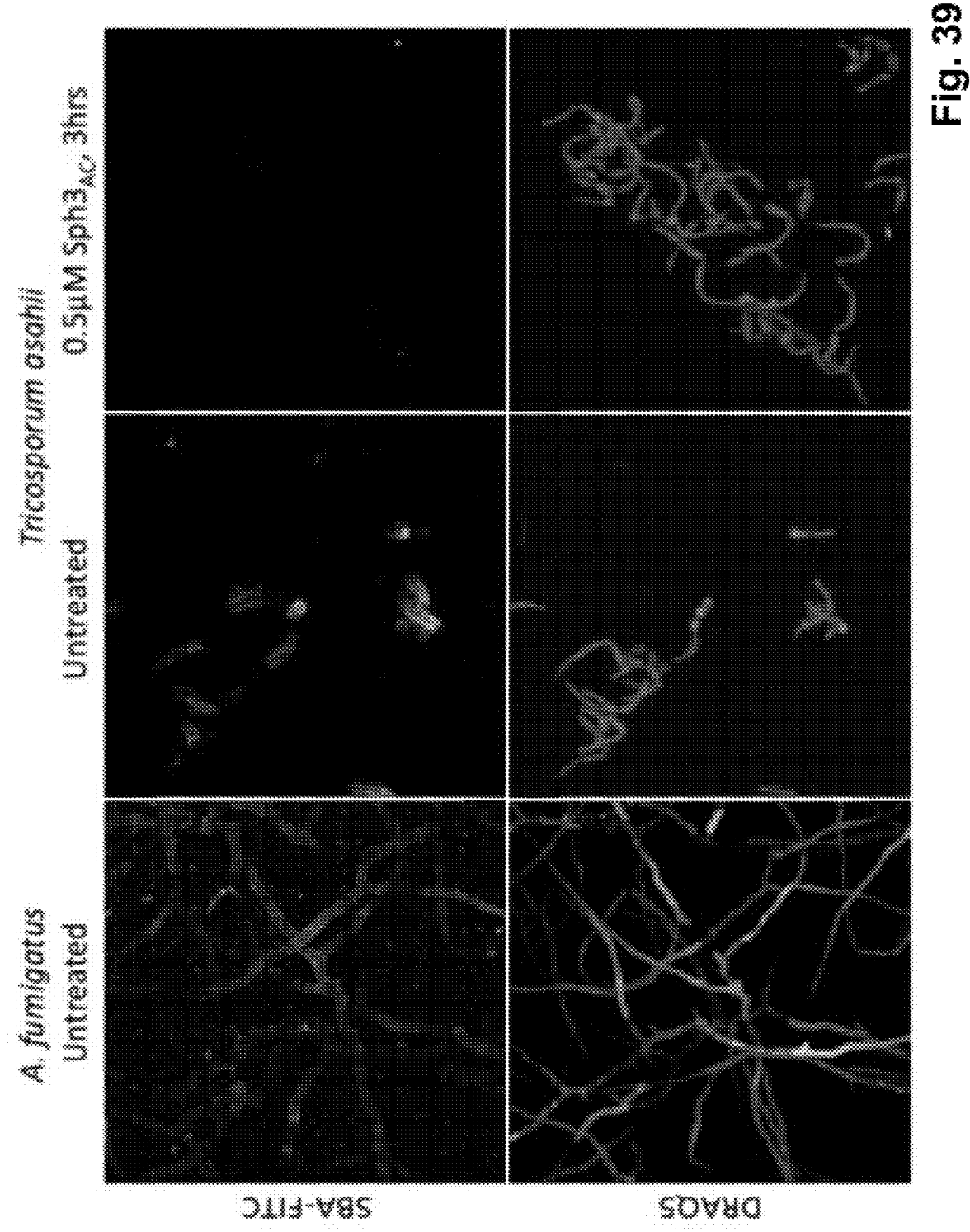

FIG. 39 demonstrates that the opportunistic fungal pathogen Trichosporon asahii produces an exopolysaccharide which is recognized by GalNAc-specific lectin indicating the presence of GAG on the surface of T. ashaii. This exopolysccharide can be degraded by treatment with 0.5 μM SPh3$_{AC(54-304)}$ for 3 hours results in a complete loss of detectable surface GalNAc (top right). Fungi were counterstained with DRAQ5 (bottom panels). $Sph3_{AC}$ refers to $SPh3_{AC(54-304)}$.

Figures 40A, 40B:
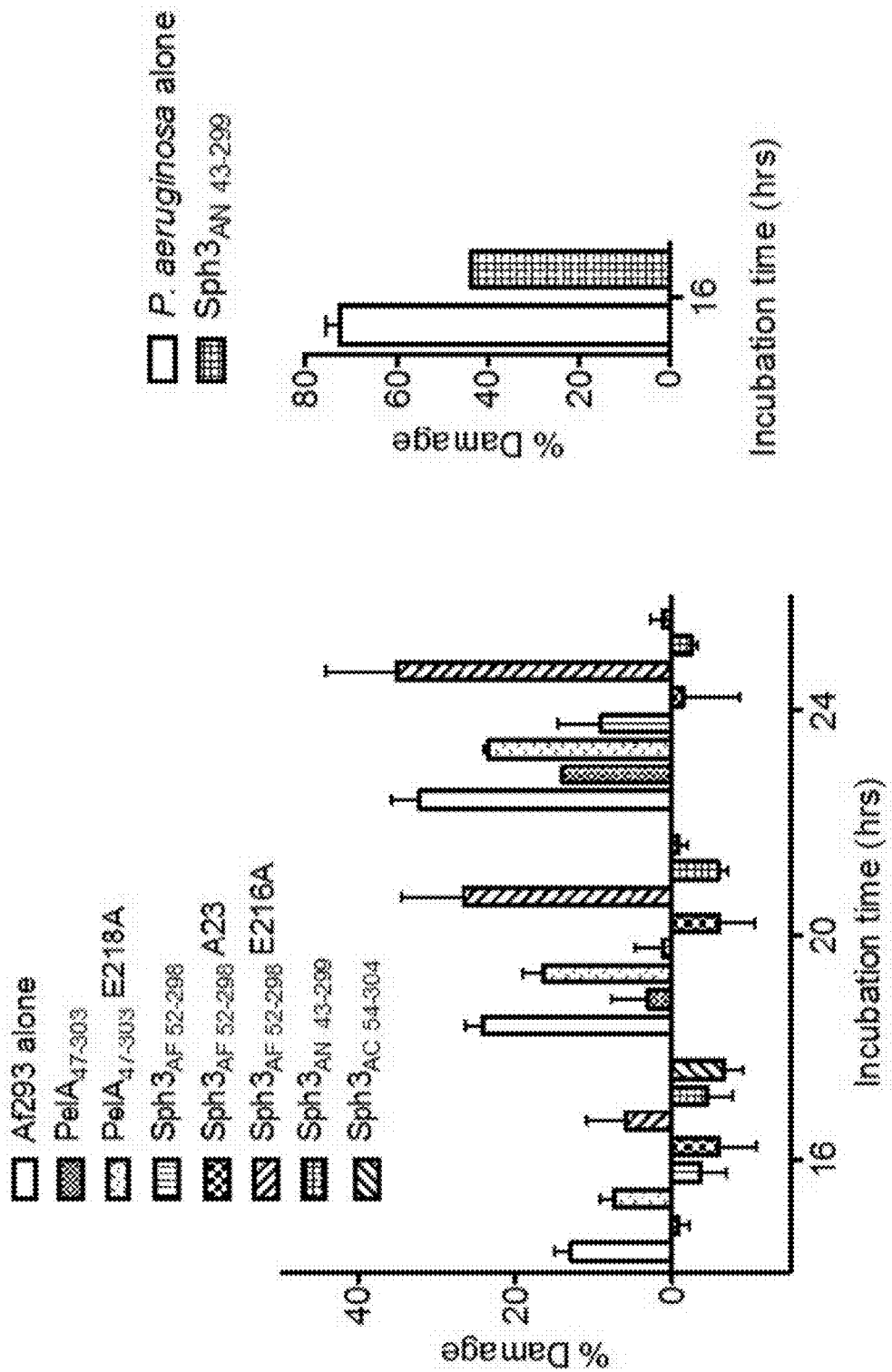

FIGS. 40A-40B demonstrate that recombinant hydrolases protect airway epithelial cells from pathogen-induced damage. (FIG. 40A) Chromium-loaded airway epithelial cell line A549 was incubated with Af2943 conidia and recombinant hydrolases. Chromium released into supernatant was measured at indicated time points. The presence of active hydrolase resulted in less chromium release while enzyme variants failed to protect the airway cells, resulting in a loss of chromium equal to that of the control. (FIG. 40B) Epithelial cell damage by *P. aeruginosa* was measured by determining the fraction of lactate dehydrogenase (LDH) in the presence and absence of $Sph3_{AN(43-299)}$. This result demonstrates that $Sph3_{AN(43-299)}$ is effective at preventing bacterial damage.

Figure 41:
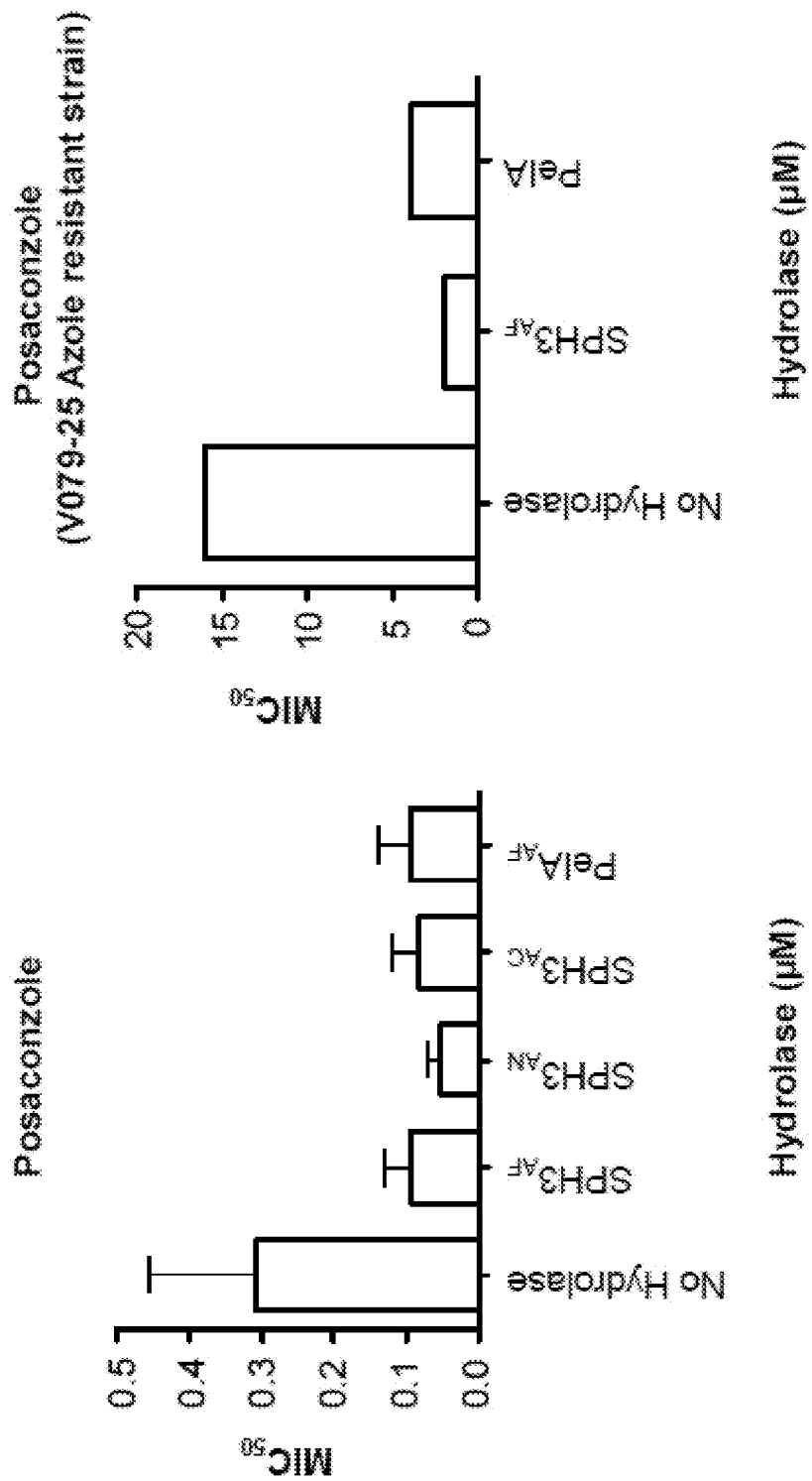
Figure 41:
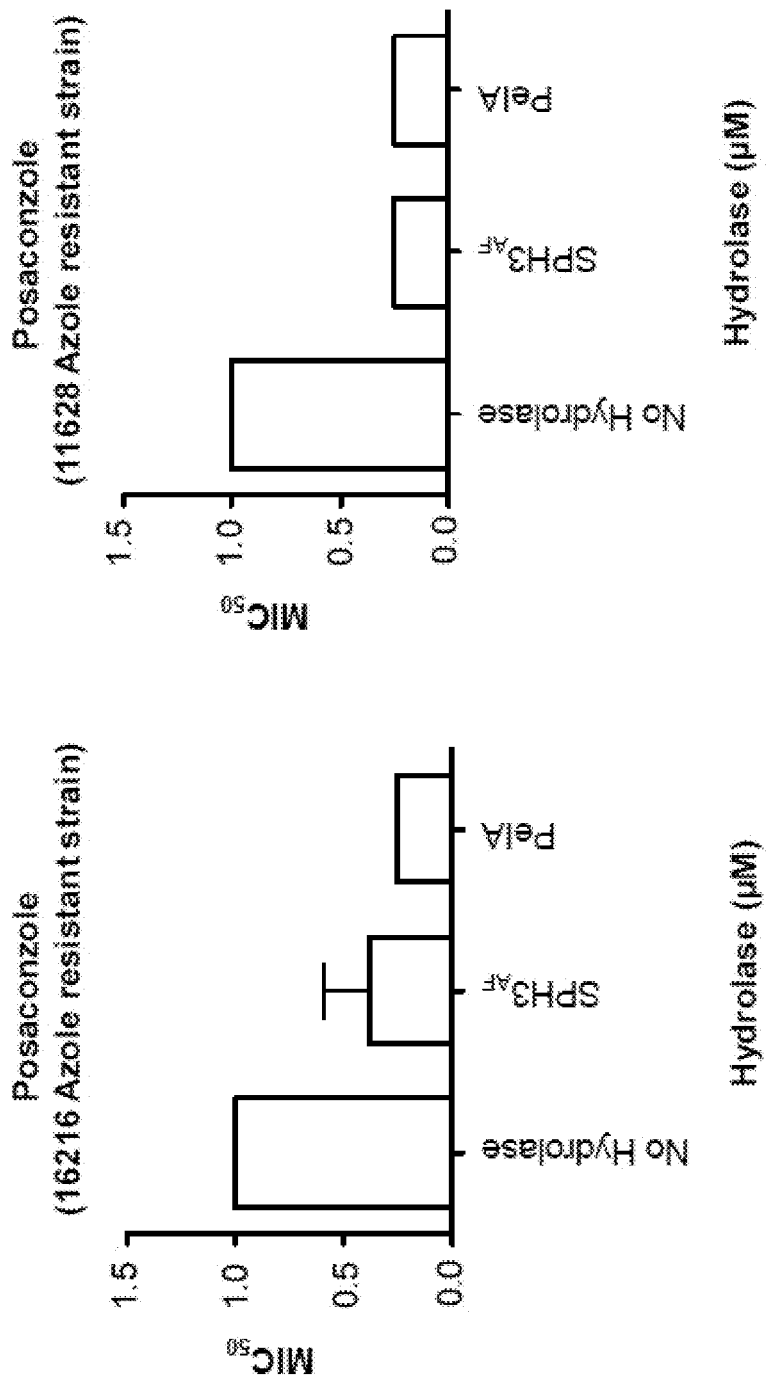
Figure 41:
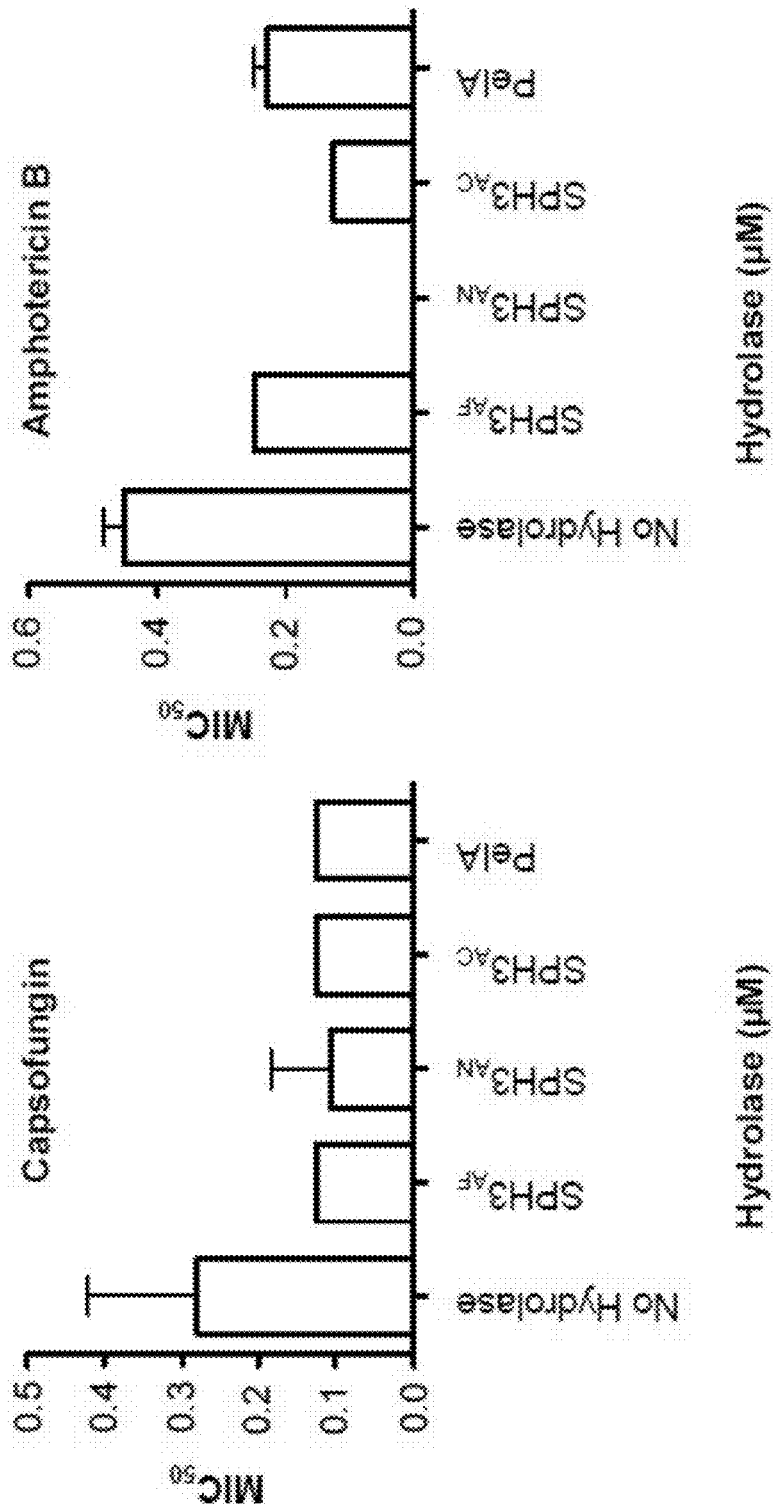

FIG. 41 indicates that hydrolases have synergistic effects in combination with antifungal drugs on the metabolic activity of *A. fumigatus*. *A. fumigatus* conidia were grown in the presence of indicated antifungal drugs and hydrolases at various concentrations for 20 h at 37° C., 5% $CO_2$, and their metabolic activity measured via XTT assay. $MIC_{50}$ defined as the drug concentration resulting in 50% of the metabolic activity of the sample not exposed to drug. $Sph3_{AC}$ refers to $Sph3_{AC(54-304)}$, $Sph3_{AN}$ refers to $Sph3_{AN(43-299)}$ and $Sph3_{AF}$ refers to $Sph3_{52-298}$. N.D.: Not Determined.

Figure 42:
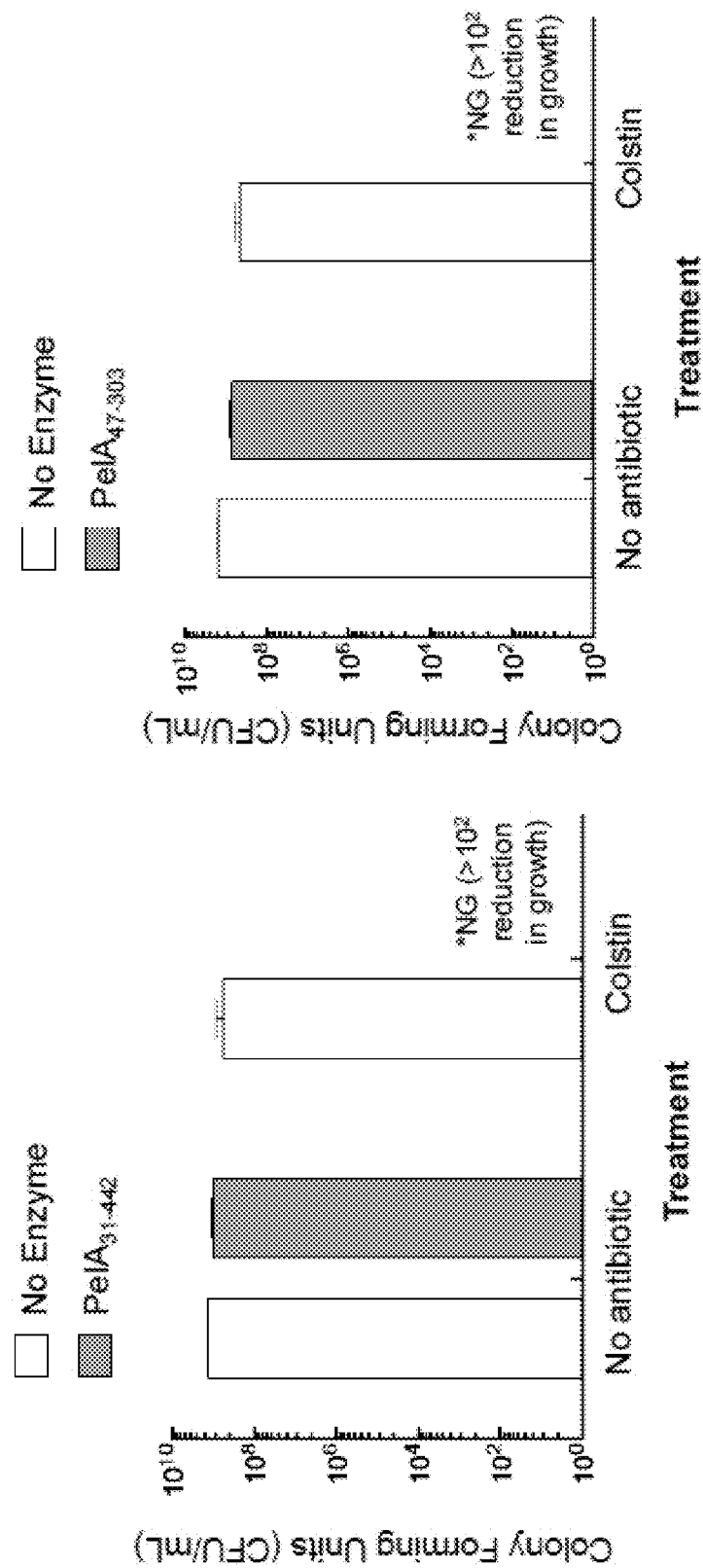

FIG. 42 demonstrates that the glycosyl hydrolases $PslG_{31-442}$ and $PelA_{47-303}$ are able to potentiate the antibiotic colistin dosed at a final concentration of 100 µg/mL. No growth (NG) was observed on LB agar plates indicating that in the presence of the glcoysyl hydrolases, colistin resulted in >100-fold more bacterial killing than in the absence of the enzyme.

Figure 43:
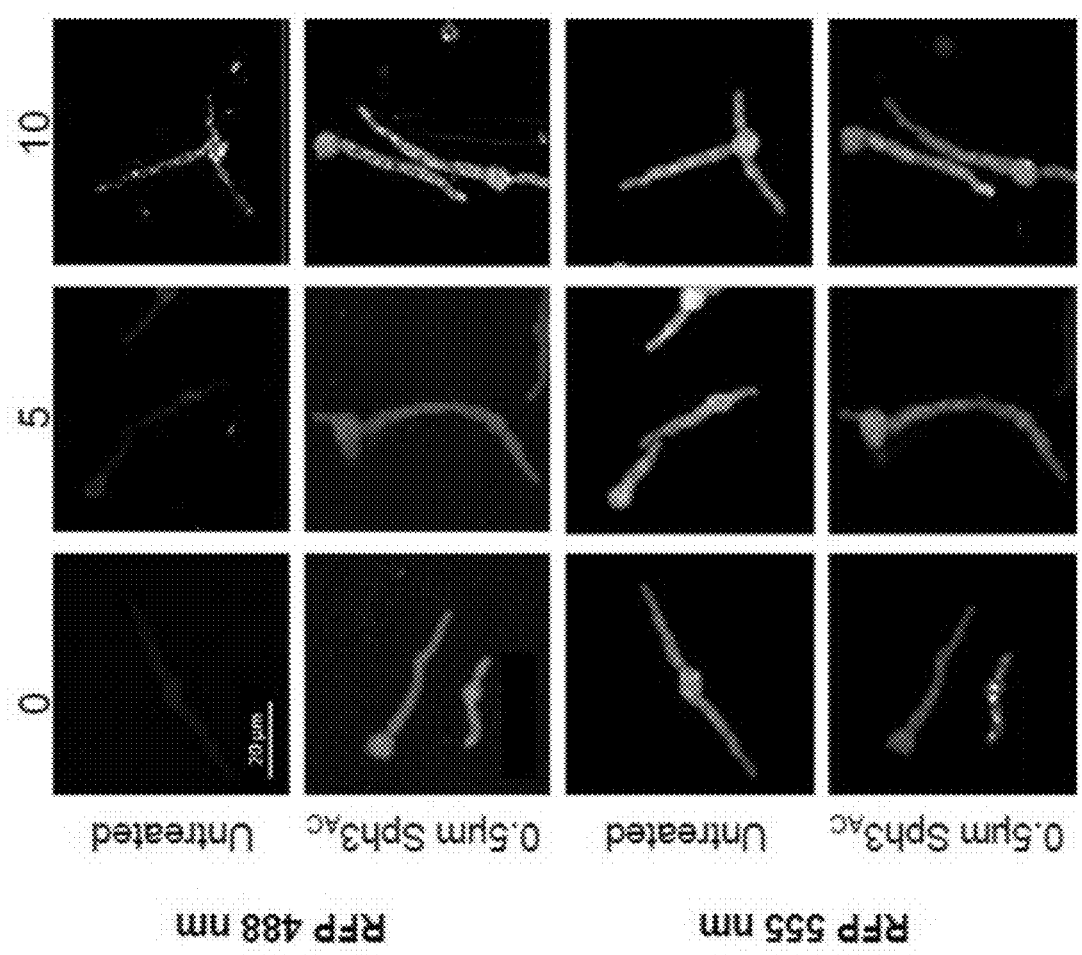

FIG. 43 demonstrates the degradation of the GAG exopolysaccharide coating *A. fumigatus* by $Sph3_{AC(54-304)}$ increases the activity of antifungals through enhancing their ability to penetrate fungal cells. $Sph3_{AC}$ refers to $Sph3_{AC(54-304)}$.

Figure 44:
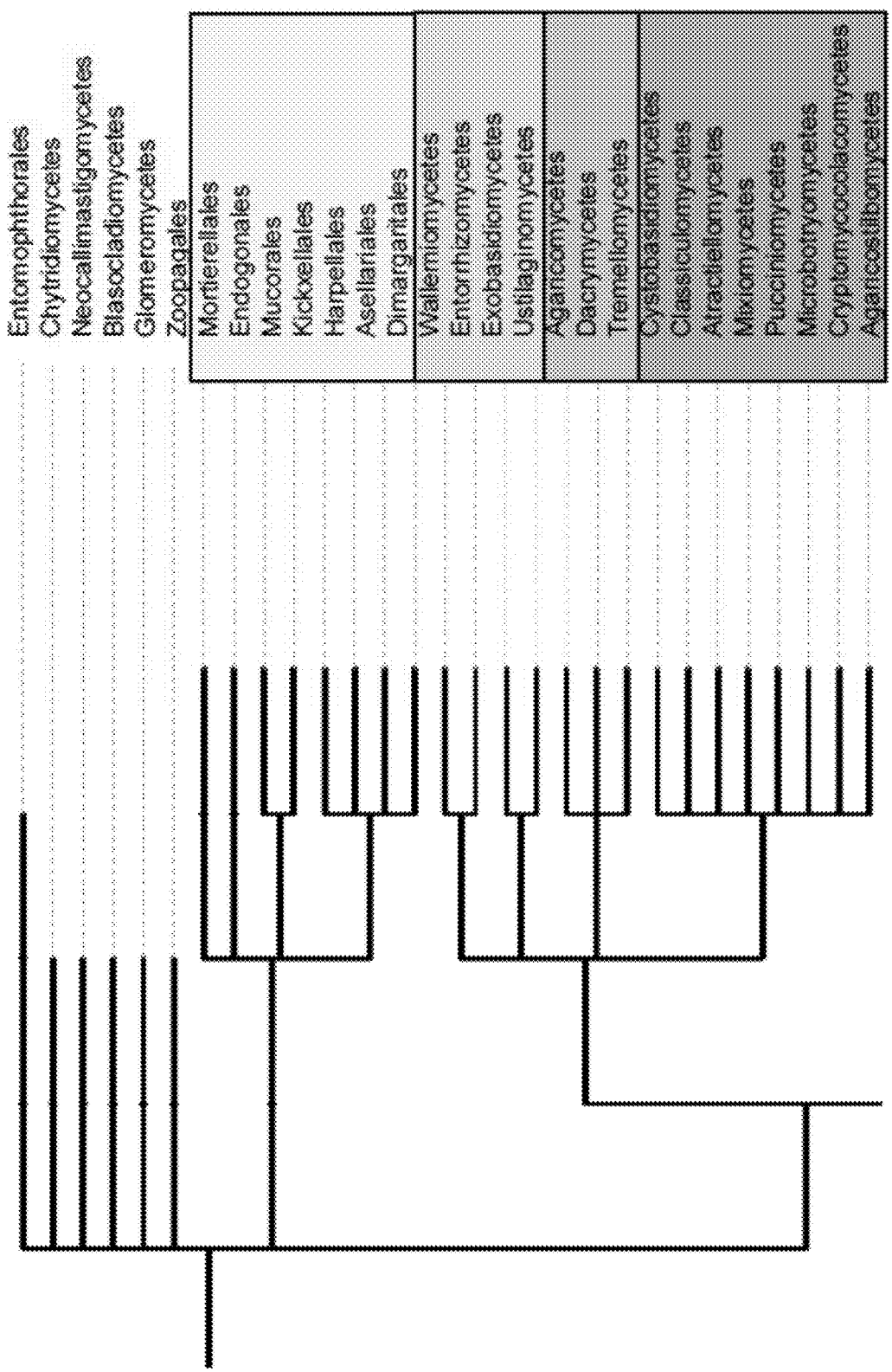
Figure 44:
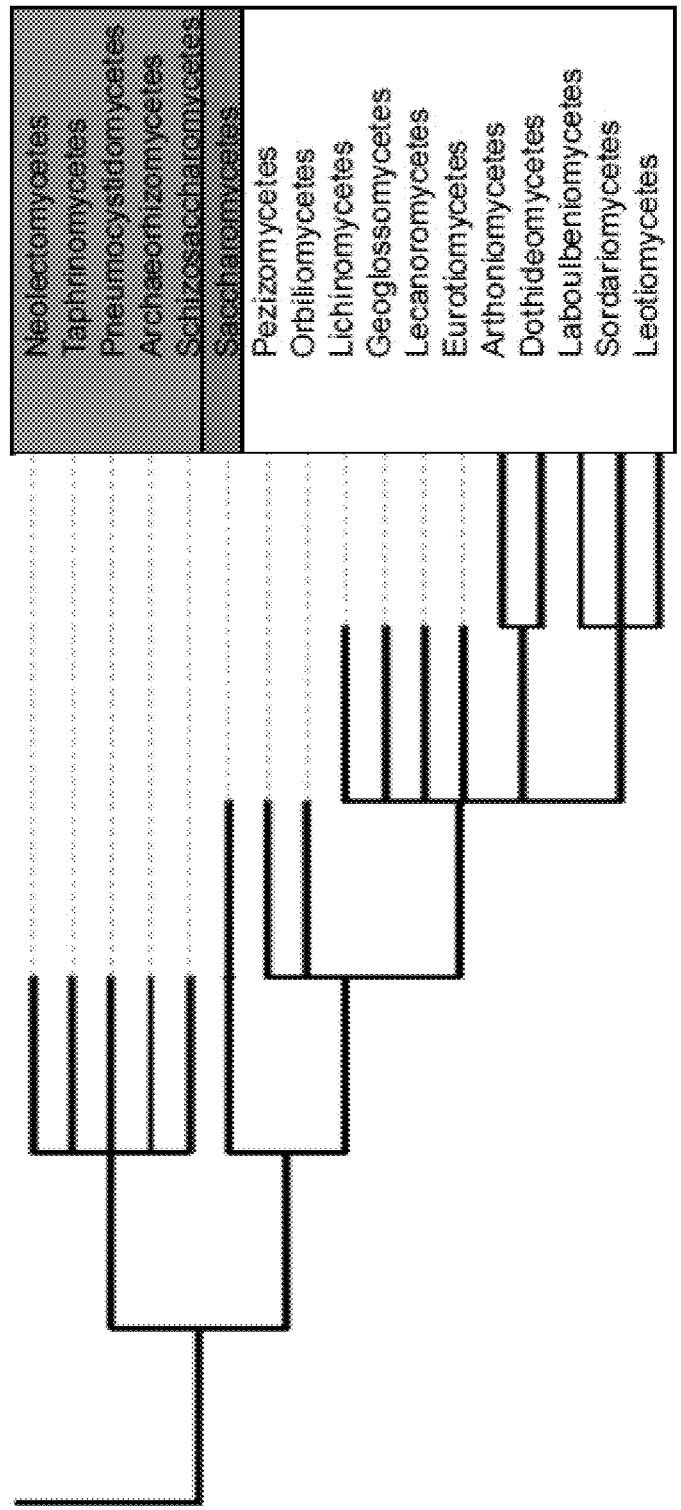

FIG. 44 shows the taxonomic relationship of fungal classes containing the GAG biosynthetic cluster as identified through bioinformatics analysis.

Figure 45:
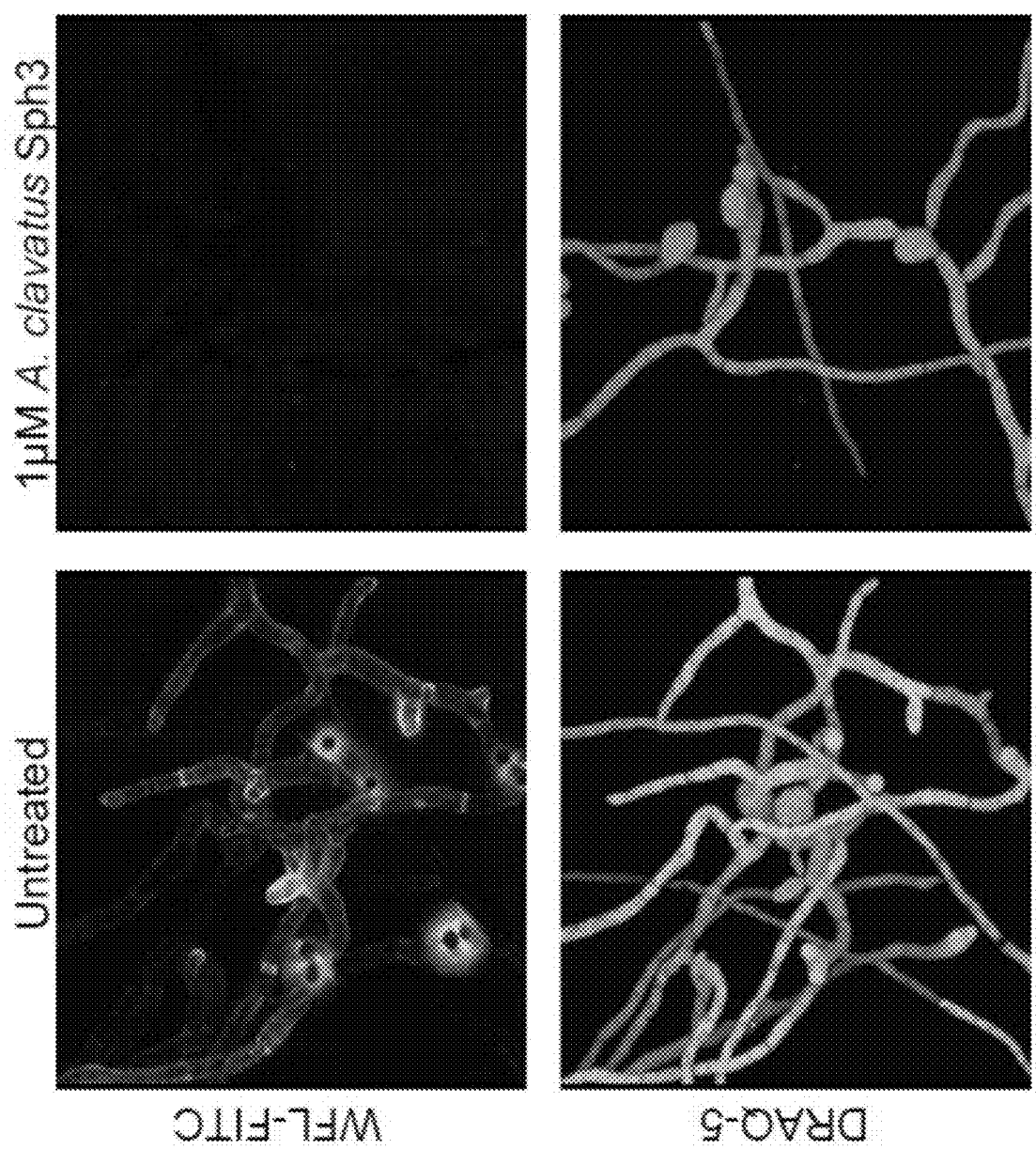

FIG. 45 demonstrates that staining *Botrytis cinerea* with a GalNAc-specific lectin detects the presence of GAG on the surface of *B. cinerea*. Treatment of hyphae of *B. cinerea* with recombinant *A. clavatus* $Sph3_{AC(54-304)}$ resulted in a complete loss of this exopolysaccharide indicating that $Sph3_{AC(54-304)}$ is able to hydrolyze the GAG on the surface of the hyphae. $Sph3_{AC}$ refers to $Sph3_{AC(54-304)}$.

Figure 46:
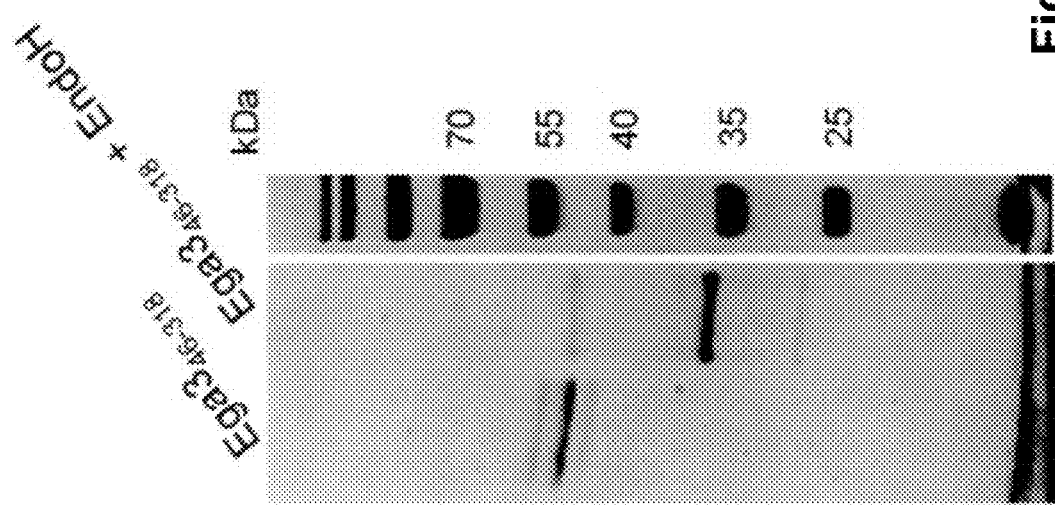

FIG. 46 shows a sodium dodecyl sulfate polyacrylamide gel electrophoresis (SDS-PAGE) gel of $Ega_{346-318}$. To determine whether the apparent mass of $Ega_{346-318}$ was larger due to glycosylation a sample of protein was treated with endoglycosidase H (EndoH). The EndoH treated $Ega_{346-318}$ produced a band near the predicted mass of the unglycosylated protein at ~31 kDa.

Figure 47A:
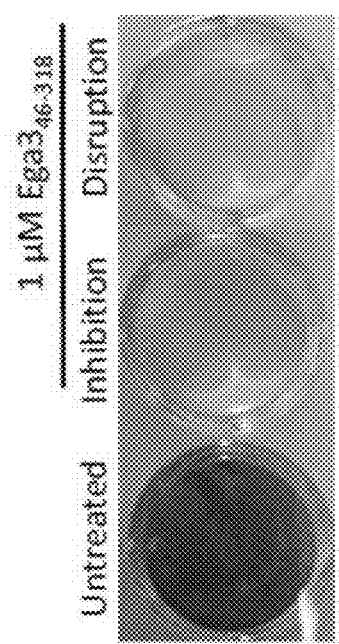
Figure 47B:
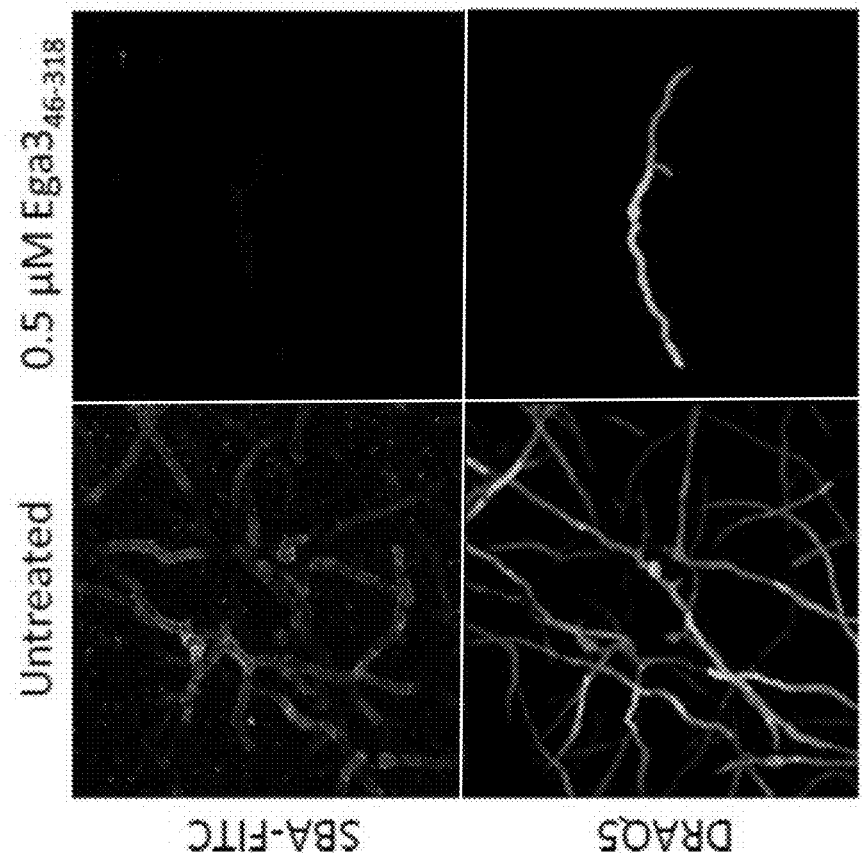

FIGS. 47A-47B show the ability of $Ega_{346-318}$ to inhibit and disperse *A. fumigatus* biofilms. (FIG. 47A) The presence of $Ega_{346-318}$ prevented biofilm formation in a microtiter dish and also allowed for disruption of the biofilm. (FIG. 47B) While untreated hyphae display extensive staining with the GalNAc specific fluorescent lectin SBA-FITC, treatment of the hyphae with 0.5 µM $Ega_{346-318}$ for 3 hours resulted in a complete loss of detectable GalNAc on the surface.

DETAILED DESCRIPTION

The present inventors have demonstrated that the exogenous application of putative hydrolases involved in the biosynthesis of the exopolysaccharides: Psi, Pel, poly-β(1, 6)-N-acetyl-D-glucosamine (PNAG) and galactosaminogalactan (GAG) may be utilized to inhibit and disperse microbial biofilms that employ these sugar polymers in biofilm formation.

Definitions

Unless defined otherwise, all technical and scientific terms used herein have the same meaning as commonly understood by one of ordinary skill in the art to which this invention belongs. The following definitions supplement those in the art and are directed to the present disclosure and are not to be imputed to any related or unrelated case. Generally, nomenclatures used in connection with, and techniques of, molecular biology, immunology, microbiology, genetics, protein and nucleic acid chemistry and hybridization described herein are those well known and commonly used in the art. Methods and techniques employed in the present disclosure are generally performed according to conventional methods known in the art and as described, for example, in general references such as Sambrook et al, Molecular Cloning: A Laboratory Manual, $2^{nd}$ ed., Cold Spring Harbor Laboratory Press, Cold Spring Harbor, N.Y. (1989) and Ausubel et al, Current Protocols in Molecular Biology, Greene Publishing Associates (1992). Although any methods and materials similar or equivalent to those described herein can be used in the practice of the invention, particular materials and methods are described herein.

As used herein and in the appended claims, the singular forms "a", "an", and "the" include plural reference unless the context clearly dictates otherwise.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "administering" means to provide or give an agent (e.g. therapeutic agent) to an animal or plant by an effective route.

The term "biofilm" as used herein refers to a composition or matrix of microorganism strains/species formed on either a biotic or abiotic surface. These microorganisms are encapsulated in a matrix generally containing proteins, nucleic acids and exopolysaccharides as the main components.

The phrase "biofilm-related infection" as used herein refers to an infection related to the formation of biofilm on a biotic surface, including, without limitation, epithelial cells of skin, eye and organs, such as the lung and respiratory system as well as surfaces and tissues of plants.

The term "lung infection" as used herein refers to respiratory infections or disease, which includes but is not limited to invasive aspergilliosis, an acute disease of the immunocompromised host or chronic *aspergillus* infection that occurs in immuno-competent individuals with compromised lung function.

The term "chronic pulmonary disease" as used herein refers to respiratory infections or disease, which includes but is not limited to cystic fibrosis and pneumonia.

The term "encoded by an exopolysaccharide biosynthetic operon or functional gene cluster" as used herein refers to a nucleic acid sequence of a microbial operon or functional gene cluster that encodes a protein involved in the production of an exopolysaccharide by the microbial organism.

The term "glycosyl hydrolase domain" or "GH domain" as used herein refers to a protein domain that encodes a putative glycosyl hydrolase, which may be identified by comparison to known glycosyl hydrolase family members. A glycosyl hydrolase enzyme is able to hydrolyze glycosidic bonds.

The term "isolated" refers to a nucleic acid or protein substantially free of cellular material or culture medium when produced by recombinant DNA techniques, or chemical precursors, or other chemicals when chemically synthesized.

Figure 1:
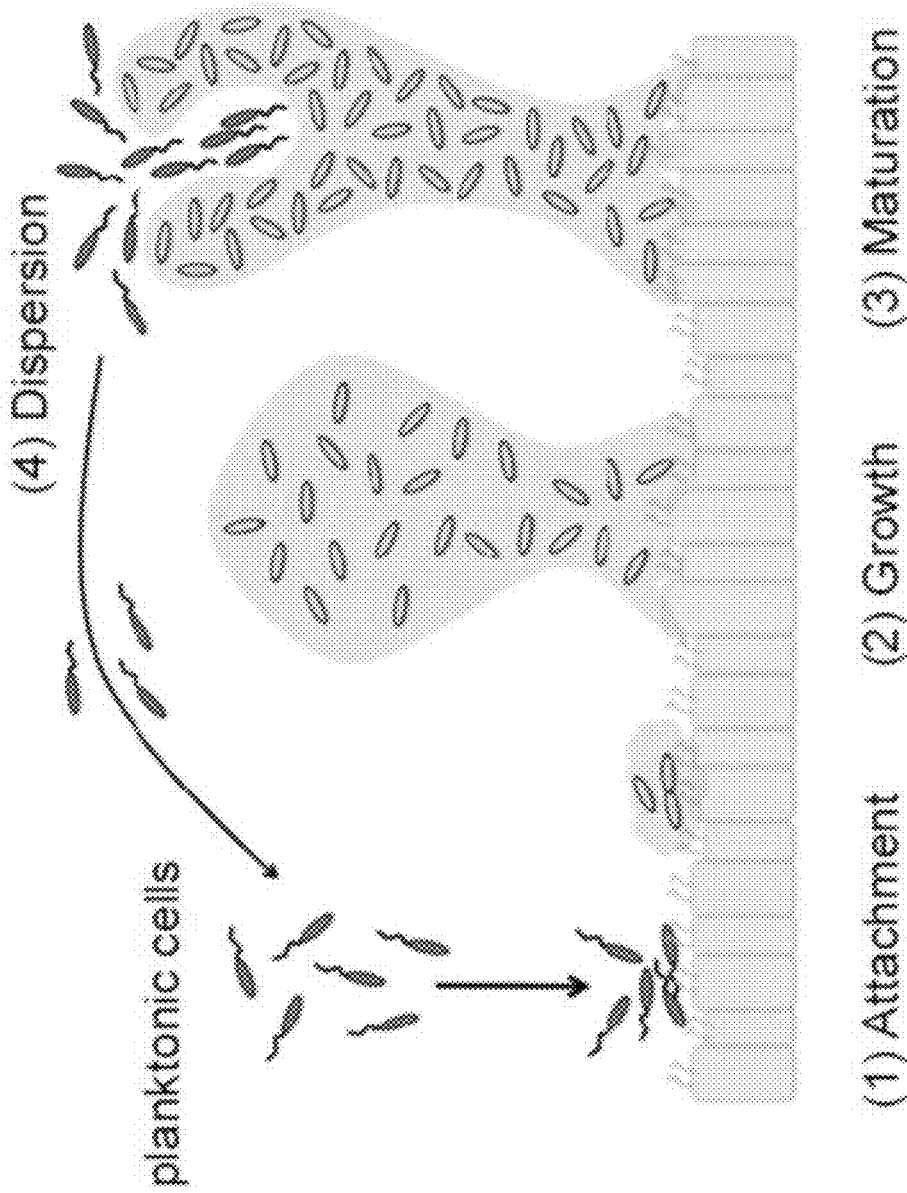
FIG. 1 shows a depiction and composition of a microbial biofilm. The formation of a biofilm can be divided into four distinct phases. Planktonic cells attach to a biotic surface such as lung epithelial cells. Here, the bacteria begin secreting the exopolysaccharides allowing attachment to biotic or abiotic surfaces, thereby initiating the biofilm.
Figure 2:
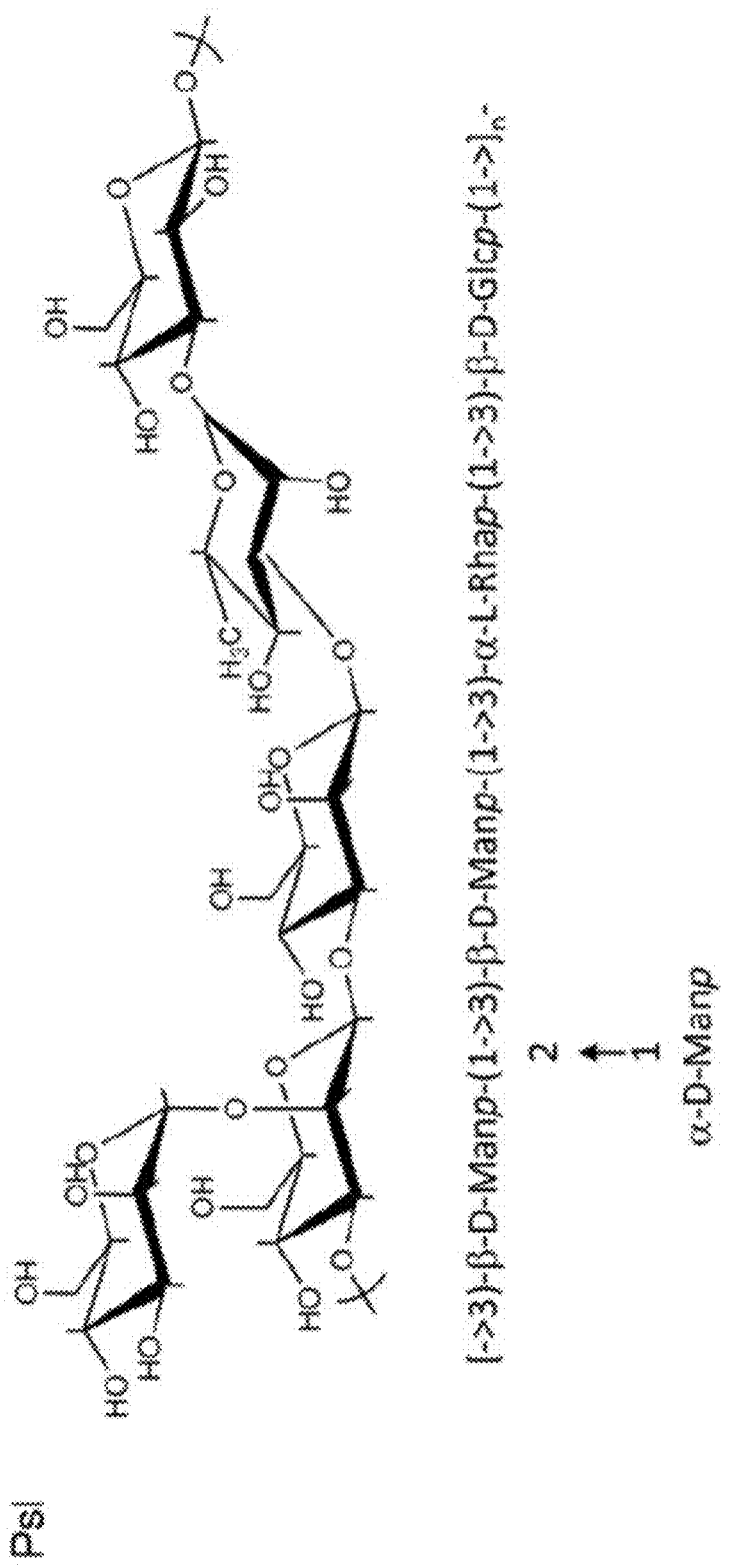
FIG. 2 shows the chemical structure of Psl. Psl is composed of a pentasaccharide-repeating unit of D-mannose, D-glucose and L-rhamnose, and is chemically distinct from other known polysaccharides.
Figure 3:
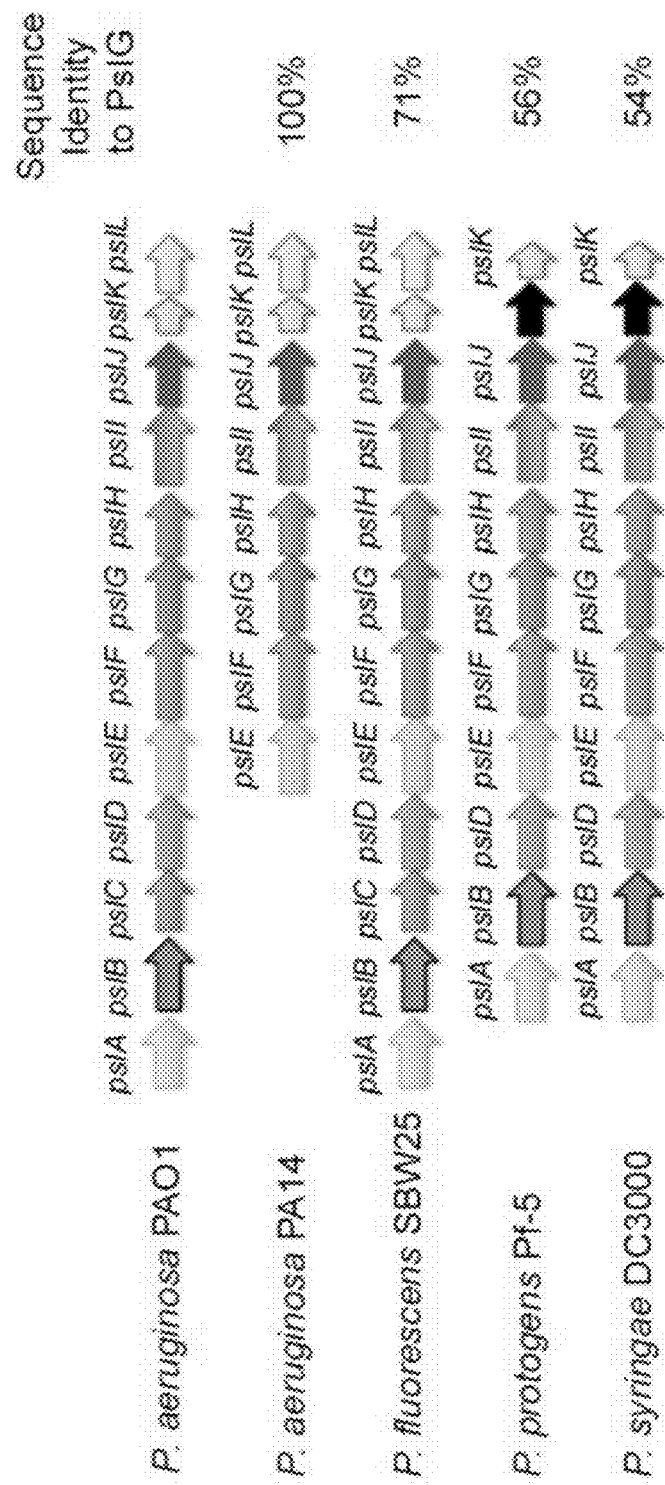
FIG. 3 shows Psl operons in several *P. aeruginosa* species. The psl operon is found in numerous *Pseudomonas* species (not all are shown), however it is unknown whether all species produce the exopolysaccharide. Due to a mutation in *P. aeruginosa* PA14, the strain has been demonstrated to be unable to synthesize the Psl polysaccharide. The location of PslG is located in the same position in the operon across species and its amino acid sequence identity relative to PslG from *P. aeruginosa* PAO1 is shown. The sequence identity refers to the amino acid sequence identity to PslG from *P. aeruginosa* PAO1.
Figure 4:
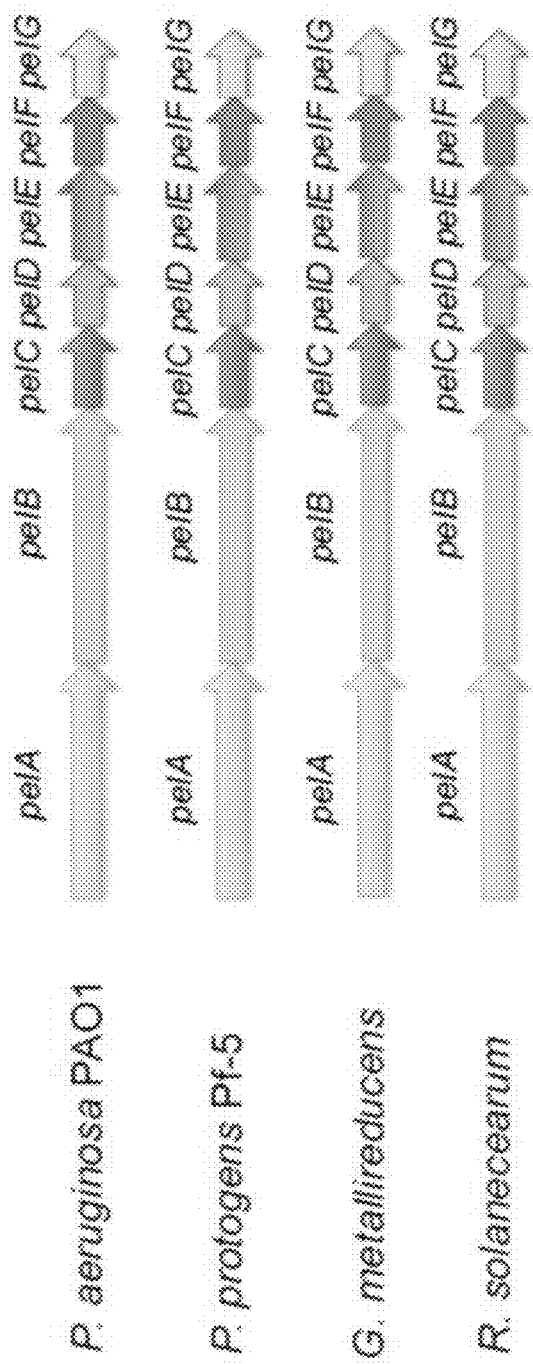
FIG. 4 shows Pel operons in several bacterial species. The pel operon is found in a number of bacterial species including those of *Geobacter metallireducens* and *Ralstonia solan-*

The term "Psl" as used herein refers to the exopolysaccharide composed of a pentassaccharide repeating unit of D-mannose, D-glucose and L-rham nose and is distinct from other known polysaccharides (FIG. 2).

The term "pslG" as used herein refers to the 7th open reading frame of the psl operon that encodes for proteins required for the biosynthesis of Psl. The psl operon is found in several *Pseudomonas* species. The term "PslG" as used herein refers to the encoded protein as will be clear in context.

The term "Pel" as used herein refers to the exopolysaccharide that is one of the main components of biofilm that forms at the air-liquid interface and is referred to as pellicles.

The term "pelA" as used herein refers to the 1st open reading frame of the pel operon that encodes for proteins required for biosynthesis of Pel. The pel operon is found in numerous *Pseudomonas* species. pelA orthologs include, without limitation, ragA from *Ralstonia solanacearum* and pelA from *Geobacter metallireducens*. The term "PelA" or "RagA" as used herein refers to the encoded proteins as will be clear in context.

The term "PNAG" as used herein refers to the homopolymer of repeating N-acetyl-D-glucosamine units, similar to chitin, however it is synthesized with a β(1,6) linkage. The partially deacetylated form is called dPNAG.

The term "bpsB" as used herein refers to the $2^{nd}$ open reading frame of the bps operon that encodes for proteins required for PNAG biosynthesis. The bps operon is found in *Bordetella* species. The term "BpsB" as used herein refers to the encoded protein as will be clear in context.

The term "pgaB" as used herein refers to the $2^{nd}$ open reading frame of the pga operon that encodes for proteins required for PNAG biosynthesis. The pga operon is found in *E. coli* and numerous Gram-negative species and is sometimes annotated as the hms operon. The term "PgaB" as used herein refers to the encoded protein as will be clear in context.

The term "GAG" as used herein refers to a heterogeneous, linear extracellular polymer that is composed of α1-4 linked galactose and α1-4 linked partially deacetylated N-acetyl-galactosamine.

The term "sph3" as used herein refers to the exon coding sequence with exon chromosomal coordinates 1,999,871 to U.S. Pat. Nos. 1,999,654 and 1,999,541 to U.S. Pat. Nos. 1,999,184 and 1,998,991 to 1,998,671 located in a functional gene cluster on chromosome 3 in *A. fumigatus* Af293, which encodes for a putative glycosyl hydrolase. sph3 orthologs include, without limitation, sph3Ac from *Aspergillus clavatus*, and sph3AN from *Aspergillus nidulans*. The terms "sph3", "Sph3$_{AC}$" or "Sph3$_{AN}$" as used herein refer to the respective encoded protein as will be clear in context.

The term "ega3" as used herein refers to the exon coding sequence with exon chromosomal coordinates 1,995,843 to 1,996,799 located in a functional gene cluster on chromosome 3 in *A. fumigatus* Af293, which encodes for a putative glycosyl hydrolase. The term "Ega3" as used herein refers to the encoded protein as will be clear in context.

The term "soluble protein" as used herein refers to a protein lacking a signal sequence or transmembrane domain(s) and if expressed from a nucleotide sequence in a cell, is not attached/associated with the membrane or other non-soluble components.

The term "antimicrobial agent" as used herein refers to any substance that kills microorganisms or inhibits their growth. These may include but are not limited to; antibiotics, antimicrobial peptides, chemotherapeutic agents, antifungals, fungicides, chemical disinfectants such as, but not limited to alcohols, aldehydes and silver, antimicrobial peptides, biocides such as benzyalkonium chloride (BAC), cetylpyridinium chloride (CPC) and chlorhexidine (CHX), or any natural or recombinant agents that demonstrate antimicrobial activity.

The term "coating" refers to the immobilization of soluble proteins to a solid abiotic support, either non-specifically through protein absorption and chemical cross-linking or specifically through recombinant or chemical means including but not limited to; the Staudinger ligation reaction, "click" chemistry, expressed protein ligation, chemoenzymatic methods or through surface modification as practiced in the art.

The phrase "surface susceptible to biofilm" as used herein refers to any biotic or abiotic surface that is prone to bacterial colonization, growth and biofilm formation.

The term "biofouling" refers to the adhesion and accumulation of microorganisms on an abiotic surface through the use of a biofilm.

The term "administering" in the context of administering to an animal is defined as any conventional route for administering an agent to an animal for use, for example, in reducing or preventing biofilm, as is known to one skilled in the art. This may include, for example, administration via the parenteral (i.e. subcutaneous, intradermal, intramuscular, etc.), the mucosal surface route, or through aerosolization, for example, through the use of a nebulizer for administration into the airways of animals. In other embodiments this may include oral administration to the animal. The dose of the agent may vary according to factors such as the health, age, weight and sex of the animal. The dosage regime may be adjusted to provide the optimum dose. One skilled in the art will appreciate that the dosage regime can be determined and/or optimized without undue experimentation.

The term "administering" in the context of a plant is defined as applying to the surface of the plant through spraying. It may also include the insertion of the gene encoding the glycosyl hydrolase into the genome or a plasmid in the plant such that the plant has the ability to produce a functional glycosyl hydrolase that can be secreted.

To "inhibit" or "suppress" or "lower" or "reduce" an activity, such as biofilm formation, is to reduce the function or activity when compared to otherwise same conditions except for a condition or parameter of interest, or alternatively, as compared to another condition or control.

To "disperse", such as biofilms, is to reduce, liberate, or degrade biomass and matrix components thereof that are part of or associated with the biofilm when compared to another condition or control.

The term "animal" as used herein includes all members of the animal kingdom including mammals, suitably humans.

The term "plant" as used herein includes all members of the plant kingdom, such as flowering and bulb-forming plants, and includes whole plants, and plant parts, such as fruit, that are susceptible to the formation of biofilm from plant pathogens.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

The term "treating a biofilm-related infection" as used herein refers to penetrating or dispersing biofilm such that the biofilm biomass is reduced or compromised thereby causing microorganisms to become exposed and vulnerable to attack, either by the immune system or by exogenous agents, either chemical or biological in nature, such as antimicrobials.

The term a "therapeutically effective amount", "effective amount" or a "sufficient amount" of a compound of the present disclosure is a quantity sufficient to, when administered to the animal, including a mammal, for example a human, or plant, effect beneficial or desired results, including clinical results, and, as such, an "effective amount" or synonym thereto depends upon the context in which it is being applied. For example, in the context of inhibiting biofilm formation or dispersing biofilm, it is an amount of the agent sufficient to achieve such an inhibition or dispersal as compared to the response obtained without administration of the agent. The amount of a given agent that will correspond to such an amount will vary depending upon various factors, such as the given agent, the pharmaceutical formulation, the route of administration, the type of condition, disease or disorder, the identity of the animal/plant or host being treated, and the like, but can nevertheless be routinely determined by one skilled in the art. As defined herein, a therapeutically effective amount of an agent may be readily determined by one of ordinary skill by routine methods known in the art.

Moreover, a "treatment" or "prevention" regime with a therapeutically effective amount of an agent may consist of a single administration, or alternatively comprise a series of applications. For example, the agent may be administered at least once a week. However, in another embodiment, the agent may be administered from about one time per week to about once or more daily for a given treatment. The length of the treatment period depends on a variety of factors, such as the severity of the disease, the age of the animal or plant, the concentration and the activity of the agent, or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required.

The term "nucleic acid" as used herein refers to a sequence of nucleotide or nucleoside monomers consisting of naturally occurring bases, sugars, and inter-sugar (backbone) linkages, and includes single stranded and double stranded molecules, RNA and DNA. The term also includes modified or substituted oligomers comprising non-naturally occurring monomers or portions thereof, which function similarly, which are referred to herein as "chemical analogues" and/or "oligonucleotide analogues" such as "peptide nucleic acids". Such modified or substituted nucleic acids may be preferred over naturally occurring forms because of properties such as enhanced cellular uptake, or increased stability in the presence of nucleases. The term also includes chimeric nucleic acids that contain two or more chemically distinct regions. For example, chimeric nucleic acids may contain at least one region of modified nucleotides that confer beneficial properties (e.g. increased nuclease resistance, increased uptake into cells), or two or more nucleic acids of the disclosure may be joined to form a chimeric nucleic acid.

The term "isolated nucleic acid molecule" as used herein refers to a nucleic acid substantially free of cellular material or culture medium when produced by recombinant DNA techniques, or chemical precursors, or other chemicals when chemically synthesized. An isolated nucleic acid is also substantially free of sequences, which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand.

The term "variant" as used herein includes modifications, substitutions, additions, derivatives, analogs, fragments or chemical equivalents of the nucleic acid or amino acid sequences disclosed herein that perform substantially the same function in substantially the same way.

As used herein, the term "glycosyl hydrolase variant thereof" means an amino acid sequence with at least 20%, 25%, 30%, 35%, 40%, 45%, 50%, 55%, 60%, 65%, 70%, 75%, 80%, 85%, 90%, 95% or 99% sequence identity to the amino acid sequence of interest and which functions to inhibit or disperse microbial biofilms. In some embodiments, certain catalytic residues are maintained while other residues are altered. Residues that are particularly relevant for catalytic function include those residues disclosed in the Examples.

As used herein, the term "protein" or "polypeptide" refers to a sequence of amino acid residues encoded by a nucleic acid molecule. Within the context of the present disclosure, a polypeptide of the disclosure may in one embodiment include various structural forms of the primary protein. For example, a polypeptide of the disclosure may be in the form of acidic or basic salts or in neutral form. In addition, individual amino acid residues may be modified by oxidation or reduction.

The proteins and polypeptides of the present disclosure may also include truncations, analogs, homologs and orthologs of the proteins and polypeptides as described herein having substantially the same function as the proteins or polypeptides of the present disclosure, such as the ability to inhibit and/or disperse microbial biofilms and/or prevent biofilm formation.

Analogs of the proteins described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the disclosure with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids, which possess dissimilar charge, size, and/or hydrophobicity characteristics.

Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. Other substitutions might well be possible.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. An optional, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search, which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another optional, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The term "pharmaceutically acceptable" means compatible with the treatment of animals, suitably humans.

The term "a cell" as used herein includes a plurality of cells. Administering a compound to a cell includes in vivo, ex vivo and in vitro treatment.

Methods and Uses:

In one aspect, the present disclosure provides a method of treating or preventing a biofilm-related infection comprising administering at least one soluble microbial protein encoded by an exopolysaccharide biosynthetic operon or functional gene cluster, such as a bacterial or fungal protein, comprising a glycosyl hydrolase domain. Also provided herein is use of at least one soluble microbial protein encoded by an exopolysaccharide biosynthetic operon or functional gene cluster, such as a bacterial or fungal protein, comprising a glycosyl hydrolase domain for treating or preventing a biofilm-related infection. Further provided is use of at least one soluble microbial protein encoded by an exopolysaccharide biosynthetic operon or functional gene cluster, such as a bacterial or fungal protein, comprising a glycosyl hydrolase domain in the manufacture of a medicament for treating or preventing a biofilm-related infection. Even further provided is at least one soluble microbial protein encoded by an exopolysaccharide biosynthetic operon or functional gene cluster, such as a bacterial or fungal protein, comprising a glycosyl hydrolase domain for use in treating or preventing a biofilm-related infection.

The present disclosure also provides a method of treating or preventing a biofilm-related infection comprising administering at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, to an animal or plant in need thereof.

Also provided is use of at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, for treating or preventing a biofilm related infection in an animal or plant in need thereof. Further provided is use of at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, in the preparation of a medicament for treating or preventing a biofilm-related infection in an animal or plant in need thereof. Even further provided is at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, for use in treating or preventing a biofilm-related infection in an animal or plant in need thereof.

In an embodiment, at least two of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be administered or used.

In another embodiment, at least three of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be administered or used.

In yet another embodiment, at least four of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be administered or used.

In a further embodiment, at least five of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be administered or used.

In yet another embodiment, (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be administered or used.

In one embodiment, the soluble protein comprising a PslG GH domain and the soluble protein comprising a PelA GH domain, or orthologs thereof, may be administered or used.

In another embodiment, the soluble protein comprising a PslG GH domain and the soluble protein comprising a BpsB and/or PgaB GH domain, or orthologs thereof, may be administered or used.

In yet another embodiment, the soluble protein comprising a PslG GH domain and the soluble protein comprising a Sph3 GH domain, or orthologs thereof, may be administered or used.

In a further embodiment, the soluble protein comprising a PslG GH domain and the soluble protein comprising an Ega3 GH domain, or orthologs thereof, may be administered or used.

In one embodiment, the soluble protein comprising a PelA GH domain or ortholog thereof and the soluble protein comprising a BpsB and/or PgaB GH domain, or orthologs thereof, may be administered or used.

In yet another embodiment, the soluble protein comprising a PelA GH domain or ortholog thereof and the soluble protein comprising a Sph3 GH domain, or orthologs thereof, may be administered or used.

In a further embodiment, the soluble protein comprising a PelA GH domain or ortholog thereof and the soluble protein comprising an Ega3 GH domain, or orthologs thereof, may be administered or used.

In one embodiment, the soluble protein comprising a BpsB and/or PgaB GH domain and the soluble protein comprising a Sph3 GH domain, or orthologs thereof, may be administered or used.

In another embodiment, the soluble protein comprising a BpsB and/or PgaB GH domain and the soluble protein comprising an Ega3 GH domain, or orthologs thereof, may be administered or used.

The biofilm-related infection may be any microbial infection in the body that has formed a layer of biofilm on the body surface or medical implant or bioprosthetic device. In one embodiment, the biofilm-related infection may be the result of a wound, burn infection or keratitis. In another embodiment, the biofilm-related infection may be a lung infection, wherein the animal has chronic pulmonary disease. In another embodiment, the biofilm-related infection may be a lung infection wherein the animal has invasion aspergillosis. In another embodiment, the biofilm-related infection may be from chronic pulmonary disease.

In an embodiment, the at least one soluble protein comprising a glycosyl hydrolase potentiates neutrophil killing of the microorganism. In a particular embodiment, the soluble protein is a PelA protein disclosed herein.

In another embodiment, the biofilm-related infection may be any microbial infection that has formed a layer of biofilm on the surface of or within a plant or plant part.

In an embodiment, the biofilm-related infection may be caused by any Pel-dependent, Psl-dependent, PNAG-dependent or GAG-dependent biofilm. In one embodiment, the biofilm-related infection may be caused by any microorganism that has the genetic capacity to synthesize the exopolysaccharides, Pel, Psi, PNAG and/or GAG and combinations thereof. These organisms include, but are not limited to; *P. aeruginosa, S. aureus, E. coli, S. epidermidis, Y. pestis, B. pertussis, Burkholderia* spp., *Candida* spp., *Aspergillus* spp, *Acinetobacter* spp., *Trichosporon asahii, Saccharata proteae, Zopfia rhizophila, Phaeosphaeria nodorum, Setosphaeria turcica, Botrytis cinerea, Cryphonectria parasitica, Melanconium* sp., *Verticillium dahlia, Nectria haematococca, Neurospora crassa, Leptosphaeria maculans, Pleomassaria siparia, Cochliobolus heterostrophus, Pyrenophora tritici-repentis, Blumeria graminis, Marssonina brunnea, Sclerotinia sclerotiorum, Taphrina deformans, Cercospora zeae-maydis* and *Fusarium* spp. In another embodiment, the biofilm may be dependent on the secretion of any exopolysaccharide that is able to be degraded by the soluble glycosyl hydrolases disclosed herein.

The soluble proteins disclosed herein provide for dispersion or degradation of the biofilm, providing an opportunity for other anti-microbial agents to access and treat the microbial infection. Accordingly, in another embodiment, the methods and uses for treating or preventing a biofilm-related infection further comprise co-administering an anti-microbial agent, such as an anti-fungal or anti-bacterial agent, to the animal or plant in need thereof. In one embodiment, the anti-microbial agent is an antibiotic.

When used in combination with other agents useful in treating microbial infection, the agents disclosed herein are suitably administered contemporaneously with those other agents. As used herein, "contemporaneous administration" or "coadministration" of two substances to an individual animal or plant means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

In an embodiment, the at least one soluble protein is expressed by a vector and the vector is administered to the animal or plant in need thereof.

In one embodiment, the vector is a lytic phage that is able to invade bacteria of the biofilm.

In one embodiment, the vector is a mycovirus that is able to invade fungal biofilms.

In an embodiment, the methods or uses disclosed herein further comprise administering other soluble proteins that degrade other components of biofilm, such as alginate and/or cellulose.

In yet another aspect, there is provided a method of preventing biofilm formation on an indwelling medical device or implant comprising coating the device with at least one soluble microbial protein encoded by an exopolysaccharide biosynthetic operon or functional gene cluster, such as a bacterial or fungal protein, comprising a glycosyl hydrolase domain.

In an embodiment, there is provided a method of preventing biofilm formation on an indwelling medical device or implant comprising coating the device with at least one of: (i) a soluble protein comprising a PslG glycosyl hydrolase (GH) domain, (ii) a soluble protein comprising a PelA GH domain, (iii) a soluble protein comprising a BpsB GH domain (iv) a soluble protein comprising a PgaB GH domain, (v) a soluble protein comprising a Sph3 GH domain and (vi) a soluble protein comprising an Ega3 GH domain, or orthologs thereof, prior to use in an animal in need thereof. Particular combinations of soluble proteins as described above may be coated on the device or implant.

In an embodiment, at least two of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be coated on the device or implant.

In another embodiment, at least three of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be coated on the device or implant.

In yet another embodiment, at least four of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be coated on the device or implant.

In a further embodiment, at least five of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be coated on the device or implant.

In yet another embodiment, (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be coated on the device or implant.

In another embodiment, the device or implant is further coated with other soluble proteins that degrade other components of biofilm, such as alginate and/or cellulose.

The indwelling medical device or implant may be any device or implant that is inserted into the body of the animal and whose surface would thus be susceptible to biofilm formation. In an embodiment, the indwelling medical device or implant may be a catheter, intravenous tube, prosthetic joint or bioprosthetic.

In an embodiment, the biofilm may be caused by any Pel-dependent, Psl-dependent, PNAG-dependent and/or GAG-dependent biofilm or any combinations thereof. In one embodiment, the biofilm may be caused by any microorganism or group of microorganisms that have the genetic capacity to synthesize the exopolysaccharides, Pel, Psl, PNAG and/or GAG and combinations thereof. These organisms include, but are not limited to; *P. aeruginosa, S. aureus, E. coli, S. epidermidis, Y. pestis, B. pertussis, Burkholderia* spp., *Candida* spp., *Aspergillus* spp., *Acinetobacter* spp. and *Fusarium* spp. In another embodiment, the biofilm may be dependent on the secretion of any exopolysaccharide that is able to be degraded by the soluble glycosyl hydrolases disclosed herein.

In yet another embodiment, the methods disclosed herein further comprise coating an antimicrobial agent on the indwelling medical device or implant. In one embodiment, the antimicrobial agent is an antibiotic. In another embodiment, the antimicrobial agent is an antifungal agent.

In yet another aspect, there is provided a method of treating or preventing biofilm formation on a non-medical surface comprising coating with or applying to the surface at least one soluble microbial protein encoded by an exopolysaccharide biosynthetic operon or functional gene cluster, such as a bacterial or fungal protein, comprising a glycosyl hydrolase domain.

Also provided herein is a method of treating or preventing biofilm formation on a non-medical surface that is susceptible to biofilm formation comprising coating with or applying to the surface at least one of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, prior to use in an animal in need thereof. Particular combinations of soluble proteins as described above may be applied or coated on the non-medical surface.

In an embodiment, at least two of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be applied or coated on the non-medical surface.

In another embodiment, at least three of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be applied or coated on the non-medical surface.

In yet another embodiment, at least four of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be applied or coated on the non-medical surface.

In a further embodiment, at least five of: (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (vi) a soluble protein comprising an Ega3 GH domain, or orthologs thereof, may be applied or coated on the non-medical surface.

In yet another embodiment, (i) a soluble protein comprising a PslG glycosyl hydrolase (GH) domain, (ii) a soluble protein comprising a PelA GH domain, (iii) a soluble protein comprising a BpsB GH domain, (iv) a soluble protein comprising a PgaB GH domain, (v) a soluble protein comprising a Sph3 GH domain and (iv) a soluble protein comprising an Ega3 GH domain, or orthologs thereof, may be applied or coated on the non-medical surface.

In another embodiment, the non-medical surface is further coated with other soluble proteins that degrade other components of biofilm, such as alginate and/or cellulose.

The above methods for coating on non-medical surfaces may be used to prevent or disrupt biofouling. Such abiotic surfaces include, but are not limited to; faucets, drains, pipes, devices related to water filtration and food-contact surfaces related to the manufacturing, preparation and serving of food for the consumption by members of the animal kingdom including mammals, suitably humans.

In an embodiment, the biofilm is caused by microorganisms or group of microorganisms with the genetic capacity to produce one or more of the following exopolysaccharides; Psi, Pel, PNAG and GAG with organisms which include but are not limited to; *P. aeruginosa, S. aureus, E. coli, S. epidermidis, Y. pestis, B. pertussis, Burkoldeira* spp., *Candida* spp., *Aspergillus* spp, *Acinetobacter* spp. and *Fusarium* spp. In another embodiment, the biofilm may be caused by a microorganism or group of microorganisms with the genetic capacity to produce any exopolysaccharide that is able to be degraded by the soluble glycosyl hydrolases disclosed herein.

In yet another embodiment, the methods disclosed herein further comprise coating an antimicrobial agent on the non-medical surface. In one embodiment, the antimicrobial agent is an antibiotic. In another embodiment, the antimicrobial agent is an antifungal agent.

In one embodiment, the soluble protein comprising a PslG GH domain disclosed herein comprises amino acids 31 to 442 of the PslG sequence deposited into GenBank under accession no. AAG05625.1 (or as shown in SEQ ID NO:11) or a glycosyl hydrolase variant thereof.

In one embodiment, the soluble protein comprising a PelA GH domain disclosed herein comprises amino acids 47 to 303 of the PelA sequence deposited into GenBank under accession no. AAG06452.1 (or as shown in SEQ ID NO:12) or amino acids 35-291 of the PelA sequence deposited into GenBank under accession no. AAY92244.2 (or as shown in SEQ ID NO:13) or glycosyl hydrolase variants thereof.

In one embodiment, the soluble protein comprising a PelA GH domain ortholog disclosed herein comprises amino acids 61 to 317 of the RagA sequence deposited into GenBank under accession no. CAQ62201.1 (or as shown in SEQ ID NO:15) or amino acids 23 to 277 of the PelA sequence deposited into GenBank under accession no. ABB32191.1 (or as shown in SEQ ID NO:14) or glycosyl hydrolase variants thereof.

In one embodiment, the soluble protein comprising a BpsB GH domain disclosed herein comprises amino acids 318 to 670 or amino acids 27 to 701 of the BpsB sequence deposited into GenBank under accession no. CAE32265.1 (or as shown in SEQ ID NO:19 or 18, respectively) or glycosyl hydrolase variants thereof.

In one embodiment, the soluble protein comprising a PgaB GH domain disclosed herein comprises amino acids 310 to 672 or amino acids 22 to 672 of the PgaB sequence deposited into GenBank under accession no. AAC74108.1 (or as shown in SEQ ID NO:17 or 16, respectively) or glycosyl hydrolase variants thereof.

In one embodiment, the soluble protein comprising a Sph3 GH domain disclosed herein comprises amino acids 52 to 298 of the Sph3 sequence deposited into GenBank under accession no. EAL92786.1 (or as shown in SEQ ID NO:20) or a glycosyl hydrolase variant thereof.

In an embodiment, the soluble protein comprising a Sph3 GH domain ortholog disclosed herein comprises amino acids 54 to 304 of the $Sph3_{AC}$ sequence from *Aspergillus clavatus* NRRL 1 deposited into GenBank under accession no. EAW09379.1 (or as shown in SEQ ID NO:22) or a glycosyl hydrolase variant thereof.

In an embodiment, the soluble protein comprising a Sph3 GH domain ortholog disclosed herein comprises amino acids 43 to 299 of the Sph3AN sequence from *Aspergillus nidulans* FGSC A4 deposited into GenBank under accession no. EAA63523.1 (or as shown in SEQ ID NO:23) or a glycosyl hydrolase variant thereof.

In one embodiment, the soluble protein comprising an Ega3 GH domain disclosed herein comprises amino acids 46 to 318 of the Ega3 sequence deposited into GenBank under accession no. EAL92787.1 (or as shown in SEQ ID NO:21) or a glycosyl hydrolase variant thereof.

As described further herein, the soluble proteins are referred to using the GenBank accession numbers noted above but are the same as those shown in the Table of Sequences, SEQ ID NOs:11-23 and as noted above.

Devices

The present inventors have demonstrated that pre-coating a plastic surface with the soluble proteins disclosed herein reduces the ability of microbes to form a biofilm layer on the surface.

Accordingly, provided herein is an indwelling medical device or implant coated with at least one soluble microbial protein encoded by an exopolysaccharide biosynthetic operon or functional gene cluster, such as a bacterial or fungal protein, comprising a glycosyl hydrolase domain.

Also provided herein is an indwelling medical device or implant coated with at least one, at least two of, at least three of, at least four of, at least five of, or all of: (i) a soluble protein comprising a PslG glycosyl hydrolase (GH) domain, such as a PslG GH soluble protein or ortholog described herein, (ii) a soluble protein comprising a PelA GH domain, such as a PelA GH soluble protein or ortholog described herein, (iii) a soluble protein comprising a BpsB GH domain, such as a BpsB GH soluble protein or ortholog described herein, (iv) a soluble protein comprising a PgaB GH domain, such as a PgaB GH soluble protein or ortholog described herein, (v) a soluble protein comprising a Sph3 GH domain, such as a Sph3 GH soluble protein or ortholog described herein, and (vi) a soluble protein comprising an Ega3 GH domain, such as a Ega3 GH soluble protein or ortholog described herein, or orthologs thereof. Particular combinations of soluble proteins as described above may be coated on the device or implant.

A person skilled in the art will appreciate that the soluble proteins disclosed herein may be immobilized to solid supports through non-specific protein absorption or chemical cross-linking. Additionally, soluble proteins may be modified through recombinant or chemical means to allow for attachment to solid supports including but not limited to; the Staudinger ligation reaction, "click" chemistry, expressed protein ligation, chemoenzymatic methods or through surface modification as practiced in the art.

A person skilled in the art will appreciate that the soluble proteins disclosed herein may be encapsulated or delivered to the skin or surface wounds using topical delivery methods such as synthetic polymers such as poloxamer, hydrogels of various compositions of matter which include but are not limited to; protein-based hydrogels, polysaccharide-based hydrogels and DNA-based hydrogels. Other delivery methods include nanoparticles, ointments, petroleum jelly and other aqueous solutions compatible with delivery. Additionally, soluble proteins may be modified through recombinant or chemical means to allow for increased stability, penetrability and compatibility with the delivery compound.

In another embodiment, the device or implant is further coated with other soluble proteins that degrade other components of biofilm, such as alginate and/or cellulose.

The indwelling medical device or implant may be any medical device that may be introduced into the body that will have a surface susceptible to biofilm formation. In one embodiment, the indwelling medical device or implant is a catheter or intravenous tube.

In another embodiment, the indwelling medical device or implant is a prosthetic joint or a bioprosthetic, including but not limited to a heart valve.

The biofilm that may be formed on the surface may be caused by any microorganism or group of microorganisms that forms Pel-dependent, Psl-dependent, PNAG-dependent biofilm or GAG-dependent, including without limitation, *P. aeruginosa, S. aureus, E. coli, S. epidermidis, Y. pestis, B. pertussis, Burkholderia* spp., *Candida* spp., *Aspergillus* spp., *Acinetobacter* spp. and *Fusarium* spp. In another embodiment, the biofilm may be caused by build up of any exopolysaccharide produced by a microorganism or group of microorganisms that is able to be degraded by the soluble glycosyl hydrolases disclosed herein.

In yet another embodiment, the indwelling medical device or implant further comprise an antimicrobial agent coated on the device or implant. In one embodiment, the antimicrobial agent is an antibiotic. In another embodiment, the antimicrobial agent is an antifungal agent.

Compositions

Also provided herein is an isolated protein consisting of amino acids 31 to 442 of the PslG sequence deposited into GenBank under accession no. AAG05625.1, an isolated protein consisting of amino acids 47 to 303 of the PelA sequence deposited into GenBank under accession no. AAG06452.1 or amino acids 35-291 of the PelA sequence deposited into GenBank under accession no. AAY92244.2, an isolated protein consisting of amino acids 61 to 317 of the RagA sequence deposited into GenBank under accession no. CAQ62201.1 or amino acids 23 to 277 of the PelA sequence deposited into GenBank under accession no. ABB32191.1, an isolated protein consisting of amino acids 318 to 670 or amino acids 27 to 701 of the BpsB sequence deposited into GenBank under accession no. CAE32265.1, an isolated protein consisting of amino acids 310 to 672 of the PgaB sequence deposited into GenBank under accession no. AAC74108.1, an isolated protein consisting of amino acids 52 to 298 of the Sph3 sequence deposited into GenBank under accession no. EAL92786.1, an isolated protein consisting of amino acids 54 to 304 of the $Sph3_{AC}$ sequence from *Aspergillus clavatus* NRRL 1 deposited into GenBank under accession no. EAW09379.1, an isolated protein consisting of amino acids 43 to 299 of the Sph3AN sequence from *Aspergillus nidulans* FGSC A4 deposited into GenBank under accession no. EAA63523.1, and/or an isolated protein consisting of amino acids 46 to 318 of the Ega3 sequence deposited into GenBank under accession no. EAL92787.1.

In yet another aspect, the present disclosure provides compositions, such as pharmaceutical compositions, comprising at least one, at least two, at least three of, at least four of, at least five of or all six of: (i) a soluble protein comprising a PslG glycosyl hydrolase (GH) domain, such as a PslG GH soluble protein or ortholog described herein, (ii) a soluble protein comprising a PelA GH domain, such as a PelA GH soluble protein or ortholog described herein, (iii) a soluble protein comprising a BpsB GH domain, such as a BpsB GH soluble protein or ortholog described herein, (iv) a soluble protein comprising a PgaB GH domain, such as a PgaB GH soluble protein or ortholog described herein, (v) a soluble protein comprising a Sph3 GH domain, such as a Sph3 GH soluble protein or ortholog described herein, and (vi) a soluble protein comprising an Ega3 GH domain, such as an Ega3 GH soluble protein or ortholog described herein, or orthologs thereof; and a pharmaceutically acceptable carrier. Particular combinations of soluble proteins as described above may be included in the compositions.

The compositions containing the agents can be prepared by known methods for the preparation of pharmaceutically acceptable compositions which can be administered to animals, optionally humans, such that an effective quantity of the active agent is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the agents in association with one or more pharmaceutically acceptable vehicles or diluents, and contained in buffered solutions with a suitable pH and iso-osmotic with the physiological fluids.

In accordance with the methods and uses of the disclosure, the disclosed agents, salts or solvates thereof may be administered to an animal, optionally a human in a variety of forms depending on the selected route of administration, as will be understood by those skilled in the art. The compositions may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

In one embodiment, the pharmaceutically acceptable carrier is a gel, such as Poloxamer.

Compositions suitable for plants containing the agents can be prepared by known methods for the preparation of acceptable compositions which can be administered to plants or plant parts.

The agents may be administered to an animal or plant alone or in combination with pharmaceutically acceptable carriers, as noted above, and/or with other pharmaceutically active agents such as antibiotics, the proportion of which is determined by the solubility and chemical nature of the agents, chosen route of administration and standard pharmaceutical practice.

The dosage of the agents and/or compositions can vary depending on many factors such as the pharmacodynamic properties of the agent, the mode of administration, the age, health and weight of the recipient animal or plant, the nature and extent of the symptoms, the frequency of the treatment and the type of concurrent treatment, if any, and the clearance rate of the compound in the animal or plant to be treated. One of skill in the art can determine the appropriate dosage based on the above factors. The agents may be administered initially in a suitable dosage that may be adjusted as required, depending on the clinical response. For ex vivo treatment of animal cells over a short period, for example for 30 minutes to 1 hour or longer, higher doses of agent may be used than for long term in vivo therapy in animals.

A person skilled in the art will appreciate that the soluble proteins disclosed herein may be prepared in any of several ways, including, without limitation, by using recombinant methods.

Accordingly, nucleic acid molecules encoding the proteins of the disclosure may be incorporated in a known manner into an appropriate expression vector which ensures good expression of the proteins. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the application and regulatory sequences selected on the basis of the host cells to be used for expression, which is operatively linked to the nucleic acid molecule. Operatively linked is intended to mean that the nucleic acid is linked to regulatory sequences in a manner that allows expression of the nucleic acid.

The disclosure therefore contemplates a recombinant expression vector containing a nucleic acid molecule disclosed herein, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the disclosure may also contain a selectable marker gene which facilitates the selection of host cells transformed or transfected with a recombinant molecule of the application. Examples of selectable marker genes are genes encoding a protein such as G418 and hygromycin, which confer resistance to certain drugs, β-galactosidase, chloramphenicol acetyltransferase, firefly luciferase, or an immunoglobulin or portion thereof such as the Fc portion of an immunoglobulin, optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the application and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the disclosure. Prokaryotic cells can be transformed with nucleic acid by, for example, electroporation or calcium chloride-mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the disclosure may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303 (5656): 371-3 (2004)). In addition, a *Pseudomonas*-based expression system such as *P. fluorescens* can be used (US Patent Application Publication No. US 2005/0186666, Schneider, Jane C et al.).

Accordingly, also provided herein is a host cell comprising a nucleic acid molecule of the disclosure.

The nucleic acid molecules encoding the proteins of the disclosure may also be incorporated in a known manner into the genome of a phage that is capable of infecting bacteria found in biofilm. Lytic phages include those which target bacteria which have the genetic capacity to produce one or more of the exopolysaccharides; Psi, Pel, PNAG and GAG. A person skilled in the art will readily identify and use a lytic phage specific to the target bacteria.

The nucleic acid molecules encoding the proteins of the disclosure may also be incorporated in a known manner into the genome of a mycovirus that is capable of infecting the fungus found in GAG biofilm. A person skilled in the art will readily identify and use a mycovirus specific to the target bacteria.

Accordingly, provided herein is a lytic phage or mycovirus encoding (i) a soluble protein comprising a PslG glycosyl hydrolase (GH) domain, such as a PslG GH soluble protein or ortholog described herein, (ii) a soluble protein comprising a PelA GH domain, such as a PelA GH soluble protein or ortholog described herein, (iii) a soluble protein comprising a BpsB GH domain, such as a BpsB GH soluble protein or ortholog described herein, (iv) a soluble protein comprising a PgaB GH domain, such as a PgaB GH soluble protein or ortholog described herein, (v) a soluble protein comprising a Sph3 GH domain, such as a Sph3 GH soluble protein or ortholog described herein, or (vi) a soluble protein comprising an Ega3 GH domain, such as an Ega3 GH soluble protein or ortholog described herein, or orthologs thereof, or combinations thereof.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1—PslG$_{31-442}$ from *P. aeruginosa* PAO1 is a Soluble Protein

Method:

The amino acid sequence of pslG from *P. aeruginosa* PAO1 was deposited into GenBank under accession no. AAG05625.1 and released in August 2000 (Stover et al 2000). The TMHMM server v2.0 (Krogh et al 2001) indicates that PslG from *Pseudomonas aeruginosa* PAO1 possesses a transmembrane helix from residues 5-24 that tethers the periplasmic catalytic domain to the cytoplasmic membrane. To obtain a soluble protein construct from the pslG gene from *P. aeruginosa* genomic DNA was amplified by PCR using the primers GGG CATATGGAGATCCAGGTACTGAAG (SEQ ID NO:1) and GGGAAGCTTTCACTCCCAGACCAGCA (SEQ ID NO:2).

*E. coli* BL21 (DE3) cells were transformed with the protein expression vector and grown in 1 L Luria-Bertani (LB) broth containing 50 µg/mL kanamycin at 37° C. When the OD$_{600}$ of the cell culture reached 0.4-0.5, the temperature was reduced to 18° C. for 20-30 min and protein expression was induced by the addition of isopropyl β-D-1-thiogalactopyranoside (IPTG) to a final concentration of 1 mM. The cultures were incubated post-induction overnight at 18° C. with shaking then harvested by centrifugation at 5,000×g for 20 min at 4° C.

Cell pellets were resuspended in 40 mL of buffer A (20 mM imidazole, 50 mM Tris pH 7.5, 300 mM NaCl, 2% (v/v) glycerol and one SIGMAFAST™ Protease Inhibitor Tablet) and the cells were lysed by at least three passes through an Emulsiflex C3 at 100 MPa (Avestin Inc). The resulting cell debris was separated from soluble protein by centrifugation at 35,000×g for 30 min. The supernatant was applied to a 5 mL Ni-NTA Superflow gravity column (Qiagen) pre-equilibrated with buffer A. The column was washed with 3 column volumes (CV) of buffer A and the expressed protein was eluted with buffer A supplemented with 250 mM imidazole. The eluted fractions were pooled and dialyzed against 4 L of buffer B (50 mM Tris pH 7.5, 150 mM NaCl 2% (v/v) glycerol) overnight at 4° C. The His-tag was removed by incubating the protein at 25° C. for 3 h with one unit of thrombin (Novagen) per 4 mg protein. Untagged protein was separated from tagged protein by purification on a 5 mL Ni-NTA Superflow gravity column pre-equilibrated with buffer A. The untagged protein was collected and buffer exchanged into buffer B by size-exclusion chromatography using a HiLoad 16/60 Superdex 200 gel-filtration column (GE Healthcare).

Result:

A soluble PslG construct encompassing residues 31-442 was expressed and purified. The expressed protein produces ~7 mg per liter of bacterial culture with a molecular weight of 46.9 kDa (FIG. 8). The purity of protein was judged to be >95% by SDS-PAGE and the protein could be concentrated to 8-10 mg/mL and stored at 4° C. for more than one month without precipitation or degradation.

Example 2—PslG$_{31-442}$ is a Two-Domain Protein with Distinct Active Site Groove Method:

Initial crystallization trials were performed with 8 mg/mL PslG$_{31}$-442 using a Gryphon robot (Art Robbins) with 96-well Art Robbins Instruments Intelli-Plates® (Hampton Research) and the MCSG1-4 sparse-matrix screen from Microlytic. Protein (1 µL) was mixed with precipitant in a 1:1 ratio and equilibrated against 60 µL of precipitant using the sitting-drop vapour diffusion method at 20° C. Optimal crystals were grown in 48-well VDX plates (Hampton Research) using 1 µL protein with equal volume of precipitant (1 mM CdCl$_2$, 0.1 M HEPES pH 7.0 and 5% (w/v) PEG3350) and equilibrated against 130 µL precipitant at 20° C. PslG$_{31-442}$ crystals were cryoprotected for 10 s in precipitant solution supplemented with 25% (v/v) ethylene glycol prior to vitrification in liquid nitrogen. Diffraction data were collected at 100 K with a wavelength of 1.075 Å on beamline X29, National Synchrotron Light Source (NSLS). A 0.16 mm collimator was used to collect a high redundancy, 360° dataset with a total of 720 images with 0.5° oscillation on an ADSC Quantum-315 detector with a 250 mm crystal-to-detector distance and an exposure time of 0.3 s per image. The beam was attenuated and 90 images with 2° oscillation were collected over 180°. The combined data were integrated, reduced and scaled using HKL2000 (Otwinowski & Minor 1997). For $PslG_{31-442}$ Autosolve (Terwilliger & Berendzen 1999) was used to generate experimental phases using the cadmium single wavelength dispersion (SAD) technique. A total of four cadmium-binding sites were found and subsequently used to generate a density-modified map. The resulting electron density of each map was of high quality and enabled PHENIX Auto-Build to build >95% of the protein. The remaining residues were built manually in COOT (Adams et al 2010, Emsley & Cowtan 2004). Refinement was carried out using PHENIX.REFINE (Afonine et al 2010). TLS groups were added to the refinement in PHENIX through the use of the TLSMD server (Painter & Merritt 2006). Structure figures were generated using the PyMOL molecular graphics system (DeLano Scientific) (Dolinsky et al 2007).

Result:

$PslG_{31-442}$ crystallized in the presence of divalent metal ions including: Ni, Cu, Co, Zn and Cd and diffraction data were collected to 2.0 Å on a crystal grown in the presence of 1 mM $CdCl_2$. The protein bound four cadmium ions, allowing the structure to be solved using the cadmium SAD technique. Refinement produced a final model with good geometry and R factors. PslG crystallized in space-group $P4_12_12$ with one protomer in the asymmetric unit. This is consistent with a calibrated analytical size exclusion column that indicates that PslG is a monomer in solution. The enzyme contains two domains: a TIM-barrel motif and a β-sandwich domain that is composed of one β-strand from the N-terminus and several β-strands from the C-terminal end of the protein (FIG. 9A). The TIM-barrel fold is the most common enzyme fold in the Protein Data Bank (PDB) of known protein structures. It is estimated that 10% of all known enzymes contain this fold (Wierenga 2001). The putative active site is located in the TIM-barrel domain and runs 40 Å equatorially across the domain (FIG. 9B). Molecular docking simulations using PatchDock (Schneidman-Duhovny et al 2005) of the Psi polysaccharide suggest that this groove is theoretically able to accommodate between 12-15 sugar units. Consistent with other members of the GH39 family, attempts to isolate the TIM-barrel domain alone were unsuccessful (St John et al 2010). This supports the hypothesis that the β-sandwich is critical for proper protein folding and/or stability of the protein.

Comparison of the amino acid sequence and crystal structure of PslG with other GH39 members suggests that two acidic residues, Glu-165 and Glu-276 are highly conserved. Structural alignment using DaliLite (Holm et al 2008) indicates that Glu-165 and Glu-276 are located in the middle of the putative active site groove, and at equivalent positions to other GH39 family members. Previous characterization of XynB, a GH39 member, suggests that Glu-165 is the acid/base while Glu-276 would function as the nucleophile in the reaction (Nieman et al 2003, Vocadlo et al 1998). The amino acids that line the groove are not well conserved in distantly related homologs. Many homologs exhibit activity towards the polysaccharide xylan, which is distinct from Psl. The lack of conservation in the active site suggests that homologs have been evolutionary selected to bind a specific polymer and would not be able to bind and catalyze the hydrolysis of Psl.

Example 3—$PslG_{31-442}$ can Prevent Biofilm Formation in Static Culture

Method:

Psl-arabinose inducible *P. aeruginosa* PAO1 pBADpsl was grown at 37° C. overnight with shaking at 200 rpm. The culture was diluted 1:100 in LB and arabinose was added to a final concentration of 0.5% (w/v) to induce Psl biosynthesis. 95 μL of diluted culture was added to sterile 96-well polystyrene microtiter plates (Thermo Scientific Cat No. 243656) and varying concentrations of $PelA_{47-303}$ or $PslG_{31-442}$ (1 nM-10 μM) were added in 5 μL aliquots to give a final volume of 100 μL. The next day fresh cultures were prepared from the overnight culture using a 1:100 dilution. 95 μL of diluted culture was added to a sterile 96-well polystyrene round bottom microtiter plate and varying concentrations of $PslG_{31-442}$ (2 nM-5 μM) were added in 5 μL aliquots to give a final volume of 100 μL. The cultures were incubated statically for 24 h at 26° C. to allow for biofilm formation. To eliminate edge-effects, ~200 μL of sterile water was placed in all outside wells and the plate was sealed with parafilm. After incubation, non-adherent cells and media were removed by thoroughly washing the plate with deionized water. The wells were stained with 150 μL of 0.1% (w/v) crystal violet for 10 min followed by rinsing with water. The remaining dye was solubilized by addition of 200 μL of 95% (v/v) ethanol and left for 10 min after which time the absorbance was measured at 595 nm using a SpectraMax M2 from Molecular Devices (Sunnyvale, Calif.). The amount of biofilm is proportional to the absorbance from staining with crystal violet (Merritt et al 2005). All reactions were completed in triplicates and purified $PelA_{47-303}$ and the buffer B were added as negative controls. The addition of 2.5 mg/mL of kanamycin to culture prior to biofilm formation was used as positive control as no cell growth occurs.

Result:

In the *P. aeruginosa* PAO1 pBADpsl which produces significantly more Psl than the clinical PAO1 strain, addition of $PslG_{31-442}$ prevented biofilm formation at 50 nM and had a $EC_{50}$ of 4.1±1.1 nM (FIG. 10). To examine whether the effect was the direct result of PslG activity a double catalytic variant $PslG_{31-442}$ E165Q/E276Q was constructed and tested. Addition of this resulted in a >100-fold increase in the $EC_{50}$ in the pBADpsl inducible strain (FIG. 10). Enzyme concentrations in excess of 10 μM, prevented Psl-dependent biofilm formation. The addition of $PelA_{47-303}$, another putative glycosyl hydrolase, did not inhibit Psl biofilm formation suggesting that biofilm inhibition is protein specific. In addition, 10 μM of $PslG_{31-442}$ did not prevent PAO1 growth suggesting that the loss of the biofilm is not due to perturbations in bacterial growth. Without wishing to be bound by theory, the enzyme variants may remain capable of binding the polysaccharide, thereby reducing the ability of the bacteria to adhere to the abiotic plate.

Example 4—$PslG_{31-442}$ can Disperse Pre-Formed Psl Biofilms

Method:

Bacterial cultures expressing Psl were inoculated as stated above and were grown at 37° C. overnight with shaking at 200 rpm. All cultures were diluted in 1:100 in LB and arabinose was added to a final concentration of 0.5% (w/v) to induce Psl biosynthesis. Media containing the Psl-producing cultures were supplemented with 200 μg/mL ampicillin and 100 μg/mL kanamycin. The cultures were incubated statically for 24 h at 26° C. to allow for biofilm formation. After incubation non-adherent cells and media were removed by washing the plate with deionized water three times. The wells were filled with 95 μL of 100 mM sodium HEPES buffer pH 7.0 followed by 5 μL of varying concentrations of each hydrolytic enzyme (2 nM-5 μM). Reactions were allowed to proceed for up to 60 min at 25° C. on a rotating nutator at which time, the reaction was quenched by washing the plates with deionized water. The wells were stained with 200 μL of 0.1% (w/v) crystal violet for 10 min, and washed with water three times. Crystal violet dye from Psi cultures was solubilized in 100 μL of 95% ethanol for 10 min with rotation, after which time the absorbance was measured at 595 nm using a SpectraMax M2 from Molecular Devices (Sunnyvale, Calif.). The amount of biofilm is proportional to the absorbance from staining with crystal violet (Merritt et al 2005). All reactions were completed in at least triplicate and 100 mM sodium HEPES buffer pH 7.0 was used as an untreated control. The addition of 2.5 mg/mL kanamycin to culture prior to biofilm formation was used as a positive control as no cell growth occurs.

Result:

The addition of 86 nM of $PslG_{31-442}$ was able to disperse a biofilm in 35 minutes (FIG. 11A). This suggests that very little protein is required to disperse these biofilms under the conditions tested. When $PslG_{31-442}$ E165Q/E276Q double catalytic variant was added in 100-fold excess compared to the wild-type enzyme (5 μM), no significant difference was observed compared to that of the untreated biofilm (FIG. 11B). This suggests that these residues are critical in catalysis. It also indicates that biofilm inhibition is not a true indicator of catalytic activity. The addition of the hydrolase domain of $PelA_{47-303}$ did not result in the loss of the Psl-dependent biofilm suggesting that dispersion is protein specific.

Example 5—$PelA_{47-303}$ from P. aeruginosa PAO1 and its Orthologs $RagA_{61-317}$ and $GmetPelA_{23-277}$ are Soluble Proteins with High Yield Method:

The protein sequence of pelA from P. aeruginosa PAO1 was deposited into GenBank under accession no. AAG06452.1 and released in August 2000 (Stover et al 2000). The PRED-TAT server (Bagos et al 2010) indicates that PelA from Pseudomonas aeruginosa PAO1 possesses a TAT signal sequence from residues 1-45, allowing the protein to be translocated from the cytosol to the periplasm in a folded state. To obtain a soluble protein construct the pelA47-303, the gene (residues 47-303) was amplified from the genomic DNA of P. aeruginosa POA1 by PCR using the primers CTGCATATGGGCGGGCCGTCCAGCGTGGCG (SEQ ID NO:3) and TTT CTCGAGTCACGGTTGCACCTCGACGTC (SEQ ID NO:4). Constructs encoding residues 61-317 of RagA from Ralstonia solanacearum were isolated using primers GCG CATATGGCGGACGCACCGAACATTGCC (SEQ ID NO:5) and GGGAAGCTTTCACG GCAGCACCTCGA TGCGCC (SEQ ID NO:6), and residues 23-277 of PelA from Geobacter metallireducens using the primers GGG CATATGCACCTCCTTTAAGCGTGGCCTTG (SEQ ID NO:7) and GCGAAGCTTTCAC GGCATAACCTCCACGCTCCC (SEQ ID NO:8) to remove the signal sequence for protein expression in the cytosol. Introduced NdeI, HindIII and XhoI restriction sites are underlined and each gene was ligated into the pET28a (Novagen) expression vector encoding an N-terminal His-tag. Protein expression of $PelA_{47-303}$ and its orthologs was the same as described in for $PslG_{31-442}$ in Example 1.

Cell pellets were resuspended in 40 mL of buffer C (20 mM imidazole, 50 mM Tris pH 8.0, 300 mM NaCl, 10% (v/v) glycerol and one protease tablet (Simga) and the cells were lysed by at least three passes through an Emulsiflex C3 at 100 MPa (Avestin Inc). The resulting cell debris was separated from soluble protein by centrifugation at 35,000×g for 30 min. The supernatant was applied to a 5 mL Ni-NTA Superflow gravity column (Qiagen) pre-equilibrated with buffer C. The column was washed with 3 column volumes of buffer A and the expressed protein was eluted with buffer A supplemented with 250 mM imidazole. The eluted fractions were pooled and dialyzed against 4 L of buffer D (50 mM Tris pH 8.0, 150 mM NaCl, 10% (v/v) glycerol) overnight at 4° C. Expression of the selenium-methionine derivative of $PelA_{47-303}$ in minimal medium was carried out using B834 Met⁻ E. coli cells (Novagen) as described previously (Lee et al 2001). Purification of (SeMet)-labeled $PelA_{47-303}$ and variants was completed as described for the wild-type enzyme.

Result:

A $PelA_{47-303}$ construct encompassing residues 47-303 was expressed and purified. The expressed protein produces ~50 mg per liter of bacterial culture with a molecular weight of 28.2 kDa (FIG. 12). The purity of protein was judged to be >95% by SDS-PAGE and the protein could be concentrated to 8-10 mg/mL and stored at 4° C. for more than one month without precipitation or degradation. In comparison, a soluble, full-length construct $PelA_{47-948}$, encompassing amino acid residues 47 to 948 yields only ~1 mg/L of bacterial culture (Colvin et al 2013).

Example 6—$PelA_{47-303}$ has a $\beta_8/\alpha_7$ TIM-Barrel Structure

Method:

Purified $PelA_{47-303}$ was concentrated to 20 mg/mL and screened using commercially available crystallization screens (Microlytic). Native crystals were set up and grown using the popular hanging-drop vapor diffusion method. Crystals were optimized using a 1:2 protein:well-solution ratio and crystallized in the solution screen composed of 25% (w/v) PEG MME 5K and Bis-Tris pH 7.5 at 20° C. Selenomethionine (SeMet)-labeled $PelA_{47-303}$ was set up in the same fashion and crystallized in a similar screen condition except this condition contained a slightly higher PEG concentration (26% (v/v)). Crystallization solution supplemented with 15% (v/v) ethylene glycol was used to cryoprotect crystals prior to vitrification in liquid nitrogen. Crystals were sent to NSLS for data collection on beamline X29. The selenium sites in $PelA_{47-303}$ were used for selenium SAD phasing. All model building and refinement was completed as described in Example 2.

Result:

$PelA_{47-303}$ from P. aeruginosa was expressed, purified and crystallized. The final protein sample was purified to homogeneity as revealed by SDS-PAGE analysis and produced high yields of ~40 mg of protein from 1 L Luria-Bretani broth. Diffraction data were collected from the native and SeMet protein crystals to 1.5 Å and 1.9 Å, respectively. The structure was solved using the SAD technique and refined to a final resolution of 1.5 Å with good refinement statistics. $PelA_{47-303}$ crystallized in the orthorhombic space group $P2_12_12$ with one protomer in the asymmetric unit. The structure indicates that $PelA_{47-303}$ has a TIM-barrel-like fold with a total of 12 β-sheets and nine α-helices (FIGS. 13A-13C). The putative active site is located in the TIM-barrel domain and is composed of a deep electronegative groove that runs equatorially across the domain (FIGS. 14A-14B). The electronegativity of this groove suggests that Pel is not negatively charged as previously suggested (Colvin et al 2011). Molecular docking simulations using PatchDock (Schneidman-Duhovny et al 2005) of a polymer of glucosamine residues suggest that this groove is theoretically able to accommodate at least 8 sugar units.

The CAZymes Analysis Toolkit (CAT) (Park et al 2010) suggests that the hydrolase domain (residues 47-303) belongs to GH family 114. Of significant importance is the high degree of amino acid conservation in the putative catalytic groove. While the catalytic residues are currently unknown, there are several highly conserved acidic residues that could function as the nucleophile and catalytic acid/base in the reaction (FIGS. 14A-14B).

Example 7—$PelA_{47-303}$ and Orthologs can Prevent Pel Biofilm Formation in Static Culture Method:
The methodology to examine the inhibition of Pel biofilm formation is identical to that previously described in Example 3 for Psl biofilms with the exception that the strain used is *P. aeruginosa* PAO1 ΔwspFΔpslpBADpel. The chemical composition of Pel is currently unknown.
Result:
An ex vivo assay was employed to examine whether exogenously added PelA prior to biofilm formation could prevent Pel polysaccharide biofilm formation. A Pel overproducing strain, which is unable to produce the Psl polysaccharide (PAO1ΔwspFΔpsl$P_{BAD}$pel) was utilized for all experiments. This strain allows for inducible over expression of the Pel polysaccharide upon addition of arabinose to the culture media. The addition of 500 nM of $PelA_{47-303}$ from *P. aeruginosa* POA1 prevented the formation of Pel-dependent biofilms. In comparison, two putative catalytic variants, D160A and E218A were unable to prevent biofilm formation at this concentration (FIG. 15). The addition of $PelA_{35-291}$ from *P. protogens* Pf-5 prevented biofilm formation at ≥70 nM and had an $EC_{50}$ of 69.3±1.2 nM (FIG. 16). The addition of $PslG_{31-442}$, another putative glycosyl hydrolase, did not inhibit Pel biofilm formation suggesting that biofilm inhibition is protein specific. Without wishing to be bound by theory, the enzyme variants may remain capable of binding the polysaccharide, thereby reducing the ability of the bacteria to adhere to the abiotic plate.

Example 8—$PelA_{47-303}$ and its Orthologs can Disperse Pre-Formed Pel Biofilms Method:
The methodology to generate pre-formed Pel biofilms is identical to that of Psl biofilms, described in Example 4 with the exception that the strain used is *P. aeruginosa* PAO1 ΔwspFΔpslpBADpel.
Result:
$PelA_{47-303}$ and the two putative catalytic variants D160A and E218A were incubated at two concentrations; 1.14 mg/mL (38 μM) and 0.57 mg/mL (19 μM). After incubation for 2 h, $PelA_{47-303}$ had successfully dispersed the Pel biofilm while the E218A variant retained a similar level of biofilm as a buffer control. The D160A variant retained ~50% of the biofilm level as the buffer control (FIG. 17A). This suggests that amino acids D160 and E218 are important for catalysis.

A similar experiment was completed with $PelA_{35-291}$ from *P. protogens* Pf-5 which revealed that 1 μM of the enzyme was able to disperse the biofilm in as little as 30 min and that a 10-fold dilution was able to disperse nearly all the biofilm in 1 h (FIG. 17B). This suggests that both wild-type hydrolase domains are catalytically active and can efficiently be added to disperse biofilms.

Figure 18A:
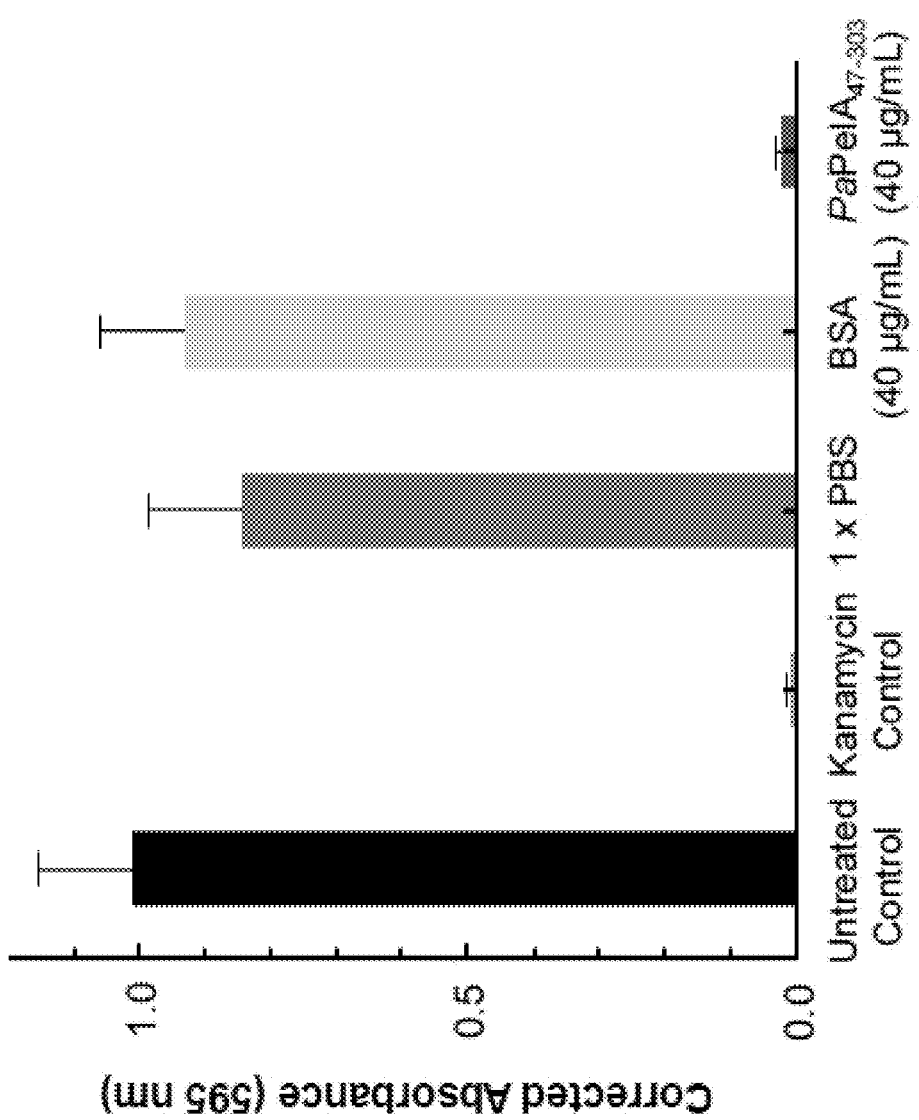
Figures 18B, 18C, 18D:
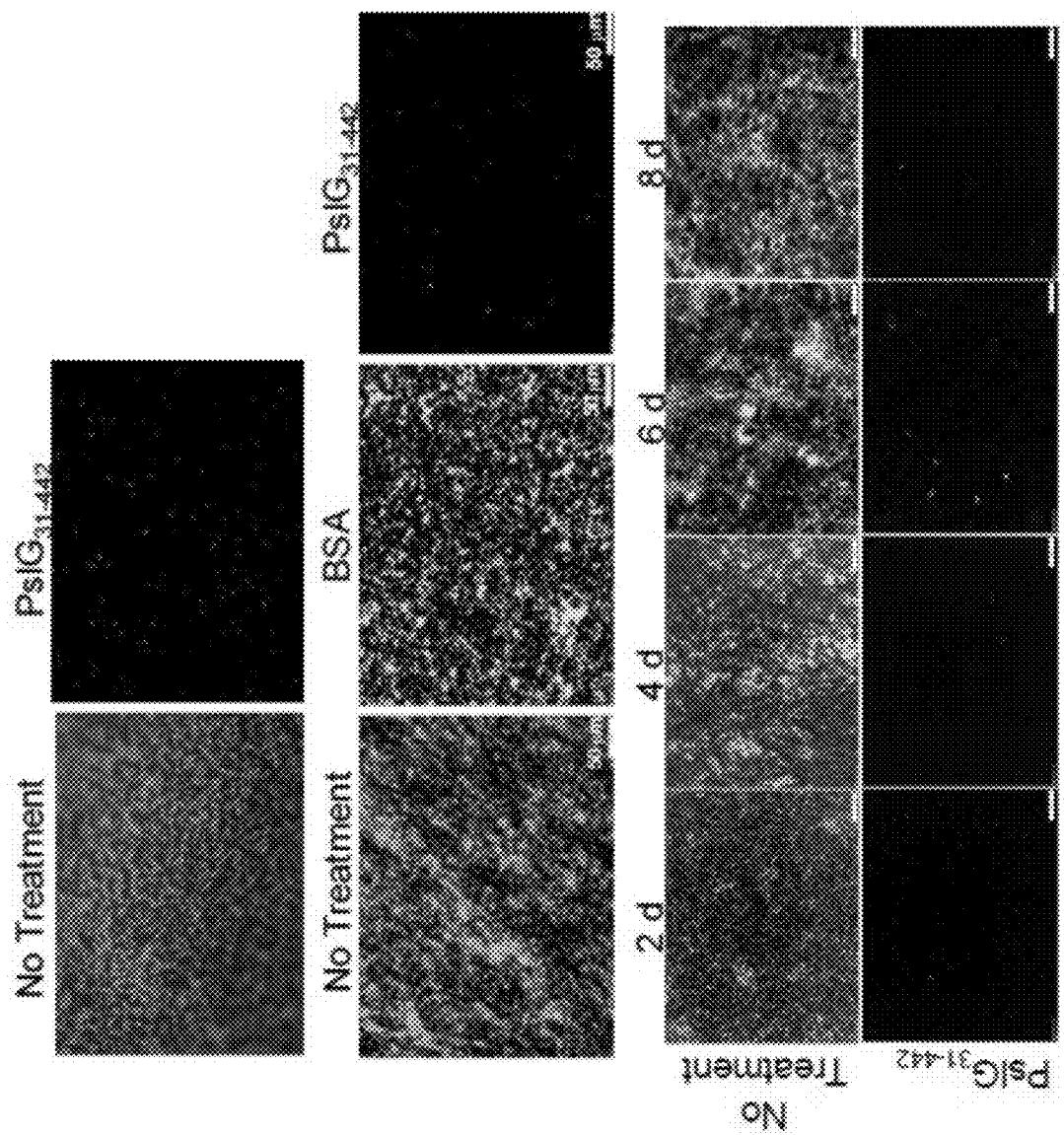

Example 9—Hydrolytic Enzymes can be Pre-Coated to Plastic to Prevent Biofilm Formation Method:
Sterile 96-well polystyrene plates were pre-coated by soaking 100 μL of 1×PBS (pH 7.4) containing 40 μg/mL of $PelA_{47-303}$ or $PslG_{31-442}$ in each well for 12 h at 4° C. The enzyme solution was removed and the wells were washed by the addition of 100 μL of 1×PBS (pH 7.4) for 5 min prior to its removal. The plates were dried at 37° C. for 1 h prior to use. Bovine Serum Albumin (BSA) at a final concentration of 40 μg/mL was used as a control. The next day, plates were inoculated with a 1:100 dilution of *P. aeruginosa* Psi or Pel arabinose inducible cultures. Immobilization of $PslG_{31-442}$ or BSA by either adsorption or cross-linking was performed on flat glass slides that are uniformly thin (0.17-0.25 mm) and corrosion-resistant. The glass surface was first activated by immersion in piranha solution ($H_2SO_4$: $H_2O_2$, 3:1) for 30 min to remove any organic matter residuals and hydroxylate the surface, then rinsed several times with double distilled water to remove any chemical residuals. For immobilization by chemical cross-linking, the surface was functionalized with amine ($NH_2$) groups by silanization, in which the glass cover was immersed in 3-aminopropyltrimethoxysilane (APTMS) solution (0.05 g/mL in 80% (v/v) ethanol) for 2 h at room temperature. The surface was washed with 80% (v/v) ethanol three times to remove unreacted APTMS. $PslG_{31-442}$ was linked onto amino functionalized glass surface through a molecular coupling agent, glutaraldehyde, by immersion of the surface in 4% glutaraldehyde in PBS buffer solution (pH 7.2) for 2 h under gentle stirring and room temperature conditions. The mixture was then rinsed 3 times with 80% ethanol to remove unreacted glutaraldehyde. Activated or modified glass ($NH_2$— glutaraldehyde) was immersed in an enzyme solution (80 μg/mL) and incubated overnight at 4° C. Finally, the surface was washed with PBS buffer several times to remove the unbound enzyme. The next day, plates were inoculated with a 1:100 dilution of *P. aeruginosa* Psl or Pel arabinose inducible cultures. The cultures were grown statically for a duration of at least 20 h after which time biofilm formation was measured using the crystal violet method described previously in Example 4 or SYTOX green to visualize bacteria via confocal microscopy.
Results:
Pre-coating wells with $PelA_{47-303}$ completely abrogated biofilm under the conditions tested (FIG. 18A). Additionally, BSA treated wells did not reduce the biofilm suggesting that coating with $PelA_{47-303}$ specifically target and inhibit *P. aeruginosa* biofilm formation. $PslG_{31-442}$ was also able to adsorb to plastic as enzyme treatment prevented cell and biofilm attachment as visualized using confocal microscopy (FIG. 18B). $PslG_{31-442}$ could also be chemically cross-linked to glass using glutaraldehyde and this treatment also prevented cell attachment and biofilm formation (FIG. 18C). Treatment with BSA demonstrated that a non-specific protein coating is insufficient to prevent biofilm formation. Glass surfaces that were covalently linked with $PslG_{31-442}$ were able to prevent biofilm formation for at least 8 days (FIG. 18D). Without wishing to be bound by theory, it is likely that other enzyme orthologs are capable of adsorbing to plastics and may be used to prevent bacterial attachment and biofilm formation.

Example 10—BpsB and its Isolated C-Terminal Domain are Stable and Soluble Proteins Method:

The protein sequence of bpsB from *B. bronchiseptica* RB50 was deposited into GenBank under accession no. CAE32265.1 and released in July 2008. The SignalP server v4.0 (Petersen et al 2011) indicates that BpsB from *B. bronchiseptica* RB50 possesses a periplasmic signal sequence from residues 1-26. For soluble protein generation, the bpsB gene containing residues 27-701 was amplified from genomic DNA by inverse PCR with flanking NdeI and HindIII endonuclease restriction sites, then digested and ligated into the pET28a (Novagen) expression vector encoding an N-terminal hexahistidine-tag. The resulting plasmid, pET28-BpsB$_{27-701}$ was then used as a template for cloning the BpsB C-terminal domain, residues 318-670, using the same procedure as above to yield plasmid pET28-BpsB$_{318-670}$. Protein expression of BpsB was the same as described in for PslG$_{31-442}$.

Active site alanine variants were generated using the QuikChange site-directed mutagenesis kit according to the manufacturer's instructions, and expressed and purified as for BpsB mentioned previously.

Cell pellets were resuspended in 40 mL of buffer E (50 mM HEPES pH 8.0, 300 mM NaCl, 10 mM imidazole, 5% (v/v) glycerol and one SIGMAFAST™ Protease Inhibitor Tablet). The cells were lysed by three passes through an Emulsiflex C3 at 100 MPa (Avestin Inc). Insoluble and cell debris was clarified from soluble protein by centrifugation at 30,000×g for 30 min. The supernatant was applied to 4 mL of Ni-NTA Superflow resin (Qiagen) packed into a 30 mL gravity column pre-equilibrated with buffer F (20 mM HEPES pH 8.0, 300 mM NaCl, 10 mM imidazole). The column was washed with 10 column volumes (CV) of buffer F and the expressed protein was eluted with buffer B supplemented with 200 mM imidazole. The eluted fractions were pooled and dialyzed against 1 L of buffer G (20 mM HEPES pH 8.0, 300 mM NaCl) overnight at 4° C. The His-tag was removed by incubating the protein at 25° C. for 2 h with one unit of thrombin (Novagen) per 4 mg protein. Untagged protein was separated from tagged protein by a second round of Ni-NTA purification with the flow-through and wash fractions being collected, concentrated, and applied to a HiLoad 16/60 Superdex 200 gel-filtration column (GE Healthcare) equilibrated in buffer H (20 mM HEPES pH 7.5, 150 mM NaCl).

Result:

A full-length BpsB encompassing residues 27-701 (BpsB$_{27-701}$) and a C-terminal hydrolase domain construct encompassing residues 318-670 (BpsB$_{318-670}$) were expressed and purified. BpsB$_{27-701}$ protein produces ~30 mg per liter of bacterial culture with a molecular weight of 78.5 kDa (FIG. 19), while BpsB$_{318-670}$ produces ~50 mg per liter of bacterial culture with a molecular weight of 42.3 kDa. The purity of each protein was judged to be >95% by SDS-PAGE and the proteins could be concentrated to 8-10 mg/mL and stored at 4° C. for more than one month without precipitation or degradation.

Example 11—BpsB$_{318-670}$ Adopts a (β/α)$_8$ Barrel with a Distinct Electronegative Groove Method:

Purified BpsB$_{318-670}$ was concentrated to 10 mg/mL and screened for crystallization conditions at 20° C. using hanging-drop vapor diffusion in 48-well VDX plates (Hampton Research) and the MCSG 1-4 sparse matrix suites (Microlytic). An initial crystallization hit was obtained in condition #77 from the MCSG-1 suite. Optimized crystals were grown using 8.6 mg/mL BpsB$_{318-670}$ with a 3 μL drop with equal amounts of protein and precipitant equilibrated against 250 μL precipitant solution (0.1 M bis(2-hydroxyethyl)aminotris(hydroxymethyl) methane (BIS-TRIS) pH 6.9, and 1.7 M ammonium sulfate). BpsB$_{318-670}$ crystals were cryoprotected for 10 s in precipitant solution supplemented with 25% (v/v) ethylene glycol prior to vitrification in liquid nitrogen. Diffraction data were collected at 100 K with a wavelength of 1.075 Å on beam line X29, at NSLS. A 0.16 mm collimator was used to collect a 360° dataset with 1.0° oscillations on an ADSC Quantum-315r detector with a 220 mm crystal-to-detector distance and an exposure time of 0.4 s per image. The beam was attenuated and 90 images with a 2° oscillation were collected over 180°. AutoMR was used to obtain phases information through molecular replacement with PgaB residues 310-646 (PDB 4F9D).

Result:

BpsB$_{318-670}$ crystallized in the space-group P21 and diffraction data were collected to 1.76 Å resolution. The structure was solved using molecular replacement and refinement produced a final model containing two molecules in the asymmetric unit with good geometry and R factors. Analytical size exclusion chromatography indicates that BpsB$_{318-670}$ is a monomer in solution. BpsB$_{318-670}$ adopts a (β/α)$_8$ barrel fold common to glycosyl hydrolases (FIG. 20), and is the most common enzyme fold in the Protein Data Bank (PDB) of known protein structures. The putative active site is located in a groove at the top of the (β/α)$_8$ barrel and is 41 Å long and 11 Å wide (FIG. 20). Molecular docking simulations using PatchDock (Schneidman-Duhovny et al 2005) of BpsB$_{318-670}$ and PNAG suggest that this groove is theoretically able to accommodate between 10-12 sugar units.

Comparison of the amino acid sequence and crystal structure of BpsB$_{318-670}$ with other GH13, GH18, and GH20 members suggests that it does not contain the canonical catalytic sequence motifs. Structural alignment using Dali-Lite (Holm et al 2008) indicate that His473 and Asp474 are located in the middle of the putative active site groove, and at equivalent positions to the GH13, GH18, and GH20 family members catalytic Asp and Glu residues. This suggests BpsB and PgaB may exhibit a novel mechanism for dPNAG hydrolysis, or belongs to a unique GH family. Variants that maintain ability to cut the exopolysaccharide will likely require such residues to be maintained. Alternatively, such residues could be further optimized and a person skilled in the art would readily be able to determine if activity is increased or decreased upon mutation.

Example 12—the C-Terminal Domain of PgaB is a Stable Soluble Protein

Method:

The plasmid pET28-PgaB$_{22-672}$ (Little et al 2012a, Little et al 2012b) was used as a template and pgaB specific primers were designed to subclone residues 310-672 into a pET28a expression vector (Novagen) using inverse PCR with an NdeI and XhoI site flanking the gene fragment. The resulting plasmid pET28-PgaB$_{310-672}$ encodes the C-terminal domain of PgaB with a thrombin cleavable hexahistidine tag. PgaB$_{310-672}$ was expressed and purified as described previously (Little et al 2012a, Little et al 2012b), with the following modification: glycerol was only included in the lysis buffer during purification.

Result:

A method for the production of PgaB encompassing residues 22-672 (PgaB$_{22-672}$) has been described previously (Little et al 2012a, Little et al 2012b). Herein, a C-terminal hydrolase domain construct encompassing residues 310-672 of PgaB (PgaB$_{310-672}$) was expressed and purified. A yield of PgaB$_{310-672}$ of ~10 mg/L of bacterial culture was obtained. The purity of the protein was judged to be >95% by SDS-PAGE (FIG. 21) and the protein could be concentrated to 8-10 mg/mL, however to minimize precipitation and degradation it was stored at 0.5-1.0 mg/mL at 4° C. for two weeks.

Example 13—BpsB$_{27-701}$, BpsB$_{318-670}$, PgaB$_{22-672}$, and PgaB$_{310-672}$ can Prevent Biofilm Formation in Static Culture Method:

The methodology to inhibit PNAG biofilms is similar to that of Psi biofilms, described in Example 3. In brief, PNAG-overproducing *E. coli* or *S. carnosus* was grown at 37° C. overnight in LB broth supplement with 200 μg/mL ampicillin and 100 μg/mL kanamycin, and 10 μg/mL tetracycline, respectively, with shaking at 200 rpm. Fresh cultures with antibiotic were prepared from the overnight culture using a 1:100 dilution, using LB broth for *E. coli*, and tryptic soy broth for *S. carnosus*. 95 μL of diluted culture was added to a sterile 96-well polystyrene round bottom microtiter plate and varying concentrations of protein (2 nM-5 μM) were added in 5 μL aliquots to give a final volume of 100 μL. The cultures were incubated statically for 24 h at 26° C. for *E. coli*, and 37° C. for *S. carnosus*, to allow for biofilm formation. To eliminate edge-effects, ~200 μL of sterile water was placed in all outside wells and the plate was sealed with parafilm. After incubation non-adherent cells and media were removed by washing the plate with deionized water three times. The wells were stained with 150 μL of 0.1% (w/v) crystal violet for 10 min, and washed with water three times. The remaining dye was solubilized with 100 μL of 33% (v/v) acetic acid for 10 min with rotation, after which time the absorbance was measured at 595 nm using a SpectraMax M2 from Molecular Devices (Sunnyvale, Calif.). The amount of biofilm is proportional to the absorbance from staining with crystal violet (Merritt et al 2005). All reactions were completed in at least triplicates and buffer G was used as an untreated control. Either an *E. coli* pgaABCD knockout strain (DPGA) or *S. carnosus* treated with gentamycin, was used as a control for background straining.

Result:

Over-producing PNAG strains from *E. coli* and *S. carnosus* that can be turned on with the addition of antibiotics were used. The addition of BpsB$_{27-701}$, BpsB$_{318-670}$, PgaB$_{22-672}$, and PgaB$_{310-670}$ to *E. coli* cultures prevented biofilm formation with EC$_{50}$ values of ~40 nM, ~60 nM, ~90 nM, and ~230 nM, respectively (FIG. 22A). Preliminary testing of biofilm inhibition for PNAG-dependent *S. carnosus* biofilms shows BpsB$_{318-670}$ can inhibit biofilm formation at 5 μM (FIG. 22B).

Example 14—BpsB$_{27-701}$, BpsB$_{318-670}$, PgaB$_{22-672}$, and PgaB$_{310-672}$ can Disperse Pre-Formed PNAG-Dependent Biofilms Method:

The methodology to form PNAG-dependent biofilms utilizes a similar methodology to that of Psi, described in Example 4, with the exception of the following differences. PNAG-overproducing *E. coli* was grown at 37° C. overnight in LB broth supplement with 200 ug/mL ampicillin and 100 ug/mL kanamycin with shaking at 200 rpm. An *E. coli* μgaABCD knockout strain was used as a non-biofilm forming control for background straining. To test different manufacturers plates, experiments were performed using sterile 96-well polystyrene round bottom microtitre plates from both Nunc and Sarstedt.

Result:

To examine whether BpsB$_{27-701}$, BpsB$_{318-670}$, PgaB$_{22-672}$, and PgaB$_{310-672}$ can degrade pre-formed PNAG biofilms, *E. coli* biofilms were grown overnight prior to addition of enzyme. The catalytic rate of an enzyme reaction is dependent on both the amount of substrate and enzyme added. It is therefore important to note that the biofilm mass is variable between experiments. The addition of BpsB$_{27-701}$, BpsB$_{318-670}$, PgaB$_{22-672}$, and PgaB$_{310-672}$, to pre-formed biofilms for 60 min with an average starting OD$_{595}$ of 0.5, degraded the biofilm with EC$_{50}$ values of ~170 nM, ~90 nM, >1000 nM, and 200 nM, respectively (FIG. 23A). Plates from different manufacturers were also tested, which resulted in varying levels of adherence, but similar levels of dispersal (FIG. 23B). Lastly, it was shown that dispersal of PNAG-dependent biofilms is specific, as the biofilm degrading enzymes PelA$_{47-303}$ and PslG$_{31-442}$ had no affect (FIG. 23C). The following alanine variants of BpsB: D326A, D328A, H473A, D474A, and E585A, were unable to disperse PNAG-dependent biofilms suggesting they play an important role in binding and/or hydrolyzing PNAG. Variants that maintain ability to cut the exopolysaccharide will likely require such residues to be maintained. Alternatively, such residues could be further optimized and a person skilled in the art would readily be able to determine if activity is increased or decreased upon mutation.

Example 15—BpsB$_{27-701}$, BpsB$_{318-670}$, PgaB$_{22-672}$, and PgaB$_{310-672}$ can Hydrolyze dPNAG Purified from *S. aureus*

Method:

Isolated dPNAG from *S. aureus* strain MN8m was solubilized in 6 N HCl at ~10 mg/mL. 10 N NaOH was used to titrate the re-suspension until neutrality was reached, ~pH 7-8. In a 50 μL reaction, 1 μM BpsB$_{318-670}$ was incubated with 1-5 mg/mL of dPNAG in 100 mM HEPES pH 7.0 for 18 hours. The sample was split into two 20 μL aliquots and treated with DTT/3-Methyl-2-benzothiazolinone hydrazone hydrochloride hydrate and heated at 80° C. for 15 minutes. A solution of 0.5% (w/w) iron (III) ammonium sulfate dodecahydrate, 0.5% (w/w) sulfamic acid, and 0.25 N hydrochloric acid was added, mixed, and cooled to room temperature. 100 μL was then transferred to a 96-well clear bottom plate and the absorbance was measured at 620 nm using a SpectraMax M2 from Molecular Devices (Sunnyvale, Calif.). Protein and dPNAG in buffer H were used as background controls.

Result:

To test whether the BpsB and PgaB anti-biofilm activity was directly due to the cleavage of the PNAG polysaccharide, reducing sugar assays were conducted. The results indicate a clear signal above background using a 24 h end-point assay indicating that the enzyme is able to hydrolyze the polysaccharide (FIG. 24). As dPNAG is estimated to be ~5% deacetylated, the average length of the dPNAG polymer (~200 units), and the signal generated in the hydrolysis assay suggests that cleavage may occur at a glucosamine residue. This would generate about 10 additional reducing ends per polymer. Without wishing to be bound by theory, since this result indicates that hydrolysis may occur at a glucosamine residue, having a BpsB or PgaB construct that includes the deacetylase domain should be beneficial in increasing the amount of glucosamine residues present on dPNAG thereby increasing sites for hydrolysis. This in turn should increase the efficiency of biofilm inhibition and degradation. Additionally, $BpsB_{27-701}$ and $BpsB_{318-670}$, showed about 4 times the hydrolysis activity compared to $PgaB_{22-672}$ and $PgaB_{310-672}$, suggesting $BpSB_{27-701}$ and $BpsB_{318-670}$ are better hydrolases under the conditions of this assay. This result correlates with the biofilm assays (FIG. 23A). The following alanine variants of BpsB: D326A, D328A, H473A, D474A, and E585A, were unable to hydrolyze dPNAG, suggesting they play an important role in binding or hydrolysis of dPNAG. As stated above, variants that maintain ability to cut the exopolysaccharide will likely require such residues to be maintained. Alternatively, such residues could be further optimized and a person skilled in the art would readily be able to determine if activity is increased or decreased upon mutation.

Example 16—$PelA_{47-303}$ can Prevent *A. fumigatus* GAG-Dependent Biofilms

Method:

To examine whether $PelA_{47-303}$, could inhibit the formation of GAG dependent biofilm, $5 \times 10^4$ *A. fumigatus* conidia/well were grown at 37° C. and 5% $CO_2$ for a duration of 20 h in Brian media supplemented with $PelA_{47-303}$. To quantify GAG biofilm formation, each well was washed twice with 400 µL of $dH_2O$ and stained for 10 min with 300 µL of 0.1% (w/v) crystal violet (Merritt et al 2005). Following this stain the wells were washed twice and the remaining dye was solubilized by addition of 300 µL of 95% (v/v) ethanol and left for 10 min after which time the absorbance was measured at 600 nm.

Result:

An ex vivo assay was employed to examine whether exogenously added PelA prior to biofilm formation could prevent GAG polysaccharide biofilm formation. The addition of ≥2 µM of $PelA_{47-303}$ was sufficient to prevent GAG biofilm formation as detected through the crystal violet assay (FIG. 25A). Two putative catalytic variants D160A and E218A were also shown to inhibit at these concentrations. A similar result was obtained for $PpPelA_{35-291}$ (FIG. 25B). Without wishing to be bound by theory, the enzyme variants may remain capable of binding the polysaccharide, thereby reducing the ability of the *A. fumigatus* to adhere to the abiotic plate.

Example 17—$PelA_{47-303}$ can Hydrolyze the GAG Polysaccharide from *A. fumigatus*

Method:

Crude GAG was isolated from *A. fumigatus* biofilms. 200 µL GAG aliquots were centrifuged to pellet the gelatinous fraction. The pellets were washed twice with 350 µL PBS. The wash procedure included vortexing for 5 min, sonicated in a bath for 3 min, and manual mixing by pipetting to reach homogeneity. The final pellet was resuspended in 200 µL of PBS. Samples were treated with 10-20 µM protein and incubated at 26° C. Samples were taken at 24 h. GAG hydrolysis was quantified using a reducing sugar assay as described previously (Anthon & Barrett 2002) with slight modifications. Briefly, 20 µL of enzyme reaction was mixed with 20 µL of 0.5 M NaOH and 20 µL of MBTH/DTT solution (1.5 mg/L 3-methyl-2-benzothiazolinone hydrazine (MBTH) and 0.5 mg/L DTT). The samples were incubated at 80° C. for 15 min before the addition of 40 µL of acidic iron reagent (0.5% $(FeNH_4(SO_4)_2).12\ H_2O$, 0.5% sulfamic acid, and 0.25 N HCl). Samples were diluted two-fold in water, before the absorbance was quantified at 620 nm.

Result:

To determine whether $PelA_{47-303}$ is capable of hydrolyzing the GAG polysaccharide, a reducing sugar assay was completed using purified GAG from *A. fumigatus* strain Af293. The number of reducing ends in solution increased over the 24 h reaction period as compared to an untreated sample (FIG. 26). The activity was specific as the release of chitin and chitosan was not significant over background hydrolysis. The single point variant E218A, abolished activity. Variants that maintain ability to cut the exopolysaccharide will likely require such residue to be maintained. Alternatively, such residue could be further optimized and a person skilled in the art would readily be able to determine if activity is increased or decreased upon mutation.

Example 18—$PelA_{47-303}$ and Orthologs can Disperse *A. fumigatus* GAG-Dependent Biofilms Method:

A total of $5 \times 10^4$ *A. fumigatus* conidia/well were grown at 37° C. and 5% $CO_2$ for a duration of 20 h in Brian media to allow for GAG production and adherence to sterile 24-well plates. To measure the dispersion of the GAG biofilm, media was aspirated and replaced with media containing $PelA_{47-303}$ or putative catalytic variants at concentrations as low as 0.28 µM and allowed to incubate in fresh media for an additional 20 h. To quench the reaction, each well was washed twice with 400 µL of $dH_2O$ and stained for 10 min with 300 µL of 0.1% (w/v) crystal violet. Following this stain, the wells were washed twice and the remaining dye was solubilized by addition of 300 µL of 95% (v/v) ethanol and left for 10 min after which time the absorbance was measured at 600 nm.

Result:

It was observed that $PelA_{47-303}$ from *P. aeruginosa* PAO1 and $PelA_{35-291}$ from *P. protogens* resulted in the elimination of the GAG biofilm while the putative catalytic variants and BSA control were unable to disrupt the biofilm (FIG. 27). PelA ortholog $RagA_{61-317}$ was also able to disperse GAG-dependent biofilms, while the PelA ortholog from *G. metallireducens* ($GmetPelA_{23-277}$) was less efficacious (FIG. 28) but nonetheless worked.

Example 19—$PelA_{47-303}$ can Prevent Epithelial Cell Damage Caused by *A. Fumigatus* Infection Method:

The immortalized airway epithelial cell line A549 was loaded with chromium-51 by incubating monolayers grown in 24-well tissue culture plates with 3 mCi of $^{51}Cr$ at 37° C. in 5% $CO_2$ for 24 h. Excess chromium was removed by washing with Hank's Balanced Salt Solution (HBSS). The labeled A549 cells were then infected with $5 \times 10^5$ conidia in 1 mL serum free DF12K medium with 0.5 µM PelA$_{47-303}$ or the E218A variant. For testing germ tubes, conidia were grown for 7 h in SAB media at 37° C., then the fungus was collected and resuspended in DF12K media before 0.5 µM of hydrolase was added. The germ tubes were incubated with hydrolase for 1 h before being added to the A549 cells. After 16, 20 and 24 h of co-incubation, an aliquot of the medium above the cells was retrieved and replaced with fresh media. The cells were then lysed with 6 N NaOH and the lysate collected. The $^{51}$Cr content of the medium and lysates was then measured in a gamma counter and the extent of epithelial cell damage was calculated as a function of the degree of $^{51}$Cr release. Each strain was tested in triplicate, and all results were corrected for spontaneous chromium release by uninfected epithelial cells.

Result:

The addition of exogenous PelA$_{47-303}$ blocked the ability of *A. fumigatus* to induce pulmonary epithelial cell injury as measured by a chromium release assay over a period of 16 h (FIG. 29). In comparison, the exogenous addition of PelA$_{47-303}$ E218A, previously shown to be unable to disrupt GAG-dependent biofilm did not prevent epithelial cell damage, confirming that the protective effect observed in the wild-type enzyme is a direct result at inhibiting and dispersing GAG-dependent biofilms. Without wishing to be bound by theory, PelA orthologs mentioned herein likely complete the same function. As stated above, variants that maintain ability to cut the exopolysaccharide will likely require such residue to be maintained. Alternatively, such residue could be further optimized and a person skilled in the art would readily be able to determine if activity is increased or decreased upon mutation.

Example 20—PelA$_{47-303}$ can Enhance Human Neutrophil Killing of *P. aeruginosa*

Method:

Overnight cultures of *P. aeruginosa* PAO1 ΔwspFΔpslp$_{BAD}$pel were diluted to an OD$_{600}$ of 0.05 in LB+0.5% arabinose and inoculated in a 96 well tissue culture-treated plate at a final volume of 100 µl/well. The plate was incubated statically at 28° C. for 20 h. Supernatants were aspirated and 100 µL of phenol red-free RPMI+ 10% Fetal Bovine Serum (FBS) containing 0.5 µM of PelA$_{47-303}$ was added. The plate was incubated at room temperature on a Nutator for 1 h. Following pretreatment with hydrolase, 100 µL RPMI+10% FBS containing 6×10$^6$ differentiated HL-60 cells were added to the wells, and plate was incubated for 90 min at 37° C., 5% CO$_2$. Wells were aspirated and supernatant was diluted between 1/200000 and 1/400000, and plated (50 µl) onto LB agar. To aspirated wells, 200 µL of "disruption solution" (PBS containing 2 µM of PelA$_{47-303}$ and 2 µM PslG$_{31-442}$) was added and plate was incubated at room temperature on the Nutator for 1-1.5 h. Wells were aspirated, diluted and plated onto LB agar as above.

Result:

To determine if hydrolase treatment could enhance the susceptibility of microorganisms to immune killing, the ability of PelA$_{47-303}$ to enhance the susceptibility of *P. aeruginosa* to neutrophils was examined. Treatment of Pel-containing *P. aeruginosa* biofilms with PelA increased the degree of microbial killing by the HL-60 neutrophil cell line from approximately 22% to 42% (FIG. 30). It is predicted that other soluble glycosyl hydrolases will also function in an analogous manner to potentiate neutrophil killing.

Example 21—PelA$_{47-303}$ can be Formulated in a Gel to Disperse Pel-Dependent *P. aeruginosa* Biofilms Method:

Poloxamer 407 (trade name Pluronic® F-127 or PF-127) is a hydrophilic non-ionic surfactant has been used as a drug delivery system for a number of routes of administration (Escobar-Chavez et al 2006). A 20% gel of PF-127 was prepared by mixing 1×PBS with Pluronic® F-127 at 4° C. until the polymer was dissolved. PelA$_{47-303}$ was added at three concentrations; 100 µg/mL, 200 µg/mL and 500 µg/mL to this solution. Pel-dependent biofilms from strain *P. aeruginosa* PAO1 ΔwspFΔpslpBADpel were formed as described in Example 8. The buffer, gel and gels containing various concentrations of PelA$_{47-303}$ were applied to the biofilm.

Result:

Treatment of biofilms with either 1×PBS buffer or 20% Pluronic® F-127 did not result in biofilm dispersal, however Pluronic® F-127 containing the three concentrations of PelA$_{47-303}$ successfully dispersed the biofilm as evident through crystal violet staining following a 1 h treatment. (FIG. 31) Without wishing to be bound by theory, it is believed that a similar delivery strategy can be utilized for any of the glycosyl hydrolases disclosed herein using agents that can encapsulate the enzymes.

Example 22—PslG$_{31-442}$ and PelA$_{47-303}$ can be Combined to Disperse Pel and Psl-Containing Biofilms from Clinical and Environmental Isolates of *P. aeruginosa*

Method:

The methodology used for the growth and dispersal of biofilms from clinical and environmental *P. aeruginosa* isolates is identical to that of laboratory strains as initially described in Example 4. One exception to this methodology is that L-arabinose is not required to induce formation of biofilms in these strains and therefore the ability to form biofilms is strain specific. The diversity of these selected isolates was previously published (Wolfgang et al 2003) and the propensity for these strains to utilize the Pel and Psi polysaccharides was characterized using genetic deletions of the pel and psl operons (Colvin et al 2012).

Result:

An ex vivo assay was employed to examine whether exogenously added PslG, PelA and combinations thereof could be utilized to disperse biofilms formed by clinical and environmental *P. aeruginosa* isolates. The addition of 100-1000 nM of PslG$_{31-442}$, PelA$_{47-303}$ or equimolar concentrations of both enzymes together resulted in ≥90% reducing in biofilm biomass as detected through crystal violet staining in a 1 hour period (FIG. 32). This demonstrates that these glycosyl hydrolases can be applied in combination to disperse biofilms in clinically relevant strains.

Example 23—Sph3$_{52-298}$ is a Soluble Protein

Method:

A comparative transcriptomic analysis of transcription factor mutants with impaired GAG production identified a cluster of 5 co-regulated genes predicted to encode proteins required for GAG biosynthesis. Several genes required for GAG biosynthesis in *A. fumigatus* are encoded on chromosome 3 in the genome (FIG. 33). A constructed Δsph3 knockout is unable to produce deacetylated GAG. The protein coding sequence of sph3 and ega3 from *A. fumigatus* Af293 were deposited into GenBank under accession no. EAL92786.1 and EAL92787.1, respectively. Sph3 is a 298 amino acid protein that is predicted, by the TMHMM server, to contain a transmembrane helix at its N-terminus (aa 20-42) (Krogh et al 2001). TMHMM classifies Sph3 as a type II membrane protein with the C-terminal domain on the extracellular surface of the cell. Structural homology searches suggest that $Sph3_{52-298}$ is composed of a $(\beta/\alpha)_8$ TIM-barrel fold. $Phyre^2$ bases these models on glycosyl hydrolases with confidence of up to 96.9% (Kelley & Sternberg 2009). The nucleotide sequence was used to design primers specific to the gene that would amplify the region encoding residues 52 to 298, which excluded the putative transmembrane helix. For Sph3, the forward primer, 5'-GGGCATATGTCCAAGGTCTTTGTGCCTCTC-TATGTG-3' (SEQ ID NO:9) encoded a NdeI site and the reverse, 5'-GGCTCGAGCTATTTTCCCATCAAATC-CACAAACTC-3' (SEQ ID NO:10), contained an XhoI site (FIG. 34). The PCR amplified product was digested using the NdeI and XhoI endonucleases and then ligated into a pET28a vector (Novagen). The sequence was confirmed by ACGT DNA Technologies Corporation before use.

Protein expression plasmids were transformed into *E. coli* BL21 (DE3) cells and grown in 1.5 L Luria-Bertani (LB) broth, with 50 µg/mL kanamycin at 37° C. to an OD600 of ~0.35-0.40. The temperature was reduced to 18° C. and at OD600 ~0.5-0.6 protein expression was induced using 0.5 mM isopropyl β-D-1-thiogalactopyranoside (IPTG). Cells were grown post-induction overnight and harvested by centrifugation for 20 min at 4000×g. Cells were re-suspended in Buffer I (50 mM CHES pH 9.0, 300 mM NaCl, 2% (v/v) glycerol, 10 mM imidazole, 2 mM TCEP) with a protease tablet (Sigma), and lysed using an Emulsiflex C3 homogenizer at 15,000 psi. Cellular debris was pelleted by centrifugation at 30,000×g and the supernatant was applied to a Ni-NTA agarose column (Qiagen). The column was washed with 10 column volumes of Buffer I and 4 column volumes of Buffer A with 20 mM imidazole. The hexa-histidine tagged protein was then eluted using Buffer I with 200 mM imidazole and the resulting fraction was concentrated using an Amicon Ultra filtration device (Millipore) to a volume of 2 mL. The concentrated protein was further purified using a HiLoad Superdex 200 size exclusion column (GE Healthcare) equilibrated with Buffer J (50 mM CHES pH 9.0, 150 mM NaCl, 1 mM TCEP).
Result:
A $Sph3_{52-298}$ construct encompassing residues 52-298 was expressed and purified. The expressed protein produces ~10 mg per liter of bacterial culture with a molecular weight of 29.6 kDa. The protein was judged to be ≥95% pure by SDS-PAGE and the protein could be concentrated to 8-10 mg/mL and stored at 4° C. (FIG. 35).

Example 24—$Sph3_{52-298}$ can Hydrolyze the GAG Polysaccharide

Method:
The methodology to examine hydrolysis of the GAG polysaccharide using $Sph3_{52-298}$ is identical to that previously described in Example 17 for the use $PelA_{47-303}$.
Result:
To determine whether $Sph3_{52-298}$ can hydrolyze the GAG polysaccharide, a reducing sugar assay was completed using purified GAG. The number of reducing ends in solution increased over the 24 h reaction period as compared to an untreated sample (FIG. 26). The single catalytic point variant D166A, abolished activity. Variants that maintain ability to cut the exopolysaccharide will likely require such residue to be maintained. Alternatively, such residue could be further optimized and a person skilled in the art would readily be able to determine if activity is increased or decreased upon mutation.

Example 25—$Sph3_{52-298}$ can Prevent and Disperse *A. fumigatus* GAG Biofilms Including *A. fumigatus* Clinical Isolates Method:
The methodology to examine the dispersal of GAG biofilms using $Sph3_{52-298}$ is identical to that previously described in Example 18 for the use $PelA_{47-303}$. Clinical isolates of *A. fumigatus* were obtained from clinical mycology lab at McGill University Health Centre.
Result:
An ex vivo assay was employed to examine whether exogenously added $Sph3_{52-298}$ could disperse pre-formed biofilms. The addition of 280 nM of $Sph3_{52-298}$ was sufficient at preventing GAG biofilm formation as detected through the crystal violet assay (FIG. 36). This suggests that $Sph3_{52-298}$ is able to disperse GAG biofilms in a similar manner as $PelA_{47-303}$ disrupting Pel polysaccharide biofilms from *P. aeruginosa* and that this enzyme may represent a novel antifungal therapy. Recombinant Sph3 from *A. fumigatus*, *A. nidulans* and *A. clavatus* all inhibit the formation of *A. fumigatus* biofilms in a dose dependent manner. Similarly, soluble Sph3 from all three *Aspergillus* species disrupted preformed biofilms of *A. fumigatus* in a dose dependent manner (FIG. 37). Introduction of point mutations in the catalytic domain of these soluble Sph3 proteins was associated with a decrease or loss of activity, suggesting that the anti-biofilm activity of these proteins is mediated by enzymatic activity. $Sph3_{52-298}$ from *A. fumigatus* was found to be active against multiple strains of *A. fumigatus* suggesting that these agents will be active against a variety of clinical isolates (FIG. 38).

Example 26—$Sph3_{AC(54-304)}$ can Disperse the GAG Biofilm of the Fungal Pathogen *Trichosporon asahii*

Method:
To assess the effects of hydrolase treatment on *Trichosporon asahii*, $1\times10^5$ *T. asahii* yeast cells or *A. fumigatus* conidia were inoculated in Dulbecco's Modified Eagle Medium (DMEM), and grown for 10 h at 37° C., 5% $CO_2$ on glass coverslips. Wells were gently washed once with Ham's F-12K (Kaighn's) Medium (F12K) media, and $Sph3_{AC(54-304)}$ was added at a final concentration of 0.5 µM in F12K, and incubated for an additional 3 h at 37° C., 5% $CO_2$. Young hyphae were washed twice with PBS, and stained with FITC tagged SBA for 1 h. The stained samples were washed with PBS and fixed with 4% PFA for 15 min. Slides were then mounted, sealed, and imaged under confocal microscopy with a 488 nm laser (Zeiss).
Result:
As shown in FIG. 39, the opportunistic fungal pathogen *Trichosporon asahii* produces a GalNAc-rich exopolysaccharide, which can be degraded by $Sph3_{AC(54-304)}$. Similar to *A. fumigatus*, untreated *T. asahii* displays GalNAc decorations on the cell surface, as determined by SBA-FITC staining (top left and center). However, treatment with 0.5 µM $Sph3_{AC(54-304)}$ for 3 h results in a complete loss of detectable surface GalNAc (top right). Fungi were counterstained with DRAQ5 (bottom panels).

Example 27—$Sph3_{52-298}$ can Prevent Epithelial Cell Damage Caused by A. Fumigatus and P. aeruginosa Infection Method:

The methodology for prevention of epithelial cell damage caused by A. fumigatus using $Sph3_{52-298}$ is identical to that previously described in Example 19 for the use $PelA_{47-303}$. For P. aeruginosa-induced damage, A549s were exposed to Pel-producing P. aeruginosa in the presence or absence of $Sph3_{AN(43-299)}$ at 0.5 µM for 16 h, and mammalian cell damage was assayed by release of lactose dehydrogenase (LDH) into the supernatant.

Result:

To determine if recombinant hydrolases could protect host cells from injury by A. fumigatus, a chromium release damage assay was used to assess injury of the A549 pulmonary epithelial cell line by A. fumigatus. Treatment of A. fumigatus with Sph3 from A. clavatus, A. nidulans, or A. fumigatus reduced fungal damage to epithelial cells (FIG. 40A). Of note, Sph3 from A. clavatus ($Sph3_{AC(54-304)}$) and A. nidulans ($Sph3_{AN(43-299)}$) completely protected epithelial cells from damage by A. fumigatus for 24 h. $Sph3_{AN(43-299)}$ was also capable of reducing damage caused by P. aeruginosa (FIG. 40B).

Example 28—the Glycoside Hydrolases $PslG_{31-442}$, $PelA_{47-303}$ and $Sph3_{52-298}$ and its Orthologs $Sph3_{AC(54-304)}$ and $Sph3_{AN(43-299)}$ can Potentiate Antimicrobial Compounds Used to Treat P. Aeruginosa and A. fumigatus Infections Method:

The effect of a combination treatment with antifungals and $Sph3_{AC(54-304)}$ or $PelA_{47-303}$ on the growth of A. fumigatus conidia was determined using a multititer plate assay. Resting A. fumigatus conidia in RPMI 1640 medium (Life Technology) buffered with MOPS (3-(N-Morpholino) Propane-Sulfonic Acid) (Fisher) (RPMI-MOPS) were added to tissue culture-treated multititer plates (BD Falcon). The conidia were incubated for 9 h at 37° C., 5% $CO_2$. Stock solutions of antifungals were prepared in dimethyl sulfoxide (DMSO) and further diluted in RPMI-MOPS. Stock solutions of hydrolase were prepared and diluted in RPMI-MOPS. The antifungal compounds were two-fold serially diluted across the rows and 0.5 µM of $Sph3_{AC(54-304)}$ or $PelA_{47-303}$ was added. The plates were then incubated at 37° C. and 5% $CO_2$ and examined after 15 h under an inverted light microscope (Zeiss, Inc.) and images acquired using an Infinity2 camera (Lumenera, Inc.). To measure fungal viability, XTT [2,3-bis-(2-methoxy-4-nitro-5-sulfophenyl)-2H-tetrazolium-5-carboxanilide] (Sigma) metabolic assay was subsequently performed; Menadione (Sigma) was added to XTT solution, and further diluted with RPMI-MOPS. The solution was added to the hyphae and incubated for 90 min. The $OD_{450}$ was measured using a spectrophotometer (ASYS UVM 340).

To examine the effect of $PelA_{47-303}$ and $PslG_{31-442}$ on antibiotic potentiation, Pel-dependent and Psl-dependent biofilms were grown as previously described in Example 4 in either the absence or presence of 1 µM $PelA_{47-303}$ or $PslG_{31-442}$, respectively. After 24 h, all samples were treated with 100 µg/mL of colistin and incubated at 25° C. for 24 h. Following this treatment, planktonic cells were removed by pipetting and remaining biofilms were suspended in buffer and subjected to a hydrolase treatment outlined in Example 4. Planktonic and biofilm biomass was pooled and serially diluted on LB agar plates for colony counts.

Result:

To determine if treatment with recombinant hydrolases could enhance the activity of antimicrobial agents, the effects of $Sph3_{AC(54-304)}$ and $PelA_{47-303}$ on antifungal susceptibility of A. fumigatus were examined. Treatment of A. fumigatus biofilms with Sph3AF, $Sph3_{AC(54-304)}$, $Sph3_{AN(43-299)}$, or $PelA_{47-303}$ resulted in an ≥50% reduction in the minimal inhibitory concentration of the antifungals posaconazole, amphotericin B and caspofungin (FIG. 41). Similar reductions in MIC were seen for sensitive and resistant strains of A. fumigatus.

$PelA_{47-303}$ and $PslG_{31-442}$ were also able to potentiate the antibiotic colistin dosed at a final concentration of 100 µg/mL. The addition of either enzyme lead to a more than 100-fold increase in bacterial killing as no growth was observed on the LB plates (FIG. 42). Without wishing to be bound by theory, it is likely that other classes of antibiotics with different mechanisms of action will also be potentiated by any glycosyl hydrolase given the involvement of exopolysaccharides in antibiotic protection.

Example 29—Treatment of A. Fumigatus with $Sph3_{AC(54-304)}$ Increases Antifungal Drug Penetration Method:

Red Fluorescent Protein (RFP)-expressing Af293 hyphae were pretreated with 0.5 µM $Sph3_{AC(54-304)}$ hydrolase for 90 min before treatment with Bodipy-conjugated posaconazole (BDP-PCZ). At various time points, samples were fixed and imaged using fluorescent confocal microscopy to determine the kinetics of drug penetration of hyphae.

Result:

To determine if this increased sensitivity to antifungals in the presence of recombinant glycosyl hydrolases resulted from enhanced cellular penetration in the absence of exopolysaccharide, the rate of uptake of posaconazole by A. fumigatus was examined in the presence or absence of $Sph3_{AC(54-304)}$. Treatment of hyphae with $Sph3_{AC(54-304)}$ increased the speed and degree of uptake of fluorescent-tagged posaconazole as visualized by confocal microscopy (FIG. 43). Collectively these data demonstrate the degradation of exopolysaccharide by recombinant hydrolases can increase the activity of antifungals through enhancing their ability to penetrate fungal cells.

Example 30—Identification of Other Species that have the Genetic Capacity to Synthesize GAG and Form GAG-Dependent Biofilms Method:

For bioinformatics analyses, amino acid sequences of the genes within the GAG biosynthesis cluster: AFU_3 G07860 (Gtb3), AFU_3 G7870 (Agd3), AFU_3 G7890 (Ega3), AFU_3 G7900 (Sph3), and AFU_3 G7910 (Uge3), were obtained from the Aspergillus Genome Database (http://www.aspergillusgenome.org) and queried by BLAST on NCBI protein database (http://blast.ncbi.nlm.nih.gov/Blast.cgi). The Conserved Domain Database (CDD) was used to predict functional domains for each putative protein. Amino acid sequences of proteins with similar domain to the cluster genes were aligned by multiple sequence alignment (MSA) using ClustalW (http://www.ebi.ac.uk/Tools/msa/clustalw2/). The resulting phylogenic relationship output was exported, formatted, and drawn for visualization using TreeVector (http://supfam.cs.bris.ac.uk/TreeVector/) for each member of the cluster. For taxonomic analysis, classes of fungi containing the GAG cluster were selected and visualized using PhyloT (http://phylot.biobyte.de).

GAG production of *Trichosporon asahii* was assessed using soybean agglutinin (SBA) lectin staining. Briefly, $1 \times 10^5$ *T. asahii* yeast cells or *A. fumigatus* conidia were inoculated in RPMI 1640, and grown for 9 h at 37° C., 5% $CO_2$ on glass coverslips. *Botrytis cinerea* isolate 7b1 (from Drs. Carisse & Tremblay from Agriculture and Agri-Food Canada, St-Jean-sur-Richelieu, Québec) was inoculated at a concentration of $6 \times 10^3$ conidia/mL in 500 μl of Brian media on poly-D-lysine-coated coverslips (Corning, Bedford, Mass.) for 17 h at room temperature, in the dark. Resulting young hyphae were fixed in 4% PFA for 30 min, washed in PBS, and stained with FITC tagged SBA for 2 h. The stained samples were washed with PBS, mounted, and imaged under confocal microscope with a 488 nm laser (Olympus, Inc.).
Result:

Bioinformatic analyses revealed the presence of the GAG biosynthetic gene cluster within the fungi of many ascomycete fungi, as well as the basidiomycete *Trichosporon* (FIG. 44). These fungi include the plant pathogenic species: *Saccharata proteae, Zopfia rhizophila, Phaeosphaeria nodorum, Setosphaeria turcica, Botrytis cinerea, Cryphonectria parasitica, Melanconium* sp., *Verticillium dahlia, Nectria haematococca, Neurospora crassa, Leptosphaeria maculans, Pleomassaria siparia, Cochliobolus heterostrophus, Pyrenophora tritici-repentis, Blumeria graminis, Marssonina brunnea, Sclerotinia sclerotiorum, Taphrina deformans, Cercospora zeae-maydis* and human pathogenic fungi: *Fusarium, Trichosporon* and *Aspergillus* species. To confirm that the presence of these clusters in other fungi predicted the production of GAG, hyphae of *T. asahii* (FIG. 39), and *B. cinerea* (FIG. 45) were stained with GalNAc-specific lectins to detect the presence of GAG. Consistent with the presence of the GAG biosynthetic cluster within the genomes of these species, lectin staining demonstrated the production of GAG-like exopolysaccharide by both organisms.

Example 31—*Botrytis cinerea* can Produce GAG-Dependent Biofilms which can be Digested by Sph3$_{AC(54-304)}$ Method:

*Botrytis cinerea* isolate 7b1 was inoculated at a concentration of $6 \times 10^3$ conidia/ml in 500 μl of Brian media on poly-D-lysine-coated coverslips (Corning, Bedford, Mass.) for 17 h at room temperature, in the dark. Samples were incubated either in the presence or absence of 1 μM Sph3$_{AC(54-304)}$. Media was then removed and the hyphae were incubated in PBS with or without 1 μM Sph3$_{AC(54-304)}$ for 1 h at room temperature. Samples were washed twice with PBS, and stained with 30 μg/mL of *Wisteria fluoribunda* (WFL) lectin conjugated to fluoresceine for 2 h at 4° C. Samples were washed twice with PBS, and fixed with 4% paraformaldehyde for 10 min at 4° C. Samples were washed once and stained with a 1:1000 dilution of DRAQ5™ (eBioscience, San Diego, Calif.) for 5 min at room temperature. Samples were washed once with PBS, mounted onto microscope slides using SlowFade® Gold antifade reagent (life Technologies™, Eugene, Oreg.), and sealed with nail polish. Images were acquired on an Olympus Fluoview confocal laser microscope using 488 and 633 nm lasers coupled with BA505-525 and BA650IF filters, respectively. Z-stacks of 0.2 μm increments were acquired, and 3D-rendered using ImageJ software (National Institutes of Health).
Result:

Treatment of hyphae of *B. cinerea* with Sph3$_{AC(54-304)}$ resulted in a complete loss of this exopolysaccharide (FIG. 45). Without wishing to be bound by theory, this data suggests that recombinant hydrolases can digest GAG biofilms from other fungal species.

Example 32—Ega3$_{46-318}$ is a Soluble Protein

Method:

Bioinformatics predictions suggest that Ega3 has a single transmembrane (TM) helix from amino acid 23 to 45. The C-terminal domain, encompassing amino acids 46-318, has been predicted to be extracellular by TMHMM. The Phyre$^2$ structural homology recognition server predicts the protein contains an $(\beta/\alpha)_8$ TIM-barrel and is aligned with glycosyl hydrolyse family GH114. A plasmid containing the ega3 gene codon optimized for expression in *E. coli* was obtained from GeneArt. The sequence encoding the predicted extracellular domain, amino acids 46-318, were subcloned into a pET28 vector between the NdeI and HindIII sites. The forward primer, 5'-GGGAGT-CATCGTATGGGCAGCAGCCATCATCATCATC-3' (SEQ ID NO: 24) encoding a Mlyl site and the reverse, 5'-GGGGGTACCTTAGCAATATTCCACCCA-3' (SEQ ID NO:25), contained an Kpnl site were used to amplify the Ega3$_{46-318}$ construct with the N-terminal hexahistidine tag. The PCR amplified product was digested using the Mlyl and Kpnl endonucleases and then ligation into a pPinka-HC vector pre-digested with the endonucleases Stul and Kpnl (Invitrogen). The sequence was confirmed by ACGT DNA Technologies Corporation before use.

Protein expression plasmids were transformed into *Pichia pastoris* (PichiaPink Strain 4) plated on *Pichia* Adenine Dropout (PAD) selection plates to identify transformed colonies. Colonies were selected and grown in 2 mL buffered complex glycerol medium (BGMY) media at 30° C. Starters were used to inoculate 500 mL of BMGY and then grown at 26° C. overnight. This larger culture was harvested and then resuspended in 450 mL buffered complex methanol medium (BMMY) media, grown at 26° C. with shaking for protein expression. Cells were harvested after 48 h by centrifugation for 20 minutes at 4000×g. The culture supernatant was applied to a 3 mL Ni-NTA agarose column (Qiagen). The column was washed with 10 column volumes of Buffer K (50 mM HEPES pH 7.5, 300 mM NaCl, 5 mM imidazole). The hexa-histidine tagged protein was then eluted using Buffer K supplemented with 200 mM imidazole and the resulting fraction was concentrated using an Amicon Ultra filtration device (Millipore) to a volume of 2 mL. The concentrated protein was further purified using a HiLoad Superdex 200 size exclusion column (GE Healthcare) equilibrated with Buffer L (50 mM HEPES pH 7.5, 300 mM NaCl).
Result:

An Ega3$_{46-318}$ construct encompassing residues 46-318 was expressed and purified. The expressed protein produces ~3 mg per liter of yeast culture with a molecular weight of 31.8 kDa. The protein was judged to be >95% pure by SDS-PAGE (FIG. 46). Protein glycosylation is common during recombinant protein expression and secretion in *P. pastoris*. To determine whether the apparent mass of Ega$_{346-318}$ was larger due to glycosylation a sample of protein was treated with endoglycosidase H (EndoH). After treatment the sample was run on SDS-PAGE. The EndoH treated Ega$_{346-318}$ produced a band near the predicted mass of the unglycosylated protein at 31 kDa.

Example 33—Ega$_{346-318}$ can Inhibit and Disperse GAG Biofilms from *A. fumigatus*

Method:

*A. fumigatus* conidia were inoculated into polystyrene, round-bottom 24-well plates at a concentration of $10^5$ conidia/well in DMEM media. To assess the inhibition of biofilm formation, Ega$_{346-318}$ was added at a final concentration of 1 μM and the conidia incubated for 18 h at 37° C., 5% $CO_2$. The resulting biofilms were then gently washed twice with distilled water, and stained with 0.1% crystal violet for 10 min. Samples were washed twice with water and the wells were imaged.

To determine the effect hydrolase has on a preformed biofilm, $10^5$ *A. fumigatus* conidia were inoculated per well in DMEM media as above, but in the absence of hydrolase. Following 18 h incubation at 37° C., 5% $CO_2$, the resulting biofilm was treated with Ega$_{346-318}$ at a final concentration of 1 μM for 1.5 h at room temperature on a nutator. The biofilms were then washed and stained as mentioned above.

Result:

While an untreated *A. fumigatus* biofilm grown for 18 h remains adherent to polystyrene after gentle washing, conidia grown in the presence of 1 μM Ega$_{346-318}$ were found to be completely non-adherent (FIGS. 47A-47B). Also, the addition of Ega$_{346-318}$ at a concentration of 1 μM to a preformed, 18 h *A. fumigatus* biofilm and incubation for 1.5 h at room temperature resulted in the disruption of the biofilm. FIGS. 47A-47B) suggests that Ega$_{346-318}$ is capable of degrading N-acetylgalactosamine (GalNAc) residues from the surface of *A. fumigatus*. While untreated hyphae display extensive surface GalNAc decorations when stained with the fluorescent lectin SBA-FITC (top left), treatment of the hyphae with 0.5 μM Ega$_{346-318}$ for 3 h resulted in a complete loss of detectable GalNAc on the surface (top right). Hyphae were counterstained with DRAQ5 (bottom panels). It is important to note that both samples were inoculated with the same density of *A. fumigatus* conidia, and that treatment with Ega$_{346-318}$ resulted in a loss of adherence and therefore hyphae retained.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

```
                        Table of Sequences

PslG31-442 (P. aeruginosa PA01)
EIQVLKAPRAVVWKDFLGVNAQFLWFSPERYNKQIDRLQDLGLEWVRLDLH
WDRLETAEDQYQLASLDQLVKDLEARQLKSVFYLVGSARFITTAPFYSPFQD
QYPPRDPEVFARRMAMLSQRYPSVAAWQVWNEPNLIGFWRPKADPEGYA
KLLQASTIALRMVDPEKPVVSAGMAFFSEMPDGRTMFDALGHLGVESLGTI
ATYHPYTQLPEGNYPWNLDFVSHANQINRALRNAGVPAIWSTEWGWSAYK
GPKELQDIIGVEGQADYVLRRLALMSALDYDRIFLFTLSDLDQRASVRDRDY
GLLDLDANPKPVYLALQRFLKVTGPKLRPADPPVTEDLPDGSFSIGWTRED
GRNVWLFWSARGGNVRLPKLKEATLHDPLSGKVTPLSGSDGLEVPVKSSL
QMLVWE (SEQ ID NO: 11)

PelA47-303 (P. aeruginosa PA01)
GGPSSVAFWYAERPPLAELSQFDWVVLEAAHLKPADVGYLKEQGSTPFAY
LSVGEFDGDAAAIADSGLARGKSAVRNQAWNSQVMDLAAPSWRAHLLKRA
AELRKQGYAGLFLDTLDSFQLQAEERREGQRRALASFLAQLHRQEPGLKLF
FNRGFEVLPELPGVASAVAVESIHAGWDAAAGQYREVPQDDRDWLKGHLD
ALRAQGMPIVAIDYLPPERRDEARALAARLRSEGYVPFVSTPALDYLGVSDV
EVQP (SEQ ID NO: 12)

PelA35-291 (P. protogens Pf-5)
AAPASVGFWYAEQPPLQELAQFEWAVVEPGHMASADVATLRKLGSQPFAY
LSVGEFDGNRAALAKQALAQGASPVRNKAWDSQVMDIATPAWREHLFKRA
KALQDQGYAGLFLDTLDSFQLLPEADREPQRKALASFLRELHSRLPNLKLFF
NRGFEVLGELDGVASAVAVESIHAGWDASAKRYRPVSEADRTWLEGELKP
LRARNIPLVAIDYLPANRREEARKLVRQLSQEGFIPVVTTPDLNALSMSTVEV
QP (SEQ ID NO: 13)

PelA23-277 (Geobacter metaffireducens)
PPLSVALYYGKQPPVNDLHAFDIVVIDPDSGLTPSEYGSGRSELFAYVSVGE
ADTARSYTKQMPDRWIIGKNPVWKSKIVDVSSEEWKQFFLDDVVEPLWQA
GYRGFFLDTLDSYLIAAPTEAHPRMEAGLVSVVRAIRQRHPEARLILNRGFEI
FDRVKDLVYAVAAESLFQNFNTVSGKYGAVDDKDRSWLTSRLNVIRETGVP
VIAIDYVDPGNRPLMRETADKIRSLGFTPWVTDKDLAGLGIGSVEVMPRTVL
GLYDGGEGAG (SEQ ID NO: 14)

RagA61-317 (Ralstonia solanacearum GMI1000)
ADAPNIAWFYGDKPPVAQLRAFDAVVVEPDHGFDPSRAKTPTTQWFAYVS
VGEVAPERRWYKELPKAWLAGSNAAWASHVIDQSQPQWPAFYVDRVIAPL
WDRGYRGFFLDTLDSYQLVAKDDAARAAQEAGMVRVIRAIKARYPEAKLIFN
RGFEILPQVHDLAYAVAFESLYRAWDQGNKQYREVNDADRAWLMGQARKI
QDEYHLPVISIDYCPPADRACARETAKRIKAQGLIPYVTDPALSTIGVGRIEVL
P (SEQ ID NO: 15)
```

Table of Sequences

PgaB$_{22-672}$ (*Escherichia coli* K-12 MG1655)
ISQSRTSFIPPQDRESLLAEQPWPHNGFVAISWHNVEDEAADQRFMSVRTS
ALREQFAWLRENGYQPVSIAQIREAHRGGKPLPEKAVVLTFDDGYQSFYTR
VFPILQAFQWPAVVAPVGSWVDTPADKQVKFGDELVDREYFATWQQVRE
VARSRLVELASHTWNSHYGIQANATGSLLPVYVNRAYFTDHARYETAAEYR
ERIRLDAVKMTEYLRTKVEVNPHVFVWPYGEANGIAIEEELKKLGYDMFFTLE
SGLANASQLDSIPRVLIANNPSLKEFAQQIITVQEKSPQRIMHIDLDYVYDENL
QQMDRNIDVLIQRVKDMQISTVYLQAFADPDGDGLVKEVWFPNRLLPMKAD
IFSRVAWQLRTRSGVNIYAWMPVLSWDLDPTLTRVKYLPTGEKKAQIHPEQ
YHRLSPFDDRVRAQVGMLYEDLAGHAAFDGILFHDDALLSDYEDASAPAITA
YQQAGFSGSLSEIRQNPEQFKQWARFKSRALTDFTLELSARVKAIRGPHIKT
ARNIFALPVIQPESEAWFAQNYADFLKSYDWTAIMAMPYLEGVAEKSADQW
LIQLTNQIKNIPQAKDKSILELQAQNWQKNGQHQAISSQQLAHWMSLLQLNG
VKNYGYYPDNFLHNQPEIDLIRPEFSTAWYPKND (SEQ ID NO: 16)

PgaB$_{310-672}$ (*Escherichia coli* K-12 MG1655 )
EKSPQRIMHIDLDYVYDENLQQMDRNIDVLIQRVKDMQISTVYLQAFADPDG
DGLVKEVWFPNRLLPMKADIFSRVAWQLRTRSGVNIYAWMPVLSWDLDPT
LTRVKYLPTGEKKAQIHPEQYHRLSPFDDRVRAQVGMLYEDLAGHAAFDGI
LFHDDALLSDYEDASAPAITAYQQAGFSGSLSEIRQNPEQFKQWARFKSRA
LTDFTLELSARVKAIRGPHIKTARNIFALPVIQPESEAWFAQNYADFLKSYDW
TAIMAMPYLEGVAEKSADQWLIQLTNQIKNIPQAKDKSILELQAQNWQKNGQ
HQAISSQQLAHWMSLLQLNGVKNYGYYPDNFLHNQPEIDLIRPEFSTAWYP
KND (SEQ ID NO: 17)

BpsB$_{27-701}$ (*Bordetella bronchiseptica* RB50 )
YKVDMLPPPDPDDGLTFRVLCMHDVRDNLRASFADMPDQFAIETRTLTDLF
EWIRVKGFNPISMQQIIDSRAGVRPLPPRPILLTFDDGYASTYTKVFPLLKKF
NYPAVVAVVTSWTDAPAGTKIRLSPKIEVPHDFFMTWAQLREMAQSGLVEL
ASHSHNLHRGVLANPQGNEQPAASSRQYLPASGRYENDAEYRARVRQDLK
TSADLIREHTGVTIRSIVWPYGAHNRDTDQVAAEVGLNIGLTLQPGPNTPDV
ALTQIRRSLVDYEVNVATVARAMREPVSYHGQVRPIERIVQVDLDYIYDPDP
EQQNRNLGQLIDRMKDLAPSAVYLQAFADPKGDGDITEVYFPNRHLPMRAD
LFNRVAWQLKTRAGVMVYAWLPVLTFSVPPGNPAYGKVVQSTTRKPGERG
LGSPTRLSPFHPDAHRVISEIYEDLAKAAHFDGLLFHDDAVLDDTEDSSPEAL
ATYQGWGLPPDIAAIRADPKLAQQWSKGKIRYLIDFTMHLRHIVSGYQNDRD
MVVARNLYAQPVLDPVSEAWYGQSLPEFLKSYDFVALMAMPNMEGAARPE
QWMRQLVAAVARQKGLDRTIFELQARDWRVGKPIDTEILRRQMVQLRSLGA
INYGYYPDDFIANHPDAEALRDVMSLKSTLEKRRLTKAQELSRQTTLYGSAS
QAEPTQR (SEQ ID NO: 18)

BpsB$_{318-670}$ (*Bordetella bronchiseptica* RB50)
PIERIVQVDLDYIYDPDPEQQNRNLGQLIDRMKDLAPSAVYLQAFADPKGDG
DITEVYFPNRHLPMRADLFNRVAWQLKTRAGVMVYAWLPVLTFSVPPGNPA
YGKVVQSTTRKPGERGLGSPTRLSPFHPDAHRVISEIYEDLAKAAHFDGLLF
HDDAVLDDTEDSSPEALATYQGWGLPPDIAAIRADPKLAQQWSKGKIRYLID
FTMHLRHIVSGYQNDRDMVVARNLYAQPVLDPVSEAWYGQSLPEFLKSYD
FVALMAMPNMEGAARPEQWMRQLVAAVARQKGLDRTIFELQARDWRVGK
PIDTEILRRQMVQLRSLGAINYGYYPDDFIANHPDAEALRDVMSLKS (SEQ ID NO: 19)

Sph3$_{52-298}$ (*Aspergillus fumigatus* Af293)
SKVFVPLYVYPAPGAWTPLEDVISKHPDVNFTVVINPGSGPGPNALPDGNY
TREIPKLASYENVRLLGYVATTYAKRNISLVRRDIETYAAWPTNSSNPALAVR
GIFFFDETPQQYDEDALAYLQELTDVVKNTPGLGPDHYVVHNPGAIPDSRYLS
TADSTVVFEATYDTFQERHGAKLFEAIPDSNRSQLCAVIHSVPESVEGSALR
SLVKQVRKVADEIFITHLDTDYYASFGRQWPEFVDLMGK (SEQ ID NO: 20)

Sph3$_{AC\ (54-304)}$ (*Aspergillus clavatus* NRRL 1)
MGPKSKVFVPLYVYPAPGAWDPLEDVISKHPDVNFTVVINPGSGPGPE
ALPDGNYTREIPKLASYENVRLLGYVATTYAKRNISEVRRDIETYAAWPTQS
SNANLAVRGIFFDETPQQ
YDADILAYLRELTDVVKGTSGLGPDHYVVHNPGAIPDSRYLSTADSTVVFEA
TYATFQERHGAELFDTIP
DSHRDQLCAVIHSVPTSVEGSDLRGLVKQVRQVADEIFITHLETDYYAGFGG
QWSEFVDLMAS (SEQ ID NO: 22)

SPh3$_{AN(43-299)}$ (*Aspergillus nidulans* FGSC A4)
RRKNNNMGPKAKVFVPLYVYPAPGAWDPLVNVITAHPDVNFTVVVNPGSG
PGPNPLPDRNYTQEIPRLTAHDNVRVLGYVATTYAKRNISSVRNDIETYAAW
PTISANPKLAVRGIFFDETPQQYNASDLAYLEELTSVVKNTPGLGPDHFVFH
NPGWPDPRYLSTADSTVVFEATYDTFQDRDGARLFETIPNSNRSQLCAVV
HSVPDSVEGSELRKFVKQARRVADEIFVTHLSTNYYASFGDKWDDFVRLMA
Q (SEQ ID NO: 23)

Ega3$_{46-318}$ *Aspergillus fumigatus* Af293)
GLGGGGGGEGEEGSGGETTPPEGNYTTAKWQPAVGTKWQIELLYALNDT -continued Table of Sequences SVDAEIYDIDLFINDKSTIAGLQRAGRKVICYFSAGSYENWRPDKDKFKDSDL
GHDLDDWPGEKWLNISSANVRQIMLDRLDMARDKGCDGVDPDNVDGYDN
DNGLDLTQADSISFVNFLANAAHARNMSIGLKNAGDIIPSVIKNMQWSVNEQ
CAQYNECDTYAVFPQNGKPVFHIEYPKGDKTNNDLSVTASQKNAACDFAG
SANFSTVIKNMNLNNWVEYC (SEQ ID NO: 21)

REFERENCES

Adams P D, Afonine P V, Bunkoczi G, Chen V B, Davis I W, et al. 2010. PHENIX: a comprehensive Python-based system for macromolecular structure solution. *Acta Crystallogr D Biol Crystallogr* 66: 213-21

Afonine P V, Mustyakimov M, Grosse-Kunstleve R W, Moriarty N W, Langan P, Adams P D. 2010. Joint X-ray and neutron refinement with phenix.refine. *Acta crystallographica. Section D, Biological crystallography* 66: 1153-63

Alhede M, Kragh K N, Qvortrup K, Allesen-Holm M, van Gennip M, et al. 2011. Phenotypes of non-attached *Pseudomonas aeruginosa* aggregates resemble surface attached biofilm. *PloS one* 6: e27943

Altschul S F, Gish W, Miller W, Myers E W, Lipman D J. 1990. Basic local alignment search tool. *J Mol Biol* 215: 403-10

Anthon G E, Barrett D M. 2002. Determination of reducing sugars with 3-methyl-2-benzothiazolinonehydrazone. *Analytical biochemistry* 305: 287-9

Ashkenazy H, Erez E, Martz E, Pupko T, Ben-Tal N. 2010. ConSurf 2010: calculating evolutionary conservation in sequence and structure of proteins and nucleic acids. *Nucleic Acids Res* 38: W529-33

Bagos P G, Nikolaou E P, Liakopoulos T D, Tsirigos K D. 2010. Combined prediction of Tat and Sec signal peptides with hidden Markov models. *Bioinformatics* 26: 2811-7

Bakkevig K, Sletta H, Gimmestad M, Aune R, Ertesvag H, et al. 2005. Role of the *Pseudomonas fluorescens* alginate lyase (AlgL) in clearing the periplasm of alginates not exported to the extracellular environment. *J Bacteriol* 187: 8375-84

Bardas G A, Veloukas T, Koutita O, Karaoglanidis G S. 2010. Multiple resistance of *Botrytis cinerea* from kiwifruit to SDHIs, QoIs and fungicides of other chemical groups. *Pest management science* 66: 967-73

Billings N, Millan M, Caldara M, Rusconi R, Tarasova Y, et al. 2013. The extracellular matrix Component Psl provides fast-acting antibiotic defense in *Pseudomonas aeruginosa* biofilms. *PLoS Pathog* 9: e1003526

Bjarnsholt T. 2013. The role of bacterial biofilms in chronic infections. *APMIS. Supplementum:* 1-51

Bjarnsholt T, Ciofu O, Molin S, Givskov M, Hoiby N. 2013. Applying insights from biofilm biology to drug development—can a new approach be developed? *Nature reviews. Drug discovery* 12: 791-808

Bragonzi A, Farulla I, Paroni M, Twomey K B, Pirone L, et al. 2012. Modelling co-infection of the cystic fibrosis lung by *Pseudomonas aeruginosa* and *Burkholderia cenocepacia* reveals influences on biofilm formation and host response. *PloS one* 7: e52330

Branda S S, Vik S, Friedman L, Kolter R. 2005. Biofilms: the matrix revisited. *Trends in microbiology* 13: 20-6

Byrd M S, Pang B, Hong W, Waligora E A, Juneau R A, et al. 2011. Direct evaluation of *Pseudomonas aeruginosa* biofilm mediators in a chronic infection model. *Infection and immunity* 79: 3087-95

Byrd M S, Pang B, Mishra M, Swords W E, Wozniak D J. 2010. The *Pseudomonas aeruginosa* exopolysaccharide Psl facilitates surface adherence and NF-kappaB activation in A549 cells. *mBio* 1

Byrd M S, Sadovskaya I, Vinogradov E, Lu H, Sprinkle A B, et al. 2009. Genetic and biochemical analyses of the *Pseudomonas aeruginosa* Psl exopolysaccharide reveal overlapping roles for polysaccharide synthesis enzymes in Psl and LPS production. *Mol Microbiol* 73: 622-38

Cerca N, Jefferson K K, Maira-Litran T, Pier D B, Kelly-Quintos C, et al. 2007. Molecular basis for preferential protective efficacy of antibodies directed to the poorly acetylated form of staphylococcal poly-N-acetyl-beta-(1-6)-glucosaminev. *Infect Immun* 75: 3406-13

Choi A H, Slamti L, Avci F Y, Pier G B, Maira-Litran T. 2009. The pgaABCD locus of *Acinetobacter baumannii* encodes the production of poly-beta-1-6-N-acetylglucosamine, which is critical for biofilm formation. *J Bacteriol* 191: 5953-63

Colvin K M, Alnabelseya N, Baker P, Whitney J C, Howell P L, Parsek M R. 2013. PelA deacetylase activity is required for Pel polysaccharide synthesis in *Pseudomonas aeruginosa*. *J Bacteriol* 195: 2329-39

Colvin K M, Gordon V D, Murakami K, Borlee B R, Wozniak D J, et al. 2011. The pel polysaccharide can serve a structural and protective role in the biofilm matrix of *Pseudomonas aeruginosa*. *PLoS pathogens* 7: e1001264

Colvin K M, Irie Y, Tart C S, Urbano R, Whitney J C, et al. 2012. The Pel and Psl polysaccharides provide *Pseudomonas aeruginosa* structural redundancy within the biofilm matrix. *Environmental microbiology* 14: 1913-28

Conover M S, Sloan G P, Love C F, Sukumar N, Deora R. 2010. The Bps polysaccharide of *Bordetella pertussis* promotes colonization and biofilm formation in the nose by functioning as an adhesin. *Mol Microbiol* 77: 1439-55

Costerton J W, Cheng K J, Geesey G G, Ladd T I, Nickel J C, et al. 1987. Bacterial biofilms in nature and disease. *Annual review of microbiology* 41: 435-64

Costerton J W, Stewart P S, Greenberg E P. 1999. Bacterial biofilms: a common cause of persistent infections. *Science* 284: 1318-22

Cywes-Bentley C, Skurnik D, Zaidi T, Roux D, Deoliveira R B, et al. 2013. Antibody to a conserved antigenic target is protective against diverse prokaryotic and eukaryotic pathogens. *Proc Natl Acad Sci USA* 110: E2209-18

Darouiche R O, Mansouri M D, Gawande P V, Madhyastha S. 2009. Antimicrobial and antibiofilm efficacy of triclosan and DispersinB combination. *The Journal of antimicrobial chemotherapy* 64: 88-93

Davies D. 2003. Understanding biofilm resistance to antibacterial agents. *Nature reviews. Drug discovery* 2: 114-22

Davies G, Henrissat B. 1995. Structures and mechanisms of glycosyl hydrolases. *Structure* 3: 853-9

Dean R, Van Kan J A, Pretorius Z A, Hammond-Kosack K E, Di Pietro A, et al. 2012. The Top 10 fungal pathogens in molecular plant pathology. *Molecular plant pathology* 13: 414-30

Digiandomenico A, Warrener P, Hamilton M, Guillard S, Ravn P, et al. 2012. Identification of broadly protective human antibodies to Pseudomonas aeruginosa exopolysaccharide Psl by phenotypic screening. *The Journal of experimental medicine* 209: 1273-87

Dolinsky T J, Czodrowski P, Li H, Nielsen J E, Jensen J H, et al. 2007. PDB2PQR: expanding and upgrading automated preparation of biomolecular structures for molecular simulations. *Nucleic Acids Res* 35: W522-5

Donelli G, Francolini I, Romoli D, Guaglianone E, Piozzi A, et al. 2007. Synergistic activity of dispersin B and cefamandole nafate in inhibition of staphylococcal biofilm growth on polyurethanes. *Antimicrobial agents and chemotherapy* 51: 2733-40

Ellis M, Richardson M, de Pauw B. 2000. Epidemiology. *Hospital medicine* 61: 605-9 Emsley P, Cowtan K. 2004. Coot: model-building tools for molecular graphics. *Acta Crystallogr D Biol Crystallogr* 60: 2126-32

Escobar-Chavez J J, Lopez-Cervantes M, Naik A, Kalia Y N, Quintanar-Guerrero D, Ganem-Quintanar A. 2006. Applications of thermo-reversible pluronic F-127 gels in pharmaceutical formulations. *Journal of pharmacy & pharmaceutical sciences: a publication of the Canadian Society for Pharmaceutical Sciences, Societe canadienne des sciences pharmaceutiques* 9: 339-58

Flemming H C, Wingender J. 2010. The biofilm matrix. *Nature reviews. Microbiology* 8: 623-33

Fontaine T, Delangle A, Simenel C, Coddeville B, van Vliet S J, et al. 2011. Galactosaminogalactan, a new immunosuppressive polysaccharide of Aspergillus fumigatus. *PLoS pathogens* 7: e1002372

Franklin M J, Nivens D E, Weadge J T, Howell P L. 2011. Biosynthesis of the Pseudomonas aeruginosa Extracellular Polysaccharides, Alginate, Pel, and Psl. *Front Microbiol* 2: 167

Friedman L, Kolter R. 2004a. Genes involved in matrix formation in Pseudomonas aeruginosa PA14 biofilms. *Mol Microbiol* 51: 675-90

Friedman L, Kolter R. 2004b. Two genetic loci produce distinct carbohydrate-rich structural components of the Pseudomonas aeruginosa biofilm matrix. *J Bacteriol* 186: 4457-65

Gawande P V, Leung K P, Madhyastha S. 2014. Antibiofilm and Antimicrobial Efficacy of DispersinB-KSL-W Peptide-Based Wound Gel Against Chronic Wound Infection Associated Bacteria. *Current microbiology*

Geiser D M, Klich M A, Frisvad J C, Peterson S W, Varga J, Samson R A. 2007. The current status of species recognition and identification in Aspergillus. *Studies in mycology* 59: 1-10

Grabke A, Fernandez-Ortuno D, Amiri A, Li X, Peres N A, et al. 2014. Characterization of iprodione resistance in Botrytis cinerea from strawberry and blackberry. *Phytopathology* 104: 396-402

Gravelat F N, Beauvais A, Liu H, Lee M J, Snarr B D, et al. 2013. Aspergillus galactosaminogalactan mediates adherence to host constituents and conceals hyphal beta-glucan from the immune system. *PLoS pathogens* 9: e1003575

Gravelat F N, Doedt T, Chiang L Y, Liu H, Filler S G, et al. 2008. In vivo analysis of Aspergillus fumigatus developmental gene expression determined by real-time reverse transcription-PCR. *Infect. Immun.* 76: 3632-39

Hall-Stoodley L, Costerton J W, Stoodley P. 2004. Bacterial biofilms: from the natural environment to infectious diseases. *Nat Rev Microbiol* 2: 95-108

Hare N J, Solis N, Harmer C, Marzook N B, Rose B, et al. 2012. Proteomic profiling of Pseudomonas aeruginosa AES-1R, PAO1 and PA14 reveals potential virulence determinants associated with a transmissible cystic fibrosis-associated strain. *BMC microbiology* 12: 16

Henrissat B, Bairoch A. 1996. Updating the sequence-based classification of glycosyl hydrolases. *The Biochemical journal* 316 (Pt 2): 695-6

Hoffman L R, D'Argenio D A, MacCoss M J, Zhang Z, Jones R A, Miller S I. 2005. Aminoglycoside antibiotics induce bacterial biofilm formation. *Nature* 436: 1171-5

Hoiby N, Bjarnsholt T, Givskov M, Molin S, Ciofu O. 2010. Antibiotic resistance of bacterial biofilms. *Int J Antimicrob Agents* 35: 322-32

Hoiby N, Ciofu O, Johansen H K, Song Z J, Moser C, et al. 2011. The clinical impact of bacterial biofilms. *International journal of oral science* 3: 55-65

Holm L, Kaariainen S, Rosenstrom P, Schenkel A. 2008. Searching protein structure databases with DaliLite v.3. *Bioinformatics* 24: 2780-1

Huse H K, Kwon T, Zlosnik J E, Speert D P, Marcotte E M, Whiteley M. 2013. Pseudomonas aeruginosa Enhances Production of a Non-Alginate Exopolysaccharide during Long-Term Colonization of the Cystic Fibrosis Lung. *PloS one* 8: e82621

Irie Y, Borlee B R, O'Connor J R, Hill P J, Harwood C S, et al. 2012. Self-produced exopolysaccharide is a signal that stimulates biofilm formation in Pseudomonas aeruginosa. *Proceedings of the National Academy of Sciences of the United States of America* 109: 20632-6

Itoh Y, Rice J D, Goller C, Pannuri A, Taylor J, et al. 2008. Roles of pgaABCD genes in synthesis, modification, and export of the Escherichia coli biofilm adhesin poly-beta-1,6-N-acetyl-D-glucosamine. *Journal of bacteriology* 190: 3670-80

Itoh Y, Wang X, Hinnebusch B J, Preston J F, 3rd, Romeo T. 2005. Depolymerization of beta-1,6-N-acetyl-D-glucosamine disrupts the integrity of diverse bacterial biofilms. *Journal of bacteriology* 187: 382-7

Izano E A, Sadovskaya I, Vinogradov E, Mulks M H, Velliyagounder K, et al. 2007. Poly-N-acetylglucosamine mediates biofilm formation and antibiotic resistance in Actinobacillus pleuropneumoniae. *Microbial pathogenesis* 43: 1-9

Izano E A, Sadovskaya I, Wang H, Vinogradov E, Ragunath C, et al. 2008. Poly-N-acetylglucosamine mediates biofilm formation and detergent resistance in Aggregatibacter actinomycetemcomitans. *Microbial pathogenesis* 44: 52-60

Jackson K D, Starkey M, Kremer S, Parsek M R, Wozniak D J. 2004. Identification of psl, a locus encoding a potential exopolysaccharide that is essential for Pseudomonas aeruginosa PAO1 biofilm formation. *Journal of bacteriology* 186: 4466-75

Jain S, Ohman D E. 1998. Deletion of algK in mucoid Pseudomonas aeruginosa blocks alginate polymer formation and results in uronic acid secretion. *Journal of bacteriology* 180: 634-41

Jarrett C O, Deak E, Isherwood K E, Oyston P C, Fischer E R, et al. 2004. Transmission of Yersinia pestis from an infectious biofilm in the flea vector. *J Infect Dis* 190: 783-92

Kall L, Krogh A, Sonnhammer E L. 2004. A combined transmembrane topology and signal peptide prediction method. *Journal of molecular biology* 338: 1027-36

Kaplan J B, Velliyagounder K, Ragunath C, Rohde H, Mack D, et al. 2004. Genes involved in the synthesis and degradation of matrix polysaccharide in *Actinobacillus actinomycetemcomitans* and *Actinobacillus pleuropneumoniae* biofilms. *Journal of bacteriology* 186: 8213-20

Kelley L A, Sternberg M J. 2009. Protein structure prediction on the Web: a case study using the Phyre server. *Nature protocols* 4: 363-71

Kim J, Hahn J S, Franklin M J, Stewart P S, Yoon J. 2009. Tolerance of dormant and active cells in *Pseudomonas aeruginosa* PA01 biofilm to antimicrobial agents. *The Journal of antimicrobial chemotherapy* 63: 129-35

Krogh A, Larsson B, von Heijne G, Sonnhammer E L. 2001. Predicting transmembrane protein topology with a hidden Markov model: application to complete genomes. *Journal of molecular biology* 305: 567-80

Kukavica-lbrulj I, Bragonzi A, Paroni M, Winstanley C, Sanschagrin F, et al. 2008. In vivo growth of *Pseudomonas aeruginosa* strains PAO1 and PA14 and the hypervirulent strain LESB58 in a rat model of chronic lung infection. *Journal of bacteriology* 190: 2804-13

Kumar C G, Anand S K. 1998. Significance of microbial biofilms in food industry: a review. *International journal of food microbiology* 42: 9-27

Lee D G, Urbach J M, Wu G, Liberati N T, Feinbaum R L, et al. 2006. Genomic analysis reveals that *Pseudomonas aeruginosa* virulence is combinatorial. *Genome biology* 7: R90

Lee J E, Cornell K A, Riscoe M K, Howell P L. 2001. Structure of *E. coli* 5'-methylthioadenosine/S-adenosylhomocysteine nucleosidase reveals similarity to the purine nucleoside phosphorylases. *Structure* 9: 941-53

Leroch M, Plesken C, Weber R W, Kauff F, Scalliet G, Hahn M. 2013. Gray mold populations in german strawberry fields are resistant to multiple fungicides and dominated by a novel clade closely related to *Botrytis cinerea*. *Appl Environ Microbiol* 79: 159-67

Lin S J, Schranz J, Teutsch S M. 2001. Aspergillosis case—fatality rate: systematic review of the literature. *Clinical infectious diseases: an official publication of the Infectious Diseases Society of America* 32: 358-66

Little D J, Li G, Ing C, DiFrancesco B R, Bamford N C, et al. 2014. Modification and periplasmic translocation of the biofilm exopolysaccharide poly-β-1,6-N-acetyl-D-glucosamine. *Proc Natl Acad Sci USA* Submitted Little D J, Poloczek J, Whitney J C, Robinson H, Nitz M, Howell P L. 2012a. The structure- and metal-dependent activity of *Escherichia coli* PgaB provides insight into the partial de-N-acetylation of poly-beta-1,6-N-acetyl-D-glucosamine. *The Journal of biological chemistry* 287: 31126-37

Little D J, Whitney J C, Robinson H, Yip P, Nitz M, Howell P L. 2012b. Combining in situ proteolysis and mass spectrometry to crystallize *Escherichia coli* PgaB. *Acta crystallographica. Section F, Structural biology and crystallization communications* 68: 842-5

Lombard V, Golaconda Ramulu H, Drula E, Coutinho P M, Henrissat B. 2014. The carbohydrate-active enzymes database (CAZy) in 2013. *Nucleic acids research* 42: D490-5

Loussert C, Schmitt C, Prevost M C, Balloy V, Fadel E, et al. 2010. In vivo biofilm composition of *Aspergillus fumigatus*. *Cellular microbiology* 12: 405-10

Ma L, Conover M, Lu H, Parsek M R, Bayles K, Wozniak D J. 2009. Assembly and development of the *Pseudomonas aeruginosa* biofilm matrix. *PLoS pathogens* 5: e1000354

Ma L, Jackson K D, Landry R M, Parsek M R, Wozniak D J. 2006. Analysis of *Pseudomonas aeruginosa* conditional psi variants reveals roles for the psi polysaccharide in adhesion and maintaining biofilm structure postattachment. *Journal of bacteriology* 188: 8213-21

Ma L, Wang S, Wang D, Parsek M R, Wozniak D J. 2012. The roles of biofilm matrix polysaccharide Psl in mucoid *Pseudomonas aeruginosa* biofilms. *FEMS immunology and medical microbiology* 65: 377-80

Mack D, Fischer W, Krokotsch A, Leopold K, Hartmann R, et al. 1996. The intercellular adhesin involved in biofilm accumulation of *Staphylococcus epidermidis* is a linear beta-1,6-linked glucosaminoglycan: purification and structural analysis. *J Bacteriol* 178: 175-83

Mah T F, Pitts B, Pellock B, Walker G C, Stewart P S, O'Toole G A. 2003. A genetic basis for *Pseudomonas aeruginosa* biofilm antibiotic resistance. *Nature* 426: 306-10

Maharaj R, May T B, Wang S K, Chakrabarty A M. 1993. Sequence of the alg8 and alg44 genes involved in the synthesis of alginate by *Pseudomonas aeruginosa*. *Gene* 136: 267-9

Mann E E, Wozniak D J. 2012. *Pseudomonas* biofilm matrix composition and niche biology. *FEMS microbiology reviews* 36: 893-916

Manuel S G, Ragunath C, Sait H B, Izano E A, Kaplan J B, Ramasubbu N. 2007. Role of active-site residues of dispersin B, a biofilm-releasing beta-hexosaminidase from a periodontal pathogen, in substrate hydrolysis. *The FEBS journal* 274: 5987-99

Matsukawa M, Greenberg E P. 2004. Putative exopolysaccharide synthesis genes influence *Pseudomonas aeruginosa* biofilm development. *Journal of bacteriology* 186: 4449-56

McKenney D, Pouliot K L, Wang Y, Murthy V, Ulrich M, et al. 1999. Broadly protective vaccine for *Staphylococcus aureus* based on an in vivo-expressed antigen. *Science* 284: 1523-7

Merritt J H, Kadouri D E, O'Toole G A. 2005. Growing and analyzing static biofilms. *Current protocols in microbiology* Chapter 1: Unit 1B 1

Michielse C B, Rep M. 2009. Pathogen profile update: *Fusarium oxysporum*. *Molecular plant pathology* 10: 311-24

Mishra M, Byrd M S, Sergeant S, Azad A K, Parsek M R, et al. 2012. *Pseudomonas aeruginosa* Psl polysaccharide reduces neutrophil phagocytosis and the oxidative response by limiting complement-mediated opsonization. *Cellular microbiology* 14: 95-106

Monday S R, Schiller N L. 1996. Alginate synthesis in *Pseudomonas aeruginosa*: the role of AlgL (alginate lyase) and AlgX. *Journal of bacteriology* 178: 625-32

Nieman C E, Wong A W, He S, Clarke L, Hopwood J J, Withers S G. 2003. Family 39 alpha-l-iduronidases and beta-D-xylosidases react through similar glycosyl-enzyme intermediates: identification of the human iduronidase nucleophile. *Biochemistry* 42: 8054-65

Otwinowski Z, Minor W. 1997. Processing of X-ray diffraction data collected in oscillation mode, pp. 307-26: Elsevier Painter J, Merritt E A. 2006. Optimal description of a protein structure in terms of multiple groups undergoing TLS motion. *Acta Crystallogr D Biol Crystallogr* 62: 439-50

Parise G, Mishra M, Itoh Y, Romeo T, Deora R. 2007. Role of a putative polysaccharide locus in *Bordetella* biofilm development. *J Bacteriol* 189: 750-60

Park B H, Karpinets T V, Syed M H, Leuze M R, Uberbacher E C. 2010. CAZymes Analysis Toolkit (CAT): web service for searching and analyzing carbohydrate-active enzymes in a newly sequenced organism using CAZy database. *Glycobiology* 20: 1574-84

Petersen T N, Brunak S, von Heijne G, Nielsen H. 2011. SignalP 4.0: discriminating signal peptides from transmembrane regions. *Nature methods* 8: 785-6

Pokrovskaya V, Poloczek J, Little D J, Griffiths H, Howell P L, Nitz M. 2013. Functional characterization of *Staphylococcus epidermidis* IcaB, a de-N-acetylase important for biofilm formation. *Biochemistry* 52: 5463-71

Rahme L G, Stevens E J, Wolfort S F, Shao J, Tompkins R G, Ausubel F M. 1995. Common virulence factors for bacterial pathogenicity in plants and animals. *Science* 268: 1899-902

Rodriguez A, Acosta A, Rodriguez C. 2014. Fungicide resistance of *Botrytis cinerea* in tomato greenhouses in the Canary Islands and effectiveness of non-chemical treatments against gray mold. *World journal of microbiology & biotechnology* 30: 2397-406

Rybtke M T, Jensen P O, Hoiby N, Givskov M, Tolker-Nielsen T, Bjarnsholt T. 2011. The implication of *Pseudomonas aeruginosa* biofilms in infections. *Inflammation & allergy drug targets* 10: 141-57

Sang H, Hulvey J, Popko J T, Jr., Lopes J, Swaminathan A, et al. 2015. A pleiotropic drug resistance transporter is involved in reduced sensitivity to multiple fungicide classes in *Sclerotinia homoeocarpa* (F. T. Bennett). *Molecular plant pathology* 16: 251-61

Schneidman-Duhovny D, Inbar Y, Nussinov R, Wolfson H J. 2005. PatchDock and SymmDock: servers for rigid and symmetric docking. *Nucleic acids research* 33: W363-7

Singh N. 2000. The current management of infectious diseases in the liver transplant recipient. *Clinics in liver disease* 4: 657-73, ix Skurnik D, Roux D, Aschard H, Cattoir V, Yoder-Himes D, et al. 2013. A comprehensive analysis of in vitro and in vivo genetic fitness of *Pseudomonas aeruginosa* using high-throughput sequencing of transposon libraries. *PLoS pathogens* 9: e1003582

Sloan G P, Love C F, Sukumar N, Mishra M, Deora R. 2007. The *Bordetella* Bps polysaccharide is critical for biofilm development in the mouse respiratory tract. *J Bacteriol* 189: 8270-6

St John F J, Gonzalez J M, Pozharski E. 2010. Consolidation of glycosyl hydrolase family 30: a dual domain 4/7 hydrolase family consisting of two structurally distinct groups. *FEBS letters* 584: 4435-41

Starkey M, Hickman J H, Ma L, Zhang N, De Long S, et al. 2009. *Pseudomonas aeruginosa* rugose small-colony variants have adaptations that likely promote persistence in the cystic fibrosis lung. *J Bacteriol* 191: 3492-503

Stewart P S. 2003. New ways to stop biofilm infections. *Lancet* 361: 97

Stewart P S, Costerton J W. 2001. Antibiotic resistance of bacteria in biofilms. *Lancet* 358: 135-8

Stover C K, Pham X Q, Erwin A L, Mizoguchi S D, Warrener P, et al. 2000. Complete genome sequence of *Pseudomonas aeruginosa* PA01, an opportunistic pathogen. *Nature* 406: 959-64

Sutherland I. 2001a. Biofilm exopolysaccharides: a strong and sticky framework. *Microbiology* 147: 3-9

Sutherland I W. 2001b. The biofilm matrix—an immobilized but dynamic microbial environment. *Trends Microbiol* 9: 222-7

Terwilliger T C, Berendzen J. 1999. Automated MAD and MIR structure solution. *Acta Crystallogr D Biol Crystallogr* 55: 849-61

Tian L, Xu S, Hutchins W C, Yang C H, Li J. 2014. Impact of the exopolysaccharides Pel and Psl on the initial adhesion of *Pseudomonas aeruginosa* to sand. *Biofouling* 30: 213-22

Tong K B, Lau C J, Murtagh K, Layton A J, Seifeldin R. 2009. The economic impact of aspergillosis: analysis of hospital expenditures across patient subgroups. *International journal of infectious diseases: IJID: official publication of the International Society for Infectious Diseases* 13: 24-36

Turk R, Singh A, Rousseau J, Weese J S. 2013. In vitro evaluation of DispersinB on methicillin-resistant *Staphylococcus pseudintermedius* biofilm. *Veterinary microbiology* 166: 576-9

Van Houdt R, Michiels C W. 2010. Biofilm formation and the food industry, a focus on the bacterial outer surface. *Journal of applied microbiology* 109: 1117-31

Vocadlo D J, MacKenzie L F, He S, Zeikus G J, Withers S G. 1998. Identification of glu-277 as the catalytic nucleophile of *Thermoanaerobacterium saccharolyticum* beta-xylosidase using electrospray MS. *The Biochemical journal* 335 (Pt 2): 449-55

Vocadlo D J, Wicki J, Rupitz K, Withers S G. 2002. A case for reverse protonation: identification of Glu160 as an acid/base catalyst in *Thermoanaerobacterium saccharolyticum* beta-xylosidase and detailed kinetic analysis of a site-directed mutant. *Biochemistry* 41: 9736-46

Vu B, Chen M, Crawford R J, Ivanova E P. 2009. Bacterial extracellular polysaccharides involved in biofilm formation. *Molecules* 14: 2535-54

Vuong C, Kocianova S, Voyich J M, Yao Y F, Fischer E R, et al. 2004. A crucial role for exopolysaccharide modification in bacterial biofilm formation, immune evasion, and virulence. *J Biol Chem* 279: 54881-86

Wang S, Parsek M R, Wozniak D J, Ma L Z. 2013. A spider web strategy of type IV pili-mediated migration to build a fibre-like Psl polysaccharide matrix in *Pseudomonas aeruginosa* biofilms. *Environ Microbiol* 15: 2238-53

Wang X, Preston J F, 3rd, Romeo T. 2004. The pgaABCD locus of *Escherichia coli* promotes the synthesis of a polysaccharide adhesin required for biofilm formation. *J Bacteriol* 186: 2724-34

Wasylnka J A, Hissen A H, Wan A N, Moore M M. 2005. Intracellular and extracellular growth of *Aspergillus fumigatus*. *Medical mycology* 43 Suppl 1: S27-30

Wasylnka J A, Moore M M. 2000. Adhesion of *Aspergillus* species to extracellular matrix proteins: evidence for involvement of negatively charged carbohydrates on the conidial surface. *Infection and immunity* 68: 3377-84

Wasylnka J A, Moore M M. 2002. Uptake of *Aspergillus fumigatus* Conidia by phagocytic and nonphagocytic cells in vitro: quantitation using strains expressing green fluorescent protein. *Infection and immunity* 70: 3156-63

Wasylnka J A, Moore M M. 2003. *Aspergillus fumigatus* conidia survive and germinate in acidic organelles of A549 epithelial cells. *Journal of cell science* 116: 1579-87

Wiehlmann L, Wagner G, Cramer N, Siebert B, Gudowius P, et al. 2007. Population structure of *Pseudomonas aeruginosa*. *Proceedings of the National Academy of Sciences of the United States of America* 104: 8101-6

Wierenga R K. 2001. The TIM-barrel fold: a versatile framework for efficient enzymes. *FEBS letters* 492: 193-8

Wolcott R, Costerton J W, Raoult D, Cutler S J. 2013. The polymicrobial nature of biofilm infection. *Clinical microbiology and infection: the official publication of the European Society of Clinical Microbiology and Infectious Diseases* 19: 107-12

Wolfgang M C, Kulasekara B R, Liang X, Boyd D, Wu K, et al. 2003. Conservation of genome content and virulence determinants among clinical and environmental isolates of *Pseudomonas aeruginosa. Proc Natl Acad Sci USA* 100: 8484-9

Yakandawala N, Gawande P V, LoVetri K, Cardona S T, Romeo T, et al. 2011. Characterization of the poly-beta-1,6-N-acetylglucosamine polysaccharide component of *Burkholderia* biofilms. *Appl Environ Microbiol* 77: 8303-9

Zegans M E, Wozniak D, Griffin E, Toutain-Kidd C M, Hammond J H, et al. 2012. *Pseudomonas aeruginosa* exopolysaccharide Psl promotes resistance to the biofilm inhibitor polysorbate 80. *Antimicrobial agents and chemotherapy* 56: 4112-22

Zhao K, Tseng B S, Beckerman B, Jin F, Gibiansky M L, et al. 2013. Psl trails guide exploration and microcolony formation in *Pseudomonas aeruginosa* biofilms. *Nature* 497: 388-91

The invention claimed is:

1. A method of treating a biofilm-related infection comprising administering to an animal or plant in need thereof a soluble protein comprising a PelA glycosyl hydrolase (GH) domain, wherein the soluble protein consists of the amino acid sequence as shown in SEQ ID NO:12, 13, 14, or 15 or the soluble protein consists of an amino acid sequence having at least 95% sequence identity to the full length of SEQ ID NO: 12, 13, 14 or 15, wherein the soluble protein is able to hydrolyze a glycosidic bond.

2. The method of claim 1, wherein the biofilm-related infection is the result of a wound, burn infection, keratitis, bioprosthetic or indwelling medical device infection in the animal or wherein the biofilm-related infection is in the lung of the animal and wherein the animal has chronic pulmonary disease or lung infection.

3. The method of claim 1, wherein the biofilm-related infection is on the surface of, or within the plant or a plant part.

4. The method of claim 1, wherein the biofilm-related infection is caused by *P. aeruginosa*, and/or *Aspergillus* spp.

5. The method of claim 1 further comprising co-administering an antimicrobial agent to the animal or plant in need thereof.

6. The method of claim 1, wherein the soluble protein is expressed by a phage vector that is able to invade bacteria associated with the biofilm-related infection or is expressed by a mycoviral vector that is able to invade fungi associated with the biofilm-related infection.

7. The method of claim 1, further comprising administering at least one of:
(i) a soluble protein comprising a Sph3 GH domain comprising the amino acid sequence as shown in SEQ ID NO:20, SEQ ID NO:22 or SEQ ID NO:23 or an amino acid sequence having at least 95% sequence identity thereto,
(ii) a soluble protein comprising a BpsB GH domain comprising the amino acid sequence as shown in SEQ ID NO:18 or SEQ ID NO:19 or an amino acid sequence having at least 95% sequence identity thereto,
(iii) a soluble protein comprising a PgaB GH domain comprising the amino acid sequence as shown in SEQ ID NO:16 or SEQ ID NO: 17 or an amino acid sequence having at least 95% sequence identity thereto, and/or
(iv) a soluble protein comprising an Ega3 GH domain comprising the amino acid sequence as shown in SEQ ID NO:21 or an amino acid sequence having at least 95% sequence identity thereto; wherein the soluble protein is able to hydrolyze a glycosidic bond.

8. The method of claim 1, wherein the soluble protein consists of the amino acid sequence of SEQ ID NO: 12, 13, 14 or 15.

9. The method of claim 7, wherein the biofilm-related infection is caused by *P. aeruginosa, S. aureus, E. coli, Candida* spp., *Aspergillus* spp., *Acinetobacter* spp., *T. asahii, B. cineria* and/or *Fusarium* spp.

* * * * *

```
                            SEQUENCE LISTING

<160> NUMBER OF SEQ ID NOS: 25

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
gggcatatgg agatccaggt actgaag                                              27

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
gggaagcttt cactcccaga ccagca                                               26

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ctgcatatgg gcgggccgtc cagcgtggcg                                           30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
tttctcgagt cacggttgca cctcgacgtc                                           30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gcgcatatgg cggacgcacc gaacattgcc                                           30
```

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
gggaagcttt cacggcagca cctcgatgcg cc                          32

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
gggcatatgc acctccttta agcgtggcct tg                          32

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gcgaagcttt cacggcataa cctccacgct ccc                         33

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
gggcatatgt ccaaggtctt tgtgcctctc tatgtg                      36

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
ggctcgagct attttcccat caaatccaca aactc                       35

<210> SEQ ID NO 11
<211> LENGTH: 412
<212> TYPE: PRT
<213> ORGANISM: Pseudomonas aeruginosa

<400> SEQUENCE: 11

Glu Ile Gln Val Leu Lys Ala Pro Arg Ala Val Trp Lys Asp Phe
1               5                   10                  15

Leu Gly Val Asn Ala Gln Phe Leu Trp Phe Ser Pro Glu Arg Tyr Asn
                20                  25                  30

Lys Gln Ile Asp Arg Leu Gln Asp Leu Gly Leu Glu Trp Val Arg Leu
            35                  40                  45

Asp Leu His Trp Asp Arg Leu Glu Thr Ala Glu Asp Gln Tyr Gln Leu

```
            50                  55                  60
Ala Ser Leu Asp Gln Leu Val Lys Asp Leu Glu Ala Arg Gln Leu Lys
 65                  70                  75                  80

Ser Val Phe Tyr Leu Val Gly Ser Ala Arg Phe Ile Thr Thr Ala Pro
                 85                  90                  95

Phe Tyr Ser Pro Phe Gln Asp Gln Tyr Pro Pro Arg Asp Pro Glu Val
                100                 105                 110

Phe Ala Arg Arg Met Ala Met Leu Ser Gln Arg Tyr Pro Ser Val Ala
                115                 120                 125

Ala Trp Gln Val Trp Asn Glu Pro Asn Leu Ile Gly Phe Trp Arg Pro
130                 135                 140

Lys Ala Asp Pro Glu Gly Tyr Ala Lys Leu Leu Gln Ala Ser Thr Ile
145                 150                 155                 160

Ala Leu Arg Met Val Asp Pro Glu Lys Pro Val Val Ser Ala Gly Met
                165                 170                 175

Ala Phe Phe Ser Glu Met Pro Asp Gly Arg Thr Met Phe Asp Ala Leu
                180                 185                 190

Gly His Leu Gly Val Glu Ser Leu Gly Thr Ile Ala Thr Tyr His Pro
                195                 200                 205

Tyr Thr Gln Leu Pro Glu Gly Asn Tyr Pro Trp Asn Leu Asp Phe Val
210                 215                 220

Ser His Ala Asn Gln Ile Asn Arg Ala Leu Arg Asn Ala Gly Val Pro
225                 230                 235                 240

Ala Ile Trp Ser Thr Glu Trp Gly Trp Ser Ala Tyr Lys Gly Pro Lys
                245                 250                 255

Glu Leu Gln Asp Ile Ile Gly Val Glu Gly Gln Ala Asp Tyr Val Leu
                260                 265                 270

Arg Arg Leu Ala Leu Met Ser Ala Leu Asp Tyr Asp Arg Ile Phe Leu
                275                 280                 285

Phe Thr Leu Ser Asp Leu Asp Gln Arg Ala Ser Val Arg Asp Arg Asp
                290                 295                 300

Tyr Gly Leu Leu Asp Leu Asp Ala Asn Pro Lys Pro Val Tyr Leu Ala
305                 310                 315                 320

Leu Gln Arg Phe Leu Lys Val Thr Gly Pro Lys Leu Arg Pro Ala Asp
                325                 330                 335

Pro Pro Val Thr Glu Asp Leu Pro Asp Gly Ser Phe Ser Ile Gly Trp
                340                 345                 350

Thr Arg Glu Asp Gly Arg Asn Val Trp Leu Phe Trp Ser Ala Arg Gly
                355                 360                 365

Gly Asn Val Arg Leu Pro Lys Leu Lys Glu Ala Thr Leu His Asp Pro
370                 375                 380

Leu Ser Gly Lys Val Thr Pro Leu Ser Gly Asp Gly Leu Glu Val
385                 390                 395                 400

Pro Val Lys Ser Ser Leu Gln Met Leu Val Trp Glu
                405                 410

<210> SEQ ID NO 12
<211> LENGTH: 257
<212> TYPE: PRT
<213> ORGANISM: Pseudomonas aeruginosa

<400> SEQUENCE: 12

Gly Gly Pro Ser Ser Val Ala Phe Trp Tyr Ala Glu Arg Pro Pro Leu
 1                   5                  10                  15
```

Ala Glu Leu Ser Gln Phe Asp Trp Val Val Leu Glu Ala Ala His Leu
            20                  25                  30

Lys Pro Ala Asp Val Gly Tyr Leu Lys Glu Gln Gly Ser Thr Pro Phe
        35                  40                  45

Ala Tyr Leu Ser Val Gly Glu Phe Asp Gly Asp Ala Ala Ile Ala
    50                  55                  60

Asp Ser Gly Leu Ala Arg Gly Lys Ser Ala Val Arg Asn Gln Ala Trp
65                  70                  75                  80

Asn Ser Gln Val Met Asp Leu Ala Ala Pro Ser Trp Arg Ala His Leu
                85                  90                  95

Leu Lys Arg Ala Ala Glu Leu Arg Lys Gln Gly Tyr Ala Gly Leu Phe
            100                 105                 110

Leu Asp Thr Leu Asp Ser Phe Gln Leu Gln Ala Glu Glu Arg Arg Glu
        115                 120                 125

Gly Gln Arg Arg Ala Leu Ala Ser Phe Leu Ala Gln Leu His Arg Gln
130                 135                 140

Glu Pro Gly Leu Lys Leu Phe Phe Asn Arg Gly Phe Glu Val Leu Pro
145                 150                 155                 160

Glu Leu Pro Gly Val Ala Ser Ala Val Ala Val Glu Ser Ile His Ala
                165                 170                 175

Gly Trp Asp Ala Ala Ala Gly Gln Tyr Arg Glu Val Pro Gln Asp Asp
            180                 185                 190

Arg Asp Trp Leu Lys Gly His Leu Asp Ala Leu Arg Ala Gln Gly Met
        195                 200                 205

Pro Ile Val Ala Ile Asp Tyr Leu Pro Pro Glu Arg Arg Asp Glu Ala
    210                 215                 220

Arg Ala Leu Ala Ala Arg Leu Arg Ser Glu Gly Tyr Val Pro Phe Val
225                 230                 235                 240

Ser Thr Pro Ala Leu Asp Tyr Leu Gly Val Ser Asp Val Glu Val Gln
                245                 250                 255

Pro

<210> SEQ ID NO 13
<211> LENGTH: 257
<212> TYPE: PRT
<213> ORGANISM: Pseudomonas protogens

<400> SEQUENCE: 13

Ala Ala Pro Ala Ser Val Gly Phe Trp Tyr Ala Glu Gln Pro Pro Leu
1               5                   10                  15

Gln Glu Leu Ala Gln Phe Glu Trp Ala Val Val Glu Pro Gly His Met
            20                  25                  30

Ala Ser Ala Asp Val Ala Thr Leu Arg Lys Leu Gly Ser Gln Pro Phe
        35                  40                  45

Ala Tyr Leu Ser Val Gly Glu Phe Asp Gly Asn Arg Ala Ala Leu Ala
    50                  55                  60

Lys Gln Ala Leu Ala Gln Gly Ala Ser Pro Val Arg Asn Lys Ala Trp
65                  70                  75                  80

Asp Ser Gln Val Met Asp Ile Ala Thr Pro Ala Trp Arg Glu His Leu
                85                  90                  95

Phe Lys Arg Ala Lys Ala Leu Gln Asp Gln Gly Tyr Ala Gly Leu Phe
            100                 105                 110

Leu Asp Thr Leu Asp Ser Phe Gln Leu Leu Pro Glu Ala Asp Arg Glu
        115                 120                 125

```
Pro Gln Arg Lys Ala Leu Ala Ser Phe Leu Arg Glu Leu His Ser Arg
            130                 135                 140

Leu Pro Asn Leu Lys Leu Phe Phe Asn Arg Gly Phe Glu Val Leu Gly
145                 150                 155                 160

Glu Leu Asp Gly Val Ala Ser Ala Val Ala Val Glu Ser Ile His Ala
                165                 170                 175

Gly Trp Asp Ala Ser Ala Lys Arg Tyr Arg Pro Val Ser Glu Ala Asp
                180                 185                 190

Arg Thr Trp Leu Glu Gly Glu Leu Lys Pro Leu Arg Ala Arg Asn Ile
            195                 200                 205

Pro Leu Val Ala Ile Asp Tyr Leu Pro Ala Asn Arg Arg Glu Glu Ala
210                 215                 220

Arg Lys Leu Val Arg Gln Leu Ser Gln Glu Gly Phe Ile Pro Val Val
225                 230                 235                 240

Thr Thr Pro Asp Leu Asn Ala Leu Ser Met Ser Thr Val Glu Val Gln
                245                 250                 255

Pro

<210> SEQ ID NO 14
<211> LENGTH: 268
<212> TYPE: PRT
<213> ORGANISM: Geobacter metallireducens

<400> SEQUENCE: 14

Pro Pro Leu Ser Val Ala Leu Tyr Tyr Gly Lys Gln Pro Pro Val Asn
1               5                   10                  15

Asp Leu His Ala Phe Asp Ile Val Val Ile Asp Pro Asp Ser Gly Leu
                20                  25                  30

Thr Pro Ser Glu Tyr Gly Ser Gly Arg Ser Glu Leu Phe Ala Tyr Val
            35                  40                  45

Ser Val Gly Glu Ala Asp Thr Ala Arg Ser Tyr Thr Lys Gln Met Pro
50                  55                  60

Asp Arg Trp Ile Ile Gly Lys Asn Pro Val Trp Lys Ser Lys Ile Val
65                  70                  75                  80

Asp Val Ser Ser Glu Glu Trp Lys Gln Phe Phe Leu Asp Asp Val Val
                85                  90                  95

Glu Pro Leu Trp Gln Ala Gly Tyr Arg Gly Phe Phe Leu Asp Thr Leu
            100                 105                 110

Asp Ser Tyr Leu Ile Ala Ala Pro Thr Glu Ala His Pro Arg Met Glu
            115                 120                 125

Ala Gly Leu Val Ser Val Val Arg Ala Ile Arg Gln Arg His Pro Glu
            130                 135                 140

Ala Arg Leu Ile Leu Asn Arg Gly Phe Glu Ile Phe Asp Arg Val Lys
145                 150                 155                 160

Asp Leu Val Tyr Ala Val Ala Ala Glu Ser Leu Phe Gln Asn Phe Asn
                165                 170                 175

Thr Val Ser Gly Lys Tyr Gly Ala Val Asp Asp Lys Asp Arg Ser Trp
            180                 185                 190

Leu Thr Ser Arg Leu Asn Val Ile Arg Glu Thr Gly Val Pro Val Ile
            195                 200                 205

Ala Ile Asp Tyr Val Asp Pro Gly Asn Arg Pro Leu Met Arg Glu Thr
            210                 215                 220

Ala Asp Lys Ile Arg Ser Leu Gly Phe Thr Pro Trp Val Thr Asp Lys
225                 230                 235                 240
```

Asp Leu Ala Gly Leu Gly Ile Gly Ser Val Glu Val Met Pro Arg Thr
            245                 250                 255

Val Leu Gly Leu Tyr Asp Gly Gly Glu Gly Ala Gly
        260                 265

<210> SEQ ID NO 15
<211> LENGTH: 257
<212> TYPE: PRT
<213> ORGANISM: Ralstonia solanacearum

<400> SEQUENCE: 15

Ala Asp Ala Pro Asn Ile Ala Trp Phe Tyr Gly Asp Lys Pro Pro Val
1               5                   10                  15

Ala Gln Leu Arg Ala Phe Asp Ala Val Val Glu Pro Asp His Gly
            20                  25                  30

Phe Asp Pro Ser Arg Ala Lys Thr Pro Thr Thr Gln Trp Phe Ala Tyr
        35                  40                  45

Val Ser Val Gly Glu Val Ala Pro Glu Arg Arg Trp Tyr Lys Glu Leu
    50                  55                  60

Pro Lys Ala Trp Leu Ala Gly Ser Asn Ala Ala Trp Ala Ser His Val
65                  70                  75                  80

Ile Asp Gln Ser Gln Pro Gln Trp Pro Ala Phe Tyr Val Asp Arg Val
                85                  90                  95

Ile Ala Pro Leu Trp Asp Arg Gly Tyr Arg Gly Phe Phe Leu Asp Thr
            100                 105                 110

Leu Asp Ser Tyr Gln Leu Val Ala Lys Asp Asp Ala Ala Arg Ala Ala
        115                 120                 125

Gln Glu Ala Gly Met Val Arg Val Ile Arg Ala Ile Lys Ala Arg Tyr
    130                 135                 140

Pro Glu Ala Lys Leu Ile Phe Asn Arg Gly Phe Glu Ile Leu Pro Gln
145                 150                 155                 160

Val His Asp Leu Ala Tyr Ala Val Ala Phe Glu Ser Leu Tyr Arg Ala
                165                 170                 175

Trp Asp Gln Gly Asn Lys Gln Tyr Arg Glu Val Asn Asp Ala Asp Arg
            180                 185                 190

Ala Trp Leu Met Gly Gln Ala Arg Lys Ile Gln Asp Glu Tyr His Leu
        195                 200                 205

Pro Val Ile Ser Ile Asp Tyr Cys Pro Pro Ala Asp Arg Ala Cys Ala
    210                 215                 220

Arg Glu Thr Ala Lys Arg Ile Lys Ala Gln Gly Leu Ile Pro Tyr Val
225                 230                 235                 240

Thr Asp Pro Ala Leu Ser Thr Ile Gly Val Gly Arg Ile Glu Val Leu
                245                 250                 255

Pro

<210> SEQ ID NO 16
<211> LENGTH: 651
<212> TYPE: PRT
<213> ORGANISM: Escherichia coli

<400> SEQUENCE: 16

Ile Ser Gln Ser Arg Thr Ser Phe Ile Pro Pro Gln Asp Arg Glu Ser
1               5                   10                  15

Leu Leu Ala Glu Gln Pro Trp Pro His Asn Gly Phe Val Ala Ile Ser
            20                  25                  30

Trp His Asn Val Glu Asp Glu Ala Ala Asp Gln Arg Phe Met Ser Val

```
        35                  40                  45
Arg Thr Ser Ala Leu Arg Glu Gln Phe Ala Trp Leu Arg Glu Asn Gly
 50                  55                  60

Tyr Gln Pro Val Ser Ile Ala Gln Ile Arg Glu Ala His Arg Gly Gly
 65                  70                  75                  80

Lys Pro Leu Pro Glu Lys Ala Val Val Leu Thr Phe Asp Asp Gly Tyr
                 85                  90                  95

Gln Ser Phe Tyr Thr Arg Val Phe Pro Ile Leu Gln Ala Phe Gln Trp
                100                 105                 110

Pro Ala Val Trp Ala Pro Val Gly Ser Trp Val Asp Thr Pro Ala Asp
            115                 120                 125

Lys Gln Val Lys Phe Gly Asp Glu Leu Val Asp Arg Glu Tyr Phe Ala
130                 135                 140

Thr Trp Gln Gln Val Arg Glu Val Ala Arg Ser Arg Leu Val Glu Leu
145                 150                 155                 160

Ala Ser His Thr Trp Asn Ser His Tyr Gly Ile Gln Ala Asn Ala Thr
                165                 170                 175

Gly Ser Leu Leu Pro Val Tyr Val Asn Arg Ala Tyr Phe Thr Asp His
            180                 185                 190

Ala Arg Tyr Glu Thr Ala Ala Glu Tyr Arg Glu Arg Ile Arg Leu Asp
        195                 200                 205

Ala Val Lys Met Thr Glu Tyr Leu Arg Thr Lys Val Glu Val Asn Pro
210                 215                 220

His Val Phe Val Trp Pro Tyr Gly Glu Ala Asn Gly Ile Ala Ile Glu
225                 230                 235                 240

Glu Leu Lys Lys Leu Gly Tyr Asp Met Phe Thr Leu Glu Ser Gly
                245                 250                 255

Leu Ala Asn Ala Ser Gln Leu Asp Ser Ile Pro Arg Val Leu Ile Ala
            260                 265                 270

Asn Asn Pro Ser Leu Lys Glu Phe Ala Gln Gln Ile Ile Thr Val Gln
        275                 280                 285

Glu Lys Ser Pro Gln Arg Ile Met His Ile Asp Leu Asp Tyr Val Tyr
290                 295                 300

Asp Glu Asn Leu Gln Gln Met Asp Arg Asn Ile Asp Val Leu Ile Gln
305                 310                 315                 320

Arg Val Lys Asp Met Gln Ile Ser Thr Val Tyr Leu Gln Ala Phe Ala
                325                 330                 335

Asp Pro Asp Gly Asp Gly Leu Val Lys Glu Val Trp Phe Pro Asn Arg
            340                 345                 350

Leu Leu Pro Met Lys Ala Asp Ile Phe Ser Arg Val Ala Trp Gln Leu
        355                 360                 365

Arg Thr Arg Ser Gly Val Asn Ile Tyr Ala Trp Met Pro Val Leu Ser
370                 375                 380

Trp Asp Leu Asp Pro Thr Leu Thr Arg Val Lys Tyr Leu Pro Thr Gly
385                 390                 395                 400

Glu Lys Lys Ala Gln Ile His Pro Glu Gln Tyr His Arg Leu Ser Pro
                405                 410                 415

Phe Asp Asp Arg Val Arg Ala Gln Val Gly Met Leu Tyr Glu Asp Leu
            420                 425                 430

Ala Gly His Ala Ala Phe Asp Gly Ile Leu Phe His Asp Asp Ala Leu
        435                 440                 445

Leu Ser Asp Tyr Glu Asp Ala Ser Ala Pro Ala Ile Thr Ala Tyr Gln
450                 455                 460
```

```
Gln Ala Gly Phe Ser Gly Ser Leu Ser Glu Ile Arg Gln Asn Pro Glu
465                 470                 475                 480

Gln Phe Lys Gln Trp Ala Arg Phe Lys Ser Arg Ala Leu Thr Asp Phe
                485                 490                 495

Thr Leu Glu Leu Ser Ala Arg Val Lys Ala Ile Arg Gly Pro His Ile
            500                 505                 510

Lys Thr Ala Arg Asn Ile Phe Ala Leu Pro Val Ile Gln Pro Glu Ser
        515                 520                 525

Glu Ala Trp Phe Ala Gln Asn Tyr Ala Asp Phe Leu Lys Ser Tyr Asp
530                 535                 540

Trp Thr Ala Ile Met Ala Met Pro Tyr Leu Glu Gly Val Ala Glu Lys
545                 550                 555                 560

Ser Ala Asp Gln Trp Leu Ile Gln Leu Thr Asn Gln Ile Lys Asn Ile
                565                 570                 575

Pro Gln Ala Lys Asp Lys Ser Ile Leu Glu Leu Gln Ala Gln Asn Trp
            580                 585                 590

Gln Lys Asn Gly Gln His Gln Ala Ile Ser Ser Gln Leu Ala His
        595                 600                 605

Trp Met Ser Leu Leu Gln Leu Asn Gly Val Lys Asn Tyr Gly Tyr Tyr
610                 615                 620

Pro Asp Asn Phe Leu His Asn Gln Pro Glu Ile Asp Leu Ile Arg Pro
625                 630                 635                 640

Glu Phe Ser Thr Ala Trp Tyr Pro Lys Asn Asp
                645                 650

<210> SEQ ID NO 17
<211> LENGTH: 363
<212> TYPE: PRT
<213> ORGANISM: Escherichia coli

<400> SEQUENCE: 17

Glu Lys Ser Pro Gln Arg Ile Met His Ile Asp Leu Asp Tyr Val Tyr
1               5                   10                  15

Asp Glu Asn Leu Gln Gln Met Asp Arg Asn Ile Asp Val Leu Ile Gln
            20                  25                  30

Arg Val Lys Asp Met Gln Ile Ser Thr Val Tyr Leu Gln Ala Phe Ala
        35                  40                  45

Asp Pro Asp Gly Asp Gly Leu Val Lys Glu Val Trp Phe Pro Asn Arg
    50                  55                  60

Leu Leu Pro Met Lys Ala Asp Ile Phe Ser Arg Val Ala Trp Gln Leu
65                  70                  75                  80

Arg Thr Arg Ser Gly Val Asn Ile Tyr Ala Trp Met Pro Val Leu Ser
                85                  90                  95

Trp Asp Leu Asp Pro Thr Leu Thr Arg Val Lys Tyr Leu Pro Thr Gly
            100                 105                 110

Glu Lys Lys Ala Gln Ile His Pro Glu Gln Tyr His Arg Leu Ser Pro
        115                 120                 125

Phe Asp Asp Arg Val Arg Ala Gln Val Gly Met Leu Tyr Glu Asp Leu
    130                 135                 140

Ala Gly His Ala Ala Phe Asp Gly Ile Leu Phe His Asp Asp Ala Leu
145                 150                 155                 160

Leu Ser Asp Tyr Glu Asp Ala Ser Ala Pro Ala Ile Thr Ala Tyr Gln
                165                 170                 175

Gln Ala Gly Phe Ser Gly Ser Leu Ser Glu Ile Arg Gln Asn Pro Glu
```

```
                    180                 185                 190
Gln Phe Lys Gln Trp Ala Arg Phe Lys Ser Arg Ala Leu Thr Asp Phe
            195                 200                 205

Thr Leu Glu Leu Ser Ala Arg Val Lys Ala Ile Arg Gly Pro His Ile
        210                 215                 220

Lys Thr Ala Arg Asn Ile Phe Ala Leu Pro Val Ile Gln Pro Glu Ser
225                 230                 235                 240

Glu Ala Trp Phe Ala Gln Asn Tyr Ala Asp Phe Leu Lys Ser Tyr Asp
                245                 250                 255

Trp Thr Ala Ile Met Ala Met Pro Tyr Leu Glu Gly Val Ala Glu Lys
            260                 265                 270

Ser Ala Asp Gln Trp Leu Ile Gln Leu Thr Asn Gln Ile Lys Asn Ile
        275                 280                 285

Pro Gln Ala Lys Asp Lys Ser Ile Leu Glu Leu Gln Ala Gln Asn Trp
    290                 295                 300

Gln Lys Asn Gly Gln His Gln Ala Ile Ser Ser Gln Gln Leu Ala His
305                 310                 315                 320

Trp Met Ser Leu Leu Gln Leu Asn Gly Val Lys Asn Tyr Gly Tyr Tyr
                325                 330                 335

Pro Asp Asn Phe Leu His Asn Gln Pro Glu Ile Asp Leu Ile Arg Pro
            340                 345                 350

Glu Phe Ser Thr Ala Trp Tyr Pro Lys Asn Asp
        355                 360
```

<210> SEQ ID NO 18
<211> LENGTH: 675
<212> TYPE: PRT
<213> ORGANISM: Bordetella bronchiseptica

<400> SEQUENCE: 18

```
Tyr Lys Val Asp Met Leu Pro Pro Pro Asp Pro Asp Asp Gly Leu Thr
1               5                   10                  15

Phe Arg Val Leu Cys Met His Asp Val Arg Asp Asn Leu Arg Ala Ser
            20                  25                  30

Phe Ala Asp Met Pro Asp Gln Phe Ala Ile Glu Thr Arg Thr Leu Thr
        35                  40                  45

Asp Leu Phe Glu Trp Ile Arg Val Lys Gly Phe Asn Pro Ile Ser Met
    50                  55                  60

Gln Gln Ile Ile Asp Ser Arg Ala Gly Val Arg Pro Leu Pro Pro Arg
65                  70                  75                  80

Pro Ile Leu Leu Thr Phe Asp Asp Gly Tyr Ala Ser Thr Tyr Thr Lys
                85                  90                  95

Val Phe Pro Leu Leu Lys Lys Phe Asn Tyr Pro Ala Val Val Ala Val
            100                 105                 110

Val Thr Ser Trp Thr Asp Ala Pro Ala Gly Thr Lys Ile Arg Leu Ser
        115                 120                 125

Pro Lys Ile Glu Val Pro His Asp Phe Phe Met Thr Trp Ala Gln Leu
    130                 135                 140

Arg Glu Met Ala Gln Ser Gly Leu Val Glu Leu Ala Ser His Ser His
145                 150                 155                 160

Asn Leu His Arg Gly Val Leu Ala Asn Pro Gln Gly Asn Glu Gln Pro
                165                 170                 175

Ala Ala Ser Ser Arg Gln Tyr Leu Pro Ala Ser Gly Arg Tyr Glu Asn
            180                 185                 190
```

```
Asp Ala Glu Tyr Arg Ala Arg Val Arg Gln Asp Leu Lys Thr Ser Ala
            195                 200                 205

Asp Leu Ile Arg Glu His Thr Gly Val Thr Ile Arg Ser Ile Val Trp
        210                 215                 220

Pro Tyr Gly Ala His Asn Arg Asp Thr Asp Gln Val Ala Ala Glu Val
225                 230                 235                 240

Gly Leu Asn Ile Gly Leu Thr Leu Gln Pro Gly Pro Asn Thr Pro Asp
                245                 250                 255

Val Ala Leu Thr Gln Ile Arg Arg Ser Leu Val Asp Tyr Glu Val Asn
            260                 265                 270

Val Ala Thr Val Ala Arg Ala Met Arg Glu Pro Val Ser Tyr His Gly
        275                 280                 285

Gln Val Arg Pro Ile Glu Arg Ile Val Gln Val Asp Leu Asp Tyr Ile
290                 295                 300

Tyr Asp Pro Asp Pro Glu Gln Gln Asn Arg Asn Leu Gly Gln Leu Ile
305                 310                 315                 320

Asp Arg Met Lys Asp Leu Ala Pro Ser Ala Val Tyr Leu Gln Ala Phe
                325                 330                 335

Ala Asp Pro Lys Gly Asp Gly Asp Ile Thr Glu Val Tyr Phe Pro Asn
            340                 345                 350

Arg His Leu Pro Met Arg Ala Asp Leu Phe Asn Arg Val Ala Trp Gln
        355                 360                 365

Leu Lys Thr Arg Ala Gly Val Met Val Tyr Ala Trp Leu Pro Val Leu
    370                 375                 380

Thr Phe Ser Val Pro Pro Gly Asn Pro Ala Tyr Gly Lys Val Val Gln
385                 390                 395                 400

Ser Thr Thr Arg Lys Pro Gly Glu Arg Gly Leu Gly Ser Pro Thr Arg
                405                 410                 415

Leu Ser Pro Phe His Pro Asp Ala His Arg Val Ile Ser Glu Ile Tyr
            420                 425                 430

Glu Asp Leu Ala Lys Ala Ala His Phe Asp Gly Leu Leu Phe His Asp
        435                 440                 445

Asp Ala Val Leu Asp Asp Thr Glu Asp Ser Ser Pro Glu Ala Leu Ala
450                 455                 460

Thr Tyr Gln Gly Trp Gly Leu Pro Pro Asp Ile Ala Ala Ile Arg Ala
465                 470                 475                 480

Asp Pro Lys Leu Ala Gln Gln Trp Ser Lys Gly Lys Ile Arg Tyr Leu
                485                 490                 495

Ile Asp Phe Thr Met His Leu Arg His Ile Val Ser Gly Tyr Gln Asn
            500                 505                 510

Asp Arg Asp Met Val Val Ala Arg Asn Leu Tyr Ala Gln Pro Val Leu
        515                 520                 525

Asp Pro Val Ser Glu Ala Trp Tyr Gly Gln Ser Leu Pro Glu Phe Leu
530                 535                 540

Lys Ser Tyr Asp Phe Val Ala Leu Met Ala Met Pro Asn Met Glu Gly
545                 550                 555                 560

Ala Ala Arg Pro Glu Gln Trp Met Arg Gln Leu Val Ala Ala Val Ala
                565                 570                 575

Arg Gln Lys Gly Leu Asp Arg Thr Ile Phe Glu Leu Gln Ala Arg Asp
            580                 585                 590

Trp Arg Val Gly Lys Pro Ile Asp Thr Glu Ile Leu Arg Arg Gln Met
        595                 600                 605

Val Gln Leu Arg Ser Leu Gly Ala Ile Asn Tyr Gly Tyr Tyr Pro Asp
```

```
    610                 615                 620

Asp Phe Ile Ala Asn His Pro Asp Ala Glu Ala Leu Arg Asp Val Met
625                 630                 635                 640

Ser Leu Lys Ser Thr Leu Glu Lys Arg Arg Leu Thr Lys Ala Gln Glu
                645                 650                 655

Leu Ser Arg Gln Thr Thr Leu Tyr Gly Ser Ala Ser Gln Ala Glu Pro
            660                 665                 670

Thr Gln Arg
        675

<210> SEQ ID NO 19
<211> LENGTH: 353
<212> TYPE: PRT
<213> ORGANISM: Bordetella bronchiseptica

<400> SEQUENCE: 19

Pro Ile Glu Arg Ile Val Gln Val Asp Leu Asp Tyr Ile Tyr Asp Pro
1               5                   10                  15

Asp Pro Glu Gln Gln Asn Arg Asn Leu Gly Gln Leu Ile Asp Arg Met
            20                  25                  30

Lys Asp Leu Ala Pro Ser Ala Val Tyr Leu Gln Ala Phe Ala Asp Pro
        35                  40                  45

Lys Gly Asp Gly Asp Ile Thr Glu Val Tyr Phe Pro Asn Arg His Leu
    50                  55                  60

Pro Met Arg Ala Asp Leu Phe Asn Arg Val Ala Trp Gln Leu Lys Thr
65                  70                  75                  80

Arg Ala Gly Val Met Val Tyr Ala Trp Leu Pro Val Leu Thr Phe Ser
                85                  90                  95

Val Pro Pro Gly Asn Pro Ala Tyr Gly Lys Val Val Gln Ser Thr Thr
            100                 105                 110

Arg Lys Pro Gly Glu Arg Gly Leu Gly Ser Pro Thr Arg Leu Ser Pro
        115                 120                 125

Phe His Pro Asp Ala His Arg Val Ile Ser Glu Ile Tyr Glu Asp Leu
    130                 135                 140

Ala Lys Ala Ala His Phe Asp Gly Leu Leu Phe His Asp Asp Ala Val
145                 150                 155                 160

Leu Asp Asp Thr Glu Asp Ser Ser Pro Glu Ala Leu Ala Thr Tyr Gln
                165                 170                 175

Gly Trp Gly Leu Pro Pro Asp Ile Ala Ala Ile Arg Ala Asp Pro Lys
            180                 185                 190

Leu Ala Gln Gln Trp Ser Lys Gly Lys Ile Arg Tyr Leu Ile Asp Phe
        195                 200                 205

Thr Met His Leu Arg His Ile Val Ser Gly Tyr Gln Asn Asp Arg Asp
    210                 215                 220

Met Val Val Ala Arg Asn Leu Tyr Ala Gln Pro Val Leu Asp Pro Val
225                 230                 235                 240

Ser Glu Ala Trp Tyr Gly Gln Ser Leu Pro Glu Phe Leu Lys Ser Tyr
                245                 250                 255

Asp Phe Val Ala Leu Met Ala Met Pro Asn Met Glu Gly Ala Ala Arg
            260                 265                 270

Pro Glu Gln Trp Met Arg Gln Leu Val Ala Ala Val Ala Arg Gln Lys
        275                 280                 285

Gly Leu Asp Arg Thr Ile Phe Glu Leu Gln Ala Arg Asp Trp Arg Val
    290                 295                 300
```

```
Gly Lys Pro Ile Asp Thr Glu Ile Leu Arg Arg Gln Met Val Gln Leu
305                 310                 315                 320

Arg Ser Leu Gly Ala Ile Asn Tyr Gly Tyr Tyr Pro Asp Asp Phe Ile
                325                 330                 335

Ala Asn His Pro Asp Ala Glu Ala Leu Arg Asp Val Met Ser Leu Lys
                340                 345                 350

Ser
```

<210> SEQ ID NO 20
<211> LENGTH: 247
<212> TYPE: PRT
<213> ORGANISM: Aspergillus fumigatus

<400> SEQUENCE: 20

```
Ser Lys Val Phe Val Pro Leu Tyr Val Tyr Pro Ala Pro Gly Ala Trp
1               5                   10                  15

Thr Pro Leu Glu Asp Val Ile Ser Lys His Pro Asp Val Asn Phe Thr
                20                  25                  30

Val Val Ile Asn Pro Gly Ser Gly Pro Gly Pro Asn Ala Leu Pro Asp
            35                  40                  45

Gly Asn Tyr Thr Arg Glu Ile Pro Lys Leu Ala Ser Tyr Glu Asn Val
        50                  55                  60

Arg Leu Leu Gly Tyr Val Ala Thr Thr Tyr Ala Lys Arg Asn Ile Ser
65                  70                  75                  80

Leu Val Arg Arg Asp Ile Glu Thr Tyr Ala Ala Trp Pro Thr Asn Ser
                85                  90                  95

Ser Asn Pro Ala Leu Ala Val Arg Gly Ile Phe Phe Asp Glu Thr Pro
            100                 105                 110

Gln Gln Tyr Asp Glu Asp Ala Leu Ala Tyr Leu Gln Glu Leu Thr Asp
        115                 120                 125

Val Val Lys Asn Thr Pro Gly Leu Gly Pro Asp His Tyr Val Val His
    130                 135                 140

Asn Pro Gly Ala Ile Pro Asp Ser Arg Tyr Leu Ser Thr Ala Asp Ser
145                 150                 155                 160

Thr Val Val Phe Glu Ala Thr Tyr Asp Thr Phe Gln Glu Arg His Gly
                165                 170                 175

Ala Lys Leu Phe Glu Ala Ile Pro Asp Ser Asn Arg Ser Gln Leu Cys
            180                 185                 190

Ala Val Ile His Ser Val Pro Glu Ser Val Glu Gly Ser Ala Leu Arg
        195                 200                 205

Ser Leu Val Lys Gln Val Arg Lys Val Ala Asp Glu Ile Phe Ile Thr
    210                 215                 220

His Leu Asp Thr Asp Tyr Tyr Ala Ser Phe Gly Arg Gln Trp Pro Glu
225                 230                 235                 240

Phe Val Asp Leu Met Gly Lys
                245
```

<210> SEQ ID NO 21
<211> LENGTH: 273
<212> TYPE: PRT
<213> ORGANISM: Aspergillus fumigatus

<400> SEQUENCE: 21

```
Gly Leu Gly Gly Gly Gly Gly Glu Gly Glu Glu Gly Ser Gly Gly
1               5                   10                  15

Glu Thr Thr Pro Pro Glu Gly Asn Tyr Thr Thr Ala Lys Trp Gln Pro
```

```
            20                  25                  30
Ala Val Gly Thr Lys Trp Gln Ile Glu Leu Leu Tyr Ala Leu Asn Asp
            35                  40                  45

Thr Ser Val Asp Ala Glu Ile Tyr Asp Ile Asp Leu Phe Ile Asn Asp
        50                  55                  60

Lys Ser Thr Ile Ala Gly Leu Gln Arg Ala Gly Arg Lys Val Ile Cys
 65                 70                  75                  80

Tyr Phe Ser Ala Gly Ser Tyr Glu Asn Trp Arg Pro Asp Lys Asp Lys
                    85                  90                  95

Phe Lys Asp Ser Asp Leu Gly His Asp Leu Asp Trp Pro Gly Glu
                100                 105                 110

Lys Trp Leu Asn Ile Ser Ser Ala Asn Val Arg Gln Ile Met Leu Asp
                115                 120                 125

Arg Leu Asp Met Ala Arg Asp Lys Gly Cys Asp Gly Val Asp Pro Asp
            130                 135                 140

Asn Val Asp Gly Tyr Asp Asn Asp Gly Leu Asp Leu Thr Gln Ala
145                 150                 155                 160

Asp Ser Ile Ser Phe Val Asn Phe Leu Ala Asn Ala Ala His Ala Arg
                165                 170                 175

Asn Met Ser Ile Gly Leu Lys Asn Ala Gly Asp Ile Ile Pro Ser Val
            180                 185                 190

Ile Lys Asn Met Gln Trp Ser Val Asn Glu Gln Cys Ala Gln Tyr Asn
        195                 200                 205

Glu Cys Asp Thr Tyr Ala Val Phe Pro Gln Asn Gly Lys Pro Val Phe
    210                 215                 220

His Ile Glu Tyr Pro Lys Gly Asp Lys Thr Asn Asn Asp Leu Ser Val
225                 230                 235                 240

Thr Ala Ser Gln Lys Asn Ala Ala Cys Asp Phe Ala Gly Ser Ala Asn
                245                 250                 255

Phe Ser Thr Val Ile Lys Asn Met Asn Leu Asn Asn Trp Val Glu Tyr
                260                 265                 270

Cys

<210> SEQ ID NO 22
<211> LENGTH: 251
<212> TYPE: PRT
<213> ORGANISM: Aspergillus clavatus

<400> SEQUENCE: 22

Met Gly Pro Lys Ser Lys Val Phe Val Pro Leu Tyr Val Tyr Pro Ala
 1                5                  10                  15

Pro Gly Ala Trp Asp Pro Leu Glu Asp Val Ile Ser Lys His Pro Asp
            20                  25                  30

Val Asn Phe Thr Val Val Ile Asn Pro Gly Ser Gly Pro Gly Pro Glu
        35                  40                  45

Ala Leu Pro Asp Gly Asn Tyr Thr Arg Glu Ile Pro Lys Leu Ala Ser
    50                  55                  60

Tyr Glu Asn Val Arg Leu Leu Gly Tyr Val Ala Thr Thr Tyr Ala Lys
 65                 70                  75                  80

Arg Asn Ile Ser Glu Val Arg Arg Asp Ile Glu Thr Tyr Ala Ala Trp
                85                  90                  95

Pro Thr Gln Ser Ser Asn Ala Asn Leu Ala Val Arg Gly Ile Phe Phe
            100                 105                 110

Asp Glu Thr Pro Gln Gln Tyr Asp Ala Asp Ile Leu Ala Tyr Leu Arg
```

```
            115                 120                 125
Glu Leu Thr Asp Val Val Lys Gly Thr Ser Gly Leu Gly Pro Asp His
130                 135                 140

Tyr Val Val His Asn Pro Gly Ala Ile Pro Asp Ser Arg Tyr Leu Ser
145                 150                 155                 160

Thr Ala Asp Ser Thr Val Val Phe Glu Ala Thr Tyr Ala Thr Phe Gln
                165                 170                 175

Glu Arg His Gly Ala Glu Leu Phe Asp Thr Ile Pro Asp Ser His Arg
            180                 185                 190

Asp Gln Leu Cys Ala Val Ile His Ser Val Pro Thr Ser Val Glu Gly
            195                 200                 205

Ser Asp Leu Arg Gly Leu Val Lys Gln Val Arg Gln Val Ala Asp Glu
        210                 215                 220

Ile Phe Ile Thr His Leu Glu Thr Asp Tyr Tyr Ala Gly Phe Gly Gly
225                 230                 235                 240

Gln Trp Ser Glu Phe Val Asp Leu Met Ala Ser
                245                 250
```

<210> SEQ ID NO 23
<211> LENGTH: 257
<212> TYPE: PRT
<213> ORGANISM: Aspergillus nidulans

<400> SEQUENCE: 23

```
Arg Arg Lys Asn Asn Asn Met Gly Pro Lys Ala Lys Val Phe Val Pro
1               5                   10                  15

Leu Tyr Val Tyr Pro Ala Pro Gly Ala Trp Asp Pro Leu Val Asn Val
                20                  25                  30

Ile Thr Ala His Pro Asp Val Asn Phe Thr Val Val Asn Pro Gly
            35                  40                  45

Ser Gly Pro Gly Pro Asn Pro Leu Pro Asp Arg Asn Tyr Thr Gln Glu
    50                  55                  60

Ile Pro Arg Leu Thr Ala His Asp Asn Val Arg Val Leu Gly Tyr Val
65                  70                  75                  80

Ala Thr Thr Tyr Ala Lys Arg Asn Ile Ser Ser Val Arg Asn Asp Ile
                85                  90                  95

Glu Thr Tyr Ala Ala Trp Pro Thr Ile Ser Ala Asn Pro Lys Leu Ala
            100                 105                 110

Val Arg Gly Ile Phe Phe Asp Glu Thr Pro Gln Gln Tyr Asn Ala Ser
        115                 120                 125

Asp Leu Ala Tyr Leu Glu Glu Leu Thr Ser Val Val Lys Asn Thr Pro
130                 135                 140

Gly Leu Gly Pro Asp His Phe Val Phe His Asn Pro Gly Val Val Pro
145                 150                 155                 160

Asp Pro Arg Tyr Leu Ser Thr Ala Asp Ser Thr Val Val Phe Glu Ala
                165                 170                 175

Thr Tyr Asp Thr Phe Gln Asp Arg Asp Gly Ala Arg Leu Phe Glu Thr
            180                 185                 190

Ile Pro Asn Ser Asn Arg Ser Gln Leu Cys Ala Val Val His Ser Val
        195                 200                 205

Pro Asp Ser Val Glu Gly Ser Glu Leu Arg Lys Phe Val Lys Gln Ala
210                 215                 220

Arg Arg Val Ala Asp Glu Ile Phe Val Thr His Leu Ser Thr Asn Tyr
225                 230                 235                 240
```

```
Tyr Ala Ser Phe Gly Asp Lys Trp Asp Asp Phe Val Arg Leu Met Ala
                245                 250                 255

Gln

<210> SEQ ID NO 24
<211> LENGTH: 37
<212> TYPE: DNA
<213> ORGANISM: Artificial Sequence
<220> FEATURE:
<223> OTHER INFORMATION: Primer

<400> SEQUENCE: 24
gggagtcatc gtatgggcag cagccatcat catcatc                              37

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
gggggtacct tagcaatatt ccaccca                                         27
```